US011053509B2

(12) United States Patent
Van Zyl et al.

(10) Patent No.: US 11,053,509 B2
(45) Date of Patent: Jul. 6, 2021

(54) PLANT-PRODUCED CHIMAERIC ORBIVIRUS VLPS

(71) Applicants: CSIR, Pretoria (ZA); UNIVERSITY OF CAPE TOWN, Cape Town (ZA); ONDERSTEPOORT BIOLOGICAL PRODUCTS SOC LTD, Pretoria (ZA)

(72) Inventors: Albertha René Van Zyl, Wynberg (ZA); Ann Elizabeth Meyers, Plumstead (ZA); Daria Anna Rutkowska, Centurion (ZA); Edward Peter Rybicki, Cape Town (ZA); Hester Catharina Stark, Irene (ZA); Martha Magaretha O'Kennedy, Pretoria (ZA); Nobalanda Betty Mokoena, Montana (ZA)

(73) Assignees: CSIR, Pretoria (ZA); UNIVERSITY OF CAPE TOWN, Cape Town (ZA); ONDERSTEPOORT BIOLOGICAL PRODUCTS SOC LTD, Pretoria (ZA)

( * ) Notice: Subject to any disclaimer, the term of this patent is extended or adjusted under 35 U.S.C. 154(b) by 0 days.

(21) Appl. No.: 16/095,264

(22) PCT Filed: Apr. 19, 2017

(86) PCT No.: PCT/IB2017/052236
§ 371 (c)(1),
(2) Date: Oct. 19, 2018

(87) PCT Pub. No.: WO2017/182958
PCT Pub. Date: Oct. 26, 2017

(65) Prior Publication Data
US 2019/0136246 A1    May 9, 2019

(30) Foreign Application Priority Data

Apr. 19, 2016    (ZA) .................. 2016/02705

(51) Int. Cl.
*A61K 39/12*    (2006.01)
*C12N 15/82*    (2006.01)
*A61P 31/14*    (2006.01)
*A61K 35/76*    (2015.01)
*A61K 39/00*    (2006.01)

(52) U.S. Cl.
CPC .......... *C12N 15/8205* (2013.01); *A61K 35/76* (2013.01); *A61K 39/12* (2013.01); *A61P 31/14* (2018.01); *C12N 15/8258* (2013.01); *A61K 2039/5258* (2013.01); *C12N 2720/12134* (2013.01)

(58) Field of Classification Search
None
See application file for complete search history.

(56) References Cited

U.S. PATENT DOCUMENTS

| 5,686,270 A | 11/1997 | Roy et al. |
| 2013/0337010 A1 | 12/2013 | Palmarini et al. |

FOREIGN PATENT DOCUMENTS

| RU | 2575599 C2 | 2/2016 |
| WO | 1994/02173 | 2/1994 |
| WO | 2013/166609 A1 | 11/2013 |

OTHER PUBLICATIONS

Strasser et al. Generation of glyco-engineered Nicotiana benthamiana for the production of monoclonal antibodies with a homogeneous human-like N-glycan structure. Plant Biotechnol J. May 2008;6(4):392-402. (Year: 2008).*
PCT International Search Report issued in PCT/IB2017/052236 dated Jul. 26, 2017 (7 pages).
PCT Written Opinion issued in PCT/IB2017/052236 dated Jul. 26, 2017 (7 pages).
Jennings et al., "The coming of age of virus-like particle vaccines", Biological Chemi, Walter De Gruyter GMBH & Co, Berlin, DE, vol. 389, No. 5, May 1, 2008, pp. 521-536.
Thuenemann et al., "The Use of Transient Expression Systems for the Rapid Production of Virus-like Particles in Plants", Current Pharmaceutical Design, vol. 19, No. 31, Sep. 1, 2013, pp. 5564-5573.
Thuenemann et al., "A method for rapid production of heteromultimeric protein complexes in plants: assembly of protective bluetongue virus-like particles", Plant Biotechnology Journal, vol . 11, No. 7, Sep. 6, 2013, pp. 839-846.
Lua et al., "Bioengineering virus-like particles as vaccines", Biotechnology and Bioengineering, vol. 111, No. 3, Mar. 1, 2014, pp. 425-440.

* cited by examiner

*Primary Examiner* — Michelle S Horning
(74) *Attorney, Agent, or Firm* — Fisherbroyles, LLP; Victoria L. Boyd

(57) ABSTRACT

This invention relates to a second generation, plant-produced synthetic Orbivirus candidate vaccine. The vaccine comprises a plant produced chimaeric Orbivirus virus like particle (VLP) comprising at least one structural protein from one Orbivirus serotype and at least one structural protein selected from another serotype of the Orbivirus, wherein both structural capsid proteins are from the same Orbivirus species. In particular the invention relates to a vaccine against an Orbivirus, a method of producing chimaeric Orbivirus virus-like particles (VLPs) for use in a method of prevention and/or treatment of an Orbivirus infection, the use of the chimaeric Orbivirus VLPs in the manufacture of a vaccine for an Orbivirus, and a method of preventing and/or treating an Orbivirus infection.

9 Claims, 24 Drawing Sheets
Specification includes a Sequence Listing.

```
BTV4VP2    MEEFVIPVFSEREIPYALINQYPLAIQTDVRVVDVDDNHNLVKIPESDMIDVPKLDIVSA
BTV11VP2   MEEFVIPVYSETDIPYSLLSHYPLAIRTDVKIADTDEGHDVVKIPESDMIDVPRVDIVEA

BTV4VP2    LNYKPTRNDGIVVPRLLDITLKAYDDRKSVKNARGVDFMTDAKWMKWAIDDRMDIQPLKI
BTV11VP2   LAAKPMRNDGIVVPRLLDITLRAYDDRKAIKSARGVEFMTNAKWMKWAIDDRMDIQPLKV

BTV4VP2    TLDEHYSVNHQLFNCIVKAKTANADTIYYDYFPLEDRAKKCNHTNLELLRSLTTIEAFHI
BTV11VP2   AIDHYNAVNHQLFNCIVKARSANADTIYYDYFPLESKVKKCNHANLDLLRSLTNTEMFHM

BTV4VP2    LQGAAYSLKSNYDLIANSERESLEESYPIGSEKWVHLTRRTKIGNSGLSYNRSISSMVQV
BTV11VP2   LQGAAYSLKSNYELITNSERNSTEETYAPGVHNQIRLVRGTRIGYKGEAYSRFVSSLVQV

BTV4VP2    VVRGKVPDIIRGEITQLNRIRTEWIGASYDRTRIRALELCNILSAIGRKMMDTHEEPKDE
BTV11VP2   RIQGRTPPEIVDDIARLNVIRTEWINAQFDSTKIRALELCKILSAIGRKMLNTHEEPKDE

BTV4VP2    MDLSTRFQFKLDEKFNTSDFEHVNIFRTSGAATNEGRFYALIAIAATDTQKGRVWRTNPY
BTV11VP2   MDLSTKFQFKLDDKFKKTDSEHINIFNVRAPATHEGRFYALIAIAATDTQRGRIWRTNPY

BTV4VP2    PCLRGALIASECELGDVYYTLRHVYRWSLRPEYGQRERQLEDNKYVFGRVNLFDSDLAVG
BTV11VP2   PCLRGALIAAECELGDVYHTLRQVYKWSLRQDYGRTEVPLENNKYVFSRINLFDSNLDVG

BTV4VP2    DQIIHWQYEITEPVKTTYDDGYICNPEEKDDELLCKIDDERYKEMMERLIEGGWDQERFK
BTV11VP2   DQVVHWMYEVDGPAETTYDNGYMCKTEREDEELVCKISEEKYKTMLDRMIQGGWDQERFK

BTV4VP2    LHSILTEPNLLTIDFEKDAYLNSRSELVFPNYFDKWINSPMFNARLRITHGEIGSSKTID
BTV11VP2   LYSILTDPNLLTIDFEKDAHLNIRSEFVLPSYFDQWIYSPMFNARLRITHGEIATRKSAD

BTV4VP2    PWNRRVVYGYVKTSIESLDYALGRYYDIRLQLFGDTLSQKQTQSAVFTYLSEQDDFPALT
BTV11VP2   PWNKRVVFGYIKASTESPEYALGQYFDMRIQFYGDALSSKQNQSAVFQYLSQQEDFPTLT

BTV4VP2    NYSKGEAVCPHAGGAVYTFRKVALSLIANYEKLSPEMHEGLEHQMYVHPSANTTYQKQVK
BTV11VP2   SYAKGDVVCPHSGGALYTFRRVALMLMANYEKLSPDLHEGMEDYTYTHPSIGGAYQKRIL

BTV4VP2    DMKDFSQLICFIIDCIFEKRVQIRGVGEARRIIYLIQNSTGSQRQEVLKKTFPNFFMRIF
BTV11VP2   EMRDFSQLICFIIDYIFERHDQLRDAKEARRILYLIQNLDEPQRLEMLNVTFPNFFRHFL

BTV4VP2    KLREVKRICDLSVINFLPLLFLVQDNISYWHRQWSVPMILFDDAVRLIPVEVGAYANRFG
BTV11VP2   KLKDVQLISDLNVINFLPLLFLVQDNISYWHRQWAVPMILYDDVIRLIPVEVGAYANRFG

BTV4VP2    LKSFYNFVRFHPGDSKKKQDADDMHKEYGVACFEYYMNTKISQGGVNVPVVTSKLDTLKI
BTV11VP2   IKSFFNFTREHPGDAKKRQKADDTHKEFGSISFNYYASTKIAQGGVHTPVVTTKLDTLKI

BTV4VP2    HLASLCLGLADSIVYTLPVAHPKKCIVLIVVGDDKLDPQVRSEQVLSKYYYSRRHICGIV
BTV11VP2   HLSSLCAGLADSIVYTLPVAHPKKCIVLIIVGDDKLEPHVRSEQVVSKYYFSRRHVSGIV

BTV4VP2    AVSVGQEGQLQVYSSGIVRHRICEKSILKYKCKVVLVRMPGHVFGNDELMTKLLNV
BTV11VP2   SICVGQDNQLKVYSSGIVRHRVCEKFILKYKCKVVLVKMPGYVFGNDELMTKLLNV
```

```
BTV4VP2    MEEFVIPVFSEREIPYALINQYPLAIQTDVRVVDVDDNHNLVKIPESDMIDVPKLDIVSA
BTV10VP2   MEEFVIPVFSERDIPYSLLNHYPLAIRIDVKVDDEDGRHNLIKIPESDMIDVPKLSVIEA

BTV4VP2    LNYKPTRNDGIVVPRLLDITLKAYDDRKSVKNARGVDFMTDAKWMKWAIDDRMDIQPLKI
BTV10VP2   LNYRPKRNDGVVVPRLLDITLHAYDKRKSTKSAKGVEFTTDAKWMKWAIDDKMDIQPLKV

BTV4VP2    TLDEHYSVNHQLFNCIVKAKTANADTIYYDYFPLEDRAKKCNHTNLELLRSLTTIEAFHI
BTV10VP2   TLDNHYSVNHQLFNCIVKARSANADTIYYDYYPLENGAKKCNHTNLDLLRSLTTTEMFHI

BTV4VP2    LQGAAYSLKSNYDLIANSERESLEESYPIGSEKWVHLTRRTKIGNSGLSYNRSISSMVQV
BTV10VP2   LQGAAYALKTTHELVAHSERESTSETYQVGTQRWIQLRKGTKIGYRGQPYERFISSLVQV

BTV4VP2    VVRGKVPDIIRGEITQLNRIRTEWIGASYDRTRIRALELCNILSAIGRKMMDTHEEPKDE
BTV10VP2   IIKGRVPDEIRDEIAELNRIKDEWKNAAYDRTKIRALELCKILSAIGRKMLDVQEEPKDE

BTV4VP2    MDLSTRFQFKLDEKFNTSDFEHVNIFRTSGAATNEGRFYALIAIAATDTQKGRVWRTNPY
BTV10VP2   MALSTRFQFKLDEKFIRTDQEHVNIFEVGGPATDDGRFYALIAIAATDTQQGRVWRTNPY

BTV4VP2    PCLRGALIASECELGDVYYTLRHVYRWSLRPEYGQRERQLEDNKYVFGRVNLFDSDLAVG
BTV10VP2   PCLRGALIAAECELGDVYFTLRQTYKWSLRSEYGQRERPLEDNKYVFSRLNLFDTNLAIG

BTV4VP2    DQIIHWQYEITEPVKTTYDDGYICNPEEKDDELLCKIDDERYKEMMERLIEGGWDQERFK
BTV10VP2   DEIIHWRYEIYRPKETTHDDGYICVSQKDDDELLCEIDGDRYKEMFDRMIQGGWDQERFK

BTV4VP2    LHSILTEPNLLTIDFEKDAYLNSRSELVFPNYFDKWINSPMFNARLRITHGEIGSSKTID
BTV10VP2   LHNILTEPNLLTIDFEKDAYLGSRSELVFPPYYDKWINSPMFNAKLKIARGEIATRKVDD

BTV4VP2    PWNRRVVYGYVKTSIESLDYALGRYYDIRLQLFGDTLSQKQTQSAVFTYLSEQDDFPALT
BTV10VP2   PWNNRAVHGYIKTSAESLGYVLGPYYDLRLQLFGDALSLEQKQSAVFEYMAQQDDFPALT

BTV4VP2    NYSKGEAVCPHAGGAVYTFRKVALSLIANYEKLSPEMHEGLEHQMYVHPSANTTYQKQVK
BTV10VP2   DYTKEKNGCPHSGGTFYTFRKVALIILSSYERLDPSLHEGREHETYMHPAINDVFRRYAL

BTV4VP2    DMKDFSQLICFIIDCIFEKRVQIRGVGEARRIIYLIQNSTGSQRQEVLKKTFPNFFMRIF
BTV10VP2   EMKEFSQLICFVFDYIFEKHVQLRNAKEARRIIYLIQNTSGVHRLDILRETFPNFLRHVM

BTV4VP2    KLREVKRICDLSVINFLPLLFLVQDNISYWHRQWSVPMILFDDAVRLIPVEVGAYANRFG
BTV10VP2   NLRDVKRICDLNVINFFPLLFLIQDNISYWHRQWSIPMILFGEVVRLIPIEVGAYANRFG

BTV4VP2    LKSFYNFVRFHPGDSKKKQDADDMHKEYGVACFEYYMNTKISQGGVNVPVVTSKLDTLKI
BTV10VP2   FKSFLNFIRFHPGDSKKKQDADDTHKEFGSICFEYYTTTKISQGEIDVPVITSKLDTLKL

BTV4VP2    HLASLCLGLADSIVYTLPVAHPKKCIVLIVGDDKLDPQVRSEQVLSKYYYSRRHICGIV
BTV10VP2   HIASLCAGLADSLVYTLPVAHPKKSIVLIIVGDDKLEPQVRSEQIVNKYHYSRRHISGVV

BTV4VP2    AVSVGQEGQLQVYSSGIVRHRICEKSILKYKCKVVLVRMPGHVFGNDELMTKLLNV
BTV10VP2   SICVDQNGQLKVHSMGITRHRICDKSILKYKCKVVLVRMPGHVFGNDELMTKLLNV
```

Figure 18

| | |
|---|---|
| BTV4 | MEEFVIPVFSEREIPYALINQYPLAIQTDVRVVDVDGNHNLVKIPESDMIDVPKLDIVSA |
| BTV17 | MEEFVIPVYSEDEIPYALLSRYPLAIQTNVKIEDVEGKHNVVKIPESDMIDIPKLTIVEA |
| | |
| BTV4 | LNYKPTRNDGIVVPRLLDITLKAYDDRKSVKNARGVDFMTDAKWMKWAIDDRMDIQPLKI |
| BTV17 | MNYKPARNDGIVVPRLLDITLRAYDDRKSTKSARGIEFMTNARWMKWAIDDRMDIQPLKV |
| | |
| BTV4 | TLDEHYSVNHQLFNCIVKAKTANADTIYYDYFPLEDRAKKCNHTNLELLRSLTTIEAFHI |
| BTV17 | TLDHYCSVNHQLFNCVVKANAANADTIYYDYFPLEDYKKRCNHTNLDLLRSLTNMELFHA |
| | |
| BTV4 | LQGAAYSLKSNYDLIANSERESLEESYPIGSEKWVHLTRRTKIGNSGLSYNRFISSMVQV |
| BTV17 | LQGAAYSIKSSYELVAYSERGSLEETYVVGQPKWIHLTRGTRIGNSGLSYERFISSMVQV |
| | |
| BTV4 | VVRGKVPDIIRGEITQLNRIRTEWIGASYDRTRIRALELCNILSAIGRKMMDTHEEPKDE |
| BTV17 | SVNGKIPDEIANEIAQLNRIRAEWITATYDRGRIRALELCNILSTIGRKMLNTHEEPKDE |
| | |
| BTV4 | MDLSTRFQFKLDEKFNTSDSEHVNIFRTSGAATNEGRFYALIAIAATDTQKGRVWRTNPY |
| BTV17 | MDLSTRFQFKLDEKFNRADSEHVNIFGVRGPATDEGRFYALIAIAATDTQKGRVWRTNPY |
| | |
| BTV4 | PCLRGALIASECELGDVYYTLRHVYQWSLRPEYGQREQQLEDNKYVFGRVNLFDSDLAVG |
| BTV17 | PCLRGALVAAECELGDVYSTLRRVYRWSLRPEYGQHERQLENNKYVFNRINLFDSNLAVG |
| | |
| BTV4 | DQIIHWQYEITEPVKTTYDDGYICNPEEEDDELLCKIDDERYKEMMERLIEGGWDQERFK |
| BTV17 | DQIIHWRYEVKASAETTYDSGYMCRHEAEEDELLCKINEDKYKEMLDRMIQGGWDQERFK |
| | |
| BTV4 | LHSILTEPNLLTIDFEKDAYLNSRSELVFPNYFDKWINSPMFNARLRITHGEIGSSKTID |
| BTV17 | LHNILTDPNLLTIDFEKDAYLNSRSELVLPDYFDKWISSPMFNARLRITKGEIGTSKKDD |
| | |
| BTV4 | PWNRRVVYGYVKTSIESLDYALGRYYDIRLQLFGDTLSQKQTQSAVFTYLSEQDDFPALT |
| BTV17 | PWNNRAVRGYIKSPAESLDFVLGPYYDLRLLFFGETLSLKQEQSAVFQYLSQLDDFPALT |
| | |
| BTV4 | NYSKGEAVCPHAGGAVYTFRKVALSLIANYEKLSPEMHEGLEHQMYVHPSANTTYQKQVK |
| BTV17 | QLTGD-AVCPHSGGALYTFRKVALFLIGNYEKLSPDLHEGMEHQRYVHPSTGGTYQKRVL |
| | |
| BTV4 | DMKDFSQLICFIIDCIFEKRVQIRGVGEARRIIYLIQNSTGSQRQEVLKKTFPNFFMRIF |
| BTV17 | EMKDPCQLTCFVIDYIFEKREQLRDTKEARYIVYLIQSLTGTQRLSVLRSTFPNFFQRLL |
| | |
| BTV4 | KLREVKRICDLSVINFLPLLFLVQDNISYWHRQWSVPMILFDDAVRLIPVEVGAYANRFG |
| BTV17 | MLKEIKFVRDLNVINFLPLMFLVHDNISYWHRQWSIPMVLFDDTIKLIPVEVGAYANRFG |
| | |
| BTV4 | LKSFYNFVRFHPGDSKKKQDADDMHKEYGVACFKYYMNTKISQGGVNVPVVTSKLDTLKI |
| BTV17 | FKSFMNFTRFHPGELKKKQIAEDIHKEFGVVAFEYYTNTKISQGNVHTPVMTTKMDVLRV |
| | |
| BTV4 | HLASLCLGLADSIVYTLPVAHPKKCIVLIVVGDDKLDPQVRSEQVLSKYYYSRRHICGIV |
| BTV17 | HLSSLCAGLADSVVYTLPVAHPKKCIVLIIVGDDKLEPHTRSEQIVSRYNYSRKHICGIV |
| | |
| BTV4 | AVSVGQEGQLQVYSSGIVRHRICEKSILKYKCKVVLVRMPGHVFGNDELMTKLLNV |
| BTV17 | SVTIGQNSQLRVHTSGIVKHRVCDKFILKHKCKVILVRMPGYVFGNDELMTKLLNV |

AHS VLP b)

pEAQ-AHS5-VP3   AgeI ──VP3──▶ XhoI pEAQ-AHS5-VP7   AgeI ──VP7──▶ XhoI pEAQ-AHS5-VP5   AgeI ──VP5──▶ XhoI pEAQ-AHS5-VP2   AgeI ─────────▶ XhoI

Figure 29

PLANT-PRODUCED CHIMAERIC ORBIVIRUS VLPS

CROSS REFERENCE TO RELATED APPLICATIONS

The present application is filed under 35 U.S.C. § 371 as the U.S. national phase of International Patent Application No. PCT/IB2017/052236, filed Apr. 19, 2017, which designated the United States and claims priority to South African Patent Application No. 2016/02705, filed Apr. 19, 2016, each of which is hereby incorporated in its entirety including all tables, figures and claims.

BACKGROUND OF THE INVENTION

This invention relates to a second generation, plant-produced synthetic Orbivirus candidate vaccine. The vaccine comprises a plant produced chimaeric Orbivirus VLP having a common core comprising at least one structural protein from one Orbivirus serotype and an outer layer comprising at least one structural protein selected from another serotype of the Orbivirus, wherein both structural capsid proteins are from the same Orbivirus species. In particular the invention relates to a vaccine against an Orbivirus, a method of producing chimaeric Orbivirus virus-like particles (VLPs) for use in a method of prevention and/or treatment of an Orbivirus infection, the use of the chimaeric Orbivirus VLPs in the manufacture of a vaccine for an Orbivirus, and a method of preventing and/or treating an Orbivirus infection.

The invention relates to a chimaeric Orbivirus VLP vaccine which is adaptable so that it can be used to immunize animals against multiple serotypes of an Orbivirus by using a common core comprising at least one capsid protein from one Orbivirus serotype and an outer layer comprising at least one Orbivirus capsid protein from another serotype of the same species of Orbivirus. VLPs which are representative of different serotypes of the same species of Orbiviruses could be mixed and administered in combination as a multivalent vaccine. Using the chimaeric VLPs of the invention it is possible to produce a multivalent vaccine which represents all of the serotypes for a particular Orbivirus species. The plant-produced Orbivirus candidate vaccines of the present invention are particulate in nature and hence stimulate a strong cellular immune response.

The genus Orbivirus is a member of the Reoviridae family, in the subfamily Sedoreovirinae. Unlike the other reoviruses, Orbiviruses are arboviruses and, as such, are transmitted by arthropod vectors. The Orbivirus genus currently contains 22 species and at least 130 different serotypes. Orbiviruses can infect and replicate within a wide range of arthropod and vertebrate hosts. Many Orbiviruses are transmitted by ticks or haematophagus insect vectors (*Culicoides* spp, mosquitoes and sand flies) and have a wide host range that includes cattle, goats and sheep, wild ruminants, equids, camelids, marsupials, sloths, bats, birds, large canine and feline carnivores and humans.

The Orbivirus virions are non-enveloped particles that are between 70-80 nm in diameter. These virus particles are spherical in appearance and are arranged as an icosahedral structure made up of three concentric layers of 4 major structural proteins (VPs) arranged in concentric shells around the double-stranded RNA genome and other minor structural and non-structural proteins. Outer, intermediate and an inner capsid layers surround the genome, with the intermediate and inner capsids having T=13 and T=2 symmetry, respectively. The core is constructed of two concentric protein shells, the inner capsid layer which contains 120 VP3 protein copies and the intermediate capsid layer composed of 780 VP7 protein copies. VP1, VP4 and VP6 are minor enzymatic proteins that are packaged along with the ten genome segments within the central space of the virus core. The Orbivirus outer capsid layer is composed of two additional structural proteins, VP2 and VP5, which mediate viral cell-attachment and penetration, respectively, during initiation of infection. The outer capsid proteins are more variable than the core proteins, and most of the non-structural proteins, and the specificity of their reactions with neutralising antibodies determines the virus serotype.

Orbiviruses have double stranded RNA genomes and are classified as Class III viruses. Their genome is linear and is segmented into ten segments of various lengths. One copy of each gene segment is packaged per virion. In most cases each gene segment encodes a single open reading frame (ORF). The genome encodes the seven structural proteins (VP1-VP7) and the four non-structural proteins (NS1, NS2, NS3/3A, NS4).

Many Orbiviruses preferentially infect vascular endothelial cells. Orbiviruses enter the host cell by endocytosis and the outer capsid is subsequently removed. The whole cycle of viral replication takes place within the cytoplasm of the host cell. Transcription of the viral genome into mRNA occurs within the core particle and mRNA is translated into proteins using the host cell ribosomes. Viral proteins are synthesized 2-14 days after initial infection. New virons self-assemble within the cytoplasm and are then released from the host cell by budding. During the budding process they transiently acquire a lipid envelope which can be detected for a short period of time following their release but this is subsequently lost.

It has been shown that co-expression of the 4 Orbivirus capsid proteins in a recombinant baculovirus system results in the formation of virus-like particles (VLPs). When VP3 and VP7 are co-expressed, 60 dimers of VP3, the innermost protein, assemble into a particle—these particles are called subcore-like particles (SCLPs); trimers of VP7 then form an icosahedral shell on the VP3 scaffold resulting in stable core-like particles (CLPs). However, these are not immunogenic in animals, which is not surprising as they do not contain the neutralizing protein VP2 which presents the major immunogenic determinants. A third shell is formed when the VP5 and VP2 of the same Orbivirus are co-expressed with the VP3 and VP7 proteins. VP2 trimers position themselves on the CLP surface and are interspersed with VP5 trimers. BTV VLPs formed in this manner have been shown to be immunogenic in sheep. Thus, Orbivirus VLPs may be an inherently safe and effective vaccine. Orbivirus VLPs have previously been expressed in insect cells, however this method of production remains costly.

Expression of recombinant proteins in plants has developed over the last twenty years from a curiosity in the late 1980s to a medically and industrially relevant production system today. Early efforts relied on transformation of plants to produce stable transgenic lines. This was achieved through biolistic delivery or, more recently, agroinfiltration. While transgenic protein production remains a useful and viable system, advances in transient expression methods and technology have positioned transient expression as the preferred method for industrial-scale production in plants. Two key factors that have played a central role in this transition are viral, or virus-derived, expression vectors and the development of agroinfiltration technology.

Agroinfiltration was originally developed as a means of introducing foreign DNA into plant cells for transient expression of recombinant proteins. This process relies on the DNA transfer capability of *Agrobacterium tumefaciens* to introduce foreign DNA into plant cells. *A. tumefaciens* can be used to transfer a transgene located in the transfer DNA (T-DNA) segment of the Ti plasmid into plants infiltrated with a bacterial suspension of the transformed bacterium. The T-DNA is transported to the plant nucleus but is rarely integrated into the plant genome. Instead, it exists as an episome from which transcription and translation of genes of interest cloned into the T-DNA take place, allowing for transient expression of recombinant proteins of interest Viral vectors were the first transient expression method developed for plants. Early efforts simply inserted a recombinant gene or epitope into the genome of viruses such as TMV, cowpea mosaic virus (CPMV), or PVX, either fused to the viral coat protein or separately, under control of a duplicated constitutive viral promoter. While this application produced immunogenic proteins, expression levels were lower than those found in transgenic plants. Other problems with these 'first-generation' viral vectors included a tendency to revert to the natural virus, constraints on insert size, difficulty of administration, and an inability to form VLPs.

These limitations prompted further work to develop 'second generation', or deconstructed, viral vectors. This approach used only the desirable viral elements, in particular the replicative machinery, to manufacture synthetic vectors capable of inducing transgene expression in plants. While these vectors are usually not infectious on their own, when coupled with agroinfiltration technology they can result in systemic transient expression of protein at levels comparable to that of transgenic plants. This approach has the advantages of short time frames (3-7 days) when compared to stable transformation (6-9 months), significant expression levels, and rapid and easy scale-up and purification. This makes agroinfiltration-mediated transient expression via viral vectors an ideal approach for the production of medically relevant proteins and particles in plants. Of particular interest is the use of transient expression for the production of VLPs in plants, as there is potential for a reduction in cost when compared to traditional systems.

Using the above mentioned technologies the applicant has developed a plant-produced Orbivirus VLP vaccine consisting of a mixture of chimaeric VLPs, as discussed herein each VLP consists of a core comprising of at least one capsid protein from one Orbivirus serotype with an outer layer consisting of at least one capsid protein from another serotype of the same Orbivirus species.

Since the VP2 capsid protein contains the neutralising epitopes, mixtures of different chimaeric VLPs provide a plant-produced particulate vaccine which can be used in animals to protect them against more than one serotype of the same Orbivirus species. The value of this product lies in the low safety requirements for production, as well as the cost effectiveness of the production method.

Virus-like particles (VLPs) are considered excellent immunogens for a number of reasons: they resemble the mature viral particles in size and shape but lack the viral genome and are thus non-replicating and non-infectious; they have also been shown to stimulate both the humoral and cellular arms of the immune system. The repetitive nature of protein epitopes exposed on the surfaces of VLPs means they stimulate a strong antibody response as a result of B cells recognising specific repetitive units.

There are a number of other advantages to using VLPs as vaccine candidates. In the case of some VLPs (eg: Human papillomavirus—HPV) it has been shown that co-administration of an adjuvant is not required for the induction of a strong antibody response, thus reducing the vaccine dose costs. VLPs can be used to broaden the protective ability of the vaccine with the inclusion of additional epitopes which would lower vaccine dose amounts and concomitant vaccine costs. In the case of animal vaccines, VLP vaccines can be designed so as to exclude markers used for diagnosis of viral infection, allowing for the distinction between infected and vaccinated animals (DIVA): this is a very important requirement in areas affected by disease outbreaks such as in the EU. These factors have led to rapid advances in the field of VLP vaccine development and production. Accordingly, this invention aims to provide non-infectious, non-replicating vaccines against Orbviruses.

The three most economically important Orbiviruses are Bluetongue virus, African horse sickness virus and epizootic hemorrhagic disease virus, all of which are transmitted by *Culicoides* species.

Bluetongue (BT) disease is a non-contagious, insect-borne, viral disease of ruminants, mainly sheep and less frequently cattle, goats, buffalo, deer, dromedaries, and antelope. In sheep, BT disease causes an acute disease with high morbidity and mortality, with up to 90% mortality in some breeds. Bluetongue disease is caused by Bluetongue virus (BTV), of the genus Orbivirus, of the Reoviridae family. There are twenty-six recognised serotypes for this virus. Bluetongue has been observed in Australia, the USA, Africa, the Middle East, Asia and Europe. There is no efficient treatment. Prevention is effected via quarantine, inoculation with live modified virus vaccine and control of the midge vector. The existing BTV vaccine used in South Africa consists of field strains of BTV attenuated through serial passage in embryonated chicken eggs and BHK-21 cells. It consists of 3 bottles (A, B and C) each containing 5 different serotypes (A—1, 4, 6, 12 and 14; B—3, 8, 9, 10 and 11; C—2, 5, 7, 13 and 19). This does not represent all the BTV serotypes circulating in South Africa, which total 26. The reason for this is that the missing types do not cause very severe pathogenicity in sheep (serotypes 15, 16, 18, 22-26). The production process in eggs and cell culture is costly and the inclusion of so many different serotypes would also add significantly to the cost.

It has been shown previously using BTV-10 VP2, VP3, VP5 and VP7 that co-expression of these four structural proteins in insect cells results in the formation of VLPs. They were shown to induce protective immunity in sheep which were challenged with live BTV-10 virus. Similar VLPs made in insect cells by co-expression of the four structural genes representing a different BTV serotype (BTV-1) have also been shown to induce neutralizing antibodies and protect sheep challenged with BTV-1. It has however, not previously been shown that co-expression of structural proteins from two different serotypes of the same Orbivirus will form chimaeric VLPs when co-expressed in a plant cell.

African horse sickness (AHS) is an infectious, non-contagious disease of equids, with a mortality rate of up to 95% in horses, the most susceptible species. African horse sickness is caused by African horse sickness virus (AHSV), which is transmitted by *Culicoides* midges. AHSV is classified as an Orbivirus in the family Reoviridae and there are currently nine recognised AHSV serotypes, namely serotypes 1 to 9. Although endemic to Sub-Saharan Africa, devastating sporadic outbreaks of AHS disease have also occurred in North Africa, the Iberian Peninsula, the Middle East and Asia. Currently African horse sickness is classified by the World Organization for Animal Health (OIE) as a notifiable disease, and strict quarantine measures govern the transport of horses from endemic countries, such as South Africa, to non-endemic regions. AHS outbreaks not only have significant economic implications on the equine industries of affected countries, but also impact directly on the agricultural and transport activities of rural communities, particularly in South Africa. More than 50% of the horses in South Africa are estimated to belong to rural community horse owners.

In endemic regions, annual prophylactic vaccination of horses with a commercial live attenuated vaccine (Onderstepoort Biological products (OBP)) is an efficient way of preventing serious losses during the peak AHS season. The multivalent vaccine consists of two components, the trivalent component (serotypes 1, 3 and 4) and the quadrivalent component (serotypes 2, 6, 7 and 8) administered three weeks apart. Although serotypes 5 and 9 are excluded from the multivalent vaccine formulation, in vivo cross-protection afforded against serotype 5 by the included serotype 8 and cross-protection afforded by the included serotype 6 against serotype 9, ensure that the vaccine is effective against all AHS serotypes. There are, however, several drawbacks associated with the use of the current AHS vaccine and these include the risk of reversion to virulence, teratogenic effects in pregnant mares as well as the inability to differentiate between infected and vaccinated animals (DIVA). These concerns have prohibited the use of this vaccine in non-endemic areas. Production of a live attenuated vaccine requires high biosafety levels during manufacture, thus elevating cost, and also precludes a rapid production rate. A plant-produced AHS VLP-based vaccine would address these concerns. Although AHS VLPs have recently been assembled in insect cells, the complexity of production and upscaling in insect cells will make only a monovalent AHS VLP based vaccine (single serotype) possible.

Whilst live attenuated vaccines for BT and AHS are available, safety concerns have prohibited the use of these vaccines in non-endemic areas, such as Europe. The use of live virus also makes it difficult to differentiate infected from vaccinated animals (DIVA). Production of live vaccines requires high biosafety levels for handling, thus elevating the production cost. The use of live virus also precludes a rapid production rate. Alternatives to the current live attenuated vaccine include an inactivated vaccine, viral vectors expressing the outer capsid proteins and subunit vaccines. Plant produced chimaeric Orbivirus VLP vaccines will abrogate the need for high biosafety levels during manufacture. In addition, VLPs can be made more rapidly by transient expression in agroinfiltrated plants.

SUMMARY OF THE INVENTION

The present invention provides for chimaeric Orbivirus VLPs which are immunogenic and which are useful in the formulation of a vaccine composition against Orbivirus infection in a subject. The invention relates to the chimaeric Orbivirus VLPs, methods for their production and vaccine compositions containing the chimaeric Orbivirus VLPs.

In one embodiment, the present invention provides for genetically engineered Orbivirus VLPs comprising a single chimaeric Orbivirus VLP, a double chimaeric Orbivirus VLP, a triple chimaeric Orbivirus VLP or a quadruple chimaeric Orbivirus VLP. It will be appreciated that in these chimaeric Orbivirus VLPs at least one structural protein is selected from one serotype of a specific Orbivirus species and the other structural proteins are selected from at least one other serotype of the same species of Orbivirus.

For instance, exemplary, non-limiting, genetically engineered BTV VLPs of the present invention may be a single chimaeric if they comprise, for instance, of one structural protein from a first BTV serotype i.e. a BTV-2 VP2 and the other structural proteins from a second BTV serotype i.e. BTV-8 VP3, BTV-8 VP5 and BTV-8 VP-7. Similarly, an exemplary double chimaeric BTV VLP of the present invention will comprise two structural proteins from a first BTV serotype and two structural proteins from a second BTV serotype, for instance, BTV-8 VP3, BTV-8 VP7, BTV-3 VP2 and BTV-3 VP5. An exemplary triple chimaeric BTV VLP of the invention may comprise, two structural proteins from a first BTV serotype, one structural protein from a second BTV serotype and one structural protein from a third BTV serotype, for instance, BTV-8 VP3, BTV-8 VP7, BTV-3 VP2 and BTV-4 VP5. Likewise, an exemplary quadruple chimaeric BTV VLP of the present invention may comprise, one structural protein from a first BTV serotype, one structural protein from a second BTV serotype, one structural protein from a third BTV serotype and one structural protein from a fourth BTV serotype, for instance, BTV-2 VP2, BTV-3 VP5, BTV-4 VP7 and BTV-8 VP3.

Exemplary, non-limiting, genetically engineered AHSV VLPs of the present invention may be a single chimaeric if they comprise, for instance, of one structural protein from a first AHSV serotype, for instance, an AHSV-7 VP2 and the other structural proteins from a second AHSV serotype, for instance, AHSV-1 VP3, AHSV-1 VP5 and AHSV-1 VP7. Similarly, an exemplary double chimaeric AHSV VLP of the present invention will comprise two structural proteins from a first AHSV serotype and two structural proteins from a second AHSV serotype, for instance, AHSV-1 VP3, AHSV-1 VP7, AHSV-7 VP2 and AHSV-7 VP5. An exemplary triple chimaeric AHSV VLP of the invention may comprise, two structural proteins from a first AHSV serotype, one structural protein from a second AHSV serotype and one structural protein from a third AHSV serotype, for instance, AHSV-1 VP3, AHSV-1 VP7, AHSV-6 VP2 and AHSV-3 VP5. Likewise, an exemplary quadruple chimaeric AHSV VLP of the present invention may comprise, one structural protein from a first AHSV serotype, one structural protein from a second AHSV serotype, one structural protein from a third AHSV serotype and one structural protein from a fourth AHSV serotype, for instance, AHSV-6 VP2, AHSV-3 VP5, AHSV-2 VP7 and AHSV-1 VP3.

Those skilled in the art will appreciate that chimaeric single, double, triple and quadruple Orbivirus VLPs can be constructed for any Orbivirus species using the methods described herein and as exemplified for BTV and AHSV.

The invention also relates to a multivalent vaccine composition comprising a combination of the chimaeric Orbivirus VLPs, wherein the chimaeric VLPs comprise structural proteins representative of several different serotypes of a particular Orbivirus species.

According to a first aspect of the invention there is provided for a chimaeric Orbivirus VLP comprising at least one structural protein from a first serotype of an Orbivirus species and at least one structural protein from a second serotype of an Orbivirus species. The chimaeric Orbivirus VLP of the invention is produced in and recovered from a plant cell.

In a preferred embodiment of the invention there is provided for a chimaeric Orbivirus virus-like particle (VLP) comprising VP2, VP3, VP5 and VP7 structural proteins, wherein at least one of the VP2, VP3, VP5 and VP7 structural proteins is selected from a first Orbivirus serotype and at least one of the VP2, VP3, VP5 and VP7 structural proteins is selected from a second Orbivirus serotype, wherein the Orbivirus serotypes are of the same Orbivirus species, and wherein the chimaeric Orbivirus VLP is produced according to a method comprising the steps of (i) providing codon-optimised nucleotide sequences encoding the Orbivirus VP2, VP3, VP5 and VP7 structural proteins, (ii) cloning the codon-optimised nucleotide sequences into at least one expression vector adapted to express the structural proteins in a plant cell, (iii) transforming or infiltrating the plant cell with the at least one expression vector of step (ii), co-expressing the VP2, VP3, VP5 and VP7 structural proteins in the plant cell, such that the expressed structural proteins assemble to form the chimaeric Orbivirus VLP; and (v) recovering the chimaeric Orbivirus VLP from the plant cell.

In one preferred embodiment of the invention the chimaeric Orbivirus VLP comprises at least one of the VP2, VP3, VP5 and VP7 structural proteins from a third Orbivirus serotype of the same Orbivirus species. Alternatively, at least one of the VP2, VP3, VP5 and VP7 structural proteins may be from a fourth Orbivirus serotype of the same Orbivirus species.

The chimaeric Orbivirus VLP of the invention may be a single chimaeric Orbivirus VLP comprising a first VP2, VP3, VP5 or VP7 structural protein from a first Orbivirus serotype and the other three structural proteins from a second Orbivirus serotype. Alternatively, the chimaeric Orbivirus VLP of the invention may be a double chimaeric Orbivirus VLP comprising two of the VP2, VP3, VP5 or VP7 structural proteins from the first Orbivirus serotype and two of the structural proteins from the second Orbivirus serotype. Further alternatively, the chimaeric Orbivirus VLP may be a triple chimaeric Orbivirus VLP comprising two of the VP2, VP3, VP5 or VP7 structural proteins from a first Orbivirus serotype, one structural protein from a second Orbivirus serotype, and one structural protein from a third Orbivirus serotype. Alternatively, the chimaeric Orbivirus VLP may be a quadruple chimaeric Orbivirus VLP comprising the first VP2, VP3, VP5 or VP7 structural protein from a first Orbivirus serotype, the second structural protein from a second Orbivirus serotype, the third structural protein from a third Orbivirus serotype, and the fourth structural protein from a fourth Orbivirus serotype.

In another preferred embodiment the plant or plant cell is Nicotiana benthamiana plant or plant cell. In yet a further preferred embodiment the plant or plant cell may be a N. benthamiana dXT/FT mutant tobacco plant or cell, which facilitates mammalian-like or human-like glycosylation of the polypeptides.

In one embodiment of the invention, for instance, where the Orbivirus is BTV the first serotype is, for instance, BTV-8 then the second Orbivirus serotype may be a BTV serotype selected from the group consisting of BTV-1, BTV-2, BTV-3, BTV-4, BTV-5, BTV-6, BTV-7, BTV-9, BTV-10, BTV-11, BTV-12, BTV-13, BTV-14, BTV-15, BTV-16, BTV-17, BTV-18, BTV-19, BTV-20, BTV-21, BTV-22, BTV-23, BTV-24, BTV-25, BTV-26 and BTV-27.

In another embodiment of the invention, for instance, where the Orbivirus is AHSV the first serotype is, for instance, AHSV-1 then the second Orbivirus serotype is an AHSV serotype selected from the group consisting of AHSV-2, AHSV-3, AHSV-4, AHSV-5, AHSV-6, AHSV-7, AHSV-8 and AHSV-9.

The chimaeric BTV VLPs or chimaeric AHSV VLPs of the embodiments described above are produced in a plant cell which has been transformed with one or more vectors that regulate the expression of the VP2, VP3, VP5 and VP7 structural proteins. It will be understood by those of skill in the art that each of the genes encoding the structural proteins may each be contained on a separate vector. Alternatively, two or more of the genes encoding the structural proteins may be contained on a single vector, in any combination. Preferably, in order to facilitate the formation of VLPs in the plant cells, the vectors containing the genes encoding the structural proteins will be transformed into the plant cell in a ratio of 1:1:1:1 or a ratio of 1:1:2:1 or a ratio of 2:1:2:1 of the genes encoding VP2:VP3:VP5:VP7.

In one preferable embodiment, the plant cell is transformed using Agrobacterium-mediated transformation. Most preferably, the expression of the Orbivirus VP2, VP3, VP5 and VP7 structural proteins in the plant cell is mediated by the Agrobacterium, wherein the Agrobacterium is selected from Agrobacterium AGL-1, Agrobacterium LBA4404, Agrobacterium GV3101 pMP90 or any other suitable agrobacterial strain.

In a further preferable embodiment the VP2, VP3, VP5 and VP7 structural proteins are transiently co-expressed in the plant cell. However, those of skill in the art will appreciate that stable transformation of the plant cell will also lead to the formation of chimaeric Orbivirus VLPs.

It will be appreciated that the embodiments described above relate to BTV and AHSV, however those of skill in the art will appreciate that using the same approach it will be possible to produce Orbivirus VLPs from any species of Orbivirus. Specifically, the Orbivirus species may be selected from the group consisting of Lebombo virus (LEBV), Pata virus (PATAV), African horse sickness virus (AHSV), Bluetongue virus (BTV), Altamira virus (ALTV), Almeirim virus (AMRV), Caninde virus (CANV), Changuinola virus (CGLV), Irituia virus (IRIV), Jamanxi virus (JAMV), Jari virus (JARIV), Gurupi virus (GURV), Monte Dourado virus (MDOV), Ourem virus (OURV), Purus virus (PURV), Saraca virus (SRAV), Acado virus (ACDV), Corriparta virus (CORV), Eubenangee virus (EUBV), Ngoupe virus (NGOV), Tilligerry virus (TILV), Epizootic hemorrhagic disease virus (EHDV), Kawanabe virus, Equine encephalosis virus (EEV), Great Island virus, Kemerovo virus (KEMV), Essaouira virus (ESSV), Kala iris virus (KIRV), Mill Door/79 virus (MILDV). Rabbit syncytium virus (RSV), Tribeč virus (TRBV), Broadhaven virus (BRDV), Orungo virus (ORUV), Abadina virus (ABAV), Apies River virus, Bunyip Creek virus (BCV), Chuzan (Kasba) virus (SBV), CSIRO Village virus (CVGV), D'Aguilar virus (DAGV), Marrakai virus (MARV), Petevo virus (PETV), Vellore virus (VELV), Llano Seco virus (LLSV), Minnal virus (MINV), Netivot virus (NETV), Umatilla virus (UMAV), Wallal virus (WALV) and Mitchell River virus (MRV).

According to a second aspect of the invention there is provided for a method of producing a chimaeric Orbivirus VLP in a plant cell, comprising transforming the plant cell with one or more vectors that regulate the expression of, for example, VP3, VP5 and VP7 structural proteins from a first Orbivirus serotype and VP2 from a second Orbivirus serotype and expressing the VP2, VP3, VP5 and VP7 structural proteins in the plant cell, wherein the expressed VP2, VP3, VP5 and VP7 structural proteins assemble to form a chimaeric Orbivirus VLP. The method further provides for transient co-expression of the VP2, VP3, VP5 and VP7 structural proteins in the plant cell. The method further provides a step of recovering the chimaeric Orbivirus VLP from the plant cell.

In a preferred embodiment the method comprises a method of producing a chimaeric Orbivirus VLP in a plant cell, the method comprising the steps of (i) providing codon-optimised nucleotide sequences encoding Orbivirus VP2, VP3, VP5 and VP7 structural proteins, wherein at least one of the VP2, VP3, VP5 and VP7 structural proteins is selected from a first Orbivirus serotype and at least one of the VP2, VP3, VP5 and VP7 structural proteins is selected from a second Orbivirus serotype of the same Orbivirus species, (ii) cloning the codon-optimised nucleotide sequences into at least one expression vector adapted to express the structural proteins in a plant cell, (iii) transforming or infiltrating the plant cell with the at least one expression vector of step (ii), (iv) co-expressing the VP2, VP3, VP5 and VP7 structural proteins in the plant cell, such that the expressed structural proteins assemble to form the chimaeric Orbivirus VLP; and (v) recovering the chimaeric Orbivirus VLP from the plant cell.

In one embodiment of the invention at least one of the VP2, VP3, VP5 and VP7 structural proteins of step (i) of the method is selected from a third Orbivirus serotype of the same Orbivirus species. Alternatively, at least one of the VP2, VP3, VP5 and VP7 structural proteins is selected from a fourth Orbivirus serotype of the same Orbivirus species.

According to one embodiment of the invention, if the Orbivirus is BTV the first and second BTV serotypes may be selected from the group consisting of BTV-1, BTV-2, BTV-3, BTV-4, BTV-5, BTV-6, BTV-7, BTV-8 BTV-9, BTV-10, BTV-11, BTV-12, BTV-13, BTV-14, BTV-15, BTV-16, BTV-17, BTV-18, BTV-19, BTV-20, BTV-21, BTV-22, BTV-23, BTV-24, BTV-25, BTV-26 and BTV-27. According to another embodiment of the invention, if the Orbivirus is AHSV the first and second AHSV serotypes may be selected from the group consisting of AHSV-1, AHSV-2, AHSV-3, AHSV-4, AHSV-5, AHSV-6, AHSV-7, AHSV-8 and AHSV-9.

In yet another aspect of the invention it will be appreciated that if the Orbivirus is selected from one of the Orbiviruses in the group comprising Lebombo virus (LEBV), Pata virus (PATAV), African horse sickness virus (AHSV), Bluetongue virus (BTV), Altamira virus (ALTV), Almeirim virus (AMRV), Caninde virus (CANV), Changuinola virus (CGLV), Irituia virus (IRIV), Jamanxi virus (JAMV), Jari virus (JARIV), Gurupi virus (GURV), Monte Dourado virus (MDOV), Ourem virus (OURV), Purus virus (PURV), Saraca virus (SRAV), Acado virus (ACDV), Corriparta virus (CORV), Eubenangee virus (EUBV), Ngoupe virus (NGOV), Tilligerry virus (TILV), Epizootic hemorrhagic disease virus (EHDV), Kawanabe virus, Equine encephalosis virus (EEV), Great Island virus, Kemerovo virus (KEMV), Essaouira virus (ESSV), Kala iris virus (KIRV), Mill Door/79 virus (MILDV), Rabbit syncytium virus (RSV), Tribeč virus (TRBV), Broadhaven virus (BRDV), Orungo virus (ORUV), Abadina virus (ABAV), Apies River virus, Bunyip Creek virus (BCV), Chuzan (Kasba) virus (SBV), CSIRO Village virus (CVGV), D'Aguilar virus (DAGV), Marrakai virus (MARV), Petevo virus (PETV), Vellore virus (VELV), Llano Seco virus (LLSV), Minnal virus (MINV), Netivot virus (NETV), Umatilla virus (UMAV), Wallal virus (WALV) and Mitchell River virus (MRV) then the first and second serotypes may be selected from different serotypes of the same species of Orbivirus.

In instances where a double, triple or quadruple chimaeric Orbivirus of the invention is produced it will be appreciated that the structural proteins will be selected from two, three or four different serotypes of a particular Orbivirus species, respectively.

It will be appreciated that the at least one expression vector described in the method includes a promoter and/or other regulatory sequences, operably linked to each nucleotide sequence encoding each structural protein.

In another embodiment the plant or plant cell is *Nicotiana benthamiana* plant or plant cell. In yet a further preferred embodiment the plant or plant cell may be a *N. benthamiana* dXT/FT mutant tobacco plant or cell, which facilitates mammalian-like or human-like glycosylation of the polypeptides. The plant cell is preferably transformed using *Agrobacterium*-mediated transformation. Most preferably, the expression of the Orbivirus VP2, VP3, VP5 and VP7 structural proteins in the plant cell is mediated by the *Agrobacterium*, and the *Agrobacterium* may be selected from *Agrobacterium* AGL-1, *Agrobacterium* LBA4404, *Agrobacterium* GV3101 pMP90 or any other suitable agrobacterial strain.

A further aspect of the invention provides for a vaccine composition comprising a chimaeric Orbivirus VLP and a pharmaceutically acceptable diluent or excipient, wherein the vaccine composition is capable of eliciting a protective immune response against a specific Orbivirus species in a subject. Preferably the immune response is a cellular and/or humoral immune response.

In a preferred embodiment of the invention the vaccine composition comprises at least one chimaeric Orbivirus VLP of the invention or made by the method of the invention and wherein the vaccine composition elicits a protective immune response against at least one serotype of a specific Orbivirus species in a subject.

A preferred embodiment of the invention provides for a vaccine composition, preferably a multivalent vaccine composition, that comprises a combination of the chimaeric Orbivirus VLPs of the invention. In particular the combination will include at least two different chimaeric VLPs of the invention having structural proteins from the different Orbivirus serotypes from Orbiviruses of the same species. As a result the vaccine composition may comprise VLPs with VP2 structural proteins from more than one serotype of a specific Orbivirus (e.g. BTV or AHSV) the vaccine composition will provide multivalent protection against more than one serotype of BTV, AHSV or a specified species of Orbivirus.

In yet a further embodiment of the invention there is provided for the vaccine composition inducing a protective immune response against an Orbivirus infection in a subject.

The present invention also provides for a method of preventing or treating an Orbivirus infection in a subject, wherein the method comprises a step of administering the chimaeric Orbivirus VLP of the invention or made by the method of the invention to the subject.

A further aspect of the invention provides for the use of the chimaeric Orbivirus VLP of the invention or made according to the method of the invention in the manufacture of a vaccine for use in prevention or treatment of an Orbivirus infection in a subject.

According to a further aspect of the invention there is provided the chimaeric Orbivirus VLP of the invention or made according to the method of the invention for use in a method of preventing or treating Orbivirus infection in a subject, the method comprising administering the chimaeric Orbivirus VLP to the subject. Alternatively the chimaeric Orbivirus VLP of the invention or made according to the method of the invention may be for use in protecting a subject from an Orbivirus infection.

In yet a further aspect of the invention there is provided for a transformed plant cell comprising at least one expression vector adapted to express a codon optimised nucleotide sequence encoding Orbivirus VP2, VP3, VP5 and VP7 structural proteins, wherein at least one of the VP2, VP3, VP5 and VP7 structural proteins is selected from a first Orbivirus serotype and at least one of the VP2, VP3, VP5 and VP7 structural proteins is selected from a second Orbivirus serotype, and wherein the Orbivirus serotypes are of the same Orbivirus species.

In one embodiment the expression of the Orbivirus VP2, VP3, VP5 and VP7 structural proteins in the plant cell is mediated by *Agrobacterium* AGL-1, *Agrobacterium* LBA4404, *Agrobacterium* GV3101 pMP90 or any other suitable agrobacterial strain.

BRIEF DESCRIPTION OF THE FIGURES

Non-limiting embodiments of the invention will now be described by way of example only and with reference to the following figures:

FIG. 6: A schematic of the BTV particle showing the four structural proteins, the transcriptase complex and the dsRNA genome (Mertens et al., 2004).

FIG. 7: Western blot of fractions 1 to 8 from 20-60% Optiprep gradient.

FIG. 11: Western blot and cognate Coomassie-stained gel of fractions 1 to 8 from 20-60% Optiprep gradient purification of BTV VP proteins from leaves infiltrated at a 1:1:3:1 (VP3:VP7:VP5:VP2) infiltration ratio.

FIG. 15: Clustal X alignment of BTV-11 VP2 (SEQ ID NO:81) and BTV-4 VP2 (SEQ ID NO:10) indicating that the two peptide sequences detected by mass spectrometry (highlighted in bold and underlined) are identical.

FIG. 16: Sucrose gradient purified double chimaeric BTV-3 VLPs capsid proteins detected in fraction 45% sucrose and separated by SDS-PAGE 4-12% Bolt precast gels. Proteins produced in *N. benthamiana* (even numbers) and *N. benthamiana* dXT/FT (odd numbers). Lane 1-2, 4 days after infiltration; lanes 3-4, 5 days; lanes 5-6, 6 days; lanes 7-8, 7 days; and lanes 9-10, 8 days; lanes 11-12, BTV-8 CLPs and lane 13, SeeBlue® Plus molecular marker (Life Technologies, Thermo Fisher Scientific).

FIG. 17: Transmission electron microscope images of double chimaeric BTV-3 VLPs created in *N. benthamiana* dXT/FT during days 6-8. BTV-8 CLP created as core in mammalian-like *N. benthamiana*. Negative staining technique using sodium phosphotungstate onto copper grids and images were visualized with a JEM-2100 Transmission electron microscope (JEOL).

FIG. 18: Clustal X alignment of BTV-4 VP2 (SEQ ID NO:84) and BTV-10 VP2 (SEQ ID NO:82) with overlap peptide sequences detected by Mass Spectrometry.

FIG. 20: Alignment of BTV-4 (protein ID ABB71695.1) and BTV-17 (protein ID CAE51104.1) with overlap peptide sequences detected by mass spectrometry.

FIG. 20: Alignment of BTV-4 (protein ID ABB71695.1) (SEQ ID NO:10) and BTV-17 (protein ID CAE51104.1) (SEQ ID NO:83) with overlap peptide sequences detected by mass spectrometry.

FIG. 24: Immunoblot detection of AHSV-1 and/or AHSV-7 capsid proteins following sucrose density gradient centrifugation. Nicotiana benthamiana leaves, agroinfiltrated with a combination of the pEAQ-HT-AHSV-1 VP2, pEAQ-express AHSV-1 VP5, pEAQ-HT-AHSV1 VP3 and pEAQ-express AHSV-1 VP7 (1:1:1:1) or a combination of pEAQ-HT-AHSV-7 VP2, pEAQ-express AHSV-1 VP5, pEAQ-HT AHSV-1VP3 and pEAQ-express AHSV-1 VP7 (1:1:1:1), were harvested 8 days p.i and the clarified cellular lysates centrifuged through 70%-30% sucrose density gradients. The gradients were fractionated from the 55% sucrose layer to the 35% sucrose layer and ⅟₅₀ of each sucrose fraction assessed for the presence of AHSV-1/AHSV-7 capsid proteins via SDS-PAGE and immunoblotting with a guinea pig anti-AHSV-7 antiserum. Lane 1 contains the Precision Plus Protein™ Western C™ standard (Bio-Rad) and the relevant sizes are indicated. Lanes 2-6 contain the 55%, 50%, 45%, 40%, 35% sucrose fractions, respectively, of the AHSV-1 sucrose gradient whilst lanes 7-11 contain 55%, 50%, 45%, 40%, 35% sucrose fractions, respectively, from the AHSV-1/AHSV-7 sucrose gradient. Lanes 12-15 contain 55%, 50%, 45%, 40% sucrose fractions proteins of pEAQ-HT cell lysate sucrose gradient, respectively, included as a negative control in this study. Arrows indicate the position of the AHSV-7 VP2 (123.6 kDa), AHSV-1 VP3 (103.2 kDa), AHSV-1 VP5 (56.6 kDa) and AHSV-1 VP7 (37.8 kDa) proteins on the immunoblot membrane.

FIG. 26: Transmission electron micrograph (TEM) images of sucrose-gradient purified (a) AHSV-1 VLPs, (b) AHSV-1 CLPs, (c) single chimaeric AHSV-1/AHSV-7 VLPs, (d) double chimaeric AHSV-1/AHSV-7 VLPs and (e)-(f) triple chimaeric AHSV-1/AHSV-3/AHSV-6 VLPs. Particles were visualized with a JEM-2100 Transmission electron microscope (JEOL). Indicated with arrows are the virus-like particles (VLPs) and the core-like particles (CLPs).

FIG. 29: Schematic representation of the constructs created for Agrobacterium-mediated expression of African horse sickness (AHSV) serotype 5 structural proteins in N. benthamiana and their resultant assembly into virus-like particles. (a) Stoichiometric diagram of virus-like particle formation. (b) Codon-optimized genes for AHSV-5 VP2, VP3, VP5 and VP7 were cloned into the pEAQ-HT plant expression vector (Sainsbury at al., 2009).

Figure 31:
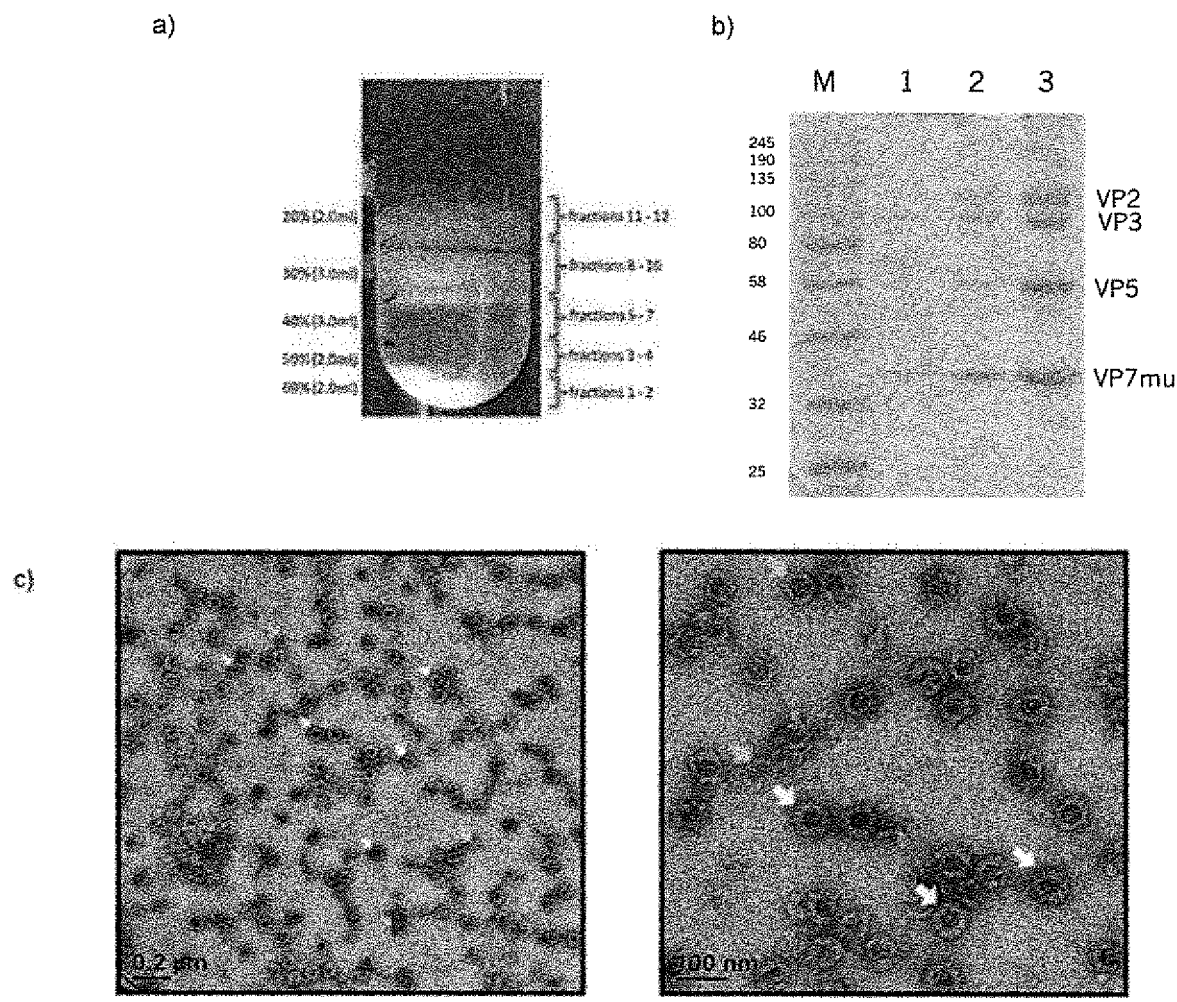

FIG. 31: Purification of AHSV-5 VLPs by density gradient ultracentrifugation. Crude plant extracts from leaves co-infiltrated with all 4 AHSV-5 *Agrobacterium* recombinants, this using the mutated VP7 recombinant, were subjected to iodixanol density gradient ultra-centrifugation. a) Gradient fractions were collected from the bottom of the tube. b) Fractions 6 (lane 1), 7 (lane 2) and 8 (lane 3) were separated by denaturing SDS-PAGE followed by Coomassie blue staining The location of the AHSV viral proteins VP2 (123 kD), VP3 (103 kD), VP5 (57 kD) and $VP7_{mu}$ (38 kD) are indicated to the right of the gel, while the molecular weight marker sizes are shown on the left. c) Gradient fraction 8 was imaged by TEM revealing the presence of fully assembled VLPs (white arrows) together with some assembly intermediates (yellow arrows). Scale bars, 50-200 nm.

Figure 32:
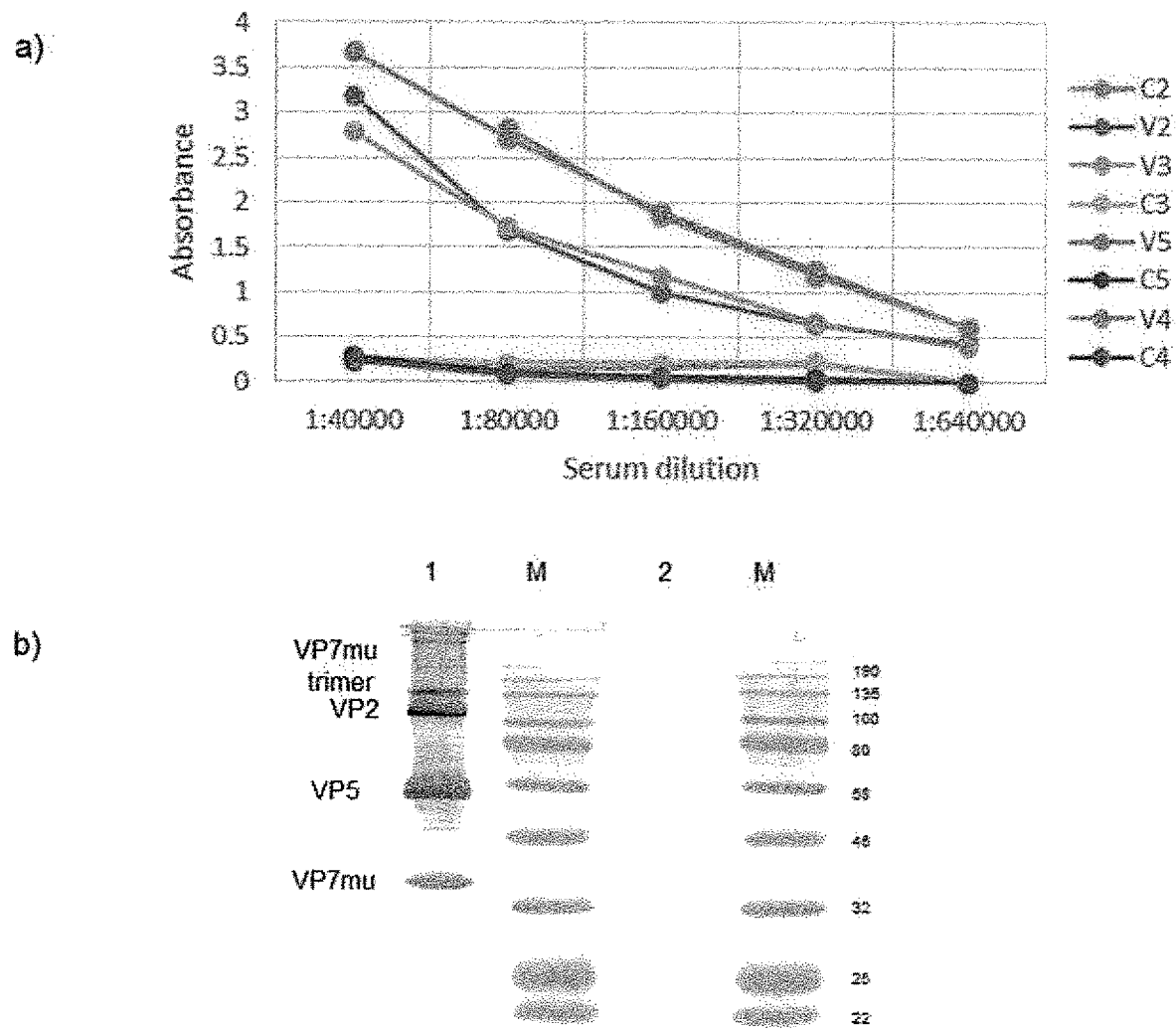

FIG. 32: Immunogenicity of plant-produced AHSV-5 VLPs in guinea pigs. a) Vaccine- and control guinea pig groups (n=4) were vaccinated with plant-produced AHSV-5 VLPs (guinea pigs V2-V5) or PBS (guinea pigs C2-C5) respectively. Both vaccines were formulated with 5% Pet Gel A adjuvant (Seppic, Paris, France). Guinea pigs V2-V5 were immunized with a dose of 16.5 µg AHSV-5 VLPs on day 0 and boosted with a dose of 50 µg VLPs on day 13, while guinea pigs C2-C5 were vaccinated with PBS per the same schedule. Serum was collected on day 41 and antibody responses were measured by standard ELISA. Absorbance values below 1:40 000 antiserum dilutions for guinea pigs in the vaccine group were too high to be measured. b) Antisera (1:10 000 dilution) from representative guinea pig V3 final bleed (lane 1) and pre-bleed (lane 2) were used to detect AHSV-5 VLPs in a standard Western blot analysis. The location of the AHSV viral proteins VP2, VP5 and $VP7_{mu}$ as well as the $VP7_{mu}$ trimer, are indicated to the left of the gel, while the molecular weight marker sizes are shown on the right. No signal was detected for the innermost core protein VP3.

Figure 33:
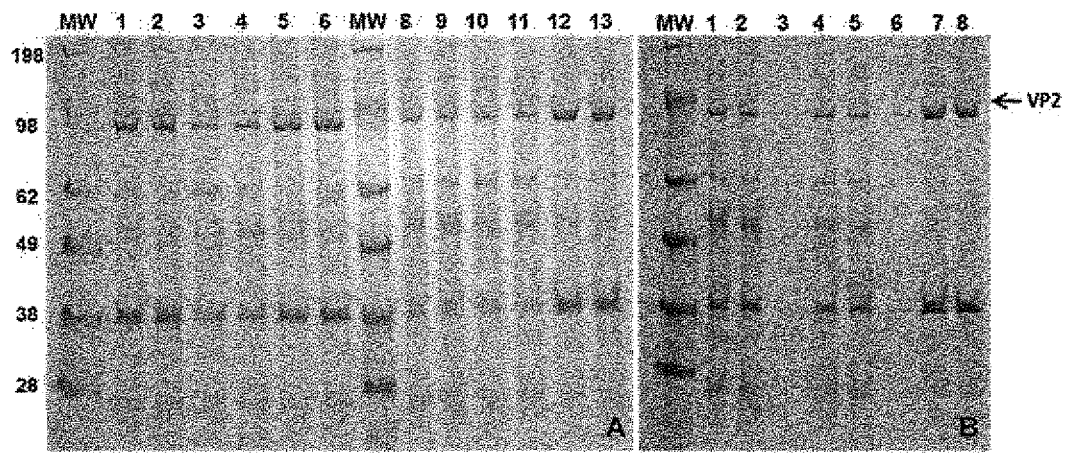

FIG. 33: Plant produced BTV-8 and BTV-3 VLPs proteins (8 µg per lane) detected in iodixanol density gradient ultracentrifugation fractions 35-40% and separated by SDS-PAGE 4-12% Bolt precast gels. MW, SeeBlue® Plus2 Pre-stained Protein Standard. A) lanes 1-2, LBA4404 mediated BTV-8 VLPs; lanes 3-4, GV3101 pMP90 mediated BTV-8 VLPs; lanes 5-6, AGL-1 mediated BTV-8 VLPs; lanes 8-9, LBA4404 mediated BTV-3 VLPs; lanes 10-11, GV3101 pMP90 mediated BTV-3 VLPs and lanes 12-13, AGL-1 mediated BTV-3 VLPs. B) lanes 1-2, LBA4404 mediated BTV-3 VLPs; lanes 4-5, GV3101 pMP90 mediated BTV-3 VLPs and lanes 7-8, AGL-1 mediated BTV-3. VLPs Viral capsid protein 2 (VP2) is indicated with an arrow.

Figure 34:
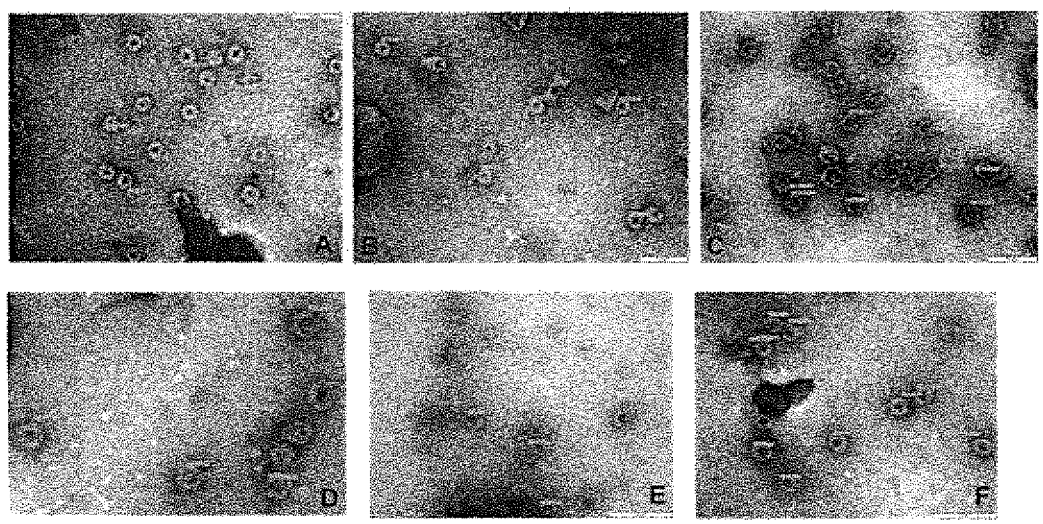

FIG. 34: TEM analysis of plant produced BTV-8 and BTV-3 VLPs subjected to Iodixanol density gradient ultracentrifugation. A, LBA4404 mediated BTV-8 VLPs (64-73 nm); B, GV3101 pMP90 mediated BTV-8 VLPs (60-71 nm); C, AGL-1 mediated BTV-8 VLPs (64-80 nm); D, LBA4404 mediated BTV-3 VLPs (65-82 nm); E, GV3101 pMP90 mediated BTV-3 VLPs (59-78 nm) and F, AGL-1 mediated BTV-3 VLPs (60-80 nm). Scale bars, 200 nm.

DETAILED DESCRIPTION OF THE INVENTION

The present invention will now be described more fully hereinafter with reference to the accompanying drawings, in which some, but not all embodiments of the invention are shown.

The invention as described should not be limited to the specific embodiments disclosed and modifications and other embodiments are intended to be included within the scope of the invention. Although specific terms are employed herein, they are used in a generic and descriptive sense only and not for purposes of limitation.

As used throughout this specification and in the claims which follow, the singular forms "a", "an" and "the" include the plural form, unless the context clearly indicates otherwise.

The terminology and phraseology used herein is for the purpose of description and should not be regarded as limiting. The use of the terms "comprising", "containing", "having" and "including" and variations thereof used herein, are meant to encompass the items listed thereafter and equivalents thereof as well as additional items.

By "bluetongue" or "BT" is meant a virus belonging to a group of approximately 26 related but genetically distinct "serotypes". The virus may also be referred to herein as "bluetongue virus" or "BTV".

BTV is a double stranded ribonucleic acid (dsRNA) virus that causes an insect-borne, infectious non-contagious disease of both domesticated and wild ruminants; it is the type species of the genus Orbivirus that is classified into the family Reoviridae. Reoviridae is one of the largest families of viruses and includes major human pathogens, such as rotavirus, as well as pathogens of insects, reptiles, fish, plants and fungi. Orbiviruses differ from other members of the Reoviridae family in that they can multiply in both arthropod and vertebrate cells, causing severe disease and high mortality. BTV is transmitted between its hosts by *Culicoides* spp., causing disease in ruminants worldwide.

Virus protein (VP) 2 is the most variable of the BTV capsid proteins and contains the epitopes involved in virus neutralisation and serotype determination (DeMaula at al., 2000, Huismans and Erasmus, 1981). Twenty six distinct serotypes of BTV have been identified based on neutralisation activity of VP2 as well as with BTV specific real time reverse transcriptase polymerase chain reaction (RT-PCR). Each serotype shows variation that is associated with the geographical origins of the virus from around the world. Molecular studies on BTV isolates from different geographic regions have further divided BTV into two major topotypes, namely the eastern and western lineages.

Figures 6, 7:
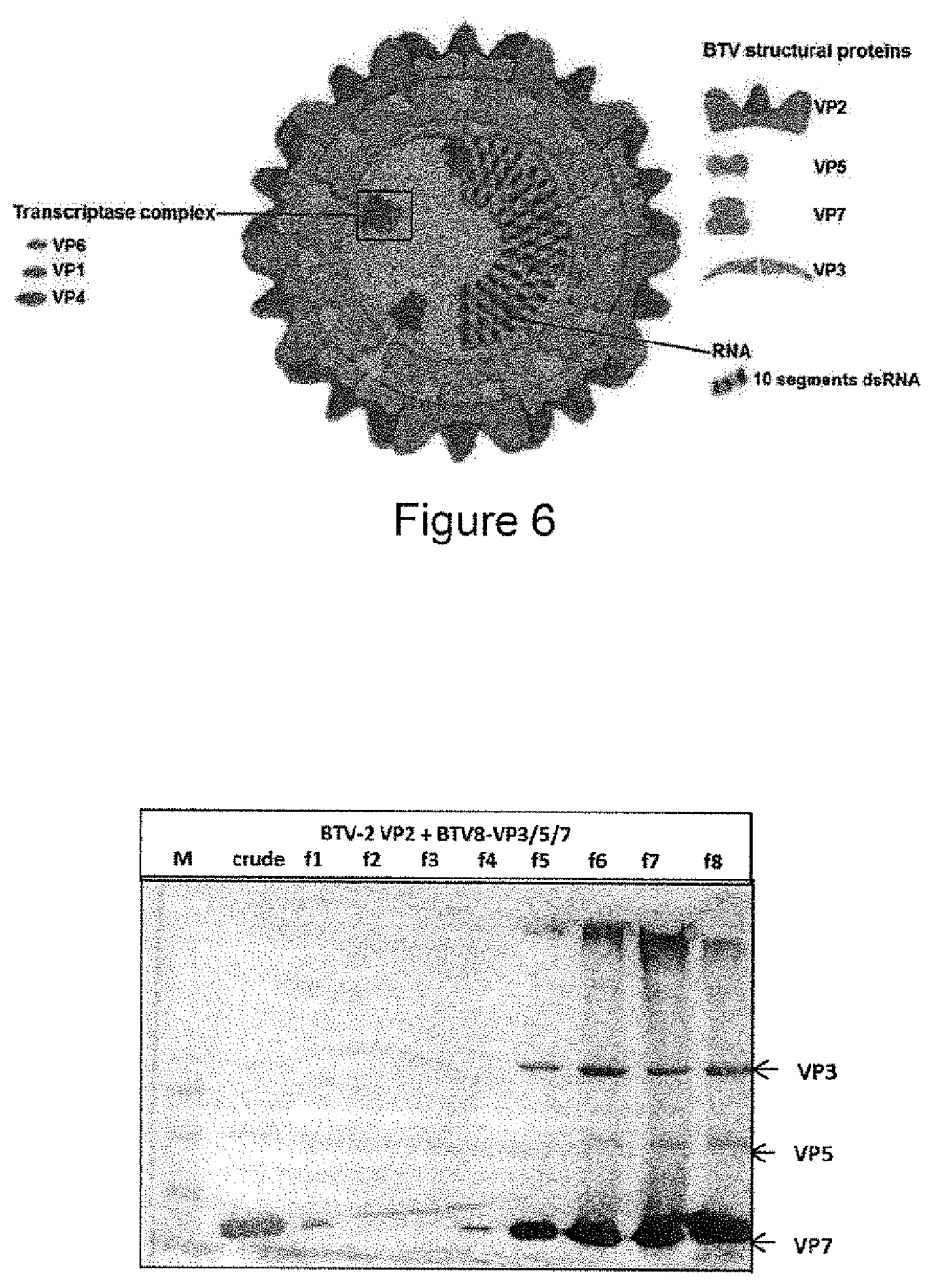

The BTV genome is a double-stranded circular dsRNA surrounded by a protein capsid. BTV can replicate in both wild and domestic ruminants as well as some species of deer. Replication takes place in both the host and the *Culicoides* insect vector. BTV virions are complex three-layered icosahedral structures that are ~80 nanometer (nm) in diameter. The virions are composed of a core of ten segments of dsRNA encapsulated by seven structural proteins (four major and three minor proteins) that are arranged into three distinct layers (FIG. 6).

The three minor proteins (viral protein (VP) 1, VP4 and VP6) are enclosed by the subcore that is made up of VP3. The core-surface layer consists of VP7. The outer capsid is composed of major proteins VP2 and VP5 which are laid onto the foundation provided by the core. The minor proteins together with the genomic RNA form the virus replication complex, whereas the four major proteins make up the capsid of the virus. In addition to the structural proteins BTV has four non-structural (NS) proteins (NS1, NS2, NS3/3a and NS4) which are involved in virus replication and assembly in BTV-infected cells.

The chimaeric VLPs and compositions according to the invention may be used to treat or prevent BTV infection or conditions associated with BTV infection. By "condition associated with BTV infection" is meant any condition, disease or disorder that has been correlated with the presence of an existing BTV infection, includes secondary effects, such as reductions in milk production, weight gain, wool break and temporary infertility.

BTV can infect all known species of domestic and wild ruminants. Severe disease usually occurs in the fine-wool and mutton breeds of sheep as well as some species of deer. BTV infection of cattle, goats and wild ruminant species is mostly asymptomatic or subclinical. In BTV endemic areas BTV-infected sheep develop only mild or no obvious disease. The bluetongue after which the disease is named is seen only in serious clinical cases.

Onset of the disease in sheep is typically characterised by high fever lasting 5-7 days. Clinical signs of disease can include fever, depression, excessive salivation, nasal discharge, facial oedema, hyperaemia and ulceration of the oral mucosa, coronitis, lameness and death. Abortion can occur in pregnant animals as well as teratogenic defects in calves. The severity of clinical disease and mortality rate is influenced by the breed and age of the animal as well as the virus strain that causes the infection. In acute cases of BT, clinical signs in sheep are mainly associated with damage to microvascular endothelial cells.

After recovery from BT animals may suffer from a number of long-lasting secondary effects, such as reductions in milk production, weight gain, wool brake and temporary infertility.

Pathogenesis of BTV infection is similar in sheep and cattle as well as other species of ruminants. After an animal gets infected with BTV, through the bite of a *Culicoides* vector, the virus will travel to the regional lymph node where initial replication takes place. The virus then spreads throughout the body to a variety of tissues, where replication occurs mainly in mononuclear phagocytic and endothelial cells.

Viraemia is cell associated and can be prolonged in domestic ruminants.

During viraemia BTV is associated with all blood cells, but late in the course of infection the virus is mostly associated with the erythrocytes. The longer lifespan of erythrocytes facilitates prolonged infection of ruminants, as well as the infection of the haematophagous insect vectors that feed on viraemic ruminants. Infectious virus can co-circulate for several weeks with high neutralising antibody titres, the maximum period of viraemia in sheep is about 50 days and in cattle about 100 days.

By "African horse sickness" or "AHS" is meant the disease itself. The virus is referred to herein as "African horse sickness virus" or "AHSV" belongs to a group of approximately 9 related but genetically distinct "serotypes".

AHSV is a double stranded ribonucleic acid (dsRNA) virus that causes an infectious, non-contagious disease of equids. It is classified as an Orbivirus in the family Reoviridae. The virus is transmitted by biting midges of the *Culicoides* species.

The AHS virion is an icosahedral, non-enveloped particle, composed of three concentric layers surrounding the segmented double-stranded RNA genome. The AHS virion has been reported to be between 70 nm-87 nm in diameter. The subcore, composed of structural protein VP3, encloses 10 linear genome segments and enzymatic minor proteins VP1, VP3 and VP6. The subcore is covered by a layer of VP7 trimers forming the core particle. The core is surrounded by the outermost layer composed of structural proteins VP5 and VP2, with VP2 being the neutralizing antigen and serotype determinant. There are nine known serotypes of AHSV and all are present within South Africa and most parts of sub-Saharan Africa.

The chimaeric VLPs and compositions according to the invention may be used to treat or prevent AHSV infection or conditions associated with AHSV infection. By "condition associated with AHSV infection" is meant any condition, disease or disorder that has been correlated with the presence of an existing AHSV infection and includes secondary effects.

AHSV infects equid species, such as horses, donkeys, mules and zebra, amongst others. The mortality rate in horses, the most susceptible species, can be up to 95% while donkeys and mules generally develop milder disease. Zebras are considered the natural vertebrate host of AHSV and rarely exhibit clinical signs of infection. Respiratory and circulatory functions are impaired in diseased animals and result in oedema of subcutaneous and intermuscular tissues, of lungs and haemorrahages of serosal surfaces. These animals also exhibit pyrexia and loss of appetite.

A compound according to the invention includes, without limitation, a single chimaeric Orbivirus VLP including a core comprising capsid proteins VP3, VP5 and VP7 from one serotype of an Orbivirus species and an outer layer comprising a VP2 selected from any one of the other serotypes of the same Orbivirus species. In an alternative embodiment a compound of the invention includes, without limitation, a double chimaeric Orbivirus VLP including a core comprising capsid proteins VP3 and VP7 from one serotype of an Orbivirus species and an outer layer comprising the VP2 and VP5 capsid proteins selected from any one of the other serotypes of the same Orbivirus species.

When the Orbivirus species is BTV, a compound according to the invention includes, without limitation, a single chimaeric VLP including a core comprising, for instance, BTV-8 capsid proteins VP3, VP5 and VP7 and an outer layer comprising a BTV VP2 selected from any one of the 26 BTV serotypes, with the exception of BTV-8. In an alternative embodiment a compound of the invention includes, without limitation, a double chimaeric VLP including a core comprising, for instance, BTV-8 VP3 and VP7 capsid proteins and an outer layer comprising BTV VP2 and VP5 capsid proteins selected from any one of the 26 BTV serotypes, with the exception of BTV-8

Similarly, when the Orbivirus species is AHSV, a compound according to the invention includes, without limitation, a single chimaeric VLP including a core comprising, for instance, AHSV-1 capsid proteins VP3, VP5 and VP7 and an outer layer comprising AHS VP2 selected from any one of the 8 remaining AHSV serotypes. In an alternative embodiment a compound of the invention includes, without limitation, a double chimaeric VLP including a core comprising, for instance, AHSV-1 VP3 and VP7 capsid proteins and an outer layer comprising AHSV VP2 and VP5 capsid proteins selected from any one of the remaining 8 AHSV serotypes.

It will be appreciated by those of skill in the art that the Orbivirus species could be an Orbivirus selected from the group consisting of Lebombo virus (LEBV), Pata virus (PATAV), African horse sickness virus (AHSV), Bluetongue virus (BTV), Altamira virus (ALTV), Almeirim virus (AMRV), Caninde virus (CANV), Changuinola virus (CGLV), Irituia virus (IRIV), Jamanxi virus (JAMV), Jari virus (JARIV), Gurupi virus (GURV), Monte Dourado virus (MDOV), Ourem virus (OURV), Purus virus (PURV), Saraca virus (SRAV), Acado virus (ACDV), Corriparta virus (CORV), Eubenangee virus (EUBV), Ngoupe virus (NGOV), Tilligerry virus (TILV), Epizootic hemorrhagic disease virus (EHDV), Kawanabe virus, Equine encephalosis virus (EEV), Great Island virus, Kemerovo virus (KEMV), Essaouira virus (ESSV), Kala iris virus (KIRV), Mill Door/79 virus (MILDV), Rabbit syncytium virus (RSV), Tribeč virus (TRBV), Broadhaven virus (BRDV), Orungo virus (ORUV), Abadina virus (ABAV), Apies River virus, Bunyip Creek virus (BCV), Chuzan (Kasba) virus (SBV), CSIRO Village virus (CVGV), D'Aguilar virus (DAGV), Marrakai virus (MARV), Petevo virus (PETV), Vellore virus (VELV), Llano Seco virus (LLSV), Minnal virus (MINV), Netivot virus (NETV), Umatilla virus (UMAV), Wallal virus (WALV) and Mitchell River virus (MRV).

A "protein," "peptide" or "polypeptide" is any chain of two or more amino acids, including naturally occurring or non-naturally occurring amino acids or amino acid analogues, irrespective of post-translational modification (e.g., glycosylation or phosphorylation).

The terms "nucleic acid" or "nucleic acid molecule" encompass both ribonucleotides (RNA) and deoxyribonucleotides (DNA), including cDNA, genomic DNA, and synthetic DNA. The nucleic acid may be double-stranded or single-stranded. Where the nucleic acid is single-stranded, the nucleic acid may be the sense strand or the antisense strand. A nucleic acid molecule may be any chain of two or more covalently bonded nucleotides, including naturally occurring or non-naturally occurring nucleotides, or nucleotide analogs or derivatives. By "RNA" is meant a sequence of two or more covalently bonded, naturally occurring or modified ribonucleotides. The term "DNA" refers to a sequence of two or more covalently bonded, naturally occurring or modified deoxyribonucleotides.

The term "complementary" refers to two nucleic acids molecules, e.g., DNA or RNA, which are capable of forming Watson-Crick base pairs to produce a region of double-strandedness between the two nucleic acid molecules. It will be appreciated by those of skill in the art that each nucleotide in a nucleic acid molecule need not form a matched Watson-Crick base pair with a nucleotide in an opposing complementary strand to form a duplex. One nucleic acid molecule is thus "complementary" to a second nucleic acid molecule if it hybridizes, under conditions of high stringency, with the second nucleic acid molecule. A nucleic acid molecule according to the invention includes both complementary molecules.

In some embodiments, a chimaeric VLP of the invention may include, without limitation, BTV-8 VP3 (SEQ ID NO: 1 or 2), VP5 (SEQ ID NO: 3 or 4) and VP7 (SEQ ID NO: 5 or 6) polypeptides or derivatives thereof and/or a VP2 polypeptide selected from the group consisting of SEQ ID NOs 7 to 11, or derivatives thereof. Another embodiment of the invention includes, without limitation, nucleic acid molecules encoding the aforementioned amino acid sequences. It will however be appreciated by those of skill in the art that the VP3, VP5 and VP7 polypeptides may be polypeptides from any of the BTV serotypes, for example BTV-3 VP5 (SEQ ID NO:12), BTV-4 VP5 (SEQ ID NO:13) and BTV-4 VP7 (SEQ ID NO:14).

In other embodiments, a chimaeric VLP of the invention may include, without limitation, AHSV-1 VP3, VP5 and VP7 polypeptides having an amino acid sequence of SEQ ID NOs: 15, 16 and 17, respectively or derivatives thereof and/or a VP2 polypeptide of SEQ ID NO:18 or 19, or derivatives thereof. Another embodiment of the invention includes, without limitation, nucleic acid molecules encoding the aforementioned amino acid sequences. It will however also be appreciated by those of skill in the art that the VP3, VP5 and VP7 polypeptides may be polypeptides from any of the AHSV serotypes, for example AHSV-7 VP5 (SEQ ID NO:20).

As used herein a "substantially identical" sequence is an amino acid or nucleotide sequence that differs from a reference sequence only by one or more conservative substitutions, or by one or more non-conservative substitutions, deletions, or insertions located at positions of the sequence that do not destroy or substantially reduce the antigenicity of one or more of the expressed polypeptides or of the polypeptides encoded by the nucleic acid molecules. Alignment for purposes of determining percent sequence identity can be achieved in various ways that are within the knowledge of those with skill in the art. These include using, for instance, computer software such as ALIGN, Megalign (DNASTAR), CLUSTALW or BLAST software. Those skilled in the art can readily determine appropriate parameters for measuring alignment, including any algorithms needed to achieve maximal alignment over the full length of the sequences being compared. In one embodiment of the invention there is provided for a polypeptide or polynucleotide sequence that has at least about 80% sequence identity, at least about 90% sequence identity, or even greater sequence identity, such as about 95%, about 96%, about 97%, about 98% or about 99% sequence identity to the sequences described herein.

Alternatively, or additionally, two nucleic acid sequences may be "substantially identical" if they hybridize under high stringency conditions. The "stringency" of a hybridisation reaction is readily determinable by one of ordinary skill in the art, and generally is an empirical calculation which depends upon probe length, washing temperature, and salt concentration. In general, longer probes required higher temperatures for proper annealing, while shorter probes require lower temperatures. Hybridisation generally depends on the ability of denatured DNA to re-anneal when complementary strands are present in an environment below their melting temperature. A typical example of such 'stringent' hybridisation conditions would be hybridisation carried out for 18 hours at 65° C. with gentle shaking, a first wash for 12 min at 65° C. in Wash Buffer A (0.5% SDS; 2×SSC), and a second wash for 10 min at 65° C. in Wash Buffer B (0.1% SDS; 0.5% SSC).

In an alternative embodiment of the invention, the chimaeric VLPs may be prepared by, for instance, inserting, deleting or replacing amino acid residues at any position of the BTV VP2, VP3, VP5 or VP7 polypeptide sequences and/or, for instance inserting, deleting or replacing nucleic acids at any position of the nucleic acid molecule encoding the BTV VP2, VP3, VP5 or VP7 polypeptides.

In an alternative embodiment of the invention, the chimaeric VLPs may be prepared by, for instance, inserting, deleting or replacing amino acid residues at any position of the AHSV VP2, VP3, VP5 or VP7 polypeptide sequences and/or, for instance inserting, deleting or replacing nucleic acids at any position of the nucleic acid molecule encoding the AHSV VP2, VP3, VP5 or VP7 polypeptides.

Those skilled in the art will appreciate that polypeptides, peptides or peptide analogues can be synthesised using standard chemical techniques, for instance, by automated synthesis using solution or solid phase synthesis methodology. Automated peptide synthesisers are commercially available and use techniques known in the art. Polypeptides, peptides and peptide analogues can also be prepared from their corresponding nucleic acid molecules using recombinant DNA technology.

In some embodiments, the nucleic acid molecules of the invention may be operably linked to other sequences. By "operably linked" is meant that the nucleic acid molecules encoding the VP2, VP3, VP5 and/or VP7 polypeptides of the invention and regulatory sequences are connected in such a way as to permit expression of the proteins when the appropriate molecules are bound to the regulatory sequences. Such operably linked sequences may be contained in vectors or expression constructs which can be transformed or transfected into host cells for expression. It will be appreciated that any vector or vectors can be used for the purposes of expressing the VP2, VP3, VP5 and/or VP7 of the invention.

The term "recombinant" means that something has been recombined. When used with reference to a nucleic acid construct the term refers to a molecule that comprises nucleic acid sequences that are joined together or produced by means of molecular biological techniques. The term "recombinant" when used in reference to a protein or a polypeptide refers to a protein or polypeptide molecule which is expressed from a recombinant nucleic acid construct created by means of molecular biological techniques. Recombinant nucleic acid constructs may include a nucleotide sequence which is ligated to, or is manipulated to become ligated to, a nucleic acid sequence to which it is not ligated in nature, or to which it is ligated at a different location in nature. Accordingly, a recombinant nucleic acid construct indicates that the nucleic acid molecule has been manipulated using genetic engineering, i.e. by human intervention. Recombinant nucleic acid constructs may be introduced into a host cell by transformation. Such recombinant nucleic acid constructs may include sequences derived from the same host cell species or from different host cell species.

The term "vector" refers to a means by which polynucleotides or gene sequences can be introduced into a cell. There are various types of vectors known in the art including plasmids, viruses, bacteriophages and cosmids. Generally polynucleotides or gene sequences are introduced into a vector by means of a cassette. The term "cassette" refers to a polynucleotide or gene sequence that is expressed from a vector, for example, the polynucleotide or gene sequences encoding the VP2, VP3, VP5 and/or VP7 polypeptides of the invention. A cassette generally comprises a gene sequence inserted into a vector, which in some embodiments, provides regulatory sequences for expressing the polynucleotide or gene sequences. In other embodiments, the vector provides the regulatory sequences for the expression of the VP2, VP3, VP5 and/or VP7 polypeptides. In further embodiments, the vector provides some regulatory sequences and the nucleotide or gene sequence provides other regulatory sequences. "Regulatory sequences" include but are not limited to promoters, transcription termination sequences, enhancers, splice acceptors, donor sequences, introns, ribosome binding sequences, poly(A) addition sequences, and/or origins of replication.

The chimaeric VLPs or compositions of the invention can be provided either alone or in combination with other compounds (for example, nucleic acid molecules, small molecules, peptides, or peptide analogues), in the presence of an adjuvant, or any carrier, such as a pharmaceutically acceptable carrier and in a form suitable for administration to mammals, for example, humans, cattle, sheep, etc.

As used herein a "pharmaceutically acceptable carrier" or "excipient" includes any and all antibacterial and antifungal agents, coatings, dispersion media, solvents, isotonic and absorption delaying agents, and the like that are physiologically compatible. A "pharmaceutically acceptable carrier" may include a solid or liquid filler, diluent or encapsulating substance which may be safely used for the administration of the chimaeric. VLPs or vaccine composition to a subject. The pharmaceutically acceptable carrier can be suitable for intramuscular, intraperitoneal, intravenous, subcutaneous, oral or sublingual administration. Pharmaceutically acceptable carriers include sterile aqueous solutions, dispersions and sterile powders for the preparation of sterile solutions. The use of media and agents for the preparation of pharmaceutically active substances is well known in the art. Where any conventional media or agent is incompatible with the active compound, use thereof in the pharmaceutical compositions of the invention is not contemplated. Supplementary active compounds can also be incorporated into the compositions.

Suitable formulations or compositions to administer the chimaeric VLPs and compositions to subjects who are to be prophylactically treated for an Orbivirus infection, who are suffering from an Orbivirus infection or subjects which are presymptomatic for a condition associated with Orbivirus infection fall within the scope of the invention. Any appropriate route of administration may be employed, such as, parenteral, intravenous, subcutaneous, intramuscular, intracranial, intraorbital, ophthalmic, intraventricular, intracapsular, intraspinal, intrathecal, intracisternal, intraperitoneal, intranasal, aerosol, topical, or oral administration.

As used herein the term "subject" includes wild and domestic ruminants, equids or any specified target animal For vaccine formulations, an effective amount of the chimaeric VLPs or compositions of the invention can be provided, either alone or in combination with other compounds, with immunological adjuvants, for example, aluminium hydroxide dimethyldioctadecylammonium hydroxide or Freund's incomplete adjuvant. The chimaeric VLPs or compositions of the invention may also be linked with suitable carriers and/or other molecules, such as bovine serum albumin or keyhole limpet hemocyanin in order to enhance immunogenicity.

In some embodiments, the chimaeric VLPs or compositions according to the invention may be provided in a kit, optionally with a carrier and/or an adjuvant, together with instructions for use.

An "effective amount" of a compound according to the invention includes a therapeutically effective amount, immunologically effective amount, or a prophylactically effective amount. A "therapeutically effective amount" refers to an amount effective, at dosages and for periods of time necessary, to achieve the desired therapeutic result, such as treatment of an Orbivirus infection or a condition associated with such infection. The outcome of the treatment may for example be measured by a decrease in viremia, inhibition of viral gene expression, delay in development of a pathology associated with the Orbivirus infection, stimulation of the immune system, or any other method of determining a therapeutic benefit. A therapeutically effective amount of a compound may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects.

The dosage of any of the chimaeric VLPs or compositions of the present invention will vary depending on the symptoms, age and body weight of the subject, the nature and severity of the disorder to be treated or prevented, the route of administration, the Orbivirus infection being treated and the form of the composition. Any of the compositions of the invention may be administered in a single dose or in multiple doses. The dosages of the compositions of the invention may be readily determined by techniques known to those of skill in the art or as taught herein.

By "immunogenically effective amount" is meant an amount effective, at dosages and for periods of time necessary, to achieve a desired immune response. The desired immune response may include stimulation or elicitation of an immune response, for instance a T or B cell response.

A "prophylactically effective amount" refers to an amount effective, at dosages and for periods of time necessary, to achieve a desired prophylactic result, such as prevention of onset of a condition associated with an Orbivirus infection. Typically, a prophylactic dose is used in subjects prior to or at an earlier stage of disease, so that a prophylactically effective amount may be less than a therapeutically effective amount.

Dosage values may vary with the severity of the condition to be alleviated. For any particular subject, specific dosage regimens may be adjusted over time according to the individual need and the judgment of the person administering or supervising the administration of the chimaeric VLPs or compositions of the invention. Dosage ranges set forth herein are exemplary only and do not limit the dosage ranges that may be selected. The amount of active compound(s) in the composition may vary according to factors such as the disease state, age, sex, and weight of the individual. Dosage regimens may be adjusted to provide the optimum therapeutic response. For example, a single dose may be administered, or multiple doses may be administered over time. It may be advantageous to formulate the compositions in dosage unit forms for ease of administration and uniformity of dosage.

The term "preventing", when used in relation to an infectious disease, or other medical disease or condition, is well understood in the art, and includes administration of a composition which reduces the frequency of or delays the onset of symptoms of a condition in a subject relative to a subject which does not receive the composition. Prevention of a disease includes, for example, reducing the number of diagnoses of the infection in a treated population versus an untreated control population, and/or delaying the onset of symptoms of the infection in a treated population versus an untreated control population.

The term "prophylactic or therapeutic" treatment is well known to those of skill in the art and includes administration to a subject of one or more of the compositions of the invention. If the composition is administered prior to clinical manifestation of the unwanted condition (e.g., disease or other unwanted state of the subject) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

Toxicity and therapeutic efficacy of compositions of the invention may be determined by standard pharmaceutical procedures in cell culture or using experimental animals, such as by determining the $LD_{50}$ and the $ED_{50}$. Data obtained from the cell cultures and/or animal studies may be used to formulating a dosage range for use in a subject. The dosage of any composition of the invention lies preferably within a range of circulating concentrations that include the $ED_{50}$ but which has little or no toxicity. The dosage may vary within this range depending upon the dosage form employed and the route of administration utilized. For compositions of the present invention, the therapeutically effective dose may be estimated initially from cell culture assays.

Provided herein are methods for producing a chimaeric BTV VLP in a plant cell, which comprises a core comprising BTV-8 capsid proteins VP3, VP5 and VP7 and an outer layer comprising BTV VP2 proteins selected from any one of the 26 BTV serotypes and methods for producing a chimaeric BTV VLP in a plant cell, which comprises a core comprising BTV-8 VP3 and VP7 capsid proteins and an outer layer comprising BTV VP2 and VP5 capsid proteins selected from any one of the 26 BTV serotypes.

Similarly, methods for producing a chimaeric AHSV VLP in a plant cell, which comprises a core comprising AHSV-1 capsid proteins VP3, VP5 and VP7 and an outer layer comprising VP2 protein selected from any one of the 8 remaining AHSV serotypes and methods for producing a chimaeric AHSV VLP in a plant cell, which comprises a core comprising AHSV-1 VP3 and VP7 capsid proteins and an outer layer comprising AHSV VP2 and VP5 capsid proteins selected from any one of the remaining 8 AHSV serotypes.

A "VLP" or "virus-like particle" refers to the capsid-like structure which results from the assembly of Orbivirus VP2, VP3, VP5 and VP7 polypeptides. These particles are antigenically and morphologically similar to native Orbivirus virus virions but do not include viral genetic material; accordingly, these particles are not replicating nor infectious.

The invention also relates in part to a method of eliciting an immune response in a subject comprising administering to a subject in need thereof a prophylactically effective amount of the chimaeric VLPs or compositions of the present invention.

The following examples are offered by way of illustration and not by way of limitation.

Example 1

Nicotiana sp. codon-optimised BTV-8 VP2 (SEQ ID NO:27), VP3 (SEQ ID NO:21), VP5 (SEQ ID NO:23) and VP7 (SEQ ID NO:25) were synthesised (Geneart, Germany). The plant codon optimised nucleotide sequences encode the following proteins: BTV-8 VP2 (SEQ ID NO:7), VP3 (SEQ ID NO:1), VP5 (SEQ ID NO:3) and VP7 (SEQ ID NO:5). Primers were designed to add restriction enzyme sites (AgeI and XhoI) on the 5' and 3' termini, respectively (Table 1) such that they could be cloned into the pEAQ-HT expression vector using these sites.

TABLE 1

BTV gene specific primers

| Protein | Primer Name | Sequence | SEQ ID NO. |
| --- | --- | --- | --- |
| BTV-8 VP2 | pEAQ-HTVP2F | 5' GCACCGGTATGGAAGAACTCGCTATCCCAA 3' | (SEQ ID NO: 41) |
|  | cVP2coR | 5' GCCTCGAGTCAAACGTTGAGGAGCTTAGTAAG 3' | (SEQ ID NO: 42) |
| BTV-8 VP3 | pEAQ-HTVP3F | 5' GCACCGGTATGGCTGCTCAAAATGAGCAAAG 3' | (SEQ ID NO: 43) |
|  | cVP3coR | 5' GCCTCGAGTTAAACAGTTGGAGCAGCAAGC 3' | (SEQ ID NO: 44) |
| BTV-8 VP5 | pEAQ-HTVP5F | 5' GCACCGGTATGGGAAAGATTATTAAGTCCCTCTC 3' | (SEQ ID NO: 45) |
|  | cVP5coR | 5' GCCTCGAGTCAAGCGTTCCTAAGGAAGAG 3' | (SEQ ID NO: 46) |
| BTV-8 VP7 | pEAQ-HTVP7F | 5' GCACCGGTATGGATACAATTGCTGCTAGGG 3' | (SEQ ID NO: 47) |
|  | cVP7coR | 5' GCCTCGAGTCACACATAAGCAGCCCTAG 3' | (SEQ ID NO: 48) |

Resulting constructs were named pEAQ-HT-VP2, pEAQ-HT-VP3, pEAQ-HT-VP5 and pEAQ-HT-VP7. These constructs were sequenced and transformed into *A. tumefaciens* LBA4404.

Ten ml cultures of all four recombinant constructs were grown up in LB containing magnesium sulphate (2 mM), rifampicin (50 µg/ml) and kanamycin (30 µg/ml) at 27° C. overnight with agitation at 200 rpm. A 10th of the volume was transferred to induction medium (LB, 10 mM MES, pH 5.6) containing the same concentration of antibiotics as well as 20 µM acetosyringone. These were incubated overnight at 27° C. with agitation at 200 rpm and then centrifuged at 4000 rpm to pellet the cells. The cell pellets were resuspended in 5 ml of infiltration medium (10 mM MES, 10 mM $MgCl_2$, 3% sucrose, pH 5.6) supplemented with 200 µM acetosyringone and incubated at room temperature for 2 h. The $OD_{600}$ of each culture was measured and the cultures diluted to an OD of 1.8 in infiltration medium. They were then combined in a ratio of 1:1:2:1 (VP2:VP3:VP5:VP7) and syringe-infiltrated into the abaxial surfaces of six-week-old *N. benthamiana* plants.

At 9 days post infiltration (dpi) the leaves were ground up and immediately cut up into fine pieces and homogenized in three volumes of ice cold bicine buffer (50 mM bicine (pH 8.4), 20 mM sodium chloride (NaCl), and 1× Complete Mini, EDTA-free protease inhibitor cocktail (Roche)) lacking NLS and DTT. The homogenate was clarified by centrifugation at 1000×g for 10 min after which the supernatant was filtered through four layers of Miracloth™ (Merck). The crude plant sap was overlayed onto 5 ml of a 40% iodixanol (Optiprep™, Sigma-Aldrich) cushion prepared in 50 mM Tris-HCl, pH 8.4 and 20 mM NaCl after which it was centrifuged for 2 h at 79 000×g in a SW 32 Ti rotor (Beckman). The 40% iodixanol cushion was collected after centrifugation from the bottom of the tube and overlayed onto 5 ml of a 20% to 60% step gradient (1 ml of each gradient in 10% incrementing steps) and centrifuged as above. Fractions of 0.5 ml were collected from the bottom of the tubes and analyzed by western blotting and TEM.

Figure 1:
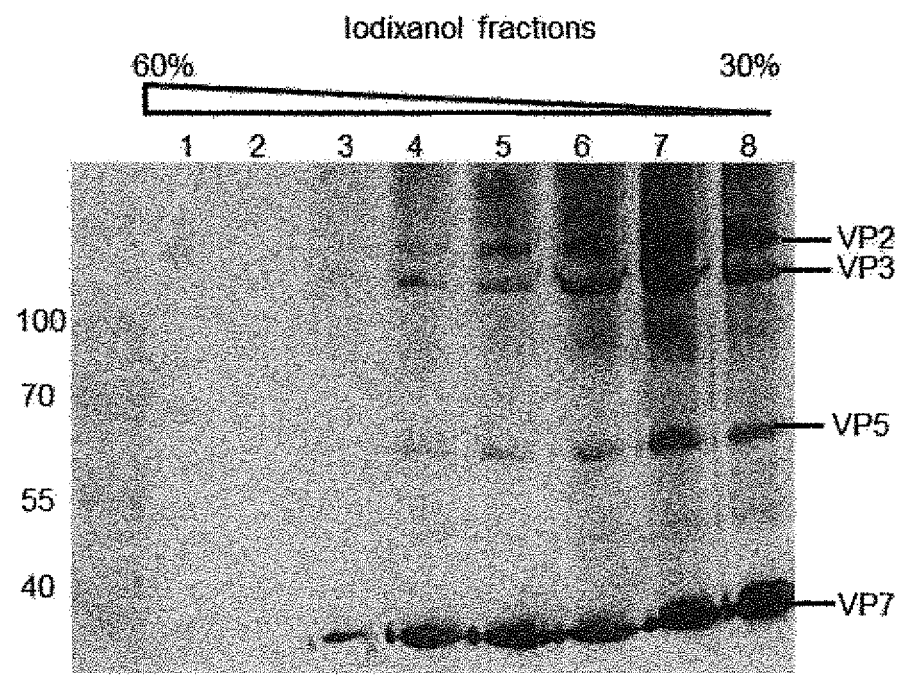
FIG. 1: Western blot analysis of density gradient fractions. Fractions 1 to 8 from 30 to 60% iodixanol gradient centrifugation of pEAQ-HT VLPs probed with anti-BTV-8 antiserum. PageRuler™ Prestained Protein Ladder (Thermo Scientific) was used as a size marker.

For western blot analysis, the iodixanol fractions were incubated at 90° C. for 10 min in loading buffer. The proteins were separated on 8% SDS polyacrylamide gels where equal amounts of total protein were loaded in each lane. After electrophoresis the proteins were transferred onto nitrocellulose membranes using a Trans-Blot® SD semi-dry transfer cell (Bio-Rad). Membranes were probed with a 1:2000 dilution of BTV-8 sheep serum (Thuenemann et al., 2013) and subsequently with a 1:10000 dilution of anti-goat/sheep alkaline phosphatase-conjugated secondary antibody (Sigma-Aldrich). Detection was performed with 5-bromo-4-chloro-3-indoxyl-phosphate (BCIP) and nitroblue tetrazolium (NBT) phosphatase substrate (BCIP/NBT 1-component, KPL). Western blot analysis of the first 8 fractions collected from the iodixanol gradient after centrifugation showed the presence of all four bands constituting the BTV-8 VLPs in fractions 4 (approximately 40%-50% iodixanol) up until fraction 8 (20%-30% iodixanol) (FIG. 1). These samples were also resolved on a Coomassie-stained SDS-PA gel. Only VP3, VP5 and VP7 could be observed on the gel. TEM analysis on fractions 5 to 8 showed only the presence of CLPs in the samples. These results indicate that VP2 and VP5 are not assembling with the CLPs to form VLPs, but that they are being co-purified with the particles.

Figure 2:
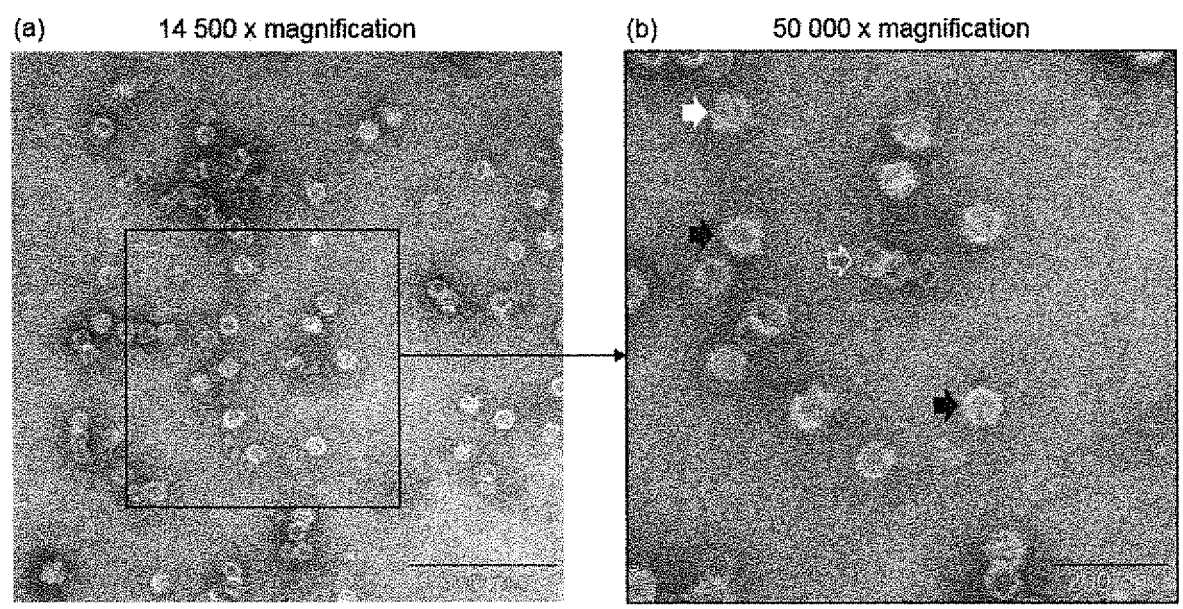
FIG. 2: TEM analysis of fraction 4 taken from 30 to 60% iodixanol gradient. (a) 14 500× magnification of BTV-8 VLPs and CLPs ranging in size from 70 to 88 nm in diameter. (b) A 50 000× magnification of the same view. Black arrows indicate VLPs measuring 80 nm in size, the white arrow shows a CLP of 65 nm and the empty white arrow indicates a subcore-like particle (measuring 53 nm). Scale bars: (a) 500 nm and (b) 200 nm. The images were obtained using a Technai $G^2$ transmission electron microscope.

For TEM, copper grids (mesh size 200) were floated for 2 min on a 1:200 dilution of BTV-8 sheep serum and washed twice with sterile water. Thereafter the grids were floated on a 1:10 dilution of crude plant extract for 5 min and washed three times with sterile water. The samples were negatively stained for 1 min with 2% uranyl acetate. Fractionated samples from the density gradients were treated similarly except they were not captured onto the grids with anti-BTV-8 sheep serum. All grids were viewed using a Technai G2 TEM. TEM of fraction 4 from the density gradient showed a mixed population of both CLPs and VLPs based on diameter measurements (FIGS. 2a and b): CLPs measured 60 to 69 nm in diameter and VLPs measured 72 to 80 nm in diameter. Ten fields of view, at a magnification of 14 500×, showed approximately 80 particles in each view of which approximately 10% were VLPs (FIG. 2a). FIG. 2b shows more detail of the particles, at 50 000× magnification, making it easier to distinguish CLPs (single shelled particles) from VLPs (double shelled particles).

TEM on samples from leaves co-infiltrated with BTV VP constructs was also carried out. The BTV-8 pEAQ-HT-VP2, pEAQ-HT-VP3, pEAQ-HT-VP5 and pEAQ-HT-VP7 constructs were cultured and combined (as described previously) in a ratio of 1:1:2:1 (VP2:VP3:VP5:VP7) and syringe-infiltrated into the abaxial surfaces of six-week-old *N. benthamiana* plants.

At 9 dpi a whole leaf was picked from the infiltrated plant and a 3 cm×3 cm piece was cut out with a scalpel blade in the presence of 2.5% gluteraldehyde (25% gluteraldehyde diluted in 0.1 M phosphate buffer (pH 7.4)). The leaf sample was soaked in 2.5% gluteraldehyde for 6 hours after which it was cut into 1 mm×3 mm fragments, also in the presence of 2.5% gluteraldehyde. The leaf fragments were left in 2.5% gluteraldehyde overnight at 4° C. The following morning the leaf fragments were washed 3 times, 5 minutes for each wash, in 0.1 M phosphate buffer (pH 7.4). The leaf fragments were fixed for one hour in one part 2% osmium tetroxide and one part 0.2 M phosphate buffer (pH 7.4) after which it was washed twice for 5 minutes each with 0.1 M phosphate buffer (pH 7.4) followed with two washes of 5 min each with water.

After washing the leaf fragments were sequentially dehydrated. The leaf fragments were incubated for 5 minutes each in 30%, 50%, 70%, 80%, 90% and 95% ethanol. The fragments were incubated for 10 minutes in 100% ethanol; this step was repeated twice. After the ethanol dehydrations series the leaf fragments were further dehydrated by 10 minute incubation in 100% acetone, repeated twice. The leaf fragments were mixed overnight in 1:1 acetone:Spurr's resin.

The following day half of the 1:1 acetone:Spurr's resin mixture was removed (after centrifugation) and replaced with 100% Spurr's resin to yield a 1:3 acetone:Spurr's resin mixture. The sample was mixed for four hours at room temperature, after which the acetone/resin mixture was removed and replaced with 100% Spun's resin. The leaf fragments were incubated in 100% Spurr's resin for three days at 4° C. The 100% Spurr's resin was replaced with fresh resin and incubated for four hours at room temperature after which the resin was replaced again and incubated overnight at room temperature. The following morning the samples were embedded and incubated for 24 hours at 60° C.

The embedded leaf samples were cut into ultrathin sections with a diamond knife and collected onto copper grids. The copper grids were stained with uranyl acetate for 10 minutes after which they were washed five times, 15 seconds each, with water. The grids were blotted dry and transferred to lead citrate for 10 minutes after which the grids were washed with water and blotted dry. Grids were viewed using the Technai G2 transmission electron microscope.

Figure 3:
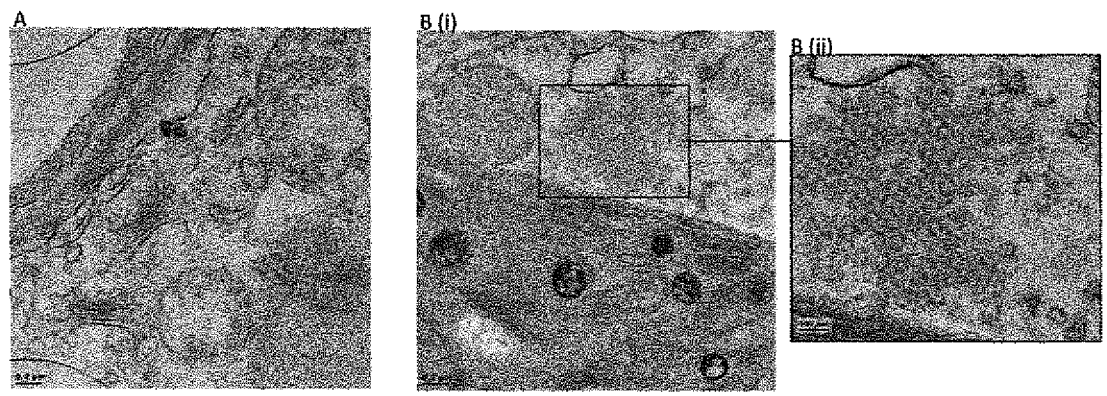
FIG. 3: A TEM of a leaf section infiltrated with only infiltration media at 17000× magnification. B(i) TEM of leaf section showing a mixed population of BTV-8 CLPs and VLPs at a 17000× magnification, B(ii) is a 40 000× magnification of B(i) displaying the particles in more detail.
Figure 4:
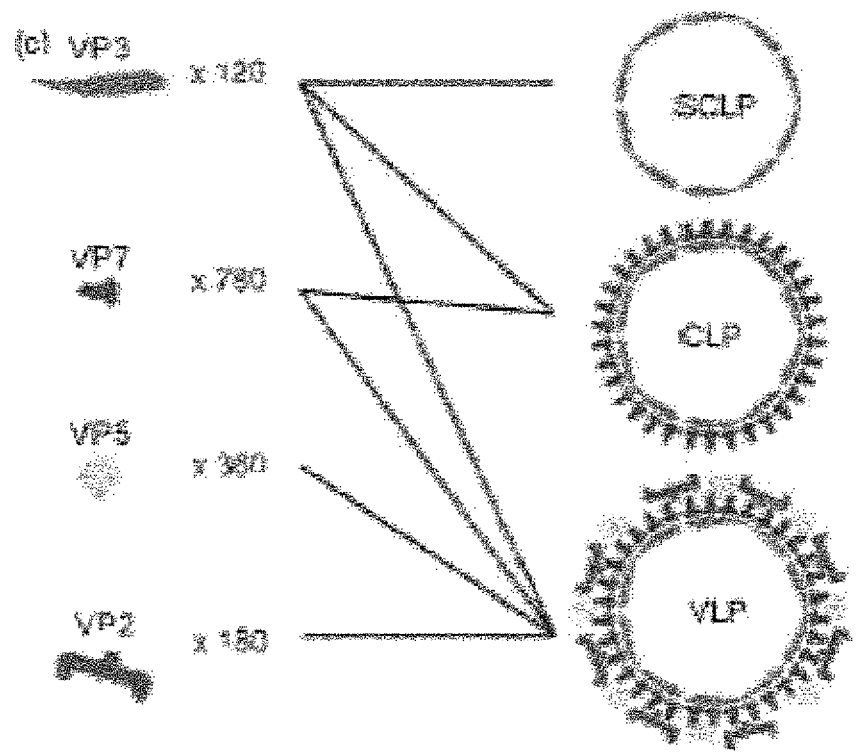
FIG. 4: Schematic representations of BTV proteins indicating how many copies of each structural protein come together to form subcore-, core- and virus-like particles (SCLP, CLP, VLP). (Thuenemann et al., 2013)

FIG. 3A shows a leaf section infiltrated only with infiltration medium as a negative control. TEM of the leaf sections (FIG. 3B (i) and (ii)) showed particles ranging in size from 60 to 78 nm in diameter, indicating that the mixed population consists of both CLPs and VLPs. The particles are present in the cytoplasm of the plant cell and are arranged in arrays.

Example 2

Figure 5:
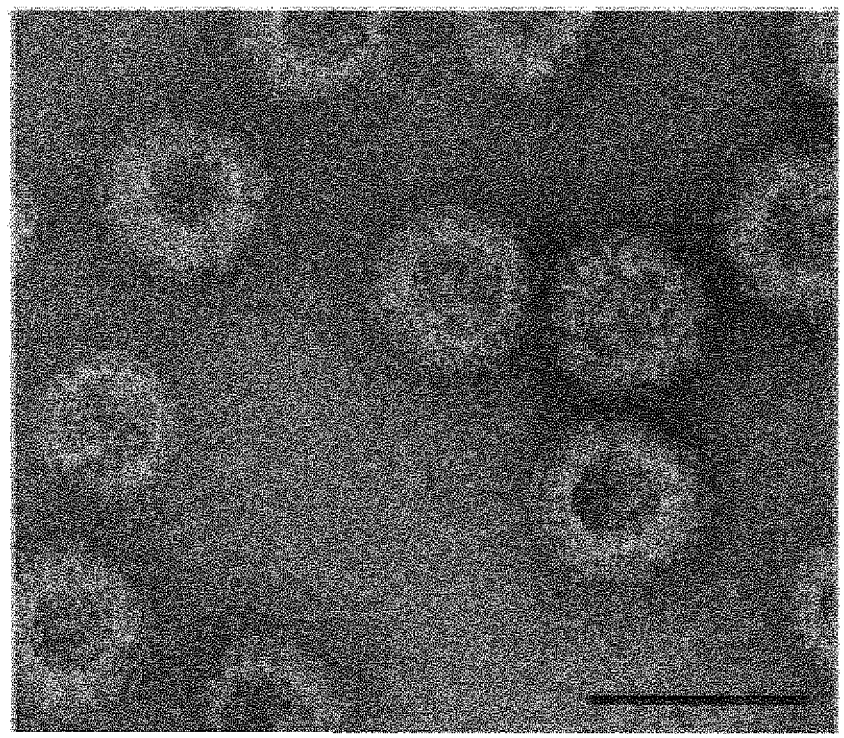
FIG. 5: BTV-like particles for serotype 8. Scale bar, 100 nm (Thuenemann et al., 2013)

In Example 1 the present inventors investigated the transient production of BTV VLPs in plants as an alternative cheaper source of safe and effective vaccine. The inventors have successfully shown that co-expression of Bluetongue virus (BTV) serotype 8 VP2, VP3, VP5 and VP7 capsid encoding genes by *Agrobacterium*-mediated infiltration of *N. benthamiana* results in the efficient assembly of virus-like particles (VLPs), and that these VLPs are highly immunogenic and are protective in sheep (FIG. 5).

The present example was performed to demonstrate that it is possible to produce BTV VLPs covering a wide range of serotypes by using the pre-existing BTV 8 VP3, 5 and 7 proteins as a common scaffold or core on which different serotype-specific VP2s could be presented representing other BTV serotypes thus producing a multivalent antigen.

To prove this concept, we tested the production of VLPs in plants with a different BTV VP2 serotype i.e. a BTV-2 VP2. The VP2 gene was codon-optimised for *N. benthamiana* (SEQ ID NO:28) and synthesised by GenScript, cloned into the plant expression vector pEAQ-HT (Sainsbury et al., 2009) and electroporated into *Agrobacterium tumefaciens* LBA4404. This recombinant strain as well as those encoding BTV serotype 8 VP3, 5 and 7 genes (made previously) which are required for VLP assembly were co-infiltrated into *N. benthamiana* and the leaves were screened for the presence of all 4 proteins by western blotting after 8 days. A preliminary western blot was carried out on the samples to determine the presence of BTV VP proteins. VP3, 5 and 7 proteins were detected but VP2 was not (data not shown). The antiserum used for this western blot is polyclonal serum from sheep which have been injected with plant-produced BTV-8 VLPs. It is possible that the VP2 is not detected by this antiserum in this western blot because it is serotype 8-specific.

We continued with scaling up of BTV VP production so that sufficient material could be obtained for purification and TEM analysis. Thirty plants were co-infiltrated with cultures of the 4 different recombinant strains and harvested after 8 days.

The leaf material was homogenised, centrifuged to get rid of particulate matter, and the supernatant filtered through Miracloth. The filtrate was then loaded on top of a 30% Optiprep™ cushion made up in bicine buffer. The tubes were centrifuged at 22 000 rpm for 2 hours in a SW32Ti rotor and the interface between the cushion and supernatant aspirated. This was loaded on top of a 20 to 60% Optiprep™ gradient (made up in bicine buffer) and centrifuged at 22 000 rpm for 2 h in a SW32Ti rotor. The tube was fractionated into 10×1 ml fractions and some of the fractions were analysed on a western blot using the same polyclonal sheep antiserum used above to detect BTV VP protein.

FIG. 7 shows the western blot where BTV-8 VP3, VP5 and VP7 are visible as 102 kDa, 59 kDa and 38 kDa sized proteins. BTV-2 VP2 (expected to be 111 kDa) is not visible, but this is not unexpected as the antiserum is serotype 8-specific.

Figure 8:
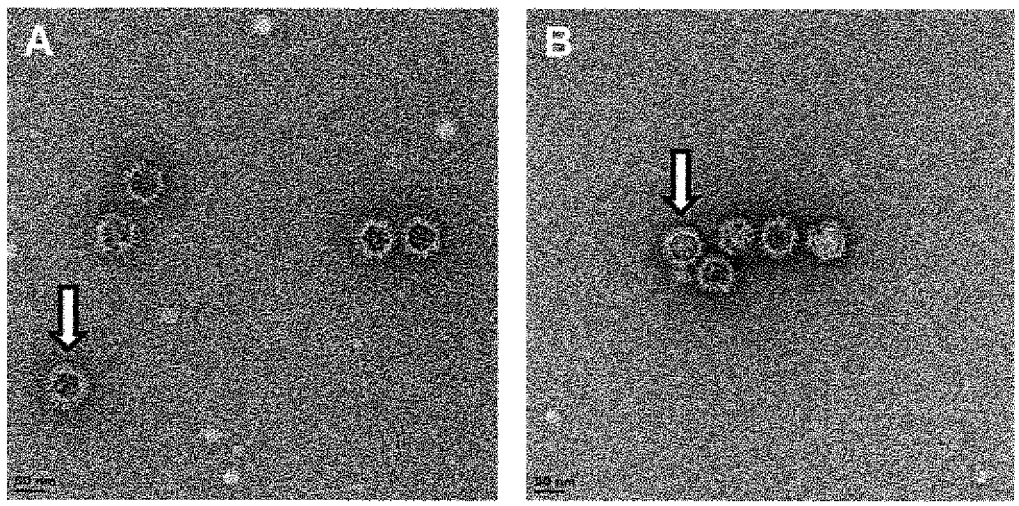
FIG. 8: Electron microscopy of plant-made BTV-like particles and assembly intermediates consisting of (A) serotype 2 and 8 capsid proteins i.e. BTV-2 VP2, BTV-8 VP5, BTV-8 VP3 and BTV-8 VP7 and (B) serotype 8 only capsid proteins i.e. BTV-8 VP2, BTV-8 VP5, BTV-8 VP3 and BTV-8 VP7. Arrows indicate fully-formed VLPs.
Figure 9:
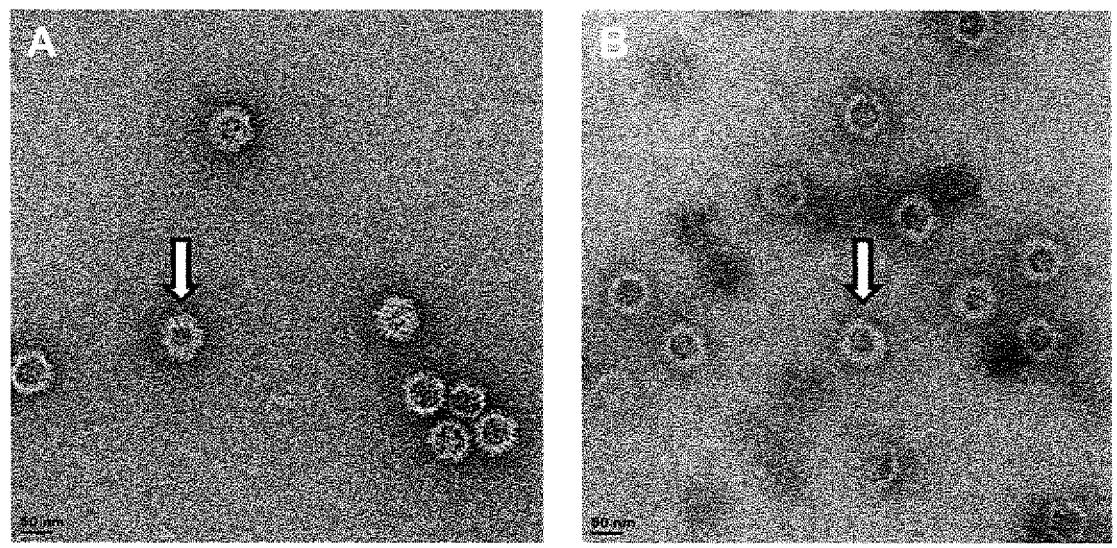
FIG. 9: Electron microscopy of plant-made BTV-like particles and assembly intermediates consisting of (A) serotype 2 and 8 capsid proteins i.e. BTV-2 VP2, BTV-8 VP5, BTV-8 VP3 and BTV-8 VP7 and (B) serotype 8 only capsid proteins i.e. BTV-8 VP2, BTV-8 VP5, BTV-8 VP3 and BTV-8 VP7. Arrows indicate fully-formed VLPs.

Fraction 5 of the gradient was analysed by transmission electron microscopy (TEM). FIGS. 8 and 9 show examples of the particles that were produced. It seems that although there were some VLPs observed (distinguished by a thicker outer ring), more than half of the particles purified consisted of subcore-like and core-like particles. However, the presence of some VLPs does indicate that the formation of chimaeric BTV particles is possible.

Figure 10:
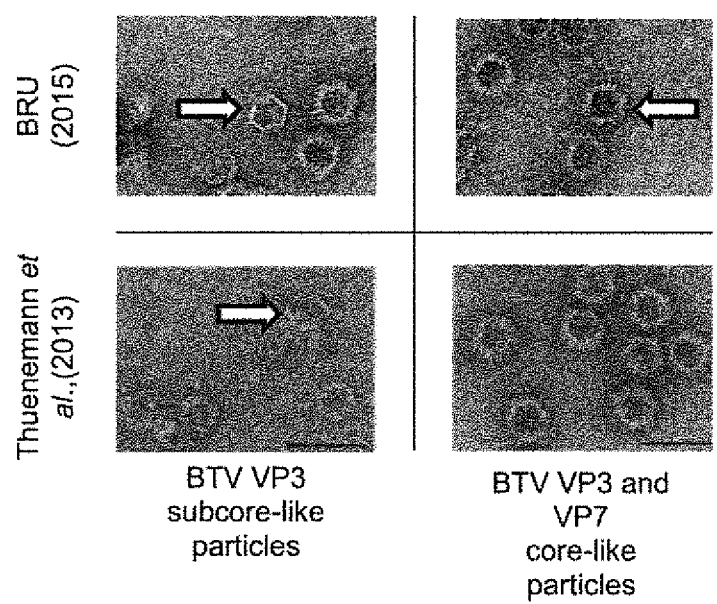
FIG. 10: Electron microscopy of chimaeric BTV subcore-like and core-like particles (BRU (2015)) and BTV-8 subcore-like and core-like particles (Thuenemann et al., 2013)

We have shown that the co-infiltration of only BTV-8 VP3- and VP7-encoding constructs results in the formation of core-like particles (FIG. 10) indicating that the core is being formed on which VP5 and VP2 can bind.

Figure 11:
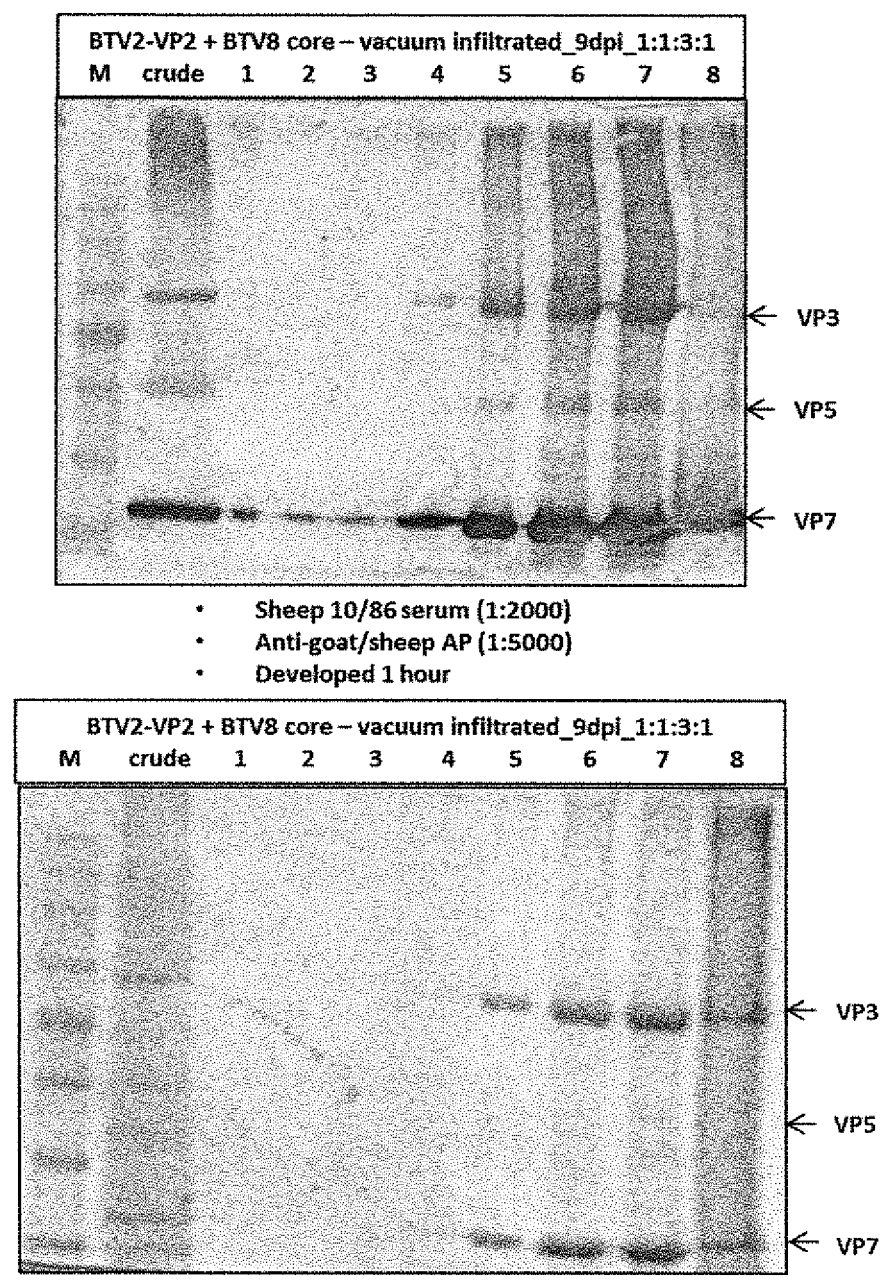

In previous work on BTV-8 VLPs only it was shown that an infiltration ratio of 1:1:2:1 of VP2:VP3:VP5:VP7 yielded the best VLPs and this was tested in this chimaeric constructs to try and skew production from more CLPs to more VLPs. FIG. 11 shows the western blot and cognate Coomassie-stained gel of fractions purified on the same gradient as above. VP3, VP5 and VP7 are clearly visible in fractions 5 to 7 on the western blot and in the Coomassie-stained gel and VP3, VP5 and VP7 are visible although there is much less VP5 than VP3 or VP7.

This example proves that it is possible to make chimaeric BTV VLPs although the infiltration process needs to be optimised in order to direct the preferential assembly of VLPs rather than CLPs.

Although BTV-8 VP3, VP5 and VP7 proteins are detectable by western blot and BTV-2 VP2 proteins are not, chimaeric BTV VLPs comprising of BTV-8 VP3, VP5 and VP7 and BTV-2 VP2 can be produced in plants although it seems there are significantly more core-like particles (CLPs) and sub-core-like particles (sCLPs) made than VLPs.

Example 3

The following plant codon optimised nucleotide sequences were synthesised by Bio Basic Int.: BTV-3 VP2

(SEQ ID NO:29), BTV-3 VP5 (SEQ ID NO:32), BTV-4 VP2 (SEQ ID NO:30), BTV-4 VP5 (SEQ ID NO:33), BTV-4 VP7 (SEQ ID NO:34), BTV-8 VP2 (SEQ ID NO:31), BTV-8 VP5 (SEQ ID NO:22), BTV-8 VP5 (SEQ ID NO:24) and BTV-8 VP7 (SEQ ID NO:26). The plant codon optimised nucleotide sequences encode the following proteins: BTV-3 VP2 (SEQ ID NO:9), BTV-3 VP5 (SEQ ID NO:12), BTV-4 VP2 (SEQ ID NO:10), BTV-4 VP5 (SEQ ID NO:13), BTV-4 VP7 (SEQ ID NO:14), BTV-8 VP2 (SEQ ID NO:11), BTV-8 VP3 (SEQ ID NO:2), BTV-8 VP5 (SEQ ID NO:4) and BTV-8 VP7 (SEQ ID NO:6).

Using the protocols described herein the nucleotide sequences where cloned into the pEAQ-HT expression vector and the vectors were subsequently electroporated into *Agrobacterium tumefaciens* LBA4404 (1.44 kV, 200Ω and 25 μF). Similarly pEAQ-HT void of an insert were also electroporated into *Agrobacterium* and served as negative controls. A pEAQ-HT-gfp vector containing the green fluorescent protein gene (gfp) served as positive control. The product was resuspended in Luria broth medium, and placed on a rotor shaker at 28° C. for three hours to recover before plated on selective medium (50 mg/l streptomycin, 25 mg/l kanamycin and 20 mg/l Rifamycin). A single colony of each Insert was PCR validated using pEAQ-HT Fw (SEQ ID NO:49) and pEAQ-HT Rv (SEQ ID NO:50) primers. These primers are specific for the pEAQ-HT vector.

The leaf material was harvested four to eight days after infiltration using a Matstone Multipurpose juice extractor in VLP extraction buffer (50 mM bicine, pH 8.4; 20 mM sodium chloride [NaCl], 0.1% (w/v) N-lauroylsarcosine (NLS) sodium salt, 1 mM dithiothreitol (DTT)) in a ratio 1:3 with complete protease inhibitor cocktail (P2714, Sigma Life Sciences) or complete EDTA-free tablets (Roche) added to the VLP extraction buffer immediately before the extraction started. In a particular experiment, 0.5 mM $CaCl_2$ was added to the extraction medium to potentially stabilize the formed VLPs. Crude extracts were centrifuged twice for 10 minutes at 4,200×g, 10° C. to remove cell debris in a JA14 rotor using a Beckman Coulter Avanti J-26 XPI centrifuge.

Particles were purified by density gradient centrifugation using ultra-high quality sucrose (Sigma Life Sciences) step gradients (30%-70%) prepared dissolved in VLP dilution buffer (50 mM Tris-HCl, pH 8.4, 20 mM NaCl). Step gradients of 1 ml with 10% incrementing steps were prepared and then overlaid with 8 ml of clarified leaf extract. The gradients were centrifuged at 85,800×g, at 10° C. for 3 hours in a SW-41Ti rotor (Beckman Coulter). Fractions of 500 μl were collected and aliquots (26 μl) from all fractions were analysed on 4-12% Bis-Tris Bolt™ (Life Technologies) protein gels or 10% Stain Free SDS-PAGE (Bio-Rad). The sucrose-gradient purified product was dialysed over-

TABLE 2 pEAQ-HT plasmid specific primers.

| Primer Name | Sequence | SEQ ID NO. |
|---|---|---|
| pEAQ-HT Fw | 5' ACTTGTTACGATTCTGCTGACTTTCGGCGG 3' | (SEQ ID NO: 49) |
| pEAQ-HT Rv | 5' CGACCTGCTAAACAGGAGCTCACAAAGA 3' | (SEQ ID NO: 50) |

Transient expression efficiency of the pEAQ series of vectors was investigated by agroinfiltration of *Nicotiana benthamiana*. The assembly of VLPs was also validated in *N. benthamiana* which facilitates mammalian-like or human-like glycosylation RNAi mutant *N. benthamiana* dXT/FT (Strasser et al., 2008). The pEAQ-HT constructs containing genes encoding individual capsid proteins of BTV serotypes 3, 4 and 8 were individually transformed into *Agrobacterium*. Prior to plant infiltration *Agrobacterium tumefaciens* strain (LBA4404) transformed with pEAQ-HT vector containing individual VP2, VP3, VP5 and VP7 of selected serotypes were streaked on YMB agar plates and incubated at 28° C. for 48 hrs. The growing bacterium was scraped off from the plate and inoculated into YMB broth with the relevant antibiotics and grown overnight. Cells were pelleted and resuspended in MMA buffer (100 mM MES, 10 mM $MgCl_2$ and 100 mM acetosyringone; pH 5.6). Each of the four *Agrobacterium* cultures were adjusted to $OD_{600}$ of approximately 0.5-0.7 with the same buffer. The formation of VLPs was validated by mixing and infiltrating the four constructs encoding the four individual capsid proteins at a ratio of 1:1:1:1 and used for plant infiltrations (20-25 plants; 15-20 cm in height). The *Agrobacterium* transformed with pEAQ-HT-gfp was used as the positive control and negative was *A. tumefecians* transformed with an empty pEAQ-HT vector. The construct pEAQ-HT-VP3 was sometimes substituted with pEAQ-VP3 wt, to suppress the expression of capsid protein VP3 and to shift the stoichiometry from core-like particles (CLPs) to VLPs as previously described (Theunemann, et al., 2013).

night against bicine buffer containing only the bicine (pH 8.4) and sodium chloride in preparation for animal trials.

The sucrose gradient fractions were adsorbed onto holey carbon-coated copper grids as follows. The grids were floated on the 1/10 dilution protein sample for 30 seconds and excess sample drained off the grid via blotting on filter paper. Subsequently the grid was floated on 2% sodium phosphotungstate, pH 7.0 for 30 seconds (0.22 μm filter sterilized before staining) and drained as described above. The air dried grid was imaged in a JEM-2100 Transmission electron microscope (JEOL) at the University of Pretoria, Laboratory for Microscopy and Microanalysis.

Protein bands of interest were in-gel trypsin digested as per the protocol described in (Shevchenko et al., 2007). In short, gel bands were destained using 50 mM $NH_4HCO_3$/50% MeOH followed by in-gel protein reduction (50 mM DTT in 25 mM $NH_4HCO_3$) and alkylation (55 mM iodoacetamide in 25 mM $NH_4HCO_3$). Proteins were digested over night at 37° C. using 5-50 μl, 10 ng/μl trypsin depending on the gel piece size. Digests were resuspended in 20 μl, 2% acetonitrile/0.2% formic acid and analysed using a Dionex Ultimate 3000 RSLC system coupled to an AB Sciex 6600 TipleTOF mass spectrometer. Peptides were first desalted on an Acclaim PepMap C18 trap column (100 μm×2 cm) for 2 min at 15 μl/min using 2% acetonitrile/0.2% formic acid, than separated on Acclain PepMap C18 RSLC column (300 μm×15 cm, 2 μm particle size). Peptide elution was achieved using a flow-rate of 8 μl/min with a gradient: 4-60% B in 15 min (A: 0.1% formic acid; B: 80% acetonitrile per 0.1% formic acid). An electrospray voltage of 5.5 kV was applied to the emitter. The 6600 TipleTOF mass spectrometer was operated in Data Dependant Acquisition mode. Precursor scans were acquired from m/z 400-1500 using an accumulation time of 250 ms followed by 30 product scans, acquired from m/z 100-1800 at 100 ms each, for a total scan time of 3.3 sec. Multiply charge ions (2+-5+, 400-1500 m/z) were automatically fragmented in Q2 collision cells using nitrogen as the collision gas. Collision energies were chosen automatically as function of m/z and charge.

Protein pilot v5 using Paragon search engine (AB Sciex) was used for comparison of the obtained MS/MS spectra with Uniprot Swissprot protein database. Proteins with threshold above ≥99.9% confidence were reported.

Assembly of BTV serotype 3, 4 and 8 VLPs were investigated by infiltrating N. benthamiana mammalian-like mutant dXT/FT or unmodified N. benthamiana plants with the relevant constructs. The Agrobacterium strain LBA4404 harboring pEAQ-HT constructs encoding for the four capsid proteins individually for BTV serotypes 3, 4 and 8 were successfully infiltrated into N. benthamiana leaves. Production of VLPs in plant leaf tissue was determined by mixing the four constructs encoding the four individual capsid proteins VP2:VP3:VP5:VP7 at a ratio of 1:1:1:1. Leaf tissue was harvested eight days after infiltration, extracted and purified as described.

The production of all four capsid proteins was determined by SDS-PAGE and immuno blot analysis where appropriate serum was available. The crude leaf extract was subjected to sucrose gradient purification and distinct protein bands were identified on Coomassie stained SDS-PAGE gels. The protein bands at 111 kDa, 100 kDa, 59 kDa and 38 kDa were confirmed to be the capsid proteins VP2, VP3, VP5 and VP7, respectively, by mass spectrophotometry. The assembly of VLPs (~70 nm) was confirmed by transmission electron microscopy (TEM) for all three serotypes 3, 4 and 8.

The following combinations of capsid proteins, extraction buffer composition and protease inhibitors were tested for assembling and purification of chimaeric CLPs and chimaeric VLPs.

BTV-3 Double Chimaeric

Figure 12:
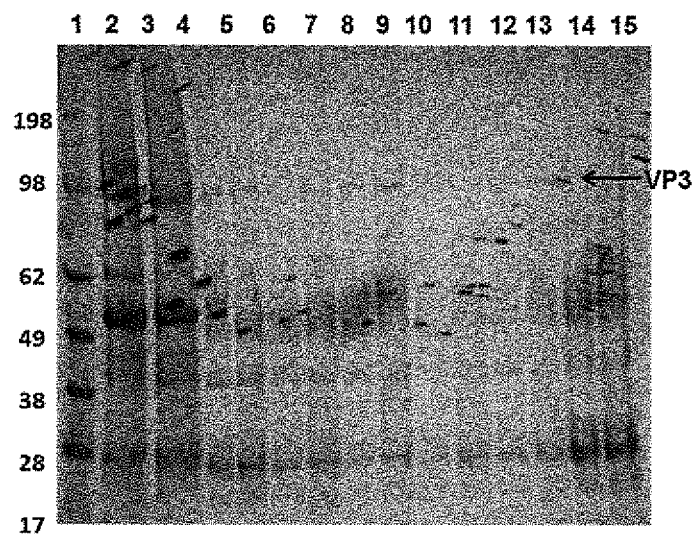
FIG. 12: SDS-PAGE 4-12% Bolt precast gels: lane 1, SeeBlue® Plus molecular marker; lanes 2-3, BTV-8 CLPs and VLPs respectively, positive controls; lanes 4-5, BTV-8 VLPs 45% and 40% sucrose gradient fractions; lanes 6-7, BTV-8 VLPs created with VP3 wt, 45% and 40%; lanes 8-9, BTV-3 single chimaeric, 45% and 40%; lanes 10-11, BTV-3 single chimaeric, BTV-8 VP3 wt core, 45% and 40%; lanes 12-13, BTV-3 double chimaeric, 45% and 40%; lanes 14-15, BTV-3 double chimaeric, BTV-8 VP3 wt core, 45% and 40%. VP3 is indicated by an arrow.

Genes encoding BTV-8 VP3 and BTV-8 VP7 forming CLPs combined with BTV-8 VP5 and BTV-3 VP2 (BTV-3 single chimaeric) or BTV-8 VP3, BTV-8 VP7 combined with BTV-3 VP2, BTV-3 VP5 (BTV-3 double chimaeric) for the outer capsids were combined as described and infiltrated into N. benthamiana leaves. Alternatively, BTV-8 VP3 cloned into pEAQ wild type (wt) was used instead of BTV-8 VP3 cloned into pEAQ-HT to form the core and in an attempt to improve the stoichiometry towards VLPs as described before (Theunemann et al., 2013). Although VP3 is dearly reduced when using BTV-8 VP3 wt in forming the cores (FIG. 12, lanes 6-7, 10-11 and 14-15), the VLP vs CLP stoichiometry did not improve in our hands.

VLPs were extracted in standard bicine buffer containing protease inhibitor (Sigma P2714-1BTL) and purified using a sucrose gradient (30-70%) and fractions (45-55%) were analyzed using Bolt gels. The presence of the core capsid proteins VP3 and VP7 as well as one of the outer capsid proteins VP5 were consistently detected at ~100 kDa, 38 kDa and 59 kDa, respectively and therefore not repeatedly subjected to mass spectrometry. The detection of VP2 with mass spectrometry and TEM analysis were considered sufficient to confirm the formation of VLPs for all future experiments.

Figure 13:
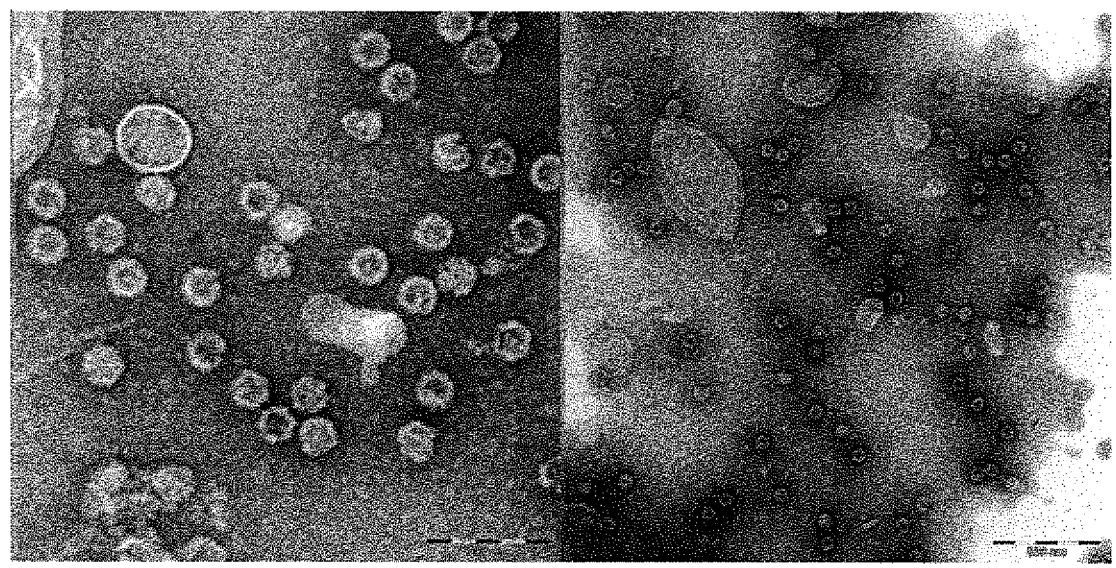
FIG. 13: Transmission electron microscope images of sucrose gradient purified BTV-8 CLPs showing the abundance of BTV-8 CLPs created in *N. benthamiana* dXT/FT to serve as core for BTV serotypes 3 and 4. Negative staining technique using sodium phosphotungstate onto copper grids and images were visualized with a JEM-2100 Transmission electron microscope (JEOL).
Figure 14:
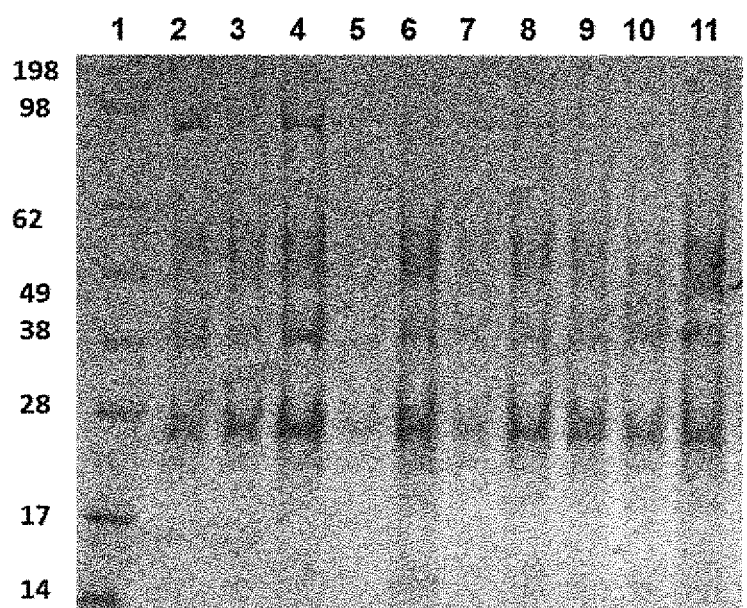
FIG. 14: SDS-PAGE 4-12% Bolt precast gels: lane 1, SeeBlue® Plus molecular marker; lanes 2 and 4, BTV-8 CLPs in *N. benthamiana* dXT/FT; lane 3, BTV-8 CLPs in *N. benthamiana*; lane 5, BTV-8 VLPs in *N. benthamiana* dXT/FT; lane 6, BTV-8 *N. benthamiana*; lane 7, chimaeric BTV-4 VLPs in *N. benthamiana* dXT/FT; lane 8, chimaeric BTV-4 VLPs in *N. benthamiana* (all BTV-4 capsids except BTV-8 VP3); lane 9 & 11, double chimaeric BTV-3 VLPs *N. benthamiana* dXT/FT in 45% and 40% respectively; lane 10, double chimaeric BTV-3 VLPs in *N. benthamiana*. Sucrose fraction 45% unless otherwise stated.

Creation of Chimaeric VLPs Comprising BTV-8 VP3 and BTV-4 VP2, VP5 and VP7 in Mammalian-Like Tobacco dXT/FT Genes encoding BTV-8 VP3 and BTV-8 VP7 were used to assemble and form CLPs in mutant N. benthamiana dXT/FT tobacco (FIG. 13). BTV-4 VP2, VP5 and VP7 were used in combination with BTV-8 VP3 to form VLPs i.e. only BTV-8 VP3 core capsid with all the remaining capsids from BTV-4 (VP2, VP5 and VP7). CLPs and VLPs were extracted in bicine buffer containing protease inhibitor (Sigma P2714-1BTL) and purified using a sucrose gradient (30-70%). Selected fractions were analyzed using Bolt gels as described (FIG. 14). The presence of BTV-4 VP2 was confirmed by mass spectrometry. Although the peptides detected were indicated as BTV-11, identical sequences appear in BTV-4 (FIG. 15).

Creation of Double Chimaeric BTV-3 VLPs

Figures 16, 17:
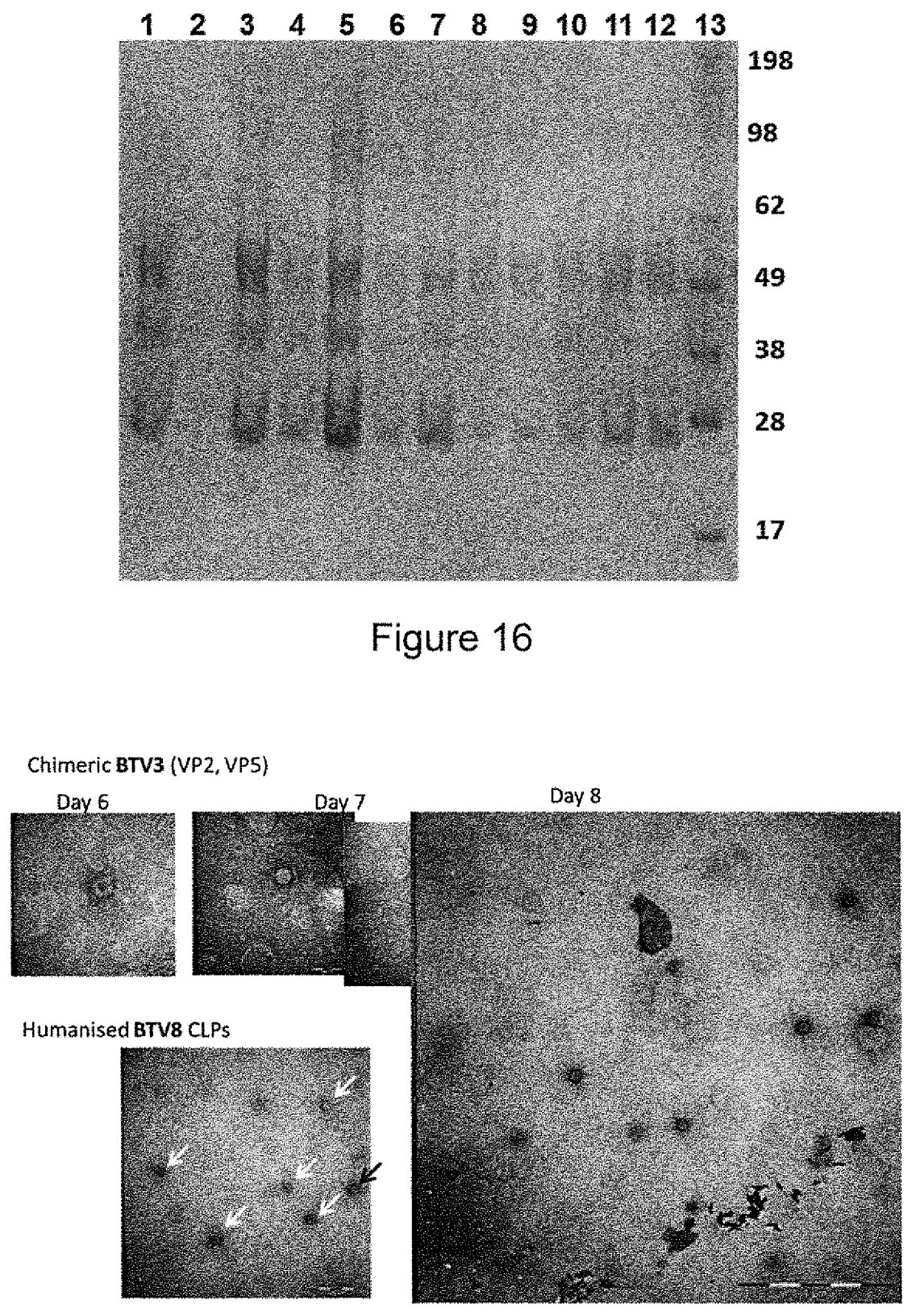

BTV-8 VP3 and VP7 inner capsid proteins were assembled with BTV-3 VP2 and VP5 outer capsid proteins. VLPs were extracted in bicine buffer containing protease inhibitor (Sigma P2714-1BTL) and purified using a sucrose gradient (30-70%) and fractions (45-40%) were analyzed using Bolt gels as described (FIG. 16). BTV-3 VP2 peptides were detected 6-8 days after infiltration of N. benthamiana and the mutant N. benthamiana dXT/FT. BTV-8 CLPs and BTV-3 VLPs were also visualized under the TEM (FIG. 17). As VLPs were detected more abundantly eight days after infiltration, the leaf material was harvested 8 days after infiltration and subjected to sucrose gradient purification for all future experiments.

Chimaeric BTV-4 and BTV-3 VLPs in Humanized Tobacco

Previously, BTV VLPs were assembled with BTV-8 VP3 and BTV-4 VP2, VP5 and VP7. In this experiment double chimaeric BTV VLPs were assembled with BTV-8 VP3 and VP7 cores and BTV-4 VP5 and VP2 outer capsids, alternatively double chimaeric BTV VLPs were assembled with BTV-8 VP3 and VP7 cores and BTV-3 VP5 and VP2 outer capsids. Double chimaerics with BTV-8 VP3 and VP7 forming the core and the outer capsid proteins being from a second serotype (3 or 4) seem to be more stable than single chimaeric BTV VLPs. The double chimaeric VLPs will be used for sheep trials. The BTV VLPs were extracted in bicine buffer supplemented with Roche EDTA-free protease inhibitor. Mass spectrometry confirmed the presence of BTV-3 VP2 and BTV-4 VP2. Although the peptides detected were indicated as BTV-10, the inventors point out that identical sequences appear in BTV-4 (FIG. 18).

Figure 19:
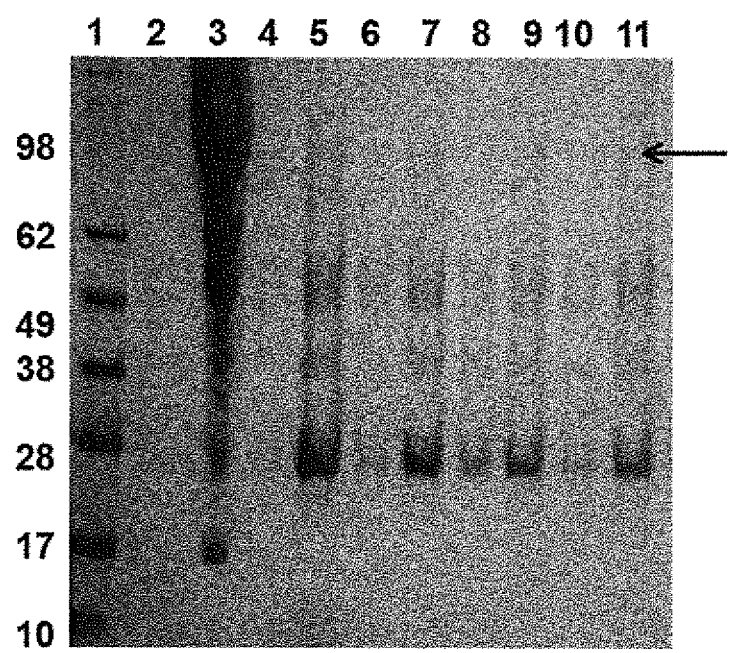
FIG. 19: Sucrose gradient purified BTV-4 VLP capsid proteins (BTV-8 VP3; BTV-4 VP2, VP5 and VP7) detected in fractions 50% (even numbers) and 45% (odd numbers) sucrose and separated by SDS-PAGE 4-12% Bolt precast gels. Proteins produced in *N. benthamiana* with VP3 indicated by the arrow. Lane 1, SeeBlue® Plus molecular marker; lanes 4-5, bicine buffer with Sigma protease inhibitor (PI); lanes 6-7, capsid proteins in bicine buffer with Roche EDTA-free protease inhibitor; lanes 8-9, capsids extracted in bicine buffer with 0.5 mM CaCl$_2$ and Sigma PI; lanes 10-11, capsids extracted in bicine buffer with 0.5 mM CaCl$_2$ and Roche PI.

Purifying Double Chimaeric BTV VLPs in Buffer Containing $CaCl_2$ and with Different Protease Inhibitors Two independent protease inhibitors and the addition or omission of $CaCl_2$ were compared to identify which method best preserved the formed VLPs during extraction. Chimaeric BTV VLPs were assembled with BTV-8 VP3 and VP7 cores and BTV-4 VP5 and VP2 outer capsids. The expression and assembly of capsid proteins was conducted in N. benthamiana dXT/FT. Selected sucrose gradient fractions were separated using the Bolt 4-12% SDS PAGE gels and fragments at ~100-120 kDa were subjected to mass spectrometry (FIG. 19). BTV-4 VP2 was detected when the BTV-4 VLPs were extracted in bicine buffer using either Sigma protease inhibitor or the Roche EDTA-free protease inhibitor. The VP2 peptides (five in total) detected with mass spectrometry, were identified as BTV-17 due to a difference of only two amino acids (FIG. 20). The addition of CaCl₂ did not enhance the amount of VLPs purified.

Example 4

Plant Expressed AHS Single, Double and Triple Chimaeric VLPs

Gene sequences, encoding the VP2, VP5, VP3 and VP7 proteins of AHSV serotype 1 (Genbank accession numbers AM883165, FJ183369, FJ183366, AM883171, respectively), the VP2 (Genbank accession number AY163330) and VP5 (Genbank accession number JQ742011) proteins of AHSV serotype 7, the VP5 protein of AHSV serotype 3 (Genbank accession number DQ868777 and the VP2 protein of AHSV serotype 6 (Genbank accession number DQ868774.1) were codon optimised for optimal expression in *Nicotiana benthamiana* plant cells and synthesized with unique AgeI and XhoI sites at the 5' and 3' termini, respectively.

The following plant codon optimised nucleotide sequences were synthesised by BioBasic Inc, Canada: AHSV-1 VP2 (SEQ ID NO:38), AHSV-1 VP3 (SEQ ID NO:35), AHSV-1 VP5 (SEQ ID NO:36), AHSV-1 VP7 (SEQ ID NO:37), AHSV-7 VP2 (SEQ ID NO:39), AHSV-7 VP5 (SEQ ID NO:40), AHSV-3 VP5 (SEQ ID NO:65) and AHSV-6 VP2 (SEQ ID NO:67). These plant codon optimised nucleotide sequences encode the following proteins: AHSV-1 VP2 (SEQ ID NO:18), AHSV-1 VP3 (SEQ ID NO:15), AHSV-1 VP5 (SEQ ID NO:16), AHSV-1 VP7 (SEQ ID NO:17), AHSV-7 VP2 (SEQ ID NO:19), AHSV-7 VP5 (SEQ ID NO:20), AHSV-3 VP5 (SEQ ID NO:66) and AHSV-6 VP2 (SEQ ID NO:68).

The VP2, VP5, VP3 and VP7 nucleotide sequences were subsequently cloned into the pEAQ expression vectors (Sainsbury et al., 2009, Plant Bioscience Limited, UK). More, specifically sequences encoding the AHSV-1 VP5, VP3 and VP7 proteins were firstly cloned into the intermediate pEAQ vectors FSC5 or FSC6 via directional AgeI/XhoI restriction enzyme-based cloning. The restriction enzymes in this study were supplied by ThermoScientific and the Fast-link DNA ligase enzyme by EpiCentre. Cloning of the AHSV-1 VP2-encoding sequence into the intermediate FSC5 vector was performed using the In-Fusion HD® cloning kit (Clontech) with the primers depicted in Table 3, according to the manufacturers instructions.

The VP5-encoding expression cassette was subsequently cloned from the recombinant FSC6-VP5 plasmid into the pEAQ express vector via directional AscI/SbfI restriction enzyme-based cloning. Cloning of the VP7-encoding expression cassette from FSC6-VP7 into the pEAQ express vector followed a similar process except that the recombinant plasmid was digested with both enzymes AscI and AlwI prior to digestion with SbfI to ensure different sizes of insert and vector backbone DNA fragments. Cloning of the VP2 and VP3 encoding sequences into the linearized pEAQ-HT vector required that the respective FSC5-VP2 and FSC-5-VP3 recombinant plasmids be digested with the AgeI and XhoI prior to ligation. The AHSV-7 VP2 and AHSV-7 VP5 encoding sequences were cloned individually into the pEAQ-HT vector via directional AgeI/XhoI restriction enzyme-based cloning. Cloning of the sequences encoding the AHSV-3 VP5 and AHSV-6 VP2 proteins individually into the pEAQ-HT vector was performed using the In-Fusion HD@ cloning kit (Clontech) with the primers depicted in Table 3, according to the manufacturers instructions.

Figure 22:
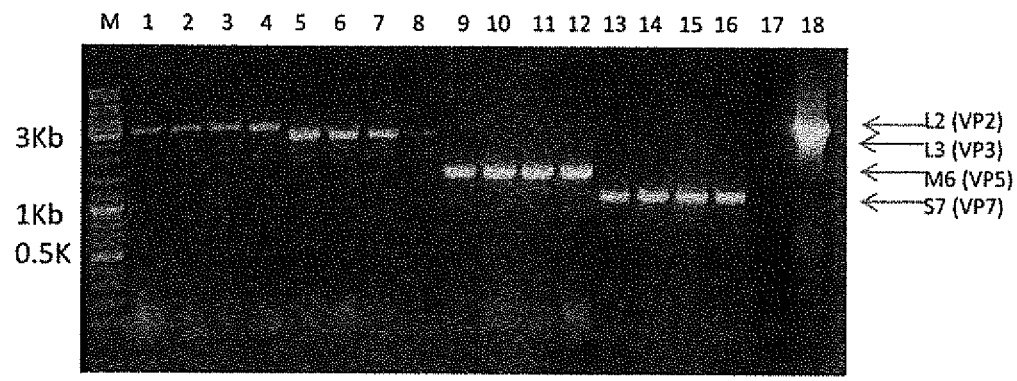
FIG. 22: Agarose gel electrophoresis of the AHSV-1 L2, L3, M6 and S7 gene-specific PCR products. The molecular weight marker (M) was the GeneRuler DNA ladder (Thermo Scientific) with the relevant sizes indicated. The arrows indicate the presence of the L2 (3.2 Kb), L3 (2.7 Kb), M6 (1.5 Kb) and S7 (1.1 Kb) PCR products in lanes 1-4, 5-8, 9-12 and 13-16, respectively.

In order to generate the dual recombinant plasmid pEAQ-express-AHSV-1VP3-AHSV1-VP7, the AHSV-1 VP7 encoding sequence was firstly cloned from pEAQ-express-AHSV-1VP7 plasmid into the pEAQ-HT vector via directional AgeI/XhoI restriction enzyme-based cloning. The VP7-encoding expression cassette was subsequently excised from pEAQ-HT-AHSV-1VP7 using the AscI/PacI enzymes and cloned into the compatible MluI/AsiSI sites of the pEAQ-express vector. The VP3-encoding expression cassette was transferred from the pEAQ-HT-AHSV1VP3 plasmid into the newly generated pEAQ-express-AHSV1VP7 plasmid via AscI/PacI mediated restriction enzyme based cloning. Following transformation into electrocompetent DH10B bacterial cells, the presence of recombinant plasmid in candidate bacterial clones was verified via colony PCR with the primers depicted in Table 4. The presence of the AHSV-1 L2 (VP2), L3 (VP3), M6 (VP5) and S7 (VP7) PCR products can be visualised in FIG. 22 following agarose gel electrophoresis.

TABLE 3

In-Fusion AHSV specific primers.

| Primer Name | Sequence | SEQ ID NO. |
|---|---|---|
| In-Fusion AHSVP2-F | 5' CAAATTCGCGACCGGTCCATGGCTAGTGAATTC 3' | (SEQ ID NO: 51) |
| In-Fusion AHSVP2-R | 5' AGTTAAAGGCCTCGAGTTATTCTATCTTTGAAAGC 3' | (SEQ ID NO: 52) |
| In-Fusion HS5VP2-F | 5' CAAATTCGCGACCGGTCCATGGTTCAGAATTCGGTG 3' | (SEQ ID NO: 69) |
| In-Fusion HS5VP2-R | 5' AGTTAAAGGCCTCGAGTCATTTCTCGGTTTTGGCC 3' | (SEQ ID NO: 70) |
| In-Fusion HS6VP2-F | 5' CAAATTCGCGACCGGTCCATGGCTTCTGAATTCGGT 3' | (SEQ ID NO: 71) |
| In-Fusion HS6VP2-R | 5' AGTTAAAGGCCTCGAGTCACTCGGCTTTGGCCAT 3' | (SEQ ID NO: 72) |

TABLE 4

Primers used for colony PCR.

| Protein | Primer Name | Sequence | SEQ ID NO. |
|---|---|---|---|
| AHSV-1 VP2 | QAHSVP2-F | 5' CGTACCGGTCCATGGCTAGTGAATTCGGT 3' | (SEQ ID NO: 53) |
| | QAHSVP2-R | 5' GCAGCTCGAGTTATTCTATCTTTGAAAGC 3' | (SEQ ID NO: 54) |
| AHSV-1 VP3 | QAHSVP3-F | 5' GGTACCGGTATGCAAGGTAACGAACGT 3' | (SEQ ID NO: 55) |
| | QAHSVP3-R | 5' CAGCTCGAGTTAAATTGTTGGCCTTGC 3' | (SEQ ID NO: 56) |
| AHSV-1 VP5 | QAHSVP5-F | 5' CGTACCGGTCCATGGGAAAATTTACTTC 3' | (SEQ ID NO: 57) |
| | QAHSVP5-R | 5' CAGCTCGAGTTAGCTAATCTTCACGCC 3' | (SEQ ID NO: 58) |
| AHSV-1 VP7 | QAHSVP7-F | 5' GCTACCGGTCCATGGATGCAATAGCAGC 3' | (SEQ ID NO: 59) |
| | QAHSVP7-R | 5' CAGCTCGAGTTAATGATAAGCTGCAAG 3' | (SEQ ID NO: 60) |
| AHSV-7 VP2 | AHSV7VP2F | 5' CCATGGCATCAGAGTTTGGTATC 3' | (SEQ ID NO: 61) |
| | AHSV7VP2R | 5' CCTCATTCTGCCTTTGATAACAGC 3' | (SEQ ID NO: 62) |
| AHSV-7 VP5 | AHSV7VP5-F | 5' ACCGGTATGGGAAAGTTC 3' | (SEQ ID NO: 63) |
| | AHSV7VP5-R | 5' CTCGAGGGCAATACGAAC 3' | (SEQ ID NO: 64) |
| AHSV-5 VP2 | FSC5F | 5' GGTTTTCGAACTTGGAGAAA 3' | (SEQ ID NO: 73) |
| | FSC5R | 5' AGAAAACCGCTCACCAAACATAGA 3' | (SEQ ID NO: 74) |
| AHSV-6 VP2 | FSC5F | 5' GGTTTTCGAACTTGGAGAAA 3' | (SEQ ID NO: 75) |
| | FSC5R | 5' AGAAAACCGCTCACCAAACATAGA 3' | (SEQ ID NO: 76) |

Figure 21:
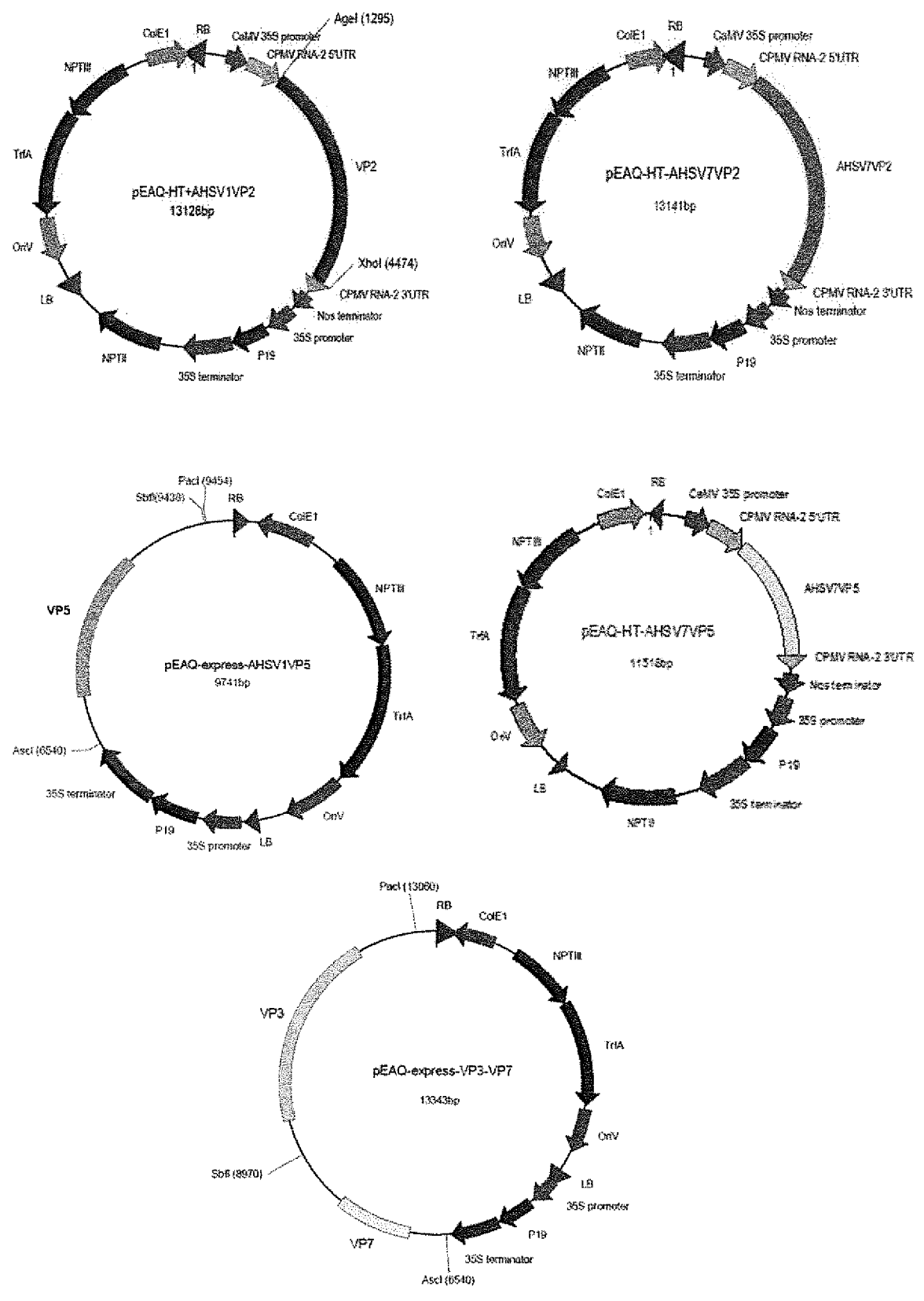

The PCR reactions contained a final concentration of 0.3 µM forward/reverse primer and the KAPA 2G Fast DNA polymerase enzyme (KAPA Biosystems) and were set up according to the manufacturer's instructions. The cycling conditions were as follows: 1 cycle of 95'C for 2 min, followed by 25 cycles of 95'C for 20 sec, 59° C. (47° C. for AHSV-7 VP2 and AHSV-7 VP5) for 15 sec and 72° C. for 3 min 30 sec followed by 1 cycle of 72° C. for 7 min. The capsid protein encoding sequences were verified via dideoxy Sanger DNA sequencing (Inqaba Biotechnical Industries (Pty) Ltd). Some of the recombinant plasmids constructed are depicted in FIG. 21.

Transient expression of the AHSV capsid proteins was accomplished via *Agrobacterium*-mediated infiltration of *Nicotiana benthamiana* or *Nicotiana benthamiana* dXT-FT plant leaves with the recombinant pEAQ expression plasmids. One hundred nanograms of the recombinant pEAQ plasmid was transformed into 60 µl electrocompetent LBA4404 *Agrobacterium* cells (1.44 kV, 200Ω and 25 µF) using a Gene Pulsar™ (Bio-Rad). The transformed bacterial cells were resuspended in 500 µl SOC medium and placed on a rotational shaker (175 rpm) at 30° C. for 3 hours to recover prior to 250 µl being plated out onto two selective medium plates (50 µg/ml Kanamycin, 50 µg/ml Rifampicin and 50 µg/ml Streptomycin). The plates were inverted and incubated at 28° C. for 96 hours. All reagents were molecular biology grade and obtained from Sigma Life Science unless otherwise indicated. Recombinant LBA4404 bacterial clones, verified via colony PCR, were inoculated into 5 ml YMB medium (0.1% yeast extract, 1% Mannitol, 1.7 mM NaCl, 0.8 mM $MgSO_4.H_2O$, 2.2 mM $K_2HPO_4$), with the appropriate antibiotics (50 µg/ml Kanamycin, 50 µg/ml Rifampicin and 50 µg/ml Streptomycin), and incubated with rotational shaking (175 rpm) for 24 hours at 28° C. Cryopreserved LBA4404 *Agrobacterium* cells, containing the pEAQ-HT vector or the pEAQ-HT-GFP plasmid, were also inoculated into 5 ml YMB media to serve as negative and positive controls, respectively. The Agrobacteria starter cultures were subsequently used to inoculate 50 ml YMB media with the appropriate antibiotics and these cultures were incubated overnight at 28° C. with rotational shaking (175 rpm). The bacterial cells were harvested from the overnight cultures via centrifugation at 8000 rpm for 7 min at 20° C. The cell pellets were each resuspended in 40 ml freshly prepared MMA infiltration buffer (10 mM MES hydrate; pH 5.6, 10 mM $MgCl_2$, 100 µM 3,5-dimethoxy-4-hydroxyacetophenone). In order to assess the assembly of CLPs, *N. benthamiana* leaves were agroinfiltrated with the VP7 and VP3-encoding genes, whilst agroinfiltration with all four capsid protein encoding sequences enabled assessment of VLP assembly. The agrobacterial suspensions were combined in a 1:1:1 ratio (for VLPs) and 1:1 (for CLPs) and subsequently diluted with the MMA buffer such that the final $OD_{600}$ was 0.45-0.5. The leaves of four week old *N. benthamiana* plants were syringe-infiltrated with these Agrobacteria combinations or the pEAQ-HT/pEAQ-HT-GFP Agrobacteria suspension. The plants were incubated at 27° C. for 8 days post-infiltration (dpi).

Figure 23:
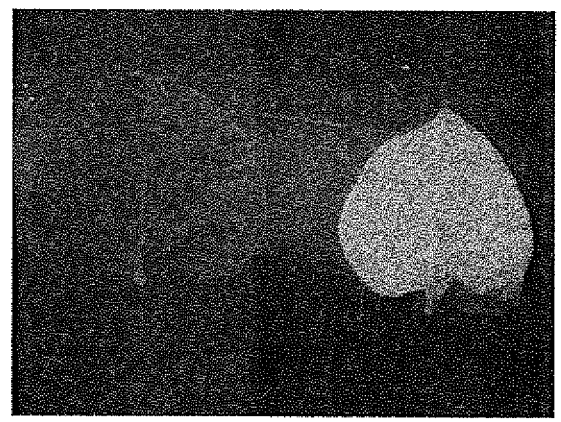
FIG. 23: Photographic record of N. benthamiana leaves agroinfiltrated with LBA4404-pEAQ-HT (left) and LBA4404-pEAQ-HT-gfp (right) and visualised under UV illumination 8 days post-infiltration.

Preliminary evidence of foreign protein expression was obtained by illuminating the pEAQ-HT-gfp-infiltrated leaf with UV light 8 dpi (FIG. 23). The visualization of fluorescing fluorescent green fluorescent protein (gfp) protein within the infiltrated leaf indicated that the infiltration procedure had been successful and it was thus likely that the AHSV capsid proteins had also been expressed in their respective infiltrated *N. benthamiana* leaves.

*Agrobacterium* infiltrated *N. benthamiana* leaves were photographed and harvested 8 days post-infiltration. The leaf tissue was extracted immediately in 3 volumes of VLP extraction buffer (20 mM sodium chloride (NaCl), 50 mM Bicine, pH 8.4, 0.1% (w/v) sodium lauroyl sarcosine (NLS), 1 mM dithiothreitol (DTT) (ThermoScientific), 0.2% protease inhibitor cocktail P2714 (Sigma Life Science)/cOmplete EDTA-free protease inhibitor cocktail (Sigma-Aldrich) or CLP extraction buffer (as VLP extraction buffer but containing 140 mM NaCl) in a multipurpose juice extractor (MATSONE). The DTT and protease inhibitor cocktails were freshly prepared according to the manufacturers' instructions and added to the extraction buffer just prior to use. Large cell debris was removed by filtering the cell lysate through two layers of miracloth and the extract further clarified via centrifugation (4200×g; 30 min; 10° C.).

Virus-like particles (VLPs) or Core-like particles (CLPs) were purified using sucrose density gradient centrifugation. Sucrose solutions (30%-70%) were prepared by dissolving ultra-high quality sucrose (Sigma Life Science) in VLP dilution buffer (20 mM NaCl, 50 mM bicine, pH 8.4) or CLP dilution buffer (140 mM NaCl, 50 mM Bicine, pH 8.4) and layered into gradients of 1 ml 10% incrementing steps. The clarified cell lysates were layered on top of the sucrose gradients and centrifuged in a SW-41Ti rotor (Beckman Coulter) at 85,800×g for 3 hours; 10° C. The 55%-35% sucrose layers were harvested in 500 μl fractions using a Minipuls2 peristaltic pump (Gilson). Ten microlitres of each fraction was subsequently analysed for protein content by denaturing SDS-PAGE and immunoblotting procedures.

Ten microliter of each sucrose fraction was mixed with an equal volume of 2× Laemmli protein sample buffer (4% SDS, 20% glycerol, 10% 2-mercaptoethanol, 0.004% bromophenol blue and 0.125 M Tris HCl, pH approx. 6.8), the protein samples denatured at 95° C. for 5 min and analysed on denaturing SDS 10% polyacrylamide gels (BioRad TGX Stain Free™ Fast Cast™), prepared according to the manufacturer's instructions. The Precision Plus Protein™ WesternC™ standard (Bio-Rad) was used as a size marker. Electrophoresis was performed in 1×TGS buffer (25 mM Tris-HCl; pH 8.3, 200 mM glycine, 0.1% SDS) using the Mini-PROTEAN® Tetra system (Bio-Rad) by applying a current of 50 V for 20 min and thereafter a current of 130 V for approximately 1.5 hours. The polyacrylamide gels were then subjected to an immunoblot protocol with an AHSV-7 specific polyclonal antiserum to confirm the identity and position of the AHSV capsid proteins on the gels.

The protein samples were immunoblotted onto a PVDF membrane within the Trans-Blot® Turbo™ Transfer Pack (Bio-Rad) using the Trans-Blot®Turbo™ Transfer system (Bio-Rad) mixed MW application (1.3 A; 25 V; 7 min). The membrane was incubated in 3% blocking solution (3% bovine serum albumin (Roche) in 1× Tris buffered saline (150 mM NaCl, 20 mM Tris pH 7.5; 0.1% Tween®-20 (Merck)) at room temperature with gentle agitation for 3 hours. Prior to incubation with the membrane, the primary antibody, an anti-AHSV-7 guinea pig polyclonal antiserum (GPαAHSV-7), was pre-treated with N. benthamiana plant extract in order to remove plant protein-specific antibodies from the serum. This was done by crushing a single uninfiltrated N. benthamiana leaf in a mortar and pestle with 1×TBS buffer in a ratio of 1:3, adding the primary antibody to this leaf extract and incubating this mixture at 37° C. for 1 hour with slight agitation. This plant extract/primary antibody mixture was then added to 3% blocking solution (1:300 dilution) and incubated overnight at 4° C. with gentle agitation to allow binding of the antibodies to immobilised protein.

The membrane was subsequently washed five times with wash buffer (0.1% Tween® 20 (Merck) in 1×TBS), 5 min for each wash. A secondary antibody, a combination of the horseradish peroxidase-conjugated Rabbit anti-Guinea Pig IgG H&L (HRP) conjugate (abcam ab6771) (1:5000 dilution) and Precision Protein™ StrepTactin-HRP Conjugate (Bio-Rad) (1:10000 dilution) was then added. After incubation at room temperature for 1 hour with gentle agitation, the membrane was washed five times in wash buffer (0.1% Tween® 20 (Merck) in 1×TBS), 5 min each wash. The membrane was then subjected to the detection procedure by adding the Clarity Western ECL chemiluminescent substrate (Bio-Rad), according to the manufacturer's instruction, and placing the membrane immediately into the ChemiDoc™ MP Imager (Bio-Rad). By using the Chemi Hi Resolution application, photographs of the chemiluminescence signals were taken approximately every second with the accumulating exposure starting at 1 second and ending at 15 seconds.

Sucrose fractions containing putative AHSV capsid proteins were electrophorized on precast denaturing 4-12% Bolt™ Bis-Tris Plus polyacrylamide Gels (Thermo Fischer Scientific), according to the manufacturers' instructions. SeeBlue® Plus2 Prestained Protein Standard (Invitrogen) was used as the size marker. Electrophoresis was performed in the Bolt® MES or MOPS SDS running buffer using the mini gel tank (Thermo Fischer Scientific) by applying a current of 200 V for approximately 35 min. The gels were then stained in Coomassie Brilliant Blue G250 staining solution (50% methanol (Minema), 10% acetic acid (Minema), 0.1% Coomassie Brilliant Blue G250 (Merck)) for 20 min and destained in destaining solution (10% methanol, 10% acetic acid) overnight. Candidate protein bands of approximately the correct size were excised from the gel and sent for Mass spectrometry (MS) analysis (Dr Stoyan Stoychev, CSIR Biosciences).

Figures 24, 25:
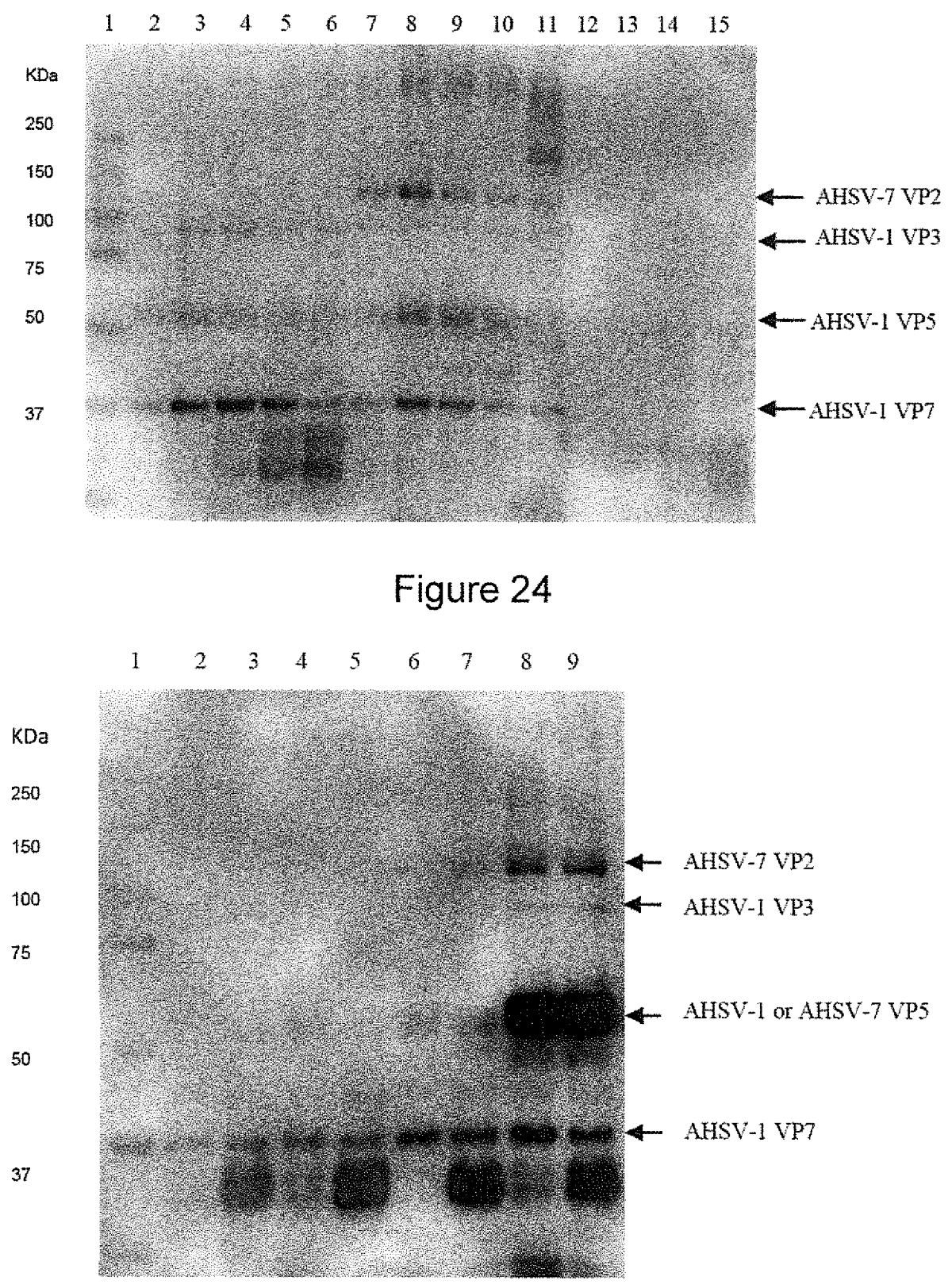

Expression of the AHSV-1 VP3, VP7, VP5 and AHSV-7 VP2 capsid proteins in the Nicotiana benthamiana leaves, harvested at 8 dpi, was confirmed via sucrose density centrifugation and immunoblot analysis with guinea pig αAHSV-7 serum (FIG. 24, lanes 7-11). Not only were these capsid proteins expressed, they were also assembling into particles, likely to be chimaeric AHSV-1/AHSV-7 VLPs, within the 55-35% sucrose fractions. The presence of the AHSV-1 VP3, VP7, VP5 capsid proteins was also confirmed in the 55-35% sucrose fractions (FIG. 24, lanes 2-6) indicating particle self-assembly. Although the AHSV-1 neutralization-specific VP2 antigen could not be detected with the AHSV-7-specific antiserum, its presence cannot be ruled out. The identity of the AHSV-1 VP3, AHSV-1 VP7, AHSV-1 VP5, AHSV-7 VP5 proteins was confirmed Mass Spectrometry (MS) analysis (Dr Stoyan Stoychev, CSIR Biosciences). The identity of the AHSV-1 VP2 and AHSV-7 VP2 proteins has not yet been confirmed via MS analysis.

It was hypothesized that a double chimaeric VLP particle, where the VP2 and VP5 outer capsid proteins originate from one serotype and the core proteins VP7 and VP3 from another serotype of AHSV, may be more stable than the single chimaeric VLP where only the outer capsid protein VP2 is exchanged. N. benthamiana leaves were hence infiltrated with combinations of recombinant Agrobacterium tumefaciens bacteria containing the AHSV-1 VP3, AHSV-1 VP7, AHSV-1 VP5 or AHSV-7 VP5 and AHSV-7 VP2 constructs and harvested 8 dpi. Sucrose gradient centrifugation of the leaf extracts and immunoblotting of the resulting sucrose fractions with guinea pig αAHSV-7 serum indicated a greater quantity of the AHSV-7 VP2 and VP5 proteins in fractions 55-50% (FIG. 25, lanes 8-9) than the AHSV-7 VP2 and AHSV-1 VP5 proteins in the same fractions of their respective sucrose gradient (FIG. 25, lanes 6-7). The quantity of the AHSV-1 VP7 and VP3 remained relatively constant in these fractions from the different sucrose gradients. This may be indicative of a larger quantity of VP2 and VP5 proteins on their outer shells of the putative double chimaeric VLPs (FIG. 25, lanes 8-9) when compared to the putative single chimaeric VLPs (FIG. 25, lanes 6-7). Presenting both outer capsid proteins from serotype 7 on a scaffold of AHSV-1 core proteins may thus help to further stabilise the proposed chimaeric AHSV-1/AHSV-7 VLP particle. In order to facilitate the assembly of chimaeric AHSV-1 based VLPs presenting the outer capsid proteins of the remaining AHSV serotypes, a double recombinant pEAQ-express-AHSV-1VP7-AHSV-1VP3 expression vector was constructed.

In order to investigate whether it may be possible to assemble a triple chimaeric AHSV VLP particle in plants, where the origin of the capsid proteins is from three different AHSV serotypes, constructs encoding the AHSV-1 VP7/AHSV-1 VP3, AHSV-3 VP5 and AHSV-6 VP2 proteins were infiltrated into Nicotiana benthamiana dXT-FT plant leaves. The leaves were harvested 8 days post-infiltration and the cell extracts centrifuged through 70-30% sucrose gradient. Sucrose fractions were electrophorized on precast denaturing 4-12% Bolt™ Bis-Tris Plus polyacrylamide Gels (Thermo Fischer Scientific), as described above, and candidate protein bands excised from the gel and sent for Mass spectrometry (MS) analysis (Table 5). The large number of AHSV-6 VP2-specific peptides confirm the assembly of the triple chimaeric AHSV-1/AHSV-3/AHSV-6 VLPs in N. benthamiana dXT-FT plant cells.

TABLE 5

Mass Spectrometry (MS) results of triple chimaeric AHSV-1/AHSV-3/AHSV-6 combination in plants

| Protein Band | % Cov (95) | Name | Peptides (95%) |
|---|---|---|---|
| 1 | 18.95 | AHSV-6 VP2 plant codon optimised | 18 |
| 2 | 32.86 | AHSV-6 VP2 plant codon optimised | 35 |

VLPs and/or CLPs were visualised by adsorbing samples from 55% sucrose fractions onto carbon-coated holey copper grids as follows: The grids were floated on the protein sample for 30 seconds, the excess sample drained off the grid via blotting on filter paper and the grid then floated on 2% sodium phosphotungstate, pH 7 for 30 sec. The excess stain was drained off by blotting the grid onto filter paper. The grid was air dried and subsequently imaged in a JEM-2100 Transmission electron microscope (JEOL). The diameters of the particles visualised on the grid were measured using the measure tool on the Gatan Digital Micrograph software. Thirty five particles of each type were measured and the mean diameter calculated.

Figure 26:
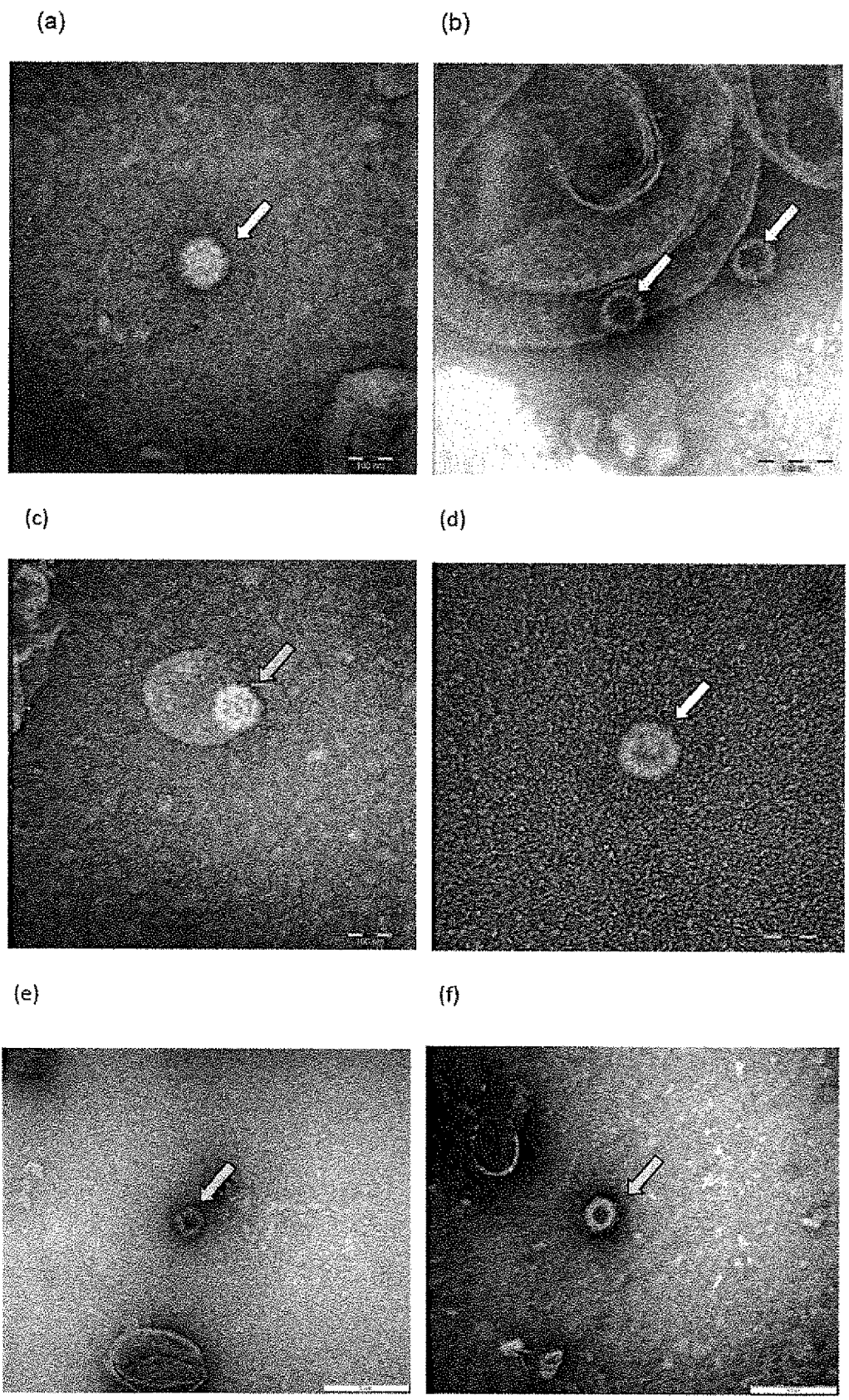
FIG. 26: Immunoblot detection of AHSV-1 and/or AHSV-7 capsid proteins following sucrose density gradient centrifugation. Nicotiana benthamiana leaves, agroinfiltrated with pEAQ-express-AHSV1VP3-AHSV-1VP7 or a combination of pEAQ-HT-AHSV-1VP2, pEAQ-express-AHSV-1 VP5, pEAQ-expressAHSV1 VP3-AHSV-1VP7 (1:1:1), or a combination of pEAQ-HT-AHSV-7VP2, pEAQ-express-AHSV-1VP5, pEAQ-express-AHSV1VP3-AHSV-1VP7 (1:1:1) or a combination of pEAQ-HT-AHSV-7VP2, pEAQ-HT-AHSV-7VP5, pEAQ-express-AHSV1VP3-AHSV-1VP7 (1:1:1) were harvested 8 days p.i and the clarified cellular lysates centrifuged through 70%-30% sucrose density gradients. The gradients were fractionated from the 55% sucrose layer to the 35% sucrose layer and ⅟₅₀ of the 55-50% sucrose fractions assessed for the presence of AHSV-1/AHSV-7 capsid proteins via SDS-PAGE and immunoblotting with a guinea pig anti-AHSV-7 antiserum. Lane 1 contains the Precision Plus Protein™ Western C™ standard (Bio-Rad) and the relevant sizes are indicated. Lanes 2-3 contain the 55%, 50% sucrose fractions, respectively, from the AHSV-1 CLP sucrose gradient. Lanes 4-5 contain the sucrose fractions, respectively, from the AHSV-1 VLP sucrose gradient Lanes 6-7 contain the 55%, 50% sucrose fractions, respectively, from the single chimaeric AHSV-1/AHSV-7 VLP sucrose gradient. Lanes 8-9 contain the 55%, 50% sucrose fractions, respectively, from the double chimaeric AHSV-1/AHSV-7 VLP sucrose gradient. Arrows indicate the position of the AHSV-7 VP2 (123.6 kDa), AHSV-1 VP3 (103.2 kDa), AHSV-1 or AHSV-7 VP5 (56.6 kDa) and AHSV-1 VP7 (37.8 kDa) proteins on the immunoblot membrane.

Transmission electron microscope (TEM) viewing of the particles present in the 55% sucrose gradient fractions of the gradients depicted above, as well as a gradient of the AHSV-1VP7-AHSV-1VP3 plant cell lysate, indicated the presence of core-like particles (CLPs) and virus-like particles (VLPs) (FIG. 26). The transiently expressed AHSV-1 VP2, VP5, VP3 and VP7 capsid proteins self-assembled into VLPs in N. benthamiana plant cells (FIG. 26(a)). These AHSV-1 VLPs were approximately 70 nm in diameter and appeared more fuzzy and dense than the 'spiky' 60 nm AHSV-1 core like particles (CLPs), consisting only of the VP7 and VP3 core proteins (FIG. 26(b)). The AHSV-1 VP3, VP7, AHSV-1 or AHSV-7 VP5 and AHSV-7 VP2 proteins also self-assembled into either single or double chimaeric AHSV-1/AHSV-7 VLPs (FIG. 3, (c) and (d), respectively), which were also approximately 70 nm in diameter. The triple chimaeric AHSV-1/AHSV-3/AHSV-6 VLPs can be visualised in FIG. 26 (e)-(f). They were also approximately 70-75 nm in size. The diameters of AHSV virion particles have previously been described as approximately 70 nm in diameter (Coetzer & Guthrie, 2004).

In the present Example the inventors have successfully produced the first documented African horse sickness virus-like particles in Nicotiana benthamiana or Nicotiana benthamiana dXT-FT plants. These VLPs, based on AHSV-1, will be used as a component of a multivalent vaccine against the nine African horse sickness serotypes. In addition, the inventors have also succeeded in generating single and double chimaeric AHSV-1/AHSV-7 VLPs, as well as triple chimaeric AHSV-1/AHSV-3/AHSV-6 VLPs in plants. In this case, particles, formed from the AHSV-1 VP3 and VP7 capsid proteins, function as a scaffold for the presentation of the entire VP2 and/or VP5 antigen of other AHSV serotypes to the immune system. An alternative scaffold, created from the capsid proteins of any one or more of the remaining eight AHSV serotypes, is not excluded. The AHSV VLP-based presentation system is in the process of being developed by the inventors for the presentation of all nine AHSV neutralization VP2 antigens to serve as an efficacious, multivalent vaccine against African horsesickness. An initial target animal trial, described in Example 8, has been conducted and preliminary data indicate that plant-expressed, double chimaeric AHSV-1/AHSV-7 VLPs are immunogenic in horses. A second target animal immunogenicity trial with a triple chimaeric AHSV-1/AHSV-3/AHSV-6 VLP particle is currently underway to confirm these results.

Example 5

Plant codon optimised nucleotide sequences were synthesised by Bio Basic Int. Both the nucleotide sequences and the proteins that they encode are described in Example 3. Using the protocols described herein the nucleotide sequences were cloned into the pEAQ-HT expression vectors. In this experiment Agrobacterium harbouring the pEAQ-HT with inserts were taken from a seed cell bank. The aim of this experiment was to compare the stable assembly of double and single chimaeric VLPs of serotypes BTV-4 and BTV-3 using BTV-8 core proteins; and also the most appropriate combinations to result in stable chimaeric VLPs.

Transient expression efficiency of the pEAQ series of vectors was investigated by agroinfiltration of Nicotiana benthamiana which facilitates mammalian-like or human-like glycosylation RNAi mutant dXT/FT. The pEAQ-HT constructs containing genes encoding individual capsid proteins of BTV serotypes 3, 4 and 8 were stored as seed cell banks. Prior to plant infiltration Agrobacterium tumefaciens strain (LBA4404) transformed with pEAQ-HT vector containing individual VP2, VP3, VP5 and VP7 of selected serotypes were streaked on YMB agar plates and incubated at 28° C. for 48 hrs. The growing bacterium was scraped off from the plate and inoculated into YMB broth with the relevant antibiotics and grown overnight. Cells were pelleted and resuspended in MMA buffer (100 mM MES, 10 mM MgCl$_2$ and 100 mM acetosyringone; pH 5.6). Each of the four Agrobacterium cultures was adjusted to OD$_{600}$ of approximately 0.5 with the same buffer. The formation of VLPs was validated by mixing and infiltrating the four constructs encoding the four individual capsid proteins at a ratio of 1:1:1:1 and used for plant infiltrations (5 plants per construct combination; 15-20 cm in height).

The leaf material was harvested eight days after infiltration using a Matstone Multipurpose juice extractor in VLP extraction buffer (50 mM bicine, pH 8.4; 20 mM sodium chloride [NaCl], 0.1% (w/v) N-lauroylsarcosine (NLS) sodium salt; 1 mM dithiothreitol (DTT)) in a ratio 1:3 with complete protease inhibitor cocktail (P2714, Sigma Life Sciences) added to the VLP extraction buffer immediately before the extraction started. Crude extracts were centrifuged twice for 10 minutes at 4,200×g, 10° C. to remove cell debris in a JA14 rotor using a Beckman Coulter Avanti J-26 XPI centrifuge.

Figure 27:
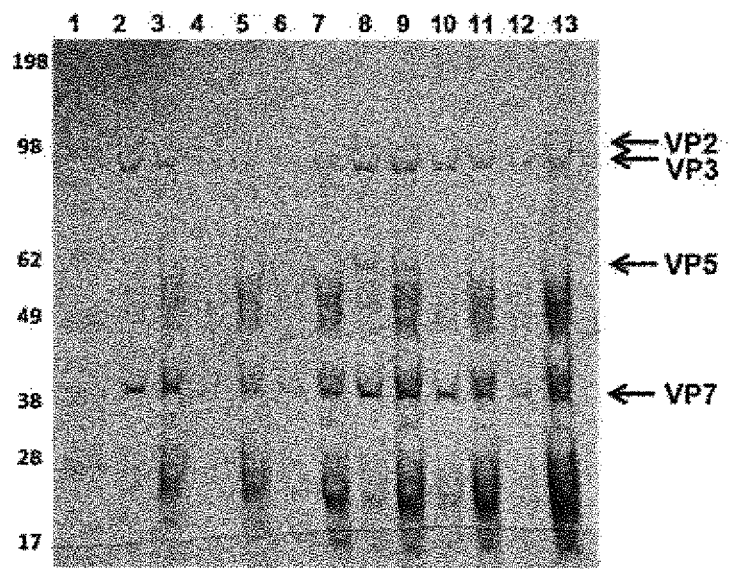
FIG. 27: Plant produced BT VLPs detected in sucrose density gradient fractions 45-50% and separated by SDS-PAGE 4-12% Bolt precast gels. Capsid proteins are indicated with arrows and annotated. Lane 1, SeeBlue® Plus molecular marker; lanes 5 & 12, homogenous BTV-8 VLPs; lanes 2-4, 6, 7; BTV-3 double chimaeric; lane 7, BTV-3 single chimaeric; and lane 8 and 13, BTV-4 (only VP3 being BTV-8); lane 9, BTV-4 double chimaeric (BTV-4 VP2 and VP5, BTV-8 core); lane 10, BTV-4 single chimaeric (BTV-8 substituting only BTV-4 VP2).

Particles were purified by density gradient centrifugation using ultra-high quality sucrose (Sigma Life Sciences) step gradients (30%-70%) prepared dissolved in VLP dilution buffer (50 mM Bicine, pH 8.4, 20 mM NaCl). Step gradients of 1 ml with 10% incrementing steps were prepared and then overlaid with 8 ml of clarified leaf extract. The gradients were centrifuged at 85,800×g, at 10° C. for 3 hours in a SW-41Ti rotor (Beckman Coulter). Sucrose gradient fractions (45%-50%) were collected and aliquots (26 µl) were analysed on a 4-12% Bis-Tris Bolt™ (Life Technologies) protein gel. Distinct protein bands were identified on Coomassie stained gels. The protein bands at 111 kDa, 100 kDa, 59 kDa and 38 kDa were confirmed to be the capsid proteins VP2, VP3, VP5 and VP7, respectively, by mass spectrophotometry. The assembly of VLPs (~70 nm) was confirmed by transmission electron microscopy (TEM) for all three serotypes 3, 4 and 8 (FIG. 27).

Figure 28:
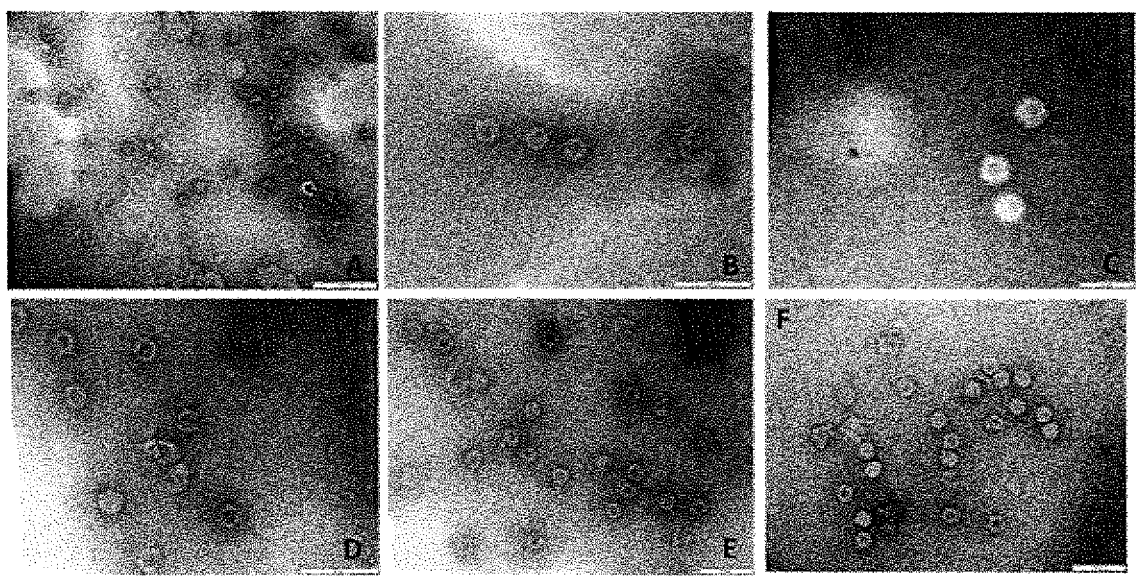
FIG. 28: TEM analysis showing assembly of structural proteins into mixture of CLPs and VLPs. (A) BTV-8; (B) BTV-4 single chimaeric (substituting only with BTV-8 VP3); (C) BTV-4 double chimaeric (BTV-4 VP2 and VP5); (D) and E BTV-3 double chimaeric (BTV-3 VP2 and VP5) and (F) BTV-3 single chimaeric (BTV-8 core with BTV-3 VP2). Scale bars, 200 nm.

The sucrose gradient fractions were adsorbed onto holey carbon-coated copper grids as follows. The grids were floated on the 1/10 dilution protein sample for 30 seconds and excess sample drained off the grid via blotting on filter paper. Subsequently the grid was floated on 2% sodium phosphotungstate, pH 7.0 for 30 seconds (0.22 µm filter sterilized before staining) and drained as described above (FIG. 28).

Protein bands of interest were in-gel trypsin digested as per the protocol described in Example 3. Protein pilot v5 using Paragon search engine (AB Sciex) was used for comparison of the obtained MS/MS spectra with Uniprot Swissprot protein database. Proteins with threshold above ≥99.9% confidence were reported (Table 6).

Similarly, almost three times more VP2 peptides were detected when the VLPs of BTV-4 was assembled via double chimaeric versus single chimaeric combinations, 48 versus 18 peptides, respectively. For both scenarios above, single chimaeric indicates that BTV-8 core (VP3, VP7 and VP5) was combined with VP2 from a second serotype. When BTV-8 VP3 was combined with the remaining capsid proteins VP2, VP7 and VP5 of serotype 4, 42 peptides were detected, 6 peptides less than BTV-4 double chimaeric VLP combination. Nevertheless, all animals trials were conducted with BTV-4 and BTV-3 double chimaeric VLP vaccines. Homogenous BTV-8 VLPs resulted in 150 VP2 peptides.

Combinations of BTV-3 Single and Double Chimaeric VLPs

BTV-3 single chimaerics was assembled by proteins BTV-8 VP3 and BTV-8 VP7 forming CLPs combined with BTV-8 VP5 and BTV-3 VP2. BTV-3 double chimaerics was assembled by proteins BTV-8 VP3, BTV-8 VP7 combined with BTV-3 VP2, BTV-3 VP5.

Combinations of BTV-4 Single and Double Chimaeric VLPs

BTV-4 single chimaerics was assembled by proteins either of 1). BTV-8 VP3 and BTV-8 VP7 forming CLPs combined with BTV-8 VP5 and BTV-4 VP2 (only VP2 of serotype 4) or 2). BTV-8 VP3 combined with BTV-4 VP7, VP5 and VP2 (only VP3 of serotype 8). BTV-4 double chimaerics was assembled by proteins BTV-8 VP3, BTV-8 VP7 combined with BTV-4 VP2, BTV-4 VP5.

Example 6

BTV-4 Double Chimaeric VLP Extraction and Purification for Sheep Trial

A large scale VLP purification system was established for biomass BTV4 VLP production for the purpose of subse-

TABLE 6

Combinations of capsid proteins and peptides identified by Mass Spectrometry. Bluetongue virus BTV-4, BTV-3 & BTV-8 seed cell bank

| Sample # | | Protein Size | Peptides | 95% coverage |
|---|---|---|---|---|
| BTV-8 homogenous VLPs | VP2 | 111 kDa | 150 | 67.6% |
| BTV-3 single chimaeric (BTV-8 VP3, VP5 & VP7, BTV-3 VP2) | VP2 | 111 kDa | 22 | 31.0% |
| BTV-3 double chimaeric (BTV-8 VP3 & VP7, BTV-3 VP2 & VP5) | VP2 | 111 kDa | 81 | 62.8% |
| BTV-4 single chimaeric (BTV-8 VP3, VP5 & VP7, BTV-4 VP2) | VP2 | 111 kDa | 18 | 29.3% |
| BTV-4 double chimaeric (BTV-8 VP3 & VP7, BTV-4 VP2 & VP5) | VP2 | 111 kDa | 48 | 54.0% |
| BTV-4 single chimaeric (BTV-8 VP3, BTV-4 VP2, VP5 & VP7) | VP2 | 111 kDa | 42 | 50.4% |

Since all the *Agrobacterium* cultures were prepared from the same seed cell bank, infiltrated in the same batch of plants, extracted with the same extraction buffer, subjected to ultracentrifugation in the same run and equal amounts were loaded on the same SDS PAGE 4-12% Bolt precast gel, we confidently make the assumption that double chimaerics have more VP2 protein assembled. The results indicate that the assembly of double chimaeric (both outer capsid proteins) VLPs is superior to the assembly of single chimaeric (only VP2 outer capsid substituted) VLPs. Almost four times more peptides of VP2 were detected when the VLPs of BTV-3 was assembled via double chimaeric versus single chimaeric combinations, 81 versus 22 peptides, respectively.

quent target animal (sheep) immunogenicity studies. Hand infiltration of *Agrobacterium* harbouring BTV serotype 8 and 4 genes encoding the four capsid proteins (BTV-8 VP3 and VP7; BTV-4 VP2 and VP5) was conducted as described in Example 3. Thirty to forty plants were infiltrated with the *Agrobacterium* culture. Once more the leaf material was harvested eight days after infiltration in Bicine buffer. Remaining plant debris was removed by filtering the cell lysate through two layers of miracloth before two successive centrifugations steps (4200×g for 10 minutes each at 10° C.). The plant extract was then filtered through a Sartoclean GF sterile midicap (3 µM+8 µM) using a Masterflex Console Drive peristaltic pump (Cole-Parmer Instrument Company).

To further purify, the lysate was filtered through a 300K Minimate™ Tangential Flow Filtration (TFF) Capsule (Pall Life Sciences) with the pressure not exceeding 2 Bar. The latter removes all proteins smaller than 300K. The NLS detergent, DTT and protease inhibitor was removed from the VLP containing extract through two subsequent wash steps (1 in 10 dilution each) with sterile VLP dilution buffer. D-(+)-Trehalose dihydrate (Sigma Life Science) (5% m/v) was added to the extract (50 ml) to stabilise the VLP extract. The extract was filter sterilised through a 0.45 µM+0.2 µM Sartobran 300 sterile capsule (Sartorius Stedim biotech GmbH) using a peristaltic pump.

In addition to TFF purification, a fraction of the crude plant lysate was also purified with sucrose gradient centrifugation. The lysate (23 ml) was layered on top of sucrose density gradients (70-30%; 3 ml each) and centrifuged at 85,800×g, at 10° C. for 3 hours in a SW-32Ti rotor (Beckman Coulter) in 38.6 ml volume ultra-clear Beckman tubes. The first 6 ml was discarded (60-70% fractions) and the following 6 ml (50-40%) containing the VLPs, was collected. The sucrose-gradient purified product was dialysed overnight against Bicine buffer containing only the Bicine (pH 8.4) and sodium chloride before filter sterilization in preparation for animal trials. The TFF and sucrose fractions used for the animal trial was mixed (1:1) with Alhydrogel and transported to Onderstepoort Biological Products (OBP) on ice. The vaccine was administered on the day of delivery at OBP.

The sheep trial was conducted according to the procedures and schedule detailed in the target animal ethics application submitted to the Animal Ethics Committee OBP. Approval was subsequently obtained from CSIR Research Ethics Committee. In short, sheep were stabled and handled according to standard operating procedures outlined by the Experimental unit. Vaccination and bleeding of animals was according to standard practices. Animals were bled on days 0, 7, 14, 21, 28, 35, 42, 49 and 56. The primary vaccine was administered on day 0 and 21 with 500 µl sterile purified BTV-4 VLPs and 500 µl Alhydrogel. Sheep 554 and 513 were vaccinated with TFF purified VLPs, sheep 521, 566 and 656 with sucrose gradient purified VLPs, sheep 551 with live attenuated BTV-4 antigens (positive control) and sheep 634 with Bicine buffer alone to serve as negative control.

Serum neutralizing tests (SNTs) were conducted to determine antibody titers and used to demonstrate seroconversion (Table 7). A titer of 1:4 will demonstrate seroconversion. Seroconversion was shown for the control sheep, three sucrose gradient and one TFF vaccinated animals. Sheep 554 was inadvertently pre-exposed to BTV.

Example 7

BTV-3 VLP Extraction and Purification for Sheep Trial

A large scale VLP purification system was established for biomass BTV-3 VLP production for the purpose of subsequent target animal (sheep) immunogenicity studies. Hand infiltration of *Agrobacterium* harbouring BTV serotype 8 and 3 genes encoding the four capsid proteins (BTV-8 VP3 and VP7; BTV-3 VP2 and VP5) was conducted as described in Example 3. Thirty to forty plants were infiltrated with the LBA4404 *Agrobacterium* culture harbouring the pEAQ-HT vector and genes encoding the capsid proteins described above. Once more the leaf material was harvested eight days after infiltration in Bicine buffer. Remaining plant debris was removed by filtering the cell lysate through two layers of miracloth before two successive centrifugations steps (4200×g for 10 minutes each at 10° C.). The plant extract was then filtered through a Sartoclean GF sterile midicap (3 µM+8 µM) using a Masterflex Console Drive peristaltic pump (Cole-Parmer Instrument Company). To further purify, the lysate was filtered through a 300K Minimate™ Tangential Flow Filtration (TFF) Capsule (Pall Life Sciences) with the pressure not exceeding 2 Bar. The latter removes all proteins smaller than 300K. The NLS detergent, DTT and protease inhibitor was removed from the VLP containing extract through two subsequent wash steps (1 in 10 dilution each) with sterile VLP dilution buffer. D-(+)-Trehalose dihydrate (Sigma Life Science) (5% m/v) was added to the extract (50 ml) to stabilise the VLP extract. The extract was filter sterilised through a 0.45 µM+0.2 µM Sartobran 300 sterile capsule (Sartorius Stedim biotech GmbH) using a peristaltic pump.

In addition to TFF purification, a fraction of the crude plant lysate was also purified with sucrose gradient centrifugation. The lysate (23 ml) was layered on top of sucrose density gradients (70-30%; 3 ml each) and centrifuged at 85,800×g, at 10° C. for 2 hours in a SW-32Ti rotor (Beckman Coulter) in 38.6 ml volume ultra-clear Beckman tubes. The first 6.5 ml was discarded (60-70% fractions) and the following 3 ml (50-40%) containing the VLPs, was collected. The sucrose-gradient purified product was dialysed overnight against phosphate buffer (pH 7.4) before filter sterilization in preparation for animal trials. The TFF and sucrose fractions used for the animal trial was mixed (1:1) with Montanide ISA 201 VG and transported to Onderstepoort Biological Products (OBP) on ice. The vaccine was administered on the day of delivery at OBP.

Sheep were stabled and handled according to standard operating procedures outlined by the Experimental unit at OBP. Vaccination and bleeding of animals was according to standard practices. Animals were bled on days 0, 7, 14, 21, 28, 35 and 42. The primary vaccine was administered on day

TABLE 7

Serum neutralizing test (SNT) results of the sheep trial.

| Sheep # | Innoculum | Day 0 | D 7 | D 14 | D 21 | D 28 | D 35 | D 42 | D 49 | D 56 |
|---|---|---|---|---|---|---|---|---|---|---|
| 554 | TFF* | 0 | 0 | 0 | 0 | 0 | 0 | 0 | 0 | 0 |
| 513 | TFF | 0 | 0 | 1:4 | 0 | 0 | 0 | 1:8 | 0 | 0 |
| 521 | Sucrose | 0 | 0 | 1:4 | 1:128 | 1:128 | 1:256 | 1:256 | 1:256 | 1:256 |
| 566 | Sucrose | 0 | 0 | 0 | 1:8 | 1:32 | 1:256 | 1:256 | 1:256 | 1:256 |
| 656 | Sucrose | 0 | 0 | 0 | 0 | 1:2 | 1:32 | 1:32 | 1:32 | 1:64 |
| 551 | OBP live attenuated BTV-4 virus (Positive control) | 0 | 0 | 0 | 1:16 | 1:128 | 1:128 | 1:256 | 1:256 | 1:256 |
| 634 | Bicine buffer (Negative control) | 0 | 0 | 0 | 0 | 0 | 0 | 0 | 0 | 0 |

0 and 21 with 500 µl sterile purified BTV-3 VLPs and 500 µl Montanide ISA 201 VG. Sheep 1646, 1639 and 1655 were vaccinated with TFF purified VLPs, sheep 1657, 1605 and 1613 with sucrose gradient purified VLPs, sheep 1632, 1647 and 1609 with sucrose gradient omitting the adjuvant; sheep 1608 and 1614 with live attenuated BTV-3 antigens (positive control) and sheep 1649 with Bicine buffer alone and sheep 1629 naïve, untouched to serve as negative control.

Serum neutralizing tests (SNTs) were conducted to determine antibody titers and used to demonstrate seroconversion. A titer of ≥1:4 will demonstrate seroconversion. Seroconversion was shown for all three TFF vaccinated animals identical to live BTV-3 monovalent vaccinations (Table 8).

Four week-old *N. benthamiana* dXT-FT plants were infiltrated with the agrobacterial combination via syringe-mediated infiltration.

The infiltrated leaves were harvested 8 days post infiltration (d.p.i), weighed and immediately processed through a juice extractor (MATSTONE 6 in 1 multipurpose juice extractor) with 3 volumes of VLP extraction buffer (20 mM NaCl, 50 mM Bicine, pH 8.4, 0.1% (w/v) Sodium lauroyl sarcosine (NLS), 1 mM Dithiothreitol (DTT) (ThermoScientific), cOmplete, EDTA-free Protease inhibitor cocktail (Sigma-Aldrich)). The DTT and cOmplete, EDTA-free Protease inhibitor cocktail tablets were freshly prepared according to the manufacturers' instructions and added to the

TABLE 8

Serum neutralising test (SNT) results of the sheep trial.

|  | Pre-bleed | Day 0 | D 7 | D 14 | D 21 | D 28 | D 35 | D 42 | D 49 | D 56 |
|---|---|---|---|---|---|---|---|---|---|---|
| TFF (ISA 201) |  |  |  |  |  |  |  |  |  |  |
| 1646 | — | — | — | — | 2 | 256 | 256 | 256 | 256 | 256 |
| 1639 | — | — | — | — | 2 | 256 | 256 | 256 | 256 | 256 |
| 1655 | — | — | — | — | 4 | 256 | 256 | 256 | 256 | 256 |
| Sucrose (ISA 201) |  |  |  |  |  |  |  |  |  |  |
| 1657 | — | — | — | — | — | — | 2 | 16 | 16 | — |
| 1605 | — | — | — | — | — | 2 | 16 | — | 2 | — |
| 1613 | — | — | — | — | — | — | — | — | — | — |
| Sucrose (no adjuvant) |  |  |  |  |  |  |  |  |  |  |
| 1632 | — | — | — | — | — | — | 8 | 8 | — | — |
| 1647 | — | — | — | — | 2 | 2 | — | 4 | — | — |
| 1609 | — | — | — | — | 4 | 8 | — | — | — | — |
| Live monovalent |  |  |  |  |  |  |  |  |  |  |
| 1608 | — | — | 128 | 256 | 256 | 256 | 256 | 256 | 256 | 256 |
| 1614 | — | — | — | 128 | Δ | 256 | 256 | 256 | 256 | 256 |
| Controls Bicine buffer |  |  |  |  |  |  |  |  |  |  |
| 1649 | — | — | — | — | — | — | — | — | — | — |
| Naïve, untouched |  |  |  |  |  |  |  |  |  |  |
| 1629 | — | — | — | — | — | — | — | — | — | — |

Example 8

VLP Purification and Immunogenicity Trial of Double Chimaeric AHSV VLPs in Horses Following agroinfiltration of *Nicotiana benthamiana* dXT-FT plants with the appropriate recombinant pEAQ vectors, the double chimaeric AHSV-1/AHSV-7 VLPs were purified by means of both tangential flow filtration (TFF) and sucrose density gradient centrifugation prior to being injected into horses. More specifically, LBA 4404 agrobacterial cells, containing the recombinant plasmids pEAQ-express-AHSV-1VP7/AHSV-1VP3, pEAQ-HT-AHSV-7VP5 and pEAQ-HT-AHSV-7VP2 were defrosted and streaked out onto selective LB plates (50 µg/ml Kanamycin, 50 µg/ml Rifampicin and 50 µg/ml Streptomycin). Following incubation at 28° C. for 48 hours, the cultures were subsequently inoculated into 50 ml YMB medium containing the appropriate antibiotics and incubated overnight at 28° C. with rotational shaking (175 rpm). The overnight cultures were harvested at 8000 rpm for 7 min at 20° C. and each cell pellet resuspended in 40 ml MMA buffer (10 mM MES hydrate; pH 5.6, 10 mM MgCl$_2$, 100 µM 3,5-Dimethoxy-4-hydroxy-acetophenone) and the OD$_{600}$ measured. The agrobacterial suspensions were combined in a 1:1:1 ratio and the final OD$_{600}$ of each combination was 0.4-0.5.

extraction buffer just prior to use. Large plant debris was removed by filtering the cell lysate through 2 layers of miracloth and the cell extract clarified via low speed centrifugation (4200×g; 30 min; 10° C.). Using a Masterflex Consol Drive peristaltic pump (Cole-Parmer Instrument Company), the cell extract was filtered through a Sartoclean GF sterile midicap (3+0.8 µM) depth filter (Sartorius).

A portion of the filtrate was layered on top of 70-30% sucrose gradients and centrifuged in a SW-38Ti rotor (Beckman Coulter) at 85,800×g for 3 hours; 10° C. Sucrose solutions (30%-70%) were prepared by dissolving ultra-high quality sucrose (Sigma Life Science) in VLP dilution buffer (20 mM NaCl, 50 mM Bicine, pH 8.4) and layered into gradients of 3 ml 10% incrementing steps. Following centrifugation the 55%-45% sucrose layers were harvested in 1 ml fractions via a Minipuls2 peristaltic pump (Gilson). Fractions containing the VLPs (55%-45%) were added together and dialysed against sterile VLP dilution buffer (20 mM NaCl, 50 mM Bicine, pH 8.4) overnight, with gentle stirring, in SnakeSkin™ dialysis tubing (Thermo Fisher Scientific).This was followed by a second dialysis step of 2 hours against new VLP dilution buffer at 4'C. The dialysed sample was harvested and D-(+)-Trehalose dihydrate (Sigma Life science) added as a stabilizing agent to a final concentration of 5%.

The remainder of the Depth filtered plant cell extract was further filtered through a 300K Minimate™ Tangential Flow filtration (TFF) Capsule (Pall Life Sciences) with the pressure not exceeding 2 Bar. This was done to remove all proteins smaller than 300K. Two subsequent wash steps (1 in 10 dilution each) with sterile VLP dilution buffer ensured the removal of the NLS detergent, DTT and Protease inhibitor from the plant extract. The plant cell lysate was concentrated to ⅕ of its original volume and D-(+)-Trehalose dihydrate (Sigma Life science) added as a stabilizing agent to a final concentration of 5%.

The sucrose and TFF purified samples were subsequently filter-sterilized through a 0.45 µM+0.2 µM Sartobran 300 Sterile capsule (Sartorius Stedim biotech GmbH) utilizing a peristaltic pump with the pressure not exceeding 2 Bar. They were also tested for sterility by streaking out 100 µl of the sample on Luria agar plates containing no antibiotics and incubating those plate overnight at 37° C. Samples, taken throughout the course of the purification procedure, were analysed for protein content by denaturing SDS-PAGE and immunoblotting procedures with AHSV-7 specific antiserum, kindly donated by OBP. The protein content of the filter sterilized samples was quantified by using the Micro BCA™ Protein Assay kit (Thermo Fisher Scientific) while the VLPs in these same samples was visualised via TEM.

The immunogenicity of the plant-produced double chimaeric AHSV-1/AHSV-7 VLPs was investigated in the target species, horses. The horse trial was conducted according to the procedures and schedule detailed in the approved target animal ethics applications (CSIR REC registration number 151/2015, OBP registration number 2015/003). Seven AHS-naïve foals (6 months old) were stabled in closed stables at OBP and handled according to standard operating procedures outlined by the Experimental Unit. Vaccination and bleeding of animals was according to standard operating protocols and conducted by OBP. Three foals were each injected subcutaneously into the inner thigh with the TFF-purified VLP/Alydrogel sample (final volume of 2 ml containing 3490 µg of total protein). Two foals were each injected subcutaneously into the inner thigh with the sucrose gradient-purified VLP/Alydrogel® sample (final volume of 2 ml containing 101 µg of total protein). One foal was inoculated with sterile bicine buffer/Alydrogel® sample as a negative control whilst another was inoculated with monovalent AHSV-7 live attenuated vaccine (OBP) as a positive control. The animals were inoculated with the booster sample on day 28 of the immunization schedule. The 2 ml TFF-purified VLP/Alydrogel® booster sample contained 3825 µg of total protein while the 2 ml sucrose gradient-purified VLP/Alydrogel® sample contained 184 µg of total protein. The two control animals received sterile bicine buffer/Alydrogel® and monovalent AHSV-7 live attenuated vaccine (OBP), respectively, during the boost inoculation. Serum samples were taken on days 0, 7, 14, 21, 28, 35, 42, 49 and 56. Serum neutralization testing was performed on the blood samples by OBP according to the RDV-ME-014 method whilst the VP7-specific ELISA tests were performed by ARC Onderstepoort Veterinary Institute (OVI).

The results of this horse trial are as follows: One horse (#31), inoculated with the TFF-purified AHSV-1/AHSV-7 VLP sample, elicited α-AHSV-7 neutralizing antibodies with a titre of 1:16 two weeks after the boost inoculation (day 42) (Table 9 & 10). This indicates that the AHSV-7 VP2 protein was presented on the surface of the double chimaeric VLPs in a conformation capable of eliciting an AHSV neutralizing humoral immune response in the horse. However, this immune response was not detected in the following two weeks (days 49 and 56). No neutralizing antibodies were detected in the sera of any of the other animals during the trial, not even the animals injected with the monovalent live attenuated AHSV-7 virus used as a positive control (Animal #32). The lack of a response in the positive control group indicates that this trial will have to be repeated. Horses #29 and #30, both inoculated with the TFF-purified AHSV-1/AHSV-7 VIPs, as well as horse #35, inoculated with sucrose gradient purified AHSV-1/AHSV-7 VLPs, elicited antibodies against the VP7 protein on day 35, a week after the booster inoculation. This indicates the presence of CLPs. As expected, the animal inoculated with bicine buffer, #43, did not elicit any neutralizing or VP7-specific antibodies during the course of the trial.

TABLE 9

Serum neutralizing test (SNT) results of the horse trial.

| Horse # | Innoculum | Day 0 | D 7 | D 14 | D 21 | D 28 | D 35 | D 42 | D 49 | D 56 |
|---|---|---|---|---|---|---|---|---|---|---|
| 23 | TFF-purified AHSV-1/7 VLPs | 0 | 0 | 0 | 0 | 0 | 0 | 0 | 0 | 0 |
| 30 | TFF-purified AHSV-1/7 VLPs | 0 | 0 | 0 | 0 | 0 | 0 | 0 | 0 | 0 |
| 31 | TFF-purified AHSV-1/7 VLPs | 0 | 0 | 0 | 0 | 0 | 0 | 1:16 | 0 | 0 |
| 35 | Sucrose gradient purified AHSV-1/7 VLPs | 0 | 0 | 0 | 0 | 0 | 0 | 0 | 0 | 0 |
| 41 | Sucrose gradient purified AHSV-1/7 VLPs | 0 | 0 | 0 | 0 | 0 | 0 | 0 | 0 | 0 |
| 32 | Monovalent live attenuated AHSV-7 OBP (Positive control) | 0 | 0 | 0 | 0 | 0 | 0 | 0 | 0 | 0 |
| 43 | Bicine buffer (Negative control) | 0 | 0 | 0 | 0 | 0 | 0 | 0 | 0 | 0 |

TABLE 10

ELISA results of the horse trial.

| Horse # | Innoculum | D 14 | D 21 | D 28 | D 35 |
|---|---|---|---|---|---|
| 23 | TFF-purified AHSV-1/7 VLPs | Neg | Neg | Neg | 9 |
| 30 | TFF-purified AHSV-1/7 VLPs | Neg | Neg | Neg | 14 |
| 31 | TFF-purified AHSV-1/7 VLPs | Neg | Neg | Neg | Neg |

TABLE 10-continued

ELISA results of the horse trial.

| Horse # | Innoculum | D 14 | D 21 | D 28 | D 35 |
|---|---|---|---|---|---|
| 35 | Sucrose gradient purified AHSV-1/7 VLPs | Neg | Neg | Neg | 22 |
| 41 | Sucrose gradient purified AHSV-1/7 VLPs | Neg | Neg | Neg | Neg |
| 32 | Monovalent live attenuated AHSV-7 OBP (Positive control) | Neg | Neg | Neg | Neg |
| 43 | Bicine buffer (Negative control) | Neg | Neg | Neg | Neg |

Example 9

Immunogenicity of Plant Produced African Horse Sickness Virus-Like Particles

A consensus gene sequence for each of the AHSV-5 viral capsid proteins VP2, VP3, VP5 and VP7 was obtained by aligning all the known sequences for these genes listed in GenBank, using CLC Mainbench bioinformatics software (Qiagen Bioinformatics, Aarhus, Denmark). Consensus sequences were codon optimized for expression in N. benthamiana and synthesized by GenScript Biotech Corporation (China) with flanking AgeI and XhoI restriction enzyme sites. The codon-optimized VP7 consensus sequence, modified as described by S. Bekker (2015) to include 7 amino acid substitutions near the 3' end, (Pro276His, Arg328Ala, Val333Asn, Ala334Pro, Pro335Met, Val336Pro and Gln338Pro) was also synthesized. Restriction enzyme cloning was used to insert the genes into the pEAQ-HT expression vector obtained from George Lomonossoff, John Innes Centre, UK (Sainsbury et al., 2009) to produce pEAQ-AHS5-VP2, pEAQ-AHS5-VP3, pEAQ-AHS5-VP5, pEAQ-AHS5-VP7 and pEAQ-AHS5-VP7mu. The AHSV-5 plasmid constructs were electroporated into Agrobacterium radiobacter AGL1-ATCC BAA-101 as described previously (Maclean et al., 2007) and recombinant clones were selected at 27° C. on Luria Bertani (LB) media plates containing 25 µg/mL carbenicillin and 50 µg/mL kanamycin.

Transient Expression in Plants

Expression of the AHSV-5 capsid proteins was achieved by agroinfiltration of 5-6-week-old N. benthamiana plants. Agrobacterium transformants each carrying one of the AHSV-5 capsid protein genes, were subcultured and grown overnight with agitation at 27° C. in Luria Bertani Broth (LBB) base supplemented with 50 µg/mL kanamycin, 20 µM acetosyringone and 2 mM MgSO$_4$. The cultures were diluted in resuspension solution (10 mM MES, pH 5.6, 10 mM MgCl$_2$, 100 µM acetosyringone) to the desired optical density and incubated for 1 h at 22° C. to allow for expression of the vir genes. For single infiltrations, each AHSV-5 Agrobacterium recombinant suspension was diluted to OD$_{600}$=0.5 or 1.0, while co-infiltration suspensions contained all four AHSV-5 recombinants in a ratio VP2:VP3:VP5:VP7 of 1:1:1:1 or 1:1:2:1. Plants were grown at 22-25° C. under 16 h/8 h light/dark cycles. Agrobacterium suspensions were infiltrated into the leaf inter-cellular spaces using either a blunt-ended syringe or by means of a vacuum infiltrator, applying a vacuum of 100 kPa. For optimization of the expression, 3 leaf discs were obtained from each plant, clipped with the lid of a micro-centrifuge tube on 3, 5 and 7 days post infiltration (dpi) and homogenized in 3 volumes of PI buffer (phosphate buffered saline (PBS), pH 7.4 containing 1× Complete protease inhibitor cocktail (Roche, Basel, Switzerland)) using a micro-pestle. The homogenate was incubated on ice for 30 min and then clarified by centrifugation at 13 000 rpm for 15 min in a benchtop microfuge. For large scale expression, leaf tissue was harvested 7 dpi, as this time span was shown to be optimal for expression of all four capsid proteins. Harvested leaves were immediately homogenized in 3 volumes PI buffer using a Moulinex™ juice extractor. The homogenized leaves were re-incubated with the extracted juice and incubated at 40 C for 1 h with gentle shaking. Crude plant extracts were filtered through four layers of Miracloth™ (Merck, Darmstadt, Germany) and the filtrate was clarified by centrifugation at 13 000 rpm for 15 min at 4° C.

Figure 30:
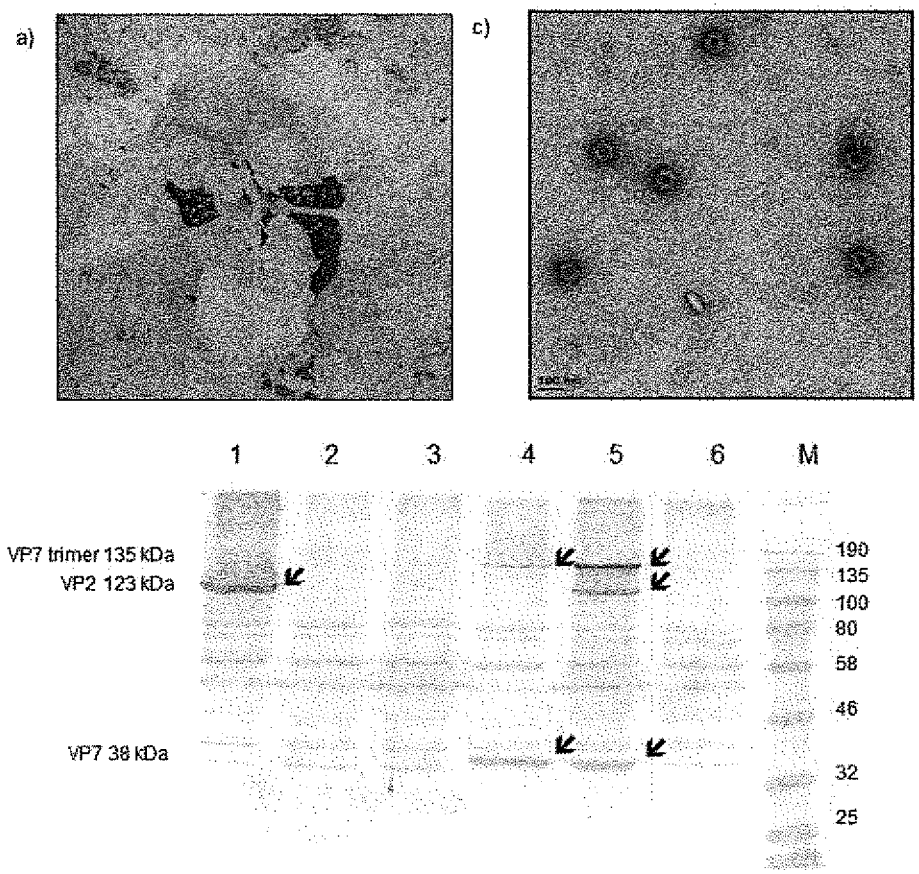
FIG. 30: Expression of recombinant AHSV-5 structural proteins and their assembly into virus-like particles in N. benthamiana. a) Western blot analysis of crude leaf extracts obtained 7 dpi with Agrobacterium radiobacter AGL1-ATCC BAA-101 containing pEAQ-AHS5 VP2 (lane 1), pEAQ-AHS5 VP3 (lane 2), pEAQ-AHS5 VP5 (lane 3), pEAQ-AHS5 VP7 (lane 4) or co-infiltrated with all 4 AHSV-5 recombinants (lane 5). Crude extract from leaves infiltrated with Agrobacterium transformed with pEAQ-HT expression vector lacking any goi, was used as a negative control (lane 6). Anti-AHSV 5 antiserum, which was unable to detect either VP3 or VP5, was used as the primary antibody. VP7 trimer (135 kDa), VP2 (123 kDa) and VP7 monomer (38 kDa) are indicated by arrow heads. Colour pre-stained protein standard, broad range (New England Biolabs, Massachusetts, USA) indicated to the right of the blots was used as a molecular weight marker b) Fully assembled AHSV 5 virus-like particles imaged by TEM analysis of crude extracts from plants co-infiltrated with pEAQ-AHS5 VP2, pEAQ-AHS5 VP3, pEAQ-AHS5 VP5 and pEAQ-AHS5 VP7. Scale bar, 100 nm. c) *N. benthamiana* plant 7 dpi with all 4 AHSV-5 *Agrobacterium* recombinants.

AHSV-5 Capsid Proteins Transiently Expressed in N. benthamiana Leaves Self-Assemble into VLPs A consensus sequence of each gene was obtained by aligning all the known sequences listed in GenBank and these were codon-optimized for Nicotiana spp. translation and synthesized with flanking AgeI and XhoI restriction enzyme sites by GenScript Biotech Corporation, China. The genes were cloned into the multiple cloning site of the pEAQ-HT vector (Sainsbury et al. 2009, obtained from G. Lomonossoff, John Innes Centre, UK) to yield four different constructs, pEAQ-AHS5-VP2, pEAQ-AHS5-VP3, pEAQ-AHS5-VP5 and pEAQ-AHS5-VP7 (FIG. 29b) Transient expression of the AHSV proteins in N. benthamiana was tested by small-scale syringe infiltration of 5 leaves with Agrobacterium strains carrying individual constructs, or co-infiltration of the same plant with all four recombinant-carrying strains. All infiltrated leaf tissue exhibited chlorosis, but little, if any, necrosis was observed (FIG. 30a). Agrobacterium suspensions carrying recombinants in two different VP2:VP3:VP5:VP7 ratios were tested, namely 1:1:1:1 and 1:1:2:1 and 3 leaf discs were extracted on days 5 and 7 post infiltration, to determine the optimal expression conditions. Western blots of crude leaf extracts infiltrated with Agrobacterium-carrying recombinants in a 1:1:1:1 ratio at an OD$_{600}$ of 0.5 each and prepared 7 days after infiltration were shown to yield optimal protein expression. Expression of VP2 (123 kD) and VP7 (37 kD), as well as the VP7 trimer (135 kD) was demonstrated, the proteins being visualized as distinct bands of the correct expected molecular weight. Bands corresponding to VP3 (103 kD) and VP5 (57 kD) were not observed (FIG. 30b). However, fully formed AHSV-5 VLPs were imaged by TEM analysis of these crude extracts, indicating that all four capsid proteins were expressed and indeed had self-assembled into complete particles (FIG. 30c). As such, this is the first known report of AHSV VLPs being produced in plants.

Purification and Western Blot Analysis

AHSV-5 VLPs were purified by iodixanol density gradient ultracentrifugation. Iodixanol (Optiprep™, Sigma-Aldrich, Missouri, USA) solutions (20-60%), prepared in PBS, were used to create a 12 ml step gradient (2-3 mL of each gradient in 10% incrementing steps) under 27 ml clarified plant extract and centrifuged at 32 000 rpm for 2 h at 4° C. in an SW 32 Ti rotor (Beckman, Calif., USA). Fractions of 1 ml were collected from the bottom of the tube and 30 µl from fractions representing the 30-40% region of the gradient were electrophoresed on a 10% SDS-polyacrylamide gel, followed by Coomassie blue staining. Particle quantification was achieved by visual comparison of the four capsid protein bands to known amounts of bovine serum albumin (BSA) run in separate lanes on the same SDS-PAGE gel. To further purify and concentrate VLP samples for use in animal studies, VLP-containing fractions were diluted with PBS to 20% iodixanol and subjected to a second round of ultracentrifugation per the same protocol described above. Both crude plant extracts and gradient-purified VLPs were analyzed by western blot: heat-denatured samples were separated on 10% polyacrylamide gels and then transferred onto HyBond™ C Extra nitrocellulose membranes (AEC-Amersham, Gauteng, South Africa) using a Trans-Blot™ SD semi-dry transfer cell (Bio-Rad, California, USA). Membranes were first probed with a 1:1000 dilution of AHSV-5 specific horse serum (received from Deltamune, Pretoria, South Africa), washed four times with PBS containing 0.05% Tween™ 20 (Sigma-Aldrich, Missouri, USA) (PBS-T) and then probed with 1:5000 dilution of anti-horse alkaline phosphatase-conjugated secondary antibody (Sigma-Aldrich, Missouri, USA). After washing again, proteins were detected with 5-bromo-4-chloro-3-indoxyl-phosphate (BCIP) and nitroblue tetrazolium (NBT) phosphatase substrate (BCIP/NBT 1-component, KPL, SeraCare, Mass., USA).

Density Gradient Ultracentrifugation of Plant-Produced AHSV-5 VLPs

To produce an AHS VLP preparation of sufficient purity and concentration for immunization of guinea pigs, several modifications were made. Firstly, the process was scaled up to infiltrate 24 plants with the recombinant constructs at the optimal $OD_{600}$ of 0.5 each and optimal ratio of 1:1:1:1. Secondly, AHSV VP7 is known to form trimers which aggregate into crystalline structures in the cytoplasm of infected cells and there is evidence to suggest that these crystals impede VLP formation by sequestering available soluble VP7 trimers and preventing them from incorporating into the core particle. Therefore, a mutated version of the VP7 gene containing 7 amino acid substitutions near the 3' end was also synthesized (SEQ ID NO:77) and cloned into pEAQ-HT to yield pEAQ-AHS5-VP7mu. The protein encoded by the mutated version of the VP7 gene has the sequence set forth in SEQ ID NO:78. Co-infiltration with *Agrobacterium* strains carrying the VP2, VP3 and VP5 recombinants together with this construct as opposed to the wild-type VP7 construct, yielded an increased concentration of VLPs. Therefore, the mutated VP7 construct was used in all further experiments. Thirdly, a vacuum infiltrator was used to introduce the *Agrobacterium* suspension into the leaf intercellular spaces as this was much less labour intensive than syringe infiltration and resulted in more uniform infiltration of plant leaves.

Lastly, clarified leaf extracts were purified by iodixanol density gradient ultracentrifugation. Green leaf impurities settled in the upper 30% region of the gradient, while a single iridescent band was observed at a higher density, near the 30-40% interface (FIG. 31a). Fractions were collected from the bottom of the tube and four distinct bands corresponding to the correct molecular weight sizes of the AHSV capsid proteins were observed following separation of fractions 6-8 by SDS-PAGE and Coomassie blue staining (FIG. 31b). Gel densitometry was used to estimate the VLP concentration. The co-sedimentation of all four proteins was highly suggestive of the presence of VLPs and this was confirmed by TEM analysis (FIG. 31c). An estimated 40-50% of the viral structures were seen to be complete AHSV VLPs or contained at least a partial VP2 outer layer, though some particles appear to have been slightly damaged during the purification process. Assembly intermediates representing core-like particles (CLPs) or CLPs in the process of acquiring the two outer coat proteins, were also observed. This purification has been repeated several times and typically, 70 g infiltrated leaf material yields±0.4 mg highly purified VLPs which equates to ±15.7 mg VLPs/kg leaf biomass.

Transmission Electron Microscopy

Glow-discharged copper grids (mesh size 200) were floated on 20 μl crude plant extract or 20 μl density gradient fractions for 3 min and then washed successively by floating on 5 drops of sterile water. Particles were negatively stained for 30 sec with 2% uranyl acetate and then imaged using a Technai G2 transmission electron microscope (TEM).

Immunization of Guinea Pigs

Approval for the immunization experiments was obtained from the Faculty of Health Sciences Animal Ethics Committee, University of Cape Town (FHS AEC ref No.: 016/019). Prior to the study, 100 μl of blood was drawn from each of 8 female guinea pigs (Hartley strain). Guinea pigs (n=4) were injected subcutaneously with purified AHSV-5 VLPs or 30% iodixanol in PBS, both formulated in 5% Montanide PET Gel A adjuvant (Seppic, Paris, France). Animals were boosted on day 13 and on day 41, they were euthanized by anaesthesia with ketamine/xylazine and exsanguinated. Serum was tested for antibodies by indirect enzyme-linked immunosorbent assay (ELISA) and western blot. Briefly, 96-well Maxisorp™ microtiter plates (Thermo Fisher Scientific, Massachusetts, USA) were coated overnight at 4° C. with 60 ng/well of AHSV-5 VLPs originally used for the inoculations. Plates were washed four times with PBS-T and blocked with 5% fat-free milk powder diluted in PBS-T for 1 h at 37° C. Guinea pig antisera were serially diluted in PBS-T/5% milk, added to the plates and allowed to incubate for 1 h at 37° C. Plates were washed four times, and an alkaline phosphatase-conjugated goat anti-guinea pig IgG (Sigma-Aldrich, Missouri, USA) was diluted (1:5000) in blocking buffer and added to plates. Plates were again incubated for 1 h at 37° C. and washed four times. After addition of 100 μl p-Nitrophenyl phosphate substrate (SIGMAFAST, Sigma-Aldrich, Missouri, USA), the plates were incubated in the dark for 30 min to allow a colorimetric reaction to develop. Optical densities at a wavelength of 450 nm were read by a Bio-Tek™ Powerwave XS spectrophotometer. For western blot analysis, guinea pig antisera were used at a dilution of 1:10 000 as per the protocol described above.

Neutralization Assays

The serum neutralizing antibody titres of individual guinea pig sera were assayed against three different AHSV serotypes, namely serotypes 4, 5 and 8 using a serum neutralization test (SNT).

Plant-Produced AHSV-5 VLPs Induce a Strong Immunogenic Response in Guinea Pigs

Guinea pigs were used as a small animal model to test the ability of the plant-produced AHSV 5 VLPs to induce an immune response. On day 0, four guinea pigs (V2-V5) were each vaccinated with 16.5 μg AHSV VLPs, while four control animals (C2-C5) were immunized with PBS. Prior to the boost inoculation, a further purification yielded sufficient AHS VLPs to increase the amount of the next inoculum. Animals were thus boosted on day 13 with 50 μg VLPs or PBS and sera from all animals was collected on day 41. Sera from guinea pigs immunized with VLPs tested positive for AHSV 5 antibodies in indirect ELISA, 1:40 000 being the lowest dilution at which an absorbance value could be read. Sera from guinea pigs vaccinated with PBS, tested negatively (FIG. 32a). Final and pre-bleed sera (1:10 000) from a representative VLP-vaccinated guinea pig (V3) were used to probe a western blot of VLPs used in the initial inoculations. Strong signals for VP2, VP5 and VP7 (both monomer and trimer) were detected by the final bleed serum but not by the pre-bleed serum from the vaccinated guinea pig (FIG. 32b).

To test the ability of the sera to neutralize live virus, serum samples from all guinea pigs were sent to the Equine Research Centre at Onderstepoort, University of Pretoria for serum neutralization tests. Sera were assayed against AHSV-5 and AHSV-8 as serological cross-protection has been shown in vitro between serotypes 5 and 8, and AHSV-4 for which no cross protection has been shown. All vaccinated guinea pig sera showed a high level of neutralization capability against AHSV-5 and neutralized AHSV-8 to a lesser extent, but to a similar degree compared to the AHS positive control (Table 11). The sera did not neutralize AHSV-4 and control guinea pig sera did not neutralize any of the AHSV serotypes. These results indicate that plant-produced AHSV-5 VLPs stimulate a highly protective immune response in guinea pigs.

TABLE 11

Virus neutralizing antibody titers of serum samples from vaccinated (V) and control (C) guinea pigs. The guinea pig sera were assayed for neutralization capability against AHSV-5, AHSV-4 and AHSV-8, as serological cross-protection has been shown in vitro between serotypes 5 and 8, but not between serotypes 5 and 4. Horse serum from animals vaccinated with the AHSV live-attenuated vaccine produced by Onderstepoort Biological Products (OBP) was used as a positive control.

| Group | Guinea Pig | AHSV-4 | AHSV-5 | AHSV-8 |
|---|---|---|---|---|
| Vaccine | V2 | Negative | 1:5120 | 1:160 |
|  | V3 | Negative | 1:640 | 1:80 |
|  | V4 | Negative | 1:1280 | 1:56 |
|  | V5 | Negative | 1:2560 | 1:80 |
| Control | C2 | Negative | Negative | Negative |
|  | C3 | Negative | Negative | Negative |
|  | C4 | Negative | Negative | Negative |
|  | C5 | Negative | Negative | Negative |
| OBP vaccine | — | 1:112 | 1:112 | 1:112 |

Example 10

Production of BT VLPs Harnessing Various *Agrobacterium* Strains

LBA4404, AGL-1 and GV3101 pMP90 *Agrobacterium* strains were compared as vehicle to deliver the expression vector pEAQ-HT, harbouring the selected genes, to the plant cells. BTV-8 (VP3, VP7, VP5 and VP2) and BTV-3 (VP5 and VP2) were individually electroporated into these *Agrobacterium* strains. The goal was to determine the *Agrobacterium* strain most suitable and resulting in the highest number of intact double chimaeric BTV-3 (BTV-8 VP3 and VP7 core combined with BTV-3 VP2 and VP5 outer capsids) and homogenous BTV-8 VLPs (BTV-8 VP3, VP5, VP2 and VP7) for commercial production. Assembly of BTV serotypes 3 and 8 VLPs were created using stocks from the LBA4404 seed cell bank, or the recently prepared *Agrobacterium* AGL-1 and GV3101 pMP90 collection. *N. benthamiana* dXT/FT plants were infiltrated with the relevant *Agrobacterium* and construct combinations. The *Agrobacterium* strains harboring pEAQ-HT constructs encoding for the four capsid proteins individually for BTV serotypes 3 and 8 were successfully infiltrated into *N. benthamiana* leaves. Production of VLPs in plant leaf tissue was determined by mixing the four constructs encoding the four individual capsid proteins VP3:VP7:VP5:VP2 at a ratio of 1:1:1:1 ($OD_{600}$=2). Leaf tissue was harvested seven days after infiltration, extracted and Iodixanol density gradient purified as described above. The Iodixanol purified BT VLPs proteins were quantified using a sensitive colorimetric protein assay, the Micro BCA™ Protein Assay Kit (ThermoScientific) using Bovine Gamma Globulin (Bio-Rad) protein standards. Eight micrograms of protein were loaded in each lane (FIG. 33).

The Iodixanol samples were stained as follows: grids were floated on the undiluted protein sample for 5 minutes were washed five times in 5 μl distilled water, drained via blotting on filter paper each time before staining. Subsequently the grids were floated on 2% uranyl acetate (30 seconds, drained and stained for another 10 seconds) and drained as described above. The air dried grid was imaged in a CM10 Transmission electron microscope (Philips) at the University of Pretoria (UP) Onderstepoort, Laboratory for Microscopy and Microanalysis (FIG. 34). Mass spectrometry was conducted as described before.

In this Example, *Agrobacterium* strains LBA4404, GV3101 pMP90 and AGL-1 were compared to mediate homogenous BTV-8 and double chimaeric BTV-3 in *N. benthamiana* facilitating mammalian glycosylation (dXT/FT, Strasser et al., 2008) by exclusively subjecting VP2 to mass spectrometry. Assembly of homogenous BTV-8 and double chimaeric BTV-3 as visualized by TEM images is comparable when mediated by the three independent *Agrobacterium* strains. Mass spectrometry analysis of homogenous BTV-8 VLPs (duplicate technical replicates) indicated that either LBA4404 (42-46 peptides) or GV3101 pMP90 (36-41 peptides) or AGL-1 (49-52 peptides) are suitable to mediate abundant VLP assembly with strain AGL-1 slightly superior. Mass spectrometry analysis of double chimaeric BTV-3 (triple technical replicates) however indicated that LBA4404 (32-39 peptides) is superior to both GV3101 pMP90 (7 peptides in only one sample) and AGL-1 (14-17 peptides).

TABLE 12

Mass spectrometry results of the production of BT VLPs harnessing various *Agrobacterium* strains

| Sample # | Duplicates or triplicates of VP2 detected | Viral protein | Note | Peptides | 95% coverage | BTV VP2 serotypes |
|---|---|---|---|---|---|---|
| BTV-8 LBA4404 | 1 | BTV-8 VP2 | 111 kDa | 46 | 48.0% | BTV8_VP2_AGJ83482_1 |
| Homogenous | 2 | BTV-8 VP2 | 111 kDa | 42 | 40.0% | BTV8_VP2_AGJ83482_1 |
| BTV-8 GV3101 pMP90 | 1 | BTV-8 VP2 | 111 kDa | 41 | 43.0% | BTV8_VP2_AGJ83482_1 |
| Homogenous | 2 | BTV-8 VP2 | 111 kDa | 36 | 37.0% | BTV8_VP2_AGJ83482_1 |
| BTV-8 AGL-1 | 1 | BTV-8 VP2 | 111 kDa | 49 | 51.0% | BTV8_VP2_AGJ83482_1 |
| Homogenous | 2 | BTV-8 VP2 | 111 kDa | 52 | 47.0% | BTV8_VP2_AGJ83482_1 |
| BTV-3 LBA4404 | 1 | BTV-3 VP2 | 111 kDa | 32 | 0.35% | BTV3_VP2_CAE51090_1 |

TABLE 12-continued

Mass spectrometry results of the production of BT VLPs harnessing various *Agrobacterium* strains

| Sample # | Duplicates or triplicates of VP2 detected | Viral protein | Note | Peptides | 95% coverage | BTV VP2 serotypes |
|---|---|---|---|---|---|---|
| Double chimaeric | 2 | BTV-3 VP2 | 111 kDa | 39 | 0.4% | BTV3_VP2_CAE51090_1 |
|  | 3 | BTV-3 VP2 | 111 kDa | 26 | 0.28% | BTV3_VP2_CAE51090_1 |
| BTV-3 GV3101 pMP90 | 1 | BTV-3 VP2 | 111 kDa | 7 | 0.06% | BTV3_VP2_CAE51090_1 |
| Double chimaeric | 2 | BTV-3 VP2 | 111 kDa | Not detected |  | BTV3_VP2_CAE51090_1 |
|  | 3 | BTV-3 VP2 | 111 kDa | Not detected |  | BTV3_VP2_CAE51090_1 |
| BTV-3 AGL-1 | 1 | BTV-3 VP2 | 111 kDa | 17 | 0.21% | BTV3_VP2_CAE51090_1 |
| Double chimaeric | 2 | BTV-3 VP2 | 111 kDa | 14 | 0.14% | BTV3_VP2_CAE51090_1 |
|  | 3 | BTV-3 VP2 | 111 kDa | Not detected |  | BTV3_VP2_CAE51090_1 |

REFERENCES

COETZER, J. A. W. & GUTHRIE, A. J. (2004) African horse sickness. In: Infectious Diseases of Livestock 2nd ed. Oxford University Press Southern Africa, Cape Town, 1231-1246.

DEMAULA, C. D., BONNEAU, K. R. & MACLACHLAN, N. J. 2000. Changes in the outer capsid proteins of bluetongue virus serotype ten that abrogate neutralization by monoclonal antibodies. Virus Res, 67, 59-66.

HUISMANS, H. & ERASMUS, B. 1981. Identification of the serotype-specific and group-specific antigens of bluetongue virus. Onderstepoort J Vet Res, 48, 51-58.

MERTENS, P. P., DIPROSE, J., MAAN, S., SINGH, K. P., ATTOUI, H. & SAMUEL, A. R. 2004. Bluetongue virus replication, molecular and structural biology. Vet Ital, 40, 426-37.

PEARSON, L. D. & ROY, P. 1993. Genetically engineered multi-component virus-like particles as veterinary vaccines. Immunology and Cell Biology 71: 381-389.

SAINSBURY, F., THUENEMANN, E. C. & LOMONOSSOFF, G. P. 2009. pEAQ: versatile expression vectors for easy and quick transient expression of heterologous proteins in plants. Plant Biotechnol., 7, 682-693.

SHEVCHENKO, A., TOMAS, H., HAVLIŠ, J., OLSEN V. J. & MANN, M. (2007) In-gel digestion for mass spectrometric characterization of proteins and proteomes. Nature Protocols. 1, 2856-2860.

STRASSER R, STADLMANN J, SCHÄHS M, STIEGLER G, QUENDLER H, MACH L, GLÖSSL J, WETERINGS K, PABST M & STEINKELLER H, 2008. Generation of glycol-engineered *Nicotiana benthamiana* for the production of monoclonal antibodies with a homogenous human N-like N-glycan structure. Plant Biotechnology Journal 6: 392-402.

THUENEMANN, E. C., MEYERS, A. E., VERWEY, J., RYBICKI, E. P. & LOMONOSSOFF, G. P. 2013. A method for rapid production of heteromultimeric protein complexes in plants: assembly of protective bluetongue virus-like particles. Plant Biotechnology Journal, n/a-n/a.

The invention claimed is:

1. A method of producing a chimaeric African Horse Sickness Virus (AHSV) VLP in a plant cell, the method comprising:
   (i) providing codon-optimised nucleotide sequences encoding AHSV VP2, VP3, VP5 and VP7 structural proteins, wherein at least one of the VP2, VP3, VP5 and VP7 structural proteins is selected from a first AHSV serotype and at least one of the VP2, VP3, VP5 and VP7 structural proteins is selected from a second AHSV serotype of the same AHSV species;
   (ii) cloning the codon-optimised nucleotide sequences into at least one expression vector adapted to express the structural proteins in a plant cell;
   (iii) transforming or infiltrating the plant cell with the at least one expression vector of step (ii);
   (iv) co-expressing the VP2, VP3, VP5 and VP7 structural proteins in the plant cell, such that the expressed structural proteins assemble to form the chimaeric AHSV VLP; and
   (v) recovering the chimaeric AHSV VLP from the plant cell.

2. The method of claim 1, wherein in step (i) at least one of the VP2, VP3, VP5 and VP7 structural proteins is selected from a third AHSV serotype.

3. The method of claim 2, wherein at least one of the VP2, VP3, VP5 and VP7 structural proteins is selected from a fourth AHSV serotype.

4. The method of claim 1, wherein the structural proteins are transiently expressed in the plant cell.

5. The method of claim 1, wherein the at least one expression vector includes a promoter and/or other regulatory sequences, operably linked to each nucleotide sequence encoding each structural protein.

6. The method of claim 1, wherein in step (iii) the at least one expression vector is transformed into the plant cell in a ratio of 1:1:1:1 or a ratio of 1:1:2:1 or a ratio of 2:1:2:1 of the nucleotide sequences encoding VP2:VP3:VP5:VP7.

7. The method of claim 1, wherein the plant cell is a *Nicotiana benthamiana* cell.

8. The method of claim 1, wherein the plant cell is a mutant *N. benthamiana* dXT/FT tobacco cell, which facilitates mammalian-like or human-like glycosylation of polypeptides.

9. The method of claim 1, wherein the expression of the AHSV VP2, VP3, VP5 and VP7 structural proteins in the plant cell is mediated by *Agrobacterium* AGL-1, LBA4404 or GV3101 pMP90.

* * * * *

SEQUENCE LISTING

```
<160> NUMBER OF SEQ ID NOS: 84

<210> SEQ ID NO 1
<211> LENGTH: 901
<212> TYPE: PRT
<213> ORGANISM: Bluetongue virus

<400> SEQUENCE: 1

Met Ala Ala Gln Asn Glu Gln Arg Pro Glu Arg Ile Lys Thr Thr Pro
1               5                   10                  15

Tyr Leu Glu Gly Asp Val Leu Ser Ser Asp Ser Gly Pro Leu Leu Ser
            20                  25                  30

Val Phe Ala Leu Gln Glu Ile Met Gln Lys Val Arg Gln Val Gln Ala
        35                  40                  45

Asp Tyr Met Thr Ala Thr Arg Glu Val Asp Phe Thr Val Pro Asp Val
    50                  55                  60

Gln Lys Ile Leu Asp Asp Ile Lys Ala Leu Ala Ala Glu Gln Val Tyr
65                  70                  75                  80

Lys Ile Val Lys Val Pro Ser Ile Ser Phe Arg His Ile Val Met Gln
                85                  90                  95

Ser Arg Asp Arg Val Leu Arg Val Asp Thr Tyr Tyr Glu Glu Met Ser
            100                 105                 110

Gln Val Gly Asp Val Ile Thr Glu Asp Glu Pro Glu Lys Phe Tyr Ser
        115                 120                 125
```

```
Thr Ile Ile Lys Lys Val Arg Phe Ile Arg Gly Lys Gly Ser Phe Ile
        130                 135                 140

Leu His Asp Ile Pro Thr Arg Asp His Arg Gly Met Glu Val Ala Glu
145                 150                 155                 160

Pro Glu Val Leu Gly Val Glu Phe Lys Asn Val Leu Pro Val Leu Thr
                165                 170                 175

Ala Glu His Arg Ala Met Ile Gln Asn Ala Leu Asp Gly Ser Ile Ile
            180                 185                 190

Glu Asn Gly Asn Val Ala Thr Arg Asp Val Asp Val Phe Ile Gly Ala
        195                 200                 205

Cys Ser Glu Pro Ile Tyr Arg Ile Tyr Asn Arg Leu Gln Gly Tyr Ile
210                 215                 220

Glu Ala Val Gln Leu Gln Glu Leu Arg Asn Ser Ile Gly Trp Leu Glu
225                 230                 235                 240

Arg Leu Gly Gln Arg Lys Arg Ile Thr Tyr Ser Gln Glu Val Leu Thr
                245                 250                 255

Asp Phe Arg Arg Gln Asp Thr Ile Trp Val Leu Ala Leu Gln Leu Pro
            260                 265                 270

Val Asn Pro Gln Val Val Trp Asp Val Pro Arg Ser Ser Ile Ala Asn
        275                 280                 285

Leu Ile Met Asn Ile Ala Thr Cys Leu Pro Thr Gly Glu Tyr Ile Ala
290                 295                 300

Pro Asn Pro Arg Ile Ser Ser Ile Thr Leu Thr Gln Arg Ile Thr Thr
305                 310                 315                 320

Thr Gly Pro Phe Ala Ile Leu Thr Gly Ser Thr Pro Thr Ala Gln Gln
                325                 330                 335

Leu Asn Asp Val Arg Lys Ile Tyr Leu Ala Leu Met Phe Pro Gly Gln
            340                 345                 350

Ile Ile Leu Asp Leu Lys Ile Asp Pro Gly Glu Arg Met Asp Pro Ala
        355                 360                 365

Val Arg Met Val Ala Gly Val Val Gly His Leu Leu Phe Thr Ala Gly
370                 375                 380

Gly Arg Phe Thr Asn Leu Thr Gln Asn Met Ala Arg Gln Leu Asp Ile
385                 390                 395                 400

Ala Leu Asn Asp Tyr Leu Leu Tyr Met Tyr Asn Thr Arg Val Gln Val
                405                 410                 415

Asn Tyr Gly Pro Thr Gly Glu Pro Leu Asp Phe Gln Ile Gly Arg Asn
            420                 425                 430

Gln Tyr Asp Cys Asn Val Phe Arg Ala Asp Phe Ala Thr Gly Thr Gly
        435                 440                 445

Tyr Asn Gly Trp Ala Thr Ile Asp Val Glu Tyr Arg Asp Pro Ala Pro
450                 455                 460

Tyr Val His Ala Gln Arg Tyr Ile Arg Tyr Cys Gly Ile Asp Ser Arg
465                 470                 475                 480

Glu Leu Ile Asn Pro Thr Thr Tyr Gly Ile Gly Met Thr Tyr His Cys
                485                 490                 495

Tyr Asn Glu Met Leu Arg Met Leu Val Ala Ala Gly Lys Asp Ser Glu
            500                 505                 510

Ala Ala Tyr Phe Arg Ser Met Leu Pro Phe His Met Val Arg Phe Ala
        515                 520                 525

Arg Ile Asn Gln Ile Ile Asn Glu Asp Leu His Ser Val Phe Ser Leu
530                 535                 540
```

```
Pro Asp Asp Met Phe Asn Ala Leu Leu Pro Asp Leu Ile Ala Gly Ala
545                 550                 555                 560

His Gln Asn Ala Asp Pro Val Val Leu Asp Val Ser Trp Ile Ser Leu
            565                 570                 575

Trp Phe Ala Phe Asn Arg Ser Phe Glu Pro Thr His Arg Asn Glu Met
                580                 585                 590

Leu Glu Ile Ala Pro Leu Ile Glu Ser Val Tyr Ala Ser Glu Leu Ser
            595                 600                 605

Val Met Lys Val Asp Met Arg His Leu Ser Leu Met Gln Arg Arg Phe
610                 615                 620

Pro Asp Val Leu Ile Gln Ala Arg Pro Ser His Phe Trp Lys Ala Val
625                 630                 635                 640

Leu Asn Asp Ser Pro Glu Ala Val Lys Ala Val Met Asn Leu Ser His
                645                 650                 655

Ser His Asn Phe Ile Asn Ile Arg Asp Met Met Arg Trp Val Leu Leu
                660                 665                 670

Pro Ser Leu Gln Pro Ser Leu Lys Leu Ala Leu Glu Glu Ala Trp
            675                 680                 685

Ala Ala Ala Asn Asp Phe Glu Asp Leu Met Leu Thr Asp Gln Val Tyr
690                 695                 700

Met His Arg Asp Met Leu Pro Glu Pro Arg Leu Asp Asp Ile Glu Arg
705                 710                 715                 720

Phe Arg Gln Glu Gly Phe Tyr Tyr Thr Asn Met Leu Glu Ala Pro Pro
                725                 730                 735

Glu Ile Asp Arg Val Val Gln Tyr Thr Tyr Glu Ile Ala Arg Leu Gln
            740                 745                 750

Ala Asn Met Gly Gln Phe Arg Ala Ala Leu Arg Arg Ile Met Asp Asp
755                 760                 765

Asp Asp Trp Val Arg Phe Gly Val Leu Arg Thr Val Arg Val Lys
770                 775                 780

Phe Phe Asp Ala Arg Pro Pro Asp Asp Ile Leu Gln Gly Leu Pro Phe
785                 790                 795                 800

Ser Tyr Asp Thr Asn Glu Lys Gly Gly Leu Ser Tyr Ala Thr Ile Lys
                805                 810                 815

Tyr Ala Thr Glu Thr Thr Ile Phe Tyr Leu Ile Tyr Asn Val Glu Phe
            820                 825                 830

Ser Asn Thr Pro Asp Ser Leu Val Leu Ile Asn Pro Thr Tyr Thr Met
            835                 840                 845

Thr Lys Val Phe Ile Asn Lys Arg Ile Val Glu Arg Val Arg Val Gly
850                 855                 860

Gln Ile Leu Ala Val Leu Asn Arg Arg Phe Val Ala Tyr Lys Gly Lys
865                 870                 875                 880

Met Arg Ile Met Asp Ile Thr Gln Ser Leu Lys Met Gly Thr Lys Leu
                885                 890                 895

Ala Ala Pro Thr Val
            900

<210> SEQ ID NO 2
<211> LENGTH: 901
<212> TYPE: PRT
<213> ORGANISM: Bluetongue virus

<400> SEQUENCE: 2

Met Ala Ala Gln Asn Glu Gln Arg Pro Glu Arg Ile Lys Thr Thr Pro
1               5                   10                  15
```

```
Tyr Leu Glu Gly Asp Val Leu Ser Ser Asp Ser Gly Pro Leu Leu Ser
         20                  25                  30

Val Phe Ala Leu Gln Glu Ile Met Gln Lys Val Arg Gln Val Gln Ala
             35                  40                  45

Asp Tyr Met Thr Ala Thr Arg Glu Val Asp Phe Thr Val Pro Asp Val
 50                  55                  60

Gln Lys Ile Leu Asp Asp Ile Lys Ala Leu Ala Ala Glu Gln Val Tyr
 65                  70                  75                  80

Lys Ile Val Lys Val Pro Ser Ile Ser Phe Arg His Ile Val Met Gln
                 85                  90                  95

Ser Arg Asp Arg Val Leu Arg Val Asp Thr Tyr Tyr Glu Glu Met Ser
            100                 105                 110

Gln Val Gly Asp Val Ile Thr Glu Asp Glu Pro Glu Lys Phe Tyr Ser
            115                 120                 125

Thr Ile Ile Lys Lys Val Arg Phe Ile Arg Gly Lys Gly Ser Phe Ile
130                 135                 140

Leu His Asp Ile Pro Thr Arg Asp His Arg Gly Met Glu Val Ala Glu
145                 150                 155                 160

Pro Glu Val Leu Gly Val Glu Phe Lys Asn Val Leu Pro Val Leu Thr
                165                 170                 175

Ala Glu His Arg Ala Met Ile Gln Asn Ala Leu Asp Gly Ser Ile Ile
            180                 185                 190

Glu Asn Gly Asn Val Ala Thr Arg Asp Val Asp Val Phe Ile Gly Ala
            195                 200                 205

Cys Ser Glu Pro Ile Tyr Arg Ile Tyr Asn Arg Leu Gln Gly Tyr Ile
210                 215                 220

Glu Ala Val Gln Leu Gln Glu Leu Arg Asn Ser Ile Gly Trp Leu Glu
225                 230                 235                 240

Arg Leu Gly Gln Arg Lys Arg Ile Thr Tyr Ser Gln Glu Val Leu Thr
                245                 250                 255

Asp Phe Arg Arg Gln Asp Thr Ile Trp Val Leu Ala Leu Gln Leu Pro
            260                 265                 270

Val Asn Pro Gln Val Val Trp Asp Val Pro Arg Ser Ser Ile Ala Asn
            275                 280                 285

Leu Ile Met Asn Ile Ala Thr Cys Leu Pro Thr Gly Glu Tyr Ile Ala
290                 295                 300

Pro Asn Pro Arg Ile Ser Ser Ile Thr Leu Thr Gln Arg Ile Thr Thr
305                 310                 315                 320

Thr Gly Pro Phe Ala Ile Leu Thr Gly Ser Thr Pro Thr Ala Gln Gln
                325                 330                 335

Leu Asn Asp Val Arg Lys Ile Tyr Leu Ala Leu Met Phe Pro Gly Gln
            340                 345                 350

Ile Ile Leu Asp Leu Lys Ile Asp Pro Gly Glu Arg Met Asp Pro Ala
            355                 360                 365

Val Arg Met Val Ala Gly Val Gly His Leu Leu Phe Thr Ala Gly
            370                 375                 380

Gly Arg Phe Thr Asn Leu Thr Gln Asn Met Ala Arg Gln Leu Asp Ile
385                 390                 395                 400

Ala Leu Asn Asp Tyr Leu Leu Tyr Met Tyr Asn Thr Arg Val Gln Val
                405                 410                 415

Asn Tyr Gly Pro Thr Gly Glu Pro Leu Asp Phe Gln Ile Gly Arg Asn
            420                 425                 430
```

```
Gln Tyr Asp Cys Asn Val Phe Arg Ala Asp Phe Ala Thr Gly Thr Gly
            435                 440                 445

Tyr Asn Gly Trp Ala Thr Ile Asp Val Glu Tyr Arg Asp Pro Ala Pro
    450                 455                 460

Tyr Val His Ala Gln Arg Tyr Ile Arg Tyr Cys Gly Ile Asp Ser Arg
465                 470                 475                 480

Glu Leu Ile Asn Pro Thr Thr Tyr Gly Ile Gly Met Thr Tyr His Cys
                485                 490                 495

Tyr Asn Glu Met Leu Arg Met Leu Val Ala Ala Gly Lys Asp Ser Glu
                500                 505                 510

Ala Ala Tyr Phe Arg Ser Met Leu Pro Phe His Met Val Arg Phe Ala
            515                 520                 525

Arg Ile Asn Gln Ile Ile Asn Glu Asp Leu His Ser Val Phe Ser Leu
        530                 535                 540

Pro Asp Asp Val Phe Asn Ala Leu Leu Pro Asp Leu Ile Ala Gly Ala
545                 550                 555                 560

His Gln Asn Ala Asp Pro Val Val Leu Asp Val Ser Trp Ile Ser Leu
                565                 570                 575

Trp Phe Ala Phe Asn Arg Ser Phe Glu Pro Thr His Arg Asn Glu Met
            580                 585                 590

Leu Glu Ile Ala Pro Leu Ile Glu Ser Val Tyr Ala Ser Glu Leu Ser
        595                 600                 605

Val Met Lys Val Asp Met Arg His Leu Ser Leu Met Gln Arg Arg Phe
    610                 615                 620

Pro Asp Val Leu Ile Gln Ala Arg Pro Ser His Phe Trp Lys Ala Val
625                 630                 635                 640

Leu Asn Asp Ser Pro Glu Ala Val Lys Ala Val Met Asn Leu Ser His
                645                 650                 655

Ser His Asn Phe Ile Asn Ile Arg Asp Met Met Arg Trp Val Leu Leu
            660                 665                 670

Pro Ser Leu Gln Pro Ser Leu Lys Leu Ala Leu Glu Glu Glu Ala Trp
        675                 680                 685

Ala Ala Ala Asn Asp Phe Glu Asp Leu Met Leu Thr Asp Gln Val Tyr
    690                 695                 700

Met His Arg Asp Met Leu Pro Glu Pro Arg Leu Asp Asp Ile Glu Arg
705                 710                 715                 720

Phe Arg Gln Glu Gly Phe Tyr Tyr Thr Asn Met Leu Glu Ala Pro Pro
                725                 730                 735

Glu Ile Asp Arg Val Val Gln Tyr Thr Tyr Glu Ile Ala Arg Leu Gln
            740                 745                 750

Ala Asn Met Gly Gln Phe Arg Ala Ala Leu Arg Arg Ile Met Asp Asp
        755                 760                 765

Asp Asp Trp Val Arg Phe Gly Gly Val Leu Arg Thr Val Arg Val Lys
770                 775                 780

Phe Phe Asp Ala Arg Pro Pro Asp Ile Leu Gln Gly Leu Pro Phe
785                 790                 795                 800

Ser Tyr Asp Thr Asn Glu Lys Gly Gly Leu Ser Tyr Ala Thr Ile Lys
                805                 810                 815

Tyr Ala Thr Glu Thr Thr Ile Phe Tyr Leu Ile Tyr Asn Val Glu Phe
            820                 825                 830

Ser Asn Thr Pro Asp Ser Leu Val Leu Ile Asn Pro Thr Tyr Thr Met
        835                 840                 845

Thr Lys Val Phe Ile Asn Lys Arg Ile Val Glu Arg Val Arg Val Gly
```

-continued

```
            850                 855                 860
Gln Ile Leu Ala Val Leu Asn Arg Arg Phe Val Ala Tyr Lys Gly Lys
865                 870                 875                 880

Met Arg Ile Met Asp Ile Thr Gln Ser Leu Lys Met Gly Thr Lys Leu
                885                 890                 895

Ala Ala Pro Thr Val
            900

<210> SEQ ID NO 3
<211> LENGTH: 526
<212> TYPE: PRT
<213> ORGANISM: Bluetongue virus

<400> SEQUENCE: 3

Met Gly Lys Ile Ile Lys Ser Leu Ser Arg Phe Gly Lys Lys Val Gly
1               5                   10                  15

Asn Ala Leu Thr Ser Asn Thr Ala Lys Lys Ile Tyr Ser Thr Ile Gly
                20                  25                  30

Lys Ala Ala Glu Arg Phe Ala Glu Ser Glu Ile Gly Ser Ala Ala Ile
            35                  40                  45

Asp Gly Leu Val Gln Gly Ser Val His Ser Leu Met Thr Gly Glu Ser
    50                  55                  60

Tyr Gly Glu Ser Val Lys Gln Ala Val Leu Leu Asn Val Met Gly Ser
65                  70                  75                  80

Gly Glu Glu Leu Pro Asp Pro Leu Ser Pro Gly Glu Arg Gly Met Gln
                85                  90                  95

Thr Lys Ile Arg Glu Leu Glu Asp Glu Gln Arg Asn Glu Leu Ile Arg
            100                 105                 110

Leu Lys Tyr Asn Asp Lys Ile Lys Gln Lys Phe Gly Lys Glu Leu Glu
        115                 120                 125

Glu Val Tyr Glu Phe Met Asn Gly Val Ala Lys Gln Glu Glu Asp Glu
    130                 135                 140

Glu Lys His Tyr Asp Val Leu Lys Lys Ala Val Asn Ser Tyr Asp Lys
145                 150                 155                 160

Ile Leu Thr Glu Glu Lys Gln Met Arg Ile Leu Ala Thr Ala Leu
                165                 170                 175

Gln Lys Glu Val Lys Glu Arg Thr Gly Thr Glu Ala Val Met Val Lys
            180                 185                 190

Glu Tyr Arg Asn Lys Ile Asp Ala Leu Lys Glu Ala Ile Glu Val Glu
        195                 200                 205

Arg Asp Gly Met Gln Glu Glu Ala Ile Gln Glu Ile Ala Gly Met Thr
    210                 215                 220

Ala Asp Val Leu Glu Ala Ala Ser Glu Glu Val Pro Leu Ile Gly Ala
225                 230                 235                 240

Gly Met Ala Thr Ala Val Ala Thr Gly Arg Ala Ile Glu Gly Ala Tyr
                245                 250                 255

Lys Leu Lys Lys Val Ile Asn Ala Leu Ser Gly Ile Asp Leu Thr His
            260                 265                 270

Leu Arg Thr Pro Lys Ile Glu Pro Thr Ile Val Ser Thr Val Leu Asp
        275                 280                 285

His Lys Phe Lys Asp Ile Pro Asp Glu Met Leu Ala Val Ser Val Leu
    290                 295                 300

Ser Lys Asn Arg Ala Ile Glu Glu Asn His Lys Glu Ile Ile His Leu
305                 310                 315                 320
```

```
Lys Asn Glu Ile Leu Pro Arg Phe Lys Lys Ala Met Asp Glu Glu Lys
                325                 330                 335

Glu Ile Cys Gly Ile Glu Asp Lys Lys Ile His Pro Lys Val Met Met
            340                 345                 350

Lys Phe Lys Ile Pro Arg Thr Gln Gln Pro Gln Ile His Ile Tyr Ser
        355                 360                 365

Ala Pro Trp Asp Ser Asp Val Phe Phe His Cys Ile Ser His
370                 375                 380

His His Ala Asn Glu Ser Phe Phe Ile Gly Phe Asp Leu Gly Ile Asp
385                 390                 395                 400

Leu Val His Tyr Glu Asp Leu Thr Ala His Trp His Ala Leu Gly Ala
                405                 410                 415

Ala Gln Ala Ala Val Gly Arg Ser Leu Asn Glu Val Tyr Lys Glu Phe
            420                 425                 430

Leu Asn Leu Ala Ile Asn Asn Thr Tyr Ser Ser Gln Met His Ala Arg
        435                 440                 445

Arg Met Ile Arg Ser Lys Thr Val His Pro Ile Tyr Leu Gly Ser Leu
450                 455                 460

His Tyr Asp Ile Ser Phe Ser Thr Leu Arg Ser Asn Ala Gln Arg Ile
465                 470                 475                 480

Val Tyr Asp Glu Glu Leu Gln Met His Ile Leu Arg Gly Pro Leu His
                485                 490                 495

Phe Gln Arg Arg Ala Ile Leu Gly Ala Ile Lys His Gly Val Lys Ile
            500                 505                 510

Leu Gly Thr Glu Val Asp Ile Pro Leu Phe Leu Arg Asn Ala
        515                 520                 525

<210> SEQ ID NO 4
<211> LENGTH: 526
<212> TYPE: PRT
<213> ORGANISM: Bluetongue virus

<400> SEQUENCE: 4

Met Gly Lys Ile Ile Lys Ser Leu Ser Arg Phe Gly Lys Lys Val Gly
1               5                   10                  15

Asn Ala Leu Thr Ser Asn Thr Ala Lys Lys Ile Tyr Ser Thr Ile Gly
                20                  25                  30

Lys Ala Ala Glu Arg Phe Ala Glu Ser Glu Ile Gly Ser Ala Ala Ile
            35                  40                  45

Asp Gly Leu Val Gln Gly Ser Val His Ser Leu Met Thr Gly Glu Ser
        50                  55                  60

Tyr Gly Glu Ser Val Lys Gln Ala Val Leu Leu Asn Val Met Gly Ser
65                  70                  75                  80

Gly Glu Glu Leu Pro Asp Pro Leu Ser Pro Gly Glu Arg Gly Met Gln
                85                  90                  95

Thr Lys Ile Arg Glu Leu Glu Asp Glu Gln Arg Ser Glu Leu Ile Arg
            100                 105                 110

Leu Lys Tyr Asn Asp Lys Ile Lys Gln Lys Phe Gly Lys Glu Leu Glu
        115                 120                 125

Glu Val Tyr Glu Phe Met Asn Gly Val Ala Lys Gln Glu Glu Asp Glu
    130                 135                 140

Glu Lys His Tyr Asp Val Leu Lys Lys Ala Val Asn Ser Tyr Asp Lys
145                 150                 155                 160

Ile Leu Thr Glu Glu Glu Lys Gln Met Arg Ile Leu Ala Thr Ala Leu
                165                 170                 175
```

Gln Lys Glu Val Lys Glu Arg Thr Gly Thr Glu Ala Val Met Val Lys
            180                 185                 190

Glu Tyr Arg Asn Lys Ile Asp Ala Leu Lys Glu Ala Ile Glu Val Glu
            195                 200                 205

Arg Asp Gly Met Gln Glu Glu Ala Ile Gln Ile Ala Gly Met Thr
210                 215                 220

Ala Asp Val Leu Glu Ala Ala Ser Glu Glu Val Pro Leu Ile Gly Ala
225                 230                 235                 240

Gly Met Ala Thr Ala Val Ala Thr Gly Arg Ala Ile Glu Gly Ala Tyr
            245                 250                 255

Lys Leu Lys Lys Val Ile Asn Ala Leu Ser Gly Ile Asp Leu Thr His
            260                 265                 270

Leu Arg Thr Pro Lys Ile Glu Pro Thr Ile Val Ser Thr Val Leu Asp
            275                 280                 285

His Lys Phe Lys Asp Ile Pro Asp Glu Met Leu Ala Val Ser Val Leu
            290                 295                 300

Ser Lys Asn Arg Ala Ile Glu Glu Asn His Lys Glu Ile Ile His Leu
305                 310                 315                 320

Lys Asn Glu Ile Leu Pro Arg Phe Lys Lys Ala Met Asp Glu Lys
            325                 330                 335

Glu Ile Cys Gly Ile Glu Asp Lys Lys Ile His Pro Lys Val Met Met
            340                 345                 350

Lys Phe Lys Ile Pro Arg Thr Gln Gln Pro Gln Ile His Ile Tyr Ser
            355                 360                 365

Ala Pro Trp Asp Ser Asp Val Phe Phe His Cys Ile Ser His
            370                 375                 380

His His Ala Asn Glu Ser Phe Phe Ile Gly Phe Asp Leu Gly Ile Asp
385                 390                 395                 400

Leu Val His Tyr Glu Asp Leu Thr Ala His Trp His Ala Leu Gly Ala
            405                 410                 415

Ala Gln Ala Ala Val Gly Arg Ser Leu Asn Glu Val Tyr Lys Glu Phe
            420                 425                 430

Leu Asn Leu Ala Ile Asn Asn Thr Tyr Ser Ser Gln Met His Ala Arg
            435                 440                 445

Arg Met Ile Arg Ser Lys Thr Val His Pro Ile Tyr Leu Gly Ser Leu
450                 455                 460

His Tyr Asp Ile Ser Phe Ser Thr Leu Arg Ser Asn Ala Gln Arg Ile
465                 470                 475                 480

Val Tyr Asp Glu Glu Leu Gln Met His Ile Leu Arg Gly Pro Leu His
            485                 490                 495

Phe Gln Arg Arg Ala Ile Leu Gly Ala Ile Lys His Gly Val Lys Ile
            500                 505                 510

Leu Gly Thr Glu Val Asp Ile Pro Leu Phe Leu Arg Asn Ala
            515                 520                 525

<210> SEQ ID NO 5
<211> LENGTH: 349
<212> TYPE: PRT
<213> ORGANISM: Bluetongue virus

<400> SEQUENCE: 5

Met Asp Thr Ile Ala Ala Arg Ala Leu Thr Val Met Arg Ala Cys Ala
1               5                   10                  15

Thr Leu Gln Glu Ala Arg Ile Val Leu Glu Ala Asn Val Met Glu Ile 20                  25                  30

Leu Gly Ile Ala Ile Asn Arg Tyr Asn Gly Leu Thr Leu Arg Gly Val
             35                  40                  45

Thr Met Arg Pro Thr Ser Leu Ala Gln Arg Asn Glu Met Phe Phe Met
 50                  55                  60

Cys Leu Asp Met Met Leu Ser Ala Ala Gly Ile Asn Val Gly Pro Ile
 65                  70                  75                  80

Ser Pro Asp Tyr Thr Gln His Met Ala Thr Ile Gly Val Leu Ala Thr
                 85                  90                  95

Pro Glu Ile Pro Phe Thr Thr Glu Ala Ala Asn Glu Ile Ala Arg Val
                100                 105                 110

Thr Gly Glu Thr Ser Thr Trp Gly Pro Ala Arg Gln Pro Tyr Gly Phe
            115                 120                 125

Phe Leu Glu Thr Glu Thr Phe Gln Pro Gly Arg Trp Phe Met Arg
            130                 135                 140

Ala Ala Gln Ala Val Thr Ala Val Val Cys Gly Pro Asp Met Ile Gln
145                 150                 155                 160

Val Ser Leu Asn Ala Gly Ala Arg Gly Asp Val Gln Ile Phe Gln
                165                 170                 175

Gly Arg Asn Asp Pro Met Met Ile Tyr Leu Val Trp Arg Arg Ile Glu
                180                 185                 190

Asn Phe Ala Met Ala Gln Gly Asn Ser Gln Gln Thr Gln Ala Gly Val
            195                 200                 205

Thr Val Ser Val Gly Gly Val Asp Met Arg Ala Gly Arg Ile Ile Ala
            210                 215                 220

Trp Asp Gly Gln Ala Ala Leu His Val His Asn Pro Thr Gln Gln Asn
225                 230                 235                 240

Ala Met Val Gln Ile Gln Val Val Phe Tyr Ile Ser Met Asp Lys Thr
                245                 250                 255

Leu Asn Gln Tyr Pro Ala Leu Thr Ala Glu Ile Phe Asn Val Tyr Ser
                260                 265                 270

Phe Arg Asp His Thr Trp His Gly Leu Arg Thr Ala Ile Leu Asn Arg
            275                 280                 285

Thr Thr Leu Pro Asn Met Leu Pro Pro Ile Phe Pro Pro Asn Asp Arg
            290                 295                 300

Asp Ser Ile Leu Thr Leu Leu Leu Ser Thr Leu Ala Asp Val Tyr
305                 310                 315                 320

Thr Val Leu Arg Pro Glu Phe Ala Ile His Gly Val Asn Pro Met Pro
                325                 330                 335

Gly Pro Leu Thr Arg Ala Ile Ala Arg Ala Ala Tyr Val
            340                 345

<210> SEQ ID NO 6
<211> LENGTH: 349
<212> TYPE: PRT
<213> ORGANISM: Bluetongue virus

<400> SEQUENCE: 6

Met Asp Thr Ile Ala Ala Arg Ala Leu Thr Val Met Arg Ala Cys Ala
 1               5                  10                  15

Thr Leu Gln Glu Ala Arg Ile Val Leu Glu Ala Asn Val Met Glu Ile
                20                  25                  30

Leu Gly Ile Ala Ile Asn Arg Tyr Asn Gly Leu Thr Leu Arg Gly Val
             35                  40                  45

```
Thr Met Arg Pro Thr Ser Leu Ala Gln Arg Asn Glu Met Phe Phe Met
    50                  55                  60

Cys Leu Asp Met Met Leu Ser Ala Ala Gly Ile Asn Val Gly Pro Ile
 65                  70                  75                  80

Ser Pro Asp Tyr Thr Gln His Met Ala Thr Ile Gly Val Leu Ala Thr
                 85                  90                  95

Pro Glu Ile Pro Phe Thr Thr Glu Ala Ala Asn Glu Ile Ala Arg Val
            100                 105                 110

Thr Gly Glu Thr Ser Thr Trp Gly Pro Ala Arg Gln Pro Tyr Gly Phe
            115                 120                 125

Phe Leu Glu Thr Glu Thr Phe Gln Pro Gly Arg Trp Phe Met Arg
130                 135                 140

Ala Ala Gln Ala Val Thr Ala Val Val Cys Gly Pro Asp Met Ile Gln
145                 150                 155                 160

Val Ser Leu Asn Ala Gly Ala Arg Gly Asp Val Gln Ile Phe Gln
                165                 170                 175

Gly Arg Asn Asp Pro Met Met Ile Tyr Leu Val Trp Arg Ile Glu
            180                 185                 190

Asn Phe Ala Met Ala Gln Gly Asn Ser Gln Gln Thr Gln Ala Gly Val
                195                 200                 205

Thr Val Ser Val Gly Gly Val Asp Met Arg Ala Gly Arg Ile Ile Ala
    210                 215                 220

Trp Asp Gly Gln Ala Ala Leu His Val His Asn Pro Thr Gln Gln Asn
225                 230                 235                 240

Ala Met Val Gln Ile Gln Val Val Phe Tyr Ile Ser Met Asp Lys Thr
                245                 250                 255

Leu Asn Gln Tyr Pro Ala Leu Thr Ala Glu Ile Phe Asn Val Tyr Ser
            260                 265                 270

Phe Arg Asp His Thr Trp His Gly Leu Arg Thr Ala Ile Leu Asn Arg
        275                 280                 285

Thr Thr Leu Pro Asn Met Leu Pro Pro Ile Phe Pro Pro Asn Asp Arg
290                 295                 300

Asp Ser Ile Leu Thr Leu Leu Leu Ser Thr Leu Ala Asp Val Tyr
305                 310                 315                 320

Thr Val Leu Arg Pro Glu Phe Ala Ile His Gly Val Asn Pro Met Pro
                325                 330                 335

Gly Pro Leu Thr Arg Ala Ile Ala Arg Ala Ala Tyr Val
            340                 345

<210> SEQ ID NO 7
<211> LENGTH: 961
<212> TYPE: PRT
<213> ORGANISM: Bluetongue virus

<400> SEQUENCE: 7

Met Glu Glu Leu Ala Ile Pro Ile Tyr Thr Asn Val Phe Pro Ala Glu
 1                   5                  10                  15

Leu Leu Asp Gly Tyr Asp Tyr Ile Ile Asp Val Ser Ser Arg Val Glu
                 20                  25                  30

Glu Glu Gly Asp Glu Pro Val Lys Arg His Asp Val Thr Glu Ile Pro
            35                  40                  45

Arg Asn Ser Met Phe Asp Ile Lys Asp Glu His Ile Arg Asp Ala Ile
 50                  55                  60

Ile Tyr Lys Pro Val Asn Asn Asp Gly Tyr Val Leu Pro Arg Val Leu
 65                  70                  75                  80
```

```
Asp Ile Thr Leu Lys Ala Phe Asp Asp Arg Lys Arg Val Val Leu Asn
                85                  90                  95

Asp Gly His Ser Glu Phe His Thr Lys Thr Asn Trp Val Gln Trp Met
            100                 105                 110

Ile Asp Asp Ala Met Asp Val Gln Pro Leu Lys Val Asp Ile Ala His
        115                 120                 125

Thr Arg Ser Arg Ile Ser His Ala Leu Phe Asn Cys Thr Val Arg Leu
    130                 135                 140

His Ser Lys Lys Ala Asp Thr Ala Ser Tyr His Val Glu Pro Val Glu
145                 150                 155                 160

Ile Glu Ser Trp Gly Cys Asn His Thr Trp Leu Ser Arg Ile His His
                165                 170                 175

Leu Val Asn Val Glu Leu Phe His Cys Ser Gln Glu Ala Ala Tyr Thr
            180                 185                 190

Leu Lys Pro Thr Tyr Lys Ile Ile Ser Asn Ala Glu Arg Ala Ser Thr
        195                 200                 205

Ser Asp Ser Phe Asn Gly Thr Met Ile Glu Leu Gly Arg Asn His Gln
    210                 215                 220

Ile Gln Met Gly Asp Gln Gly Tyr Gln Lys Leu Lys Glu Gly Leu Val
225                 230                 235                 240

Gln Val Arg Ile Glu Gly Lys Thr Pro Leu Val Ile Gln Glu Glu Ile
                245                 250                 255

Thr Ala Leu Asn Lys Ile Arg Glu Gln Trp Ile Ala Arg Asn Phe Asp
            260                 265                 270

Gln Arg Glu Ile Lys Val Leu Asp Leu Cys Arg Leu Leu Ser Thr Ile
        275                 280                 285

Gly Arg Lys Met Cys Asn Thr Glu Glu Glu Pro Lys Asn Glu Ala Asp
    290                 295                 300

Leu Ser Val Lys Phe Gln Met Glu Leu Asp Glu Ile Phe Arg Pro Gly
305                 310                 315                 320

Asn Asn Glu Arg Thr Asn Ile Met Gly Gly Val His Arg Lys Asn
                325                 330                 335

Glu Asp Arg Phe Tyr Val Leu Ile Met Ile Ala Ala Ser Asp Thr Asn
            340                 345                 350

Lys Gly Arg Ile Trp Trp Ser Asn Pro Tyr Pro Cys Leu Arg Gly Ala
        355                 360                 365

Leu Ile Ala Ala Glu Val Gln Leu Gly Asp Val Tyr Asn Leu Leu Arg
    370                 375                 380

Asn Trp Phe Gln Trp Ser Val Arg Pro Thr Tyr Val Pro Tyr Asp Arg
385                 390                 395                 400

Asn Arg Glu Ser Asp Lys Tyr Ile Tyr Ser Arg Ile Asn Leu Phe Asp
                405                 410                 415

Ser Thr Leu Arg Pro Gly Asp Lys Ile Val His Trp Glu Tyr Lys Leu
            420                 425                 430

Leu Asn Glu Val Arg Glu Val Ser Ile Asn Lys Gly Asn Glu Cys Asp
        435                 440                 445

Leu Phe Pro Glu Asp Glu Glu Phe Thr Thr Lys Phe His Glu Ala Arg
    450                 455                 460

Tyr Thr Glu Met Lys Asn Gln Ile Ile Gln Ser Gly Trp Asn Gln Arg
465                 470                 475                 480

Asp Phe Lys Met His Lys Ile Leu Glu Asp Gly Ala Asn Val Leu Thr
                485                 490                 495
```

```
Ile Asp Phe Glu Lys Asp Ala His Ile Gly Thr Gly Ser Ala Leu Ser
                500                 505                 510

Leu Pro Asp Tyr Tyr Asn Lys Trp Ile Ile Ala Pro Met Phe Asn Ala
            515                 520                 525

Lys Leu Arg Ile Thr Glu Val Val Ile Gly Thr Ala His Thr Asp Asp
        530                 535                 540

Pro Ala Val Gly Arg Ser Ala Lys Ala Phe Thr His Asp Pro Phe Asp
545                 550                 555                 560

Leu Gln Arg Tyr Cys Leu Ala Arg Tyr Tyr Asp Val Arg Pro Gly Met
                565                 570                 575

Met Gly Arg Ala Leu Ser Lys Gln Gln Asn Met Ser Ser Met Thr Asp
            580                 585                 590

Lys Leu Ser Lys Gln Glu Asp Tyr Ala Gly Ile Val Ser Arg Arg Leu
        595                 600                 605

Glu Tyr Lys Glu Arg Glu Asn Arg Cys Leu Thr Glu Thr Ala Gln Tyr
            610                 615                 620

Val Phe Glu Lys Thr Cys Leu Tyr Val Leu Glu Leu Leu Ser Arg His
625                 630                 635                 640

Thr Met Pro Ser Glu Asp Ser Glu Val Thr Phe Glu His Pro Thr Ile
                645                 650                 655

Asp Pro Ser Val Asp Ile Glu Thr Trp Lys Ile Ile Asp Val Ser Gln
            660                 665                 670

Leu Ile Ile Phe Val Phe Asp Tyr Leu Phe Glu Asn Arg Lys Ile Val
        675                 680                 685

Arg Asp Thr Thr Glu Ala Arg Trp Thr Leu Phe Lys Ile Arg Ser Glu
690                 695                 700

Val Gly Arg Ala Arg Ile Asp Ala Ile Glu Met Thr Phe Pro Arg Phe
705                 710                 715                 720

Gly Arg Met Leu Arg Asn Ala Ser Gln Ala Lys Ile Asn Gln Asp Ile
                725                 730                 735

Ala Cys Leu Asn Phe Leu Pro Leu Leu Phe Ile Ile Gly Asp Asn Ile
            740                 745                 750

Ser Tyr Ala His Arg Gln Trp Ser Ile Pro Val Leu Leu Tyr Ala His
        755                 760                 765

Asp Ile Arg Ile Ile Pro Leu Glu Val Gly Ala Tyr Asn Asn Arg Phe
770                 775                 780

Gly Leu Thr Ser Tyr Leu Glu Tyr Met Ala Phe Phe Pro Ser Tyr Ala
785                 790                 795                 800

Thr Arg Val Ala Lys Ile Asp Glu Ser Ile Lys Glu Cys Ala Ile Ala
                805                 810                 815

Met Ala Glu Phe Tyr Met Asn Thr Asp Ile His Ser Gly Ser Val Met
            820                 825                 830

Ser Asn Val Ile Thr Thr Lys Arg Leu Leu Tyr Glu Thr Tyr Leu Ala
        835                 840                 845

Ser Leu Cys Gly Gly Tyr Ser Asp Gly Leu Leu Trp Tyr Leu Pro Ile
850                 855                 860

Thr His Pro Ser Lys Cys Leu Ala Phe Glu Val Ala Asp Asp Val
865                 870                 875                 880

Val Pro Leu Ser Val Arg Arg Glu Arg Ile Leu Ser Arg Phe Pro Leu
                885                 890                 895

Ser Ser Arg His Val Lys Gly Ile Ala Leu Ile Ser Val Asp Arg Asn
            900                 905                 910

Gln Lys Val Ser Val Gln Thr Glu Gly Ile Val Thr His Arg Leu Cys
```

```
            915                 920                 925
Lys Lys Asn Leu Leu Lys Tyr Val Cys Asp Val Ile Leu Phe Lys Phe
930                 935                 940

Ser Gly His Val Phe Gly Asn Asp Glu Met Leu Thr Lys Leu Leu Asn
945                 950                 955                 960

Val

<210> SEQ ID NO 8
<211> LENGTH: 962
<212> TYPE: PRT
<213> ORGANISM: Bluetongue virus

<400> SEQUENCE: 8

Met Asp Glu Leu Gly Ile Pro Ile Tyr Gly Arg Asn Tyr Pro Glu His
1               5                   10                  15

Leu Leu Lys Gly Tyr Glu Phe Leu Ile Asn Thr Gly Val Arg Tyr Pro
            20                  25                  30

Ser Gln Gly Gly Arg His Asp Val Ser Lys Ile Pro Glu Met Phe Ala
        35                  40                  45

Tyr Asp Ile Lys Asp Glu Gly Ile Arg Glu Ala Leu Lys Tyr Met Pro
50                  55                  60

Thr Arg Asn Asp Gly Val Val Leu Pro Arg Ile Val Asp Ile Ser Leu
65                  70                  75                  80

Lys Gly Tyr Asp Ile Arg Lys Ser Val Ile Glu Ala Asn Lys Ser Asn
                85                  90                  95

Ser Phe His Thr Asp Thr Asn Trp Val Gln Trp Met Ile Lys Asp Ser
            100                 105                 110

Met Asp Gln Gln Pro Leu Lys Ile Ser Ile Asp Glu Glu His Ser Arg
        115                 120                 125

Val Val His Ser Leu Phe Asn Cys Gln Val Lys Ile Asp Ala Lys Lys
130                 135                 140

Ala Asp Thr Leu Ser Tyr His Leu Glu Ala Ile Glu Asp Ala Glu Lys
145                 150                 155                 160

Ala Cys Leu His Thr Arg Gly Gln Leu Cys Asn His Leu Ala Arg Met
                165                 170                 175

Asp Leu Leu His Ala Ala Gln Glu Ile Ala Tyr Ala Ile Lys Pro Thr
            180                 185                 190

Tyr Gln Leu Ile Val His Ser Glu Arg Ala Ser Thr Ser Asp Asn Phe
        195                 200                 205

Glu Leu Gly Arg Gln Asp Val Ile Thr Leu Arg Gly His Arg Ile
210                 215                 220

Gln Met Gly Asp Glu Ala Tyr Thr Lys Leu Met Glu Arg Leu Val Arg
225                 230                 235                 240

Leu Thr Val Gln Gly Asn Val Pro Arg Lys Ile Gln Ser Glu Ile Glu
                245                 250                 255

Gln Leu Glu Ala Ile Arg Thr Trp Ala Thr Gly Arg Tyr Asp Pro
            260                 265                 270

Ala His Ile Asn Ser Gln Asp Leu Cys Arg Ile Leu Ser Arg Ile Gly
        275                 280                 285

Arg Ile Met Leu Asp Gln Glu Ala Glu Pro Val Asp Glu Asp Ser Leu
290                 295                 300

Ser Leu Arg Phe Gln Arg Ala Leu Asp Glu Lys Phe Arg Leu Asn Asp
305                 310                 315                 320

Ser Glu Arg Asn Lys Ile Phe Glu Pro Lys Ser His Arg Lys Asp Glu
```

-continued

```
                325                 330                 335
Asp Arg Phe Tyr Val Leu Leu Ala Ile Ala Ala Ser Asp Thr Tyr Asn
                340                 345                 350
Ser Arg Ile Trp Trp Ser Asn Pro Tyr Pro Cys Leu Arg Gly Thr Leu
                355                 360                 365
Ile Ala Ala Glu Thr Lys Leu Gly Asp Val Tyr Phe Thr Leu Arg Ser
                370                 375                 380
Trp Tyr Asp Trp Ser Val Arg Ser Ser Tyr Val Pro Arg Glu Arg Glu
385                 390                 395                 400
Arg Glu Thr Glu Lys Tyr Ile Phe Ser Lys Ile Asn Leu Phe Asp Tyr
                405                 410                 415
Glu Ala Gly Pro Ser Ser Lys Val Ile His Trp Glu Tyr Gln Leu Tyr
                420                 425                 430
Lys Arg Glu Arg Val Val Thr Leu Glu Arg Gly Asn Pro Cys Asp Leu
                435                 440                 445
Tyr Pro Asp Glu Asp Asp Glu Val Ile Ile Thr Lys Phe Asp Asp Ala
                450                 455                 460
Lys Tyr Ser Glu Met Val Gly Glu Ile Ile Asp Gly Gly Trp Asn Asp
465                 470                 475                 480
Glu Glu Phe Lys Met Tyr Lys Leu Leu Gln Glu Lys Gly Asn Val Leu
                485                 490                 495
Thr Ile Asp Phe Glu Lys Asp Thr Lys Leu Asn Ser Thr Ser Glu Val
                500                 505                 510
Val Leu Pro Asp Tyr Tyr Gly Lys Trp Ile Val Ala Pro Met Phe Asn
                515                 520                 525
Ser Lys Met Arg Ile Ile Glu Thr Glu Ile Ala Thr Asn Arg Ser Asp
                530                 535                 540
Asp Pro Met Ile Lys Arg Thr Leu Lys Pro Met Thr Asp Pro Val
545                 550                 555                 560
Glu Leu Gln Arg Tyr Thr Leu Ala Arg Tyr Tyr Asp Ile Arg Pro Gly
                565                 570                 575
Leu Met Gly Arg Ser Leu Asn Arg Thr Gln Thr Gln Ser Thr Phe Asp
                580                 585                 590
Ala Lys Val Ser Glu Leu Ser Asp Tyr Glu Lys Val Val Ser Arg Phe
                595                 600                 605
Gly Val Ile Lys Lys Pro Thr Arg Pro Cys Val Thr Leu Thr Gly Arg
                610                 615                 620
Tyr Ile Leu Glu Lys Tyr Ser Leu Leu Leu Ile Asp Ile Leu Lys Tyr
625                 630                 635                 640
His Thr Glu Val Glu Glu Asn Pro Gln Glu Glu Phe Thr His Pro Arg
                645                 650                 655
Ile Asp Leu Gln Phe Lys Phe Asn Gly Asn Thr Leu Ser Asp Leu Asn
                660                 665                 670
Gln Thr Val Val Phe Ile Val Asp Tyr Leu His Glu Lys Arg Asn Tyr
                675                 680                 685
Val Arg Ser Val Tyr Glu Ala Arg Tyr Ile Ile Ser Arg Ile Arg Ser
                690                 695                 700
Ser Thr Gly Ala Ala Arg Met Ser Ile Leu Glu Phe Tyr Phe Pro Thr
705                 710                 715                 720
Phe Ala Arg Leu Ile Ser Asn Ala Arg Glu Pro Thr Tyr Val Lys Asp
                725                 730                 735
Leu Met Ala Leu Asn Phe Leu Pro Leu Leu Phe Ile Val Gly Asp Asn
                740                 745                 750
```

```
Met Ile Tyr Lys His Arg Gln Trp Ser Ile Pro Leu Leu Tyr Thr
            755                 760                 765

Asp Arg Val Lys Val Ile Pro Leu Glu Val Gly Ser Ser Asn Asn Arg
770                 775                 780

Gln Gly Leu Val Ser Tyr Leu Glu Tyr Met Phe Phe Phe Pro Ser Leu
785                 790                 795                 800

Ala Asp Arg Thr Ser Lys Val Asp Glu Ser Met Ile Lys Val Ser Lys
            805                 810                 815

Glu Val Val Asn Tyr Tyr Met Lys Thr Thr Ile Ser Glu Gly Gly Val
            820                 825                 830

Asn Leu Asn Val Val Ser Thr Lys Ser Leu Leu Tyr Asp Ile Tyr Leu
            835                 840                 845

Ser Ser Val Cys Gly Gly Val Ser Asp Gly Val Val Trp Tyr Leu Pro
            850                 855                 860

Ile Thr His Pro Tyr Lys Cys Val Val Ala Ile Glu Val Cys Asp Asp
865                 870                 875                 880

Arg Val Pro Ala Arg Leu Arg Cys Asp Arg Leu Arg Leu Arg Phe Pro
            885                 890                 895

Leu Ser Ala Gln His Leu Lys Gly Ile Val Val Ile Gln Ile Asn Glu
            900                 905                 910

Glu Gly Gly Phe Asp Val Tyr Thr Glu Gly Ile Val Thr His Arg Val
            915                 920                 925

Cys Lys Lys Ser Leu Leu Lys His Val Cys Asp Ile Val Leu Leu Lys
            930                 935                 940

Phe His Gly His Val Phe Gly Asn Asp Glu Met Leu Thr Lys Leu Leu
945                 950                 955                 960

Asn Val

<210> SEQ ID NO 9
<211> LENGTH: 959
<212> TYPE: PRT
<213> ORGANISM: Bluetongue virus

<400> SEQUENCE: 9

Met Glu Glu Leu Val Ile Pro Val Ile Ser Arg Gln Phe Asp Lys Lys
1               5                   10                  15

Leu Val Gly Arg Tyr Glu Tyr Val Ile Glu Leu Ala Glu Pro Glu Gln
            20                  25                  30

Asp Glu Trp Thr Asn His Asp Val Thr Gln Ile Pro Gly Arg Arg Met
        35                  40                  45

Phe Asp Val Ala Gln Gln Gly Ile Arg Glu Ala Ile Tyr Lys Pro
50                  55                  60

Leu Asp Asn Asp Gly Glu Val Leu Pro Arg Ile Leu Asp Met Ser Ile
65                  70                  75                  80

Ala Cys Tyr Asp Met Arg Lys Thr Met Met Lys Lys Glu Gly Val Asp
            85                  90                  95

Phe Val Ser Asn Thr Arg Trp Leu Glu Trp Met Ile Gln Asp Ser Met
                100                 105                 110

Asp Val Gln Pro Leu Arg Val Gln Met Lys Glu Asp His Ser Thr Val
            115                 120                 125

Gln Tyr Asp Met Phe Ser Ala Lys Val His Ile Asp Ser Arg Lys Ala
        130                 135                 140

Asp Thr Thr Ser Tyr His Ala Ile Ala Val Glu Thr Lys Ala Glu Arg
145                 150                 155                 160
```

```
Lys Cys Cys His Val Arg Thr Glu Val Trp Asn Ser Val Val Arg Asn
            165                 170                 175

His Leu Phe Asn Thr Ala Gln Glu Ser Cys Tyr Thr Phe Lys Gln Thr
            180                 185                 190

Tyr Glu Leu Ile Val Asn Ser Glu Arg Leu Ser Thr Glu Glu Glu Phe
            195                 200                 205

Arg Val Gly Ala Pro Gln Phe His Thr Ile Gln Arg Asn His Arg Met
            210                 215                 220

Gln Leu Gly Asp Asn Ala Tyr Asp Lys Phe Leu Lys Gly Leu Val Gln
225                 230                 235                 240

Leu Arg Val Ser Gly Thr Thr Pro Ala Lys Ile Arg Asp Glu Val Ala
            245                 250                 255

Ala Leu Asp Val Ile Arg Asp Asn Trp Ile Arg Gly Ser Phe Asp Arg
            260                 265                 270

Ser His Ile Lys Ser Leu Glu Leu Cys Arg Leu Leu Ser Ser Ile Gly
            275                 280                 285

Arg Lys Met Val Asn Met Glu Glu Pro Lys Asp Glu Lys Asp Leu
            290                 295                 300

Ser Val Lys Phe Gln Phe Arg Leu Asp Glu Lys Phe Ser Pro Asn Asp
305                 310                 315                 320

Pro Glu Arg Asn Val Ile Phe Thr Ser Lys Thr His Arg Thr Asn Glu
            325                 330                 335

Asp Arg Phe Tyr Val Leu Leu Ile Ala Ala Ser Asp Thr Asn Asn
            340                 345                 350

Gly Arg Val Trp Trp Ser Asn Pro Tyr Pro Cys Leu Arg Gly Ala Leu
            355                 360                 365

Ile Ala Ala Glu Cys Lys Leu Gly Asp Val Tyr His Thr Leu Arg Ser
            370                 375                 380

Lys Tyr Glu Trp Gly Val Arg Pro Thr Tyr Lys Pro Lys Asp Leu Glu
385                 390                 395                 400

Arg Glu Arg Glu Lys Tyr Val Val Gly Arg Val Asn Leu Phe Asp Leu
            405                 410                 415

Glu Gly Glu Pro Ala Thr Lys Val Ile His Trp Glu Tyr Glu Leu Ile
            420                 425                 430

Ser Pro Thr Tyr Ser Val Ser Asn His Lys Gly Asn His Cys Asp Leu
            435                 440                 445

Tyr Pro Asp Asp Val Glu Ile Thr Thr Lys Phe Asn Glu Asp Arg Tyr
            450                 455                 460

Arg Glu Met Ile Gln Ser Val Ile Asp Asp Gly Trp Asp Gln Lys Asn
465                 470                 475                 480

Leu Lys Met Tyr Lys Ile Leu Glu Glu Glu Gly Asn Pro Leu Leu Tyr
            485                 490                 495

Asp Leu Glu Lys Asp Ile Lys Leu Asp Ser Gln Ser Gln Val Val Phe
            500                 505                 510

Pro Ser Tyr Tyr Asn Lys Trp Thr His Ala Pro Met Phe Asn Ala Arg
            515                 520                 525

Val Lys Pro Cys Asp Ile Glu Leu Ala Glu Arg Lys Asn Asp Asp Pro
530                 535                 540

Phe Val Lys Arg Thr Leu Lys Pro Ile Lys Ala Asp Cys Val Asp Leu
545                 550                 555                 560

Leu Arg Tyr His Met Ser His Tyr Tyr Asp Leu Arg Pro Ser Leu Lys
            565                 570                 575
```

```
Gly Val Ser Leu Ser Asn Lys Gln Thr Pro Ser Gly Ile His Gln Ala
            580                 585                 590

Leu Val Gln Asp Asp Leu Tyr Ser Arg Leu Arg Arg Arg Asp Val
        595                 600                 605

Asp Leu Asp Tyr Ser Ser Pro Cys Pro Ile Ile Thr Asn Tyr Phe Leu
    610                 615                 620

Leu Glu Lys Phe His Ile Leu Ile Leu Thr Ile Met Glu Lys His Tyr
625                 630                 635                 640

Trp Glu Leu Asp Asp Ser Asp Asp Val Tyr Glu Phe Pro Lys Ile Asp
                645                 650                 655

Ala Ser Ala Phe Glu Val Asp Gly Thr Leu Tyr Asp Ile Ser Gln Thr
            660                 665                 670

Ile Val His Met Tyr Asp Arg Phe Phe Glu Lys Arg Arg Val Leu Arg
        675                 680                 685

Ser Ile Asp Glu Ser Arg Trp Ile Leu His Leu Ile Arg Ile Ser Gln
    690                 695                 700

Gly Arg Glu Arg Leu Glu Val Ile Glu Arg Phe Phe Pro Asn Tyr Gly
705                 710                 715                 720

Lys Ala Met Arg Gln Arg Asp Phe Lys Lys Val Arg Asp Val Met Phe
                725                 730                 735

Leu Asn Phe Leu Pro Phe Phe Phe Leu Thr Gly Asp Asn Ile Ser Tyr
            740                 745                 750

Glu His Arg Gln Trp Ser Ile Pro Ile Ile Leu Tyr Ala Asp Lys Leu
        755                 760                 765

Arg Ile Leu Pro Ile Glu Val Gly Ala His Tyr Asn Arg Phe Gly Val
    770                 775                 780

Thr Cys Ile Leu Glu Leu Leu Asn Phe Phe Pro Ser Tyr Glu Lys Arg
785                 790                 795                 800

Glu Glu Lys Leu Glu Glu Asp Ile Val Leu Cys Ala Asp Ala Ile Val
                805                 810                 815

Asn Phe Tyr Leu Gln Thr Thr Ile Ser Asn Gly Gly Val Gln Thr Ser
            820                 825                 830

Ile Val Ser Thr Lys Ala Leu Leu Tyr Glu Met Tyr Leu Ser Ser Ile
        835                 840                 845

Cys Gly Gly Tyr Ser Glu Gly Val Leu Trp Tyr Leu Pro Ile Thr His
    850                 855                 860

Pro Val Lys Cys Leu Val Ala Leu Glu Val Ser Asp Ala Leu Val Gly
865                 870                 875                 880

Ala Asp Val Arg Ile Asp Lys Ile Arg Arg Phe Pro Leu Ser Ala
                885                 890                 895

Lys His Leu Lys Gly Ile Val Gln Ile Ser Val His Pro Asn Arg Thr
            900                 905                 910

Phe Ser Val Thr Thr Cys Gly Ile Val Lys His Lys Val Cys Lys Lys
        915                 920                 925

Thr Leu Leu Lys His Arg Cys Asp Val Ile Leu Leu Gln Thr Pro Gly
    930                 935                 940

Tyr Val Phe Gly Asn Asp Glu Leu Leu Thr Lys Leu Leu Asn Ile
945                 950                 955

<210> SEQ ID NO 10
<211> LENGTH: 956
<212> TYPE: PRT
<213> ORGANISM: Bluetongue virus

<400> SEQUENCE: 10
```

```
Met Glu Glu Phe Val Ile Pro Val Phe Ser Glu Arg Glu Ile Pro Tyr
1               5                   10                  15

Ala Leu Ile Asn Gln Tyr Pro Leu Ala Ile Gln Thr Asp Val Arg Val
            20                  25                  30

Val Asp Val Asp Gly Asn His Asn Leu Val Lys Ile Pro Glu Ser Asp
        35                  40                  45

Met Ile Asp Val Pro Lys Leu Asp Ile Val Ser Ala Leu Asn Tyr Lys
    50                  55                  60

Pro Thr Arg Asn Asp Gly Ile Val Val Pro Arg Leu Leu Asp Ile Thr
65                  70                  75                  80

Leu Lys Ala Tyr Asp Asp Arg Lys Ser Val Lys Asn Ala Arg Gly Val
                85                  90                  95

Asp Phe Met Thr Asp Ala Lys Trp Met Lys Trp Ala Ile Asp Asp Arg
        100                 105                 110

Met Asp Ile Gln Pro Leu Lys Ile Thr Leu Asp Glu His Tyr Ser Val
    115                 120                 125

Asn His Gln Leu Phe Asn Cys Ile Val Lys Ala Lys Thr Ala Asn Ala
        130                 135                 140

Asp Thr Ile Tyr Tyr Asp Tyr Phe Pro Leu Glu Asp Arg Ala Lys Lys
145                 150                 155                 160

Cys Asn His Thr Asn Leu Glu Leu Leu Arg Ser Leu Thr Thr Ile Glu
                165                 170                 175

Ala Phe His Ile Leu Gln Gly Ala Ala Tyr Ser Leu Lys Ser Asn Tyr
        180                 185                 190

Asp Leu Ile Ala Asn Ser Glu Arg Glu Ser Leu Glu Glu Ser Tyr Pro
    195                 200                 205

Ile Gly Ser Glu Lys Trp Val His Leu Thr Arg Arg Thr Lys Ile Gly
210                 215                 220

Asn Ser Gly Leu Ser Tyr Asn Arg Phe Ile Ser Ser Met Val Gln Val
225                 230                 235                 240

Val Val Arg Gly Lys Val Pro Asp Ile Ile Arg Gly Glu Ile Thr Gln
                245                 250                 255

Leu Asn Arg Ile Arg Thr Glu Trp Ile Gly Ala Ser Tyr Asp Arg Thr
        260                 265                 270

Arg Ile Arg Ala Leu Glu Leu Cys Asn Ile Leu Ser Ala Ile Gly Arg
    275                 280                 285

Lys Met Met Asp Thr His Glu Glu Pro Lys Asp Glu Met Asp Leu Ser
290                 295                 300

Thr Arg Phe Gln Phe Lys Leu Asp Glu Lys Phe Asn Thr Ser Asp Ser
305                 310                 315                 320

Glu His Val Asn Ile Phe Arg Thr Ser Gly Ala Ala Thr Asn Glu Gly
                325                 330                 335

Arg Phe Tyr Ala Leu Ile Ala Ile Ala Ala Thr Asp Thr Gln Lys Gly
        340                 345                 350

Arg Val Trp Arg Thr Asn Pro Tyr Pro Cys Leu Arg Gly Ala Leu Ile
    355                 360                 365

Ala Ser Glu Cys Glu Leu Gly Asp Val Tyr Tyr Thr Leu Arg His Val
370                 375                 380

Tyr Gln Trp Ser Leu Arg Pro Glu Tyr Gly Gln Arg Glu Gln Gln Leu
385                 390                 395                 400

Glu Asp Asn Lys Tyr Val Phe Gly Arg Val Asn Leu Phe Asp Ser Asp
                405                 410                 415
```

-continued

Leu Ala Val Gly Asp Gln Ile Ile His Trp Gln Tyr Glu Ile Thr Glu
            420                 425                 430

Pro Val Lys Thr Thr Tyr Asp Asp Gly Tyr Ile Cys Asn Pro Glu Glu
            435                 440                 445

Glu Asp Asp Glu Leu Leu Cys Lys Ile Asp Asp Glu Arg Tyr Lys Glu
    450                 455                 460

Met Met Glu Arg Leu Ile Glu Gly Gly Trp Asp Gln Glu Arg Phe Lys
465                 470                 475                 480

Leu His Ser Ile Leu Thr Glu Pro Asn Leu Thr Ile Asp Phe Glu
                485                 490                 495

Lys Asp Ala Tyr Leu Asn Ser Arg Ser Glu Leu Val Phe Pro Asn Tyr
            500                 505                 510

Phe Asp Lys Trp Ile Asn Ser Pro Met Phe Asn Ala Arg Leu Arg Ile
            515                 520                 525

Thr His Gly Glu Ile Gly Ser Ser Lys Thr Ile Asp Pro Trp Asn Arg
            530                 535                 540

Arg Val Val Tyr Gly Tyr Val Lys Thr Ser Ile Glu Ser Leu Asp Tyr
545                 550                 555                 560

Ala Leu Gly Arg Tyr Tyr Asp Ile Arg Leu Gln Leu Phe Gly Asp Thr
                565                 570                 575

Leu Ser Gln Lys Gln Thr Gln Ser Ala Val Phe Thr Tyr Leu Ser Glu
            580                 585                 590

Gln Asp Asp Phe Pro Ala Leu Thr Asn Tyr Ser Lys Gly Glu Ala Val
            595                 600                 605

Cys Pro His Ala Gly Gly Ala Val Tyr Thr Phe Arg Lys Val Ala Leu
610                 615                 620

Ser Leu Ile Ala Asn Tyr Glu Lys Leu Ser Pro Glu Met His Glu Gly
625                 630                 635                 640

Leu Glu His Gln Met Tyr Val His Pro Ser Ala Asn Thr Thr Tyr Gln
                645                 650                 655

Lys Gln Val Lys Asp Met Lys Asp Phe Ser Gln Leu Ile Cys Phe Ile
            660                 665                 670

Ile Asp Cys Ile Phe Glu Lys Arg Val Gln Ile Arg Gly Val Gly Glu
            675                 680                 685

Ala Arg Arg Ile Ile Tyr Leu Ile Gln Asn Ser Thr Gly Ser Gln Arg
690                 695                 700

Gln Glu Val Leu Lys Lys Thr Phe Pro Asn Phe Met Arg Ile Phe
705                 710                 715                 720

Lys Leu Arg Glu Val Lys Arg Ile Cys Asp Leu Ser Val Ile Asn Phe
                725                 730                 735

Leu Pro Leu Leu Phe Leu Val Gln Asp Asn Ile Ser Tyr Trp His Arg
            740                 745                 750

Gln Trp Ser Val Pro Met Ile Leu Phe Asp Asp Ala Val Arg Leu Ile
            755                 760                 765

Pro Val Glu Val Gly Ala Tyr Ala Asn Arg Phe Gly Leu Lys Ser Phe
770                 775                 780

Tyr Asn Phe Val Arg Phe His Pro Gly Asp Ser Lys Lys Gln Asp
785                 790                 795                 800

Ala Asp Asp Met His Lys Glu Tyr Gly Val Ala Cys Phe Lys Tyr Tyr
                805                 810                 815

Met Asn Thr Lys Ile Ser Gln Gly Gly Val Asn Val Pro Val Val Thr
            820                 825                 830

Ser Lys Leu Asp Thr Leu Lys Ile His Leu Ala Ser Leu Cys Leu Gly

```
        835                 840                 845

Leu Ala Asp Ser Ile Val Tyr Thr Leu Pro Val Ala His Pro Lys Lys
    850                 855                 860

Cys Ile Val Leu Ile Val Val Gly Asp Asp Lys Leu Asp Pro Gln Val
865                 870                 875                 880

Arg Ser Glu Gln Val Leu Ser Lys Tyr Tyr Tyr Ser Arg Arg His Ile
                885                 890                 895

Cys Gly Ile Val Ala Val Ser Val Gly Gln Glu Gly Gln Leu Gln Val
            900                 905                 910

Tyr Ser Ser Gly Ile Val Arg His Arg Ile Cys Glu Lys Ser Ile Leu
        915                 920                 925

Lys Tyr Lys Cys Lys Val Val Leu Val Arg Met Pro Gly His Val Phe
    930                 935                 940

Gly Asn Asp Glu Leu Met Thr Lys Leu Leu Asn Val
945                 950                 955

<210> SEQ ID NO 11
<211> LENGTH: 961
<212> TYPE: PRT
<213> ORGANISM: Bluetongue virus

<400> SEQUENCE: 11

Met Glu Glu Leu Ala Ile Pro Ile Tyr Thr Asn Val Phe Pro Ala Glu
1               5                   10                  15

Leu Leu Asp Gly Tyr Asp Tyr Ile Ile Asp Ile Ser Ser Arg Val Glu
            20                  25                  30

Glu Glu Gly Asp Glu Pro Val Lys Arg His Asp Val Thr Glu Ile Pro
        35                  40                  45

Arg Asn Ser Met Phe Asp Ile Lys Asp Glu His Ile Arg Asp Ala Ile
    50                  55                  60

Ile Tyr Lys Pro Val Asn Asn Asp Gly Tyr Val Leu Pro Arg Val Leu
65                  70                  75                  80

Asp Ile Thr Leu Lys Ala Phe Asp Asp Arg Lys Arg Val Ile Leu Asn
                85                  90                  95

Asp Gly His Ser Glu Phe His Thr Lys Ser Asn Trp Val Gln Trp Met
            100                 105                 110

Ile Asp Asp Ala Met Asp Val Gln Pro Leu Lys Val Asp Ile Ala His
        115                 120                 125

Thr Arg Ser Arg Ile Ser His Ala Leu Phe Asn Cys Thr Val Arg Leu
    130                 135                 140

His Ser Lys Lys Ala Asp Thr Ala Ser Tyr His Val Glu Pro Val Glu
145                 150                 155                 160

Ile Glu Ser Arg Gly Cys Asn His Thr Trp Leu Gly Arg Ile His His
                165                 170                 175

Leu Val Asn Val Glu Leu Phe His Cys Ser Gln Glu Ala Ala Tyr Ala
            180                 185                 190

Leu Lys Pro Thr Tyr Lys Ile Ile Ser Asn Ala Glu Arg Ala Ser Thr
        195                 200                 205

Ser Asp Ser Phe Asn Gly Thr Met Ile Glu Leu Gly Arg Asn His Gln
    210                 215                 220

Ile Gln Met Gly Asp Gln Gly Tyr Gln Lys Leu Lys Glu Gly Leu Val
225                 230                 235                 240

Gln Val Arg Ile Glu Gly Lys Thr Pro Leu Ala Ile Gln Glu Glu Ile
                245                 250                 255
```

```
Thr Ala Leu Asn Lys Ile Arg Glu Gln Trp Ile Ala Arg Asn Phe Asp
            260                 265                 270

Gln Arg Glu Ile Lys Val Leu Asp Leu Cys Arg Leu Leu Ser Thr Ile
        275                 280                 285

Gly Arg Lys Met Cys Asn Thr Glu Glu Pro Lys Asn Glu Ala Asp
    290                 295                 300

Leu Ser Val Lys Phe Gln Met Glu Leu Asp Glu Ile Phe Arg Pro Gly
305                 310                 315                 320

Asn Asn Glu Arg Thr Asn Ile Met Gly Gly Val His Arg Lys Asn
            325                 330                 335

Glu Asp Arg Phe Tyr Val Leu Ile Met Ile Ala Ala Ser Asp Thr Asn
        340                 345                 350

Lys Gly Arg Ile Trp Trp Ser Asn Pro Tyr Pro Cys Leu Arg Gly Ala
    355                 360                 365

Leu Ile Ala Ala Glu Val Gln Leu Gly Asp Val Tyr Asn Leu Leu Arg
370                 375                 380

Asn Trp Phe Gln Trp Ser Ile Arg Pro Thr Tyr Val Pro Tyr Asp Arg
385                 390                 395                 400

Asn Arg Glu Ser Asp Lys Tyr Ile Tyr Ser Arg Ile Asn Leu Phe Asp
            405                 410                 415

Ser Thr Leu Lys Pro Gly Asp Lys Ile Val His Trp Glu Tyr Glu Leu
        420                 425                 430

Leu Asn Glu Val Arg Glu Val Ser Ile Ser Lys Gly Asn Glu Cys Asp
    435                 440                 445

Leu Phe Pro Glu Asp Glu Glu Phe Thr Thr Lys Phe His Glu Ala Arg
450                 455                 460

Tyr Thr Glu Met Lys Asn Gln Ile Ile Gln Ser Gly Trp Asn Gln Arg
465                 470                 475                 480

Asp Phe Lys Met His Lys Ile Leu Glu Asp Gly Ala Asn Val Leu Thr
            485                 490                 495

Ile Asp Phe Glu Lys Asp Ala His Ile Gly Thr Gly Ser Ala Leu Ser
        500                 505                 510

Leu Pro Asp Tyr Tyr Asn Lys Trp Ile Ile Ala Pro Met Phe Asn Ala
    515                 520                 525

Lys Leu Arg Ile Thr Glu Val Val Ile Gly Thr Ala His Thr Asp Asp
530                 535                 540

Pro Ala Val Gly Arg Ser Ala Lys Ala Phe Thr His Asp Pro Phe Asp
545                 550                 555                 560

Leu Gln Arg Tyr Cys Leu Ala Arg Tyr Tyr Asp Val Arg Pro Gly Met
            565                 570                 575

Met Gly Arg Ala Leu Ser Lys Gln Gln Asn Met Ser Ser Met Thr Asp
        580                 585                 590

Lys Leu Ser Lys Gln Glu Asp Tyr Ser Gly Ile Val Ser Arg Arg Leu
    595                 600                 605

Glu Tyr Arg Glu Arg Glu Ser Arg Cys Leu Thr Glu Thr Ala Gln Tyr
610                 615                 620

Val Phe Glu Lys Thr Cys Leu Tyr Val Leu Glu Leu Ser Lys His
625                 630                 635                 640

Thr Met Pro Ser Glu Asp Ser Glu Val Thr Phe Glu His Pro Thr Val
            645                 650                 655

Asp Pro Asn Ile Asp Ile Glu Thr Trp Lys Ile Ile Asp Val Ser Gln
        660                 665                 670

Leu Ile Ile Phe Val Phe Asp Tyr Leu Phe Glu Asn Arg Lys Ile Val
```

```
                675                 680                 685
Arg Asp Thr Thr Glu Ala Arg Trp Thr Leu Phe Lys Ile Arg Ser Glu
    690                 695                 700
Val Gly Arg Ala Arg Ile Asp Ala Ile Glu Met Thr Phe Pro Arg Phe
705                 710                 715                 720
Gly Arg Met Leu Arg Asn Val Ser Gln Ala Lys Ile Asn Gln Glu Ile
                725                 730                 735
Ala Cys Leu Asn Phe Leu Pro Leu Leu Phe Ile Ile Gly Asp Asn Ile
                740                 745                 750
Ser Tyr Ala His Arg Gln Trp Ser Ile Pro Val Leu Leu Tyr Ala His
                755                 760                 765
Asp Ile Arg Ile Ile Pro Leu Glu Val Gly Ala Tyr Asn Asn Arg Phe
                770                 775                 780
Gly Leu Thr Ser Tyr Leu Glu Tyr Met Thr Phe Phe Pro Ser Tyr Ala
785                 790                 795                 800
Thr Arg Leu Ala Lys Ile Asp Glu Ser Ile Lys Glu Cys Ala Ile Ala
                805                 810                 815
Met Ala Glu Phe Tyr Met Asn Thr Asp Ile His Ser Gly Gly Val Met
                820                 825                 830
Ser Asn Val Ile Thr Thr Lys Arg Leu Leu Tyr Glu Thr Tyr Leu Ala
                835                 840                 845
Ser Leu Cys Gly Gly Tyr Ser Asp Gly Leu Leu Trp Tyr Val Pro Ile
                850                 855                 860
Thr His Pro Ser Lys Cys Leu Val Ala Phe Glu Val Ala Asp Asp Val
865                 870                 875                 880
Val Pro Leu Ser Val Arg Arg Glu Arg Ile Leu Ser Arg Phe Pro Leu
                885                 890                 895
Ser Ser Arg His Val Lys Gly Ile Ala Leu Ile Ser Val Asp Arg Asn
                900                 905                 910
Gln Lys Val Ser Val Gln Thr Glu Gly Ile Val Thr His Arg Leu Cys
                915                 920                 925
Lys Lys Asn Leu Leu Lys Tyr Val Cys Asp Val Ile Leu Phe Lys Phe
                930                 935                 940
Ser Gly His Val Phe Gly Asn Asp Glu Met Leu Thr Lys Leu Leu Asn
945                 950                 955                 960
Val

<210> SEQ ID NO 12
<211> LENGTH: 526
<212> TYPE: PRT
<213> ORGANISM: Bluetongue virus

<400> SEQUENCE: 12

Met Gly Lys Ile Ile Lys Ser Leu Ser Arg Phe Gly Lys Lys Val Gly
1               5                   10                  15
Asn Ala Leu Thr Ser Asn Thr Ala Lys Lys Ile Tyr Ser Thr Ile Gly
                20                  25                  30
Lys Ala Ala Glu Arg Phe Ala Glu Ser Glu Ile Gly Ser Ala Ala Ile
                35                  40                  45
Asp Gly Leu Val Gln Gly Ser Val His Ser Ile Met Thr Gly Glu Ser
                50                  55                  60
Tyr Gly Glu Ser Val Lys Gln Ala Val Leu Leu Asn Val Leu Gly Ala
65                  70                  75                  80
Gly Asp Glu Ile Pro Asp Pro Leu Ser Pro Gly Glu Arg Gly Ile Gln
```

```
                85                  90                  95
Met Lys Ile Lys Glu Ile Glu Glu Gln Arg Asn Glu Leu Val Arg
            100                 105                 110
Leu Lys His Gly Lys Glu Ile Ala Lys Lys Phe Gly Asp Glu Leu Glu
            115                 120                 125
Glu Ile Tyr Gln Phe Met Asn Gly Glu Val Lys Glu Val Gln Gln
            130                 135                 140
Glu Glu Gln Tyr Lys Val Leu Cys Lys Ala Val Asn Ser Tyr Glu Lys
145                 150                 155                 160
Leu Leu Leu Ala Glu Asn Asp Glu Met Arg Thr Leu Ala Arg Ala Leu
                165                 170                 175
Gln Arg Glu Ala Thr Glu Arg Thr Glu Thr Glu Ser Lys Met Val Lys
                180                 185                 190
Glu Tyr Arg Gln Lys Ile Asp Ala Leu Lys Ala Ala Ile Glu Val Glu
                195                 200                 205
Arg Asp Gly Met Gln Glu Glu Ala Ile Gln Glu Ile Ala Gly Met Thr
            210                 215                 220
Ala Asp Val Leu Glu Ala Ala Ser Glu Glu Val Pro Leu Val Gly Ser
225                 230                 235                 240
Gly Met Ala Thr Ala Ile Ala Thr Gly Arg Ala Ile Glu Gly Ala Tyr
                245                 250                 255
Lys Leu Lys Lys Val Ile Asn Ala Leu Ser Gly Ile Asp Leu Ser His
            260                 265                 270
Leu Arg Thr Pro Lys Ile Glu Pro Thr Met Val Ala Thr Thr Leu Glu
            275                 280                 285
His Arg Phe Arg Asp Ile Pro Asp Lys Glu Leu Ala Val Ser Ile Leu
            290                 295                 300
Ala Lys Asn Asn Ala Ile Val Ala Asn Thr Arg Glu Val Gln His Ile
305                 310                 315                 320
Lys Glu Glu Ile Leu Pro Lys Phe Lys Lys Ile Met Asp Glu Glu Lys
            325                 330                 335
Glu Leu Glu Gly Ile Asp Asp Lys Lys Ile His Pro Arg Val Met Met
            340                 345                 350
Arg Phe Lys Val Pro Arg Pro Gln Gln Pro Gln Ile His Ile Tyr Ser
            355                 360                 365
Ala Pro Trp Asp Ser Asp Val Phe Phe His Cys Val Ser His
            370                 375                 380
Phe His Val Asn Glu Ser Phe Phe Leu Gly Phe Asp Leu Gly Ile Asp
385                 390                 395                 400
Val Val His Phe Glu Asp Leu Ala Ala His Trp His Ala Leu Gly Ala
                405                 410                 415
Ala Gln Glu Ala Lys Gly Arg Thr Leu Asn Glu Ala Tyr Lys Glu Phe
            420                 425                 430
Leu Asn Leu Ser Ile Gly Ser Ala Tyr Thr Ser Pro Met His Ala Arg
            435                 440                 445
Arg Met Ile Arg Ser Lys Thr Val His Pro Ile Tyr Leu Gly Ser Met
            450                 455                 460
His Tyr Asp Ile Thr Tyr Glu Thr Leu Lys Ser Asn Ala Gln Arg Ile
465                 470                 475                 480
Val Tyr Asp Asp Glu Leu Gln Met His Ile Leu Arg Gly Pro Leu His
                485                 490                 495
Phe Gln Arg Arg Ala Ile Leu Gly Ala Leu Lys Phe Gly Val Lys Val
            500                 505                 510
```

```
Leu Gly Asp Lys Ile Asp Val Pro Leu Phe Leu Lys Asn Ala
        515                 520                 525

<210> SEQ ID NO 13
<211> LENGTH: 526
<212> TYPE: PRT
<213> ORGANISM: Bluetongue virus

<400> SEQUENCE: 13

Met Gly Lys Ile Ile Lys Ser Leu Ser Arg Phe Gly Lys Lys Val Gly
1               5                   10                  15

Asn Ala Leu Ser Ser Asn Thr Ala Lys Lys Ile Tyr Ser Thr Ile Gly
            20                  25                  30

Lys Ala Ala Glu Arg Phe Ala Glu Ser Glu Ile Gly Ala Ala Thr Ile
        35                  40                  45

Asp Gly Leu Val Gln Gly Ser Val His Ser Ile Ile Thr Gly Glu Ser
    50                  55                  60

Tyr Gly Glu Ser Val Lys Gln Ala Val Leu Leu Asn Val Leu Gly Thr
65                  70                  75                  80

Gly Glu Glu Leu Pro Asp Pro Leu Ser Pro Gly Glu Arg Gly Met Gln
                85                  90                  95

Met Lys Ile Lys Glu Leu Glu Asp Glu Gln Arg Asn Glu Leu Val Arg
            100                 105                 110

Leu Lys Tyr Asn Lys Glu Ile Thr Lys Glu Phe Gly Asn Glu Leu Glu
        115                 120                 125

Glu Val Tyr Asp Phe Met Asn Gly Glu Ala Lys Glu Glu Val Val
    130                 135                 140

Gln Glu Gln Tyr Ser Met Leu Cys Lys Ala Val Asp Ser Tyr Glu Lys
145                 150                 155                 160

Ile Leu Lys Ala Glu Asp Ser Lys Met Gly Ile Leu Ala Arg Ala Leu
                165                 170                 175

Gln Arg Glu Ala Ser Glu Arg Ser Gln Asp Glu Ile Lys Met Val Lys
            180                 185                 190

Glu Tyr Arg Gln Lys Ile Asp Ala Leu Lys Asn Ala Ile Glu Ile Glu
        195                 200                 205

Arg Asp Gly Met Gln Glu Glu Ala Ile Gln Glu Ile Ala Gly Met Thr
    210                 215                 220

Ala Asp Val Leu Glu Ala Ala Ser Glu Glu Val Pro Leu Ile Gly Ala
225                 230                 235                 240

Gly Met Ala Thr Ala Val Ala Thr Gly Arg Ala Ile Glu Gly Ala Tyr
                245                 250                 255

Lys Leu Lys Lys Val Ile Asn Ala Leu Ser Gly Ile Asp Leu Ser His
            260                 265                 270

Met Arg Ser Pro Lys Ile Glu Pro Thr Ile Ile Ala Thr Thr Leu Glu
        275                 280                 285

His Arg Phe Lys Glu Ile Pro Asp Glu Gln Leu Ala Val Ser Val Leu
    290                 295                 300

Asn Lys Lys Thr Ala Val Thr Asp Asn Cys Asn Glu Ile Ala His Ile
305                 310                 315                 320

Lys Gln Glu Ile Leu Pro Lys Phe Lys Arg Ile Met Asp Glu Lys
                325                 330                 335

Glu Ile Glu Gly Ile Glu Asp Lys Val Ile His Pro Arg Val Met Met
            340                 345                 350

Arg Phe Lys Ile Pro Arg Thr Gln Gln Pro Gln Ile His Ile Tyr Ala
```

```
                355                 360                 365
Ala Pro Trp Asp Ser Asp Val Phe Phe His Cys Val Ser His
    370                 375                 380

His His Arg Asn Glu Ser Phe Phe Leu Gly Phe Asp Leu Gly Ile Asp
385                 390                 395                 400

Val Val His Phe Glu Asp Leu Thr Ser His Trp His Ala Leu Gly Leu
                405                 410                 415

Ala Gln Glu Ala Ser Gly Arg Thr Leu Thr Glu Ala Tyr Arg Glu Phe
            420                 425                 430

Leu Asn Leu Ser Ile Ser Ser Thr Tyr Ser Ser Ala Ile His Ala Arg
                435                 440                 445

Arg Met Ile Arg Ser Arg Ala Val His Pro Ile Phe Leu Gly Ser Met
        450                 455                 460

His Tyr Asp Ile Thr Tyr Glu Ala Leu Lys Asn Asn Ala Gln Arg Ile
465                 470                 475                 480

Val Tyr Asp Glu Glu Leu Gln Met His Ile Leu Arg Gly Pro Leu His
                485                 490                 495

Phe Gln Arg Arg Ala Ile Leu Gly Ala Leu Lys Phe Gly Val Lys Ile
            500                 505                 510

Leu Gly Asp Lys Ile Asp Val Pro Leu Phe Leu Arg Asn Ala
                515                 520                 525

<210> SEQ ID NO 14
<211> LENGTH: 349
<212> TYPE: PRT
<213> ORGANISM: Bluetongue virus

<400> SEQUENCE: 14

Met Asp Thr Ile Ala Ala Arg Ala Leu Thr Val Met Arg Ala Cys Ala
1               5                   10                  15

Thr Leu Gln Glu Ala Arg Ile Val Leu Glu Ala Asn Val Met Glu Ile
            20                  25                  30

Leu Gly Ile Ala Ile Asn Arg Tyr Asn Gly Leu Thr Leu Arg Gly Val
        35                  40                  45

Thr Met Arg Pro Thr Ser Leu Ala Gln Arg Asn Glu Met Phe Phe Met
    50                  55                  60

Cys Leu Asp Met Met Leu Ser Ala Ala Gly Ile Asn Val Gly Pro Ile
65                  70                  75                  80

Ser Pro Asp Tyr Thr Gln His Met Ala Thr Ile Gly Val Leu Ala Thr
                85                  90                  95

Pro Glu Ile Pro Phe Thr Glu Ala Ala Asn Glu Ile Ala Arg Val
            100                 105                 110

Thr Gly Glu Thr Ser Thr Trp Gly Pro Ala Arg Gln Pro Tyr Gly Phe
        115                 120                 125

Phe Leu Glu Thr Glu Thr Phe Gln Pro Gly Arg Trp Phe Met Arg
    130                 135                 140

Ala Ala Gln Ala Val Thr Ala Val Val Cys Gly Pro Asp Met Ile Gln
145                 150                 155                 160

Val Ser Leu Asn Ala Gly Ala Arg Gly Asp Val Gln Gln Ile Phe Gln
                165                 170                 175

Gly Arg Asn Asp Pro Met Met Ile Tyr Leu Val Trp Arg Arg Ile Glu
            180                 185                 190

Asn Phe Ala Met Ala Gln Gly Asn Ser Gln Gln Thr Gln Ala Gly Val
        195                 200                 205
```

```
Thr Val Ser Val Gly Gly Val Asp Met Arg Ala Gly Arg Ile Ile Ala
    210                 215                 220

Trp Asp Gly Gln Ala Ala Leu His Val His Asn Pro Thr Gln Gln Asn
225                 230                 235                 240

Ala Met Val Gln Ile Gln Val Val Phe Tyr Ile Ser Met Asp Lys Thr
                245                 250                 255

Leu Asn Gln Tyr Pro Ala Leu Thr Ala Glu Ile Phe Asn Val Tyr Ser
                260                 265                 270

Phe Arg Asp His Thr Trp His Gly Leu Arg Thr Ala Ile Leu Asn Arg
                275                 280                 285

Thr Thr Leu Pro Asn Met Leu Pro Pro Ile Phe Pro Pro Asn Asp Arg
    290                 295                 300

Asp Ser Ile Leu Thr Leu Leu Leu Ser Thr Leu Ala Asp Val Tyr
305                 310                 315                 320

Thr Val Leu Arg Pro Glu Phe Ala Ile His Gly Val Asn Pro Met Pro
                325                 330                 335

Gly Pro Leu Thr Arg Ala Ile Ala Arg Ala Ala Tyr Val
                340                 345
```

<210> SEQ ID NO 15
<211> LENGTH: 900
<212> TYPE: PRT
<213> ORGANISM: African horse sickness virus

<400> SEQUENCE: 15

```
Met Gln Gly Asn Glu Arg Ile Gln Asp Lys Asn Glu Lys Glu Lys Ala
1               5                   10                  15

Tyr Ala Pro Tyr Leu Asp Gly Ala Ser Val Ser Thr Asp Asn Gly Pro
                20                  25                  30

Ile Leu Ser Val Phe Ala Leu Gln Glu Ile Met Gln Lys Ile Arg Gln
            35                  40                  45

Asn Gln Ser Asp Met Ala Ala His Ala Pro Asp Val Asp Gly Ala Ile
        50                  55                  60

Pro Glu Val Met Thr Ile Ile Ser Gly Ile Lys Gly Leu Leu Glu Glu
65                  70                  75                  80

Lys Asp Tyr Lys Val Ile Asn Ala Pro Pro Asn Ser Phe Arg Thr Ile
                85                  90                  95

Pro Met Gln Ser Thr Glu Tyr Val Leu Gln Val Asn Thr Phe Tyr Glu
                100                 105                 110

Arg Met Ser Glu Ile Gly Gly Pro Val Asp Glu Thr Asp Pro Ile Phe
            115                 120                 125

Tyr Ala Leu Ile Leu Glu Lys Leu Lys Phe Leu Lys Ser Glu Gly Ala
        130                 135                 140

Phe Ile Leu Gln Gly Ile Ala Thr Lys Asp Tyr Arg Gly Ala Glu Ile
145                 150                 155                 160

Ala Asp Pro Glu Ile Ile Gly Val Ser Phe Gln Asn Ala Leu Ser His
                165                 170                 175

Leu Ala Ala Ile Asp Arg Gln Ile Ile Gln Asp Thr Leu Asn Gly Met
                180                 185                 190

Ile Ile Glu Asn Gly Leu Val Ala Asp Arg Asn Val Asp Val Phe Arg
            195                 200                 205

Ala Ala Met Ser Asp Pro Ile Tyr Arg Ile His Asn Val Leu Gln Gly
        210                 215                 220

Tyr Ile Glu Gly Ile Gln His Gly Glu Leu Arg Glu Ser Val Asn Trp
225                 230                 235                 240
```

```
Leu Met Arg Leu Gly Leu Arg Lys Arg Ile Glu Phe Ala Asn Phe Leu
            245                 250                 255

Thr Asp Phe Arg Arg Ala Asp Thr Ile Trp Ile Ser Gln Arg Leu
            260                 265                 270

Pro Ile Asn Ala Asn Val Ile Trp Asn Val Pro Arg Cys His Ile Ala
            275                 280                 285

Asn Leu Ile Thr Asn Val Ala Leu Cys Leu Pro Thr Gly Glu Tyr Leu
            290                 295                 300

Met Pro Asn Pro Arg Ile Asn Ser Ile Thr Ile Thr Gln Arg Ile Thr
305                 310                 315                 320

Gln Thr Asn Pro Phe Ser Ile Ile Ser Gly Leu Thr Pro Thr Ala Val
            325                 330                 335

Gln Met Asn Asp Val Arg Lys Ile Tyr Leu Ala Leu Met Phe Pro Asn
            340                 345                 350

Gln Ile Ile Leu Asp Ile Lys Pro Asp Ser Ser His Ala Val Asp Pro
            355                 360                 365

Val Leu Arg Met Val Ala Gly Val Leu Gly His Val Met Phe Thr Tyr
            370                 375                 380

Gly Pro Ile Met Thr Asn Ile Thr Pro Thr Met Ala Glu Leu Leu Asp
385                 390                 395                 400

Ala Ala Leu Ser Asp Tyr Leu Leu Tyr Met Tyr Asn Asn Arg Ile Pro
            405                 410                 415

Ile Asn Tyr Gly Pro Thr Gly Gln Pro Leu Asp Phe Arg Ile Gly Ala
            420                 425                 430

Arg Asn Gln Tyr Asp Cys Asn Ala Phe Arg Ala Asp Pro Gln Thr Gly
            435                 440                 445

Arg Gly Tyr Asn Gly Trp Gly Val Val Asp Val Gln Arg Val Gln Pro
            450                 455                 460

Ser Pro Tyr Asp His Val Gln Arg Val Ile Arg Tyr Cys Asp Ile Asp
465                 470                 475                 480

Ser Arg Glu Ile Ile Asp Pro Arg Thr Tyr Gly Met Asn Met Thr Tyr
            485                 490                 495

Pro Ile Phe Arg Glu Met Leu Arg Met Leu Val Ala Ala Gly Lys Asp
            500                 505                 510

Gln Glu Ala Ala Tyr Leu Arg Gln Met Leu Pro Phe His Met Ile Arg
            515                 520                 525

Phe Ala Arg Ile Asn Gln Ile Ile Asn Glu Asp Leu Leu Ser Ala Phe
            530                 535                 540

Ser Pro Asp Gln Asn Phe Asp Val Val Leu His Asn Leu Ile Gln Gly
545                 550                 555                 560

Asn Phe Gly Glu Thr Asp Pro Val Val Leu Glu Val Ser Trp Ala Ser
            565                 570                 575

Ile Trp Phe Ala Phe Val Arg Arg Phe Glu Pro Ile Ala Arg Ser Asp
            580                 585                 590

Leu Leu Glu Ala Ala Pro Leu Ile Glu Ala Arg Tyr Ala Ala Glu Leu
            595                 600                 605

Ser Thr Met Gln Met Asp Val Gln Gln Leu Arg Met Met Arg Ala Arg
            610                 615                 620

Val Pro Asp Thr Val Ile Asn Ala Thr Pro Ser Gln Cys Trp Lys Ala
625                 630                 635                 640

Val Leu Lys Asn Ala Pro Glu Pro Ile Lys Asn Leu Met Asn Leu Ser
            645                 650                 655
```

```
His Ser Phe Ser Phe Val Asn Val Arg Asp Ile Val Arg Trp Ser Gln
            660                 665                 670

Arg Asp Ile Gln Glu Ser Leu Ala Tyr Val Leu Asn Arg Glu Ala Trp
        675                 680                 685

Ala Ile Ala Asn Asp Phe Glu Asp Leu Met Leu Val Asp His Val Tyr
    690                 695                 700

Ile Gln Arg Thr Met Leu Pro Glu Pro Arg Leu Asp Asp Ile Asn Glu
705                 710                 715                 720

Phe Arg Arg Gln Gly Phe Phe His Thr Asn Met Ile Asp Gly Ala Pro
                725                 730                 735

Pro Ile Gly Asp Val Thr His Tyr Thr Tyr Ala Ile Ala Asn Leu Gln
            740                 745                 750

Ala Asn Met Gly Gln Phe Arg Ala Ala Ile Arg Arg Thr Leu Asp Asp
        755                 760                 765

Asn Gly Trp Ile Gln Phe Gly Gly Met Leu Arg Asn Ile Lys Ile Lys
    770                 775                 780

Phe Phe Asp Ser Arg Pro Pro Asp Glu Ile Leu Thr Ala Met Pro Val
785                 790                 795                 800

Tyr Thr Glu Glu Glu Arg Asp Gly Val Arg Met Val Ala Phe Lys Tyr
                805                 810                 815

Ala Thr Thr Ala Thr Ala Tyr Phe Leu Leu Tyr Asn Val Glu Tyr Ser
            820                 825                 830

Asn Thr Pro Asp Thr Leu Ile Thr Val Asn Pro Thr Phe Thr Met Thr
        835                 840                 845

Lys Ile His Met Arg Lys Lys Ile Val Arg Arg Val Arg Ala Pro Asp
    850                 855                 860

Val Leu Ser Gln Val Asn Lys Arg Leu Val Ala Tyr Lys Gly Lys Met
865                 870                 875                 880

Arg Leu Met Asp Val Thr Lys Cys Leu Lys Thr Gly Val Gln Leu Ala
                885                 890                 895

Arg Pro Thr Ile
            900

<210> SEQ ID NO 16
<211> LENGTH: 502
<212> TYPE: PRT
<213> ORGANISM: African horse sickness virus

<400> SEQUENCE: 16

Met Gly Lys Phe Thr Ser Phe Leu Lys Arg Ala Gly Thr Ala Thr Lys
1               5                   10                  15

Arg Ala Leu Ser Ser Asp Ala Ala Lys Lys Met Tyr Lys Thr Ala Gly
            20                  25                  30

Lys Ala Leu Gln Arg Val Val Glu Ser Ile Gly Ala Ala Ile
        35                  40                  45

Asp Gly Val Met Gln Gly Thr Ile Gln Ser Ile Gln Gly Glu Asn
    50                  55                  60

Leu Gly Asp Ser Ile Lys Gln Ala Val Ile Leu Asn Val Ala Gly Thr
65                  70                  75                  80

Leu Glu Ser Ala Pro Asp Pro Leu Ser Pro Gly Glu Gln Ile Leu Tyr
                85                  90                  95

Gly Lys Val His Glu Ile Glu Arg Met Glu Lys Glu Asp Arg Val Ile
            100                 105                 110

Ala Ala His Ala Asn Asp Ile Glu Lys Glu Phe Gly Lys Glu Leu Thr
        115                 120                 125
```

Ile Arg Lys Ile Val Lys Gly Glu Glu Lys Ile Glu Glu Leu Glu Gly
130                 135                 140

Lys Glu Val Glu Tyr Val Glu Lys Ala Leu Asp Gly Leu Leu Lys Ile
145                 150                 155                 160

Gly Lys Asn Gln Ser Lys Arg Ile Thr Asn Leu Tyr Lys Ala Leu Gln
            165                 170                 175

Thr Glu Glu Gln Leu Arg Thr Glu Asp Glu Ile Ala Met Ile Ser Asp
            180                 185                 190

Tyr Lys Glu Lys Phe Gly Ala Leu Lys Glu Ala Ile Gln Ile Glu Gln
            195                 200                 205

Gln Ala Ala Asn Glu Glu Ala Ile Gln Glu Met Leu Asp Ile Ser Ala
210                 215                 220

Asp Val Ile Glu Thr Ala Ser Glu Glu Val Pro Ile Phe Gly Ala Ala
225                 230                 235                 240

Ala Ala Asn Val Val Ala Thr Thr Arg Ala Ile Glu Gly Gly Lys Leu
            245                 250                 255

Lys Glu Ile Val Asp Lys Leu Thr Gly Ile Asp Leu Ser His Leu Lys
            260                 265                 270

Val Ala Glu Ile His Pro His Val Ile Gly Gln Ala Ile Ser Lys Asn
            275                 280                 285

Asp Val Asp Asp Lys Thr Leu Ala Val Ala Ile Lys Ser Lys Val Asp
290                 295                 300

Ala Val Asp Glu Met Asn Gln Glu Thr Glu His Val Ile Gln Ser Ile
305                 310                 315                 320

Leu Pro Leu Val Lys Arg Glu Tyr Gln Lys His Glu Asn Lys Phe Asn
            325                 330                 335

Ile Lys Ile Pro Ser Ala Leu Lys Ile His Ser Glu His Thr Pro Lys
            340                 345                 350

Val His Ile Tyr Thr Thr Pro Trp Asp Ser Asp Lys Val Phe Ile Cys
            355                 360                 365

Arg Cys Ile Ala Pro His His Gln Gln Arg Ser Phe Met Gly Phe Asp
370                 375                 380

Leu Glu Ile Glu Tyr Val Tyr Tyr Glu Asp Thr Ser Val Glu Ala His
385                 390                 395                 400

Ile Met His Gly Gly Ala Val Met Ile Glu Gly Arg Gly Phe Arg Gln
            405                 410                 415

Ala Tyr Asn Glu Phe Met Ser Val Ala Trp Ser Met Pro Glu Ile Pro
            420                 425                 430

Glu Leu His Lys Arg Arg Met Gln Arg Asn Gln Gly Ser His Pro Ile
            435                 440                 445

Tyr Met Gly Ser Met Asp Tyr Thr Ile Ser Phe Asp Gln Leu Ser Thr
450                 455                 460

Asn Ala Leu Gln Leu Val His Asn Thr Asp Leu Gln Met His Cys Leu
465                 470                 475                 480

Arg Gly Pro Ile Lys Phe Gln Arg Arg Thr Ile Met Asn Ala Leu Leu
            485                 490                 495

Phe Gly Val Lys Ile Ser
            500

<210> SEQ ID NO 17
<211> LENGTH: 347
<212> TYPE: PRT
<213> ORGANISM: African horse sickness virus

<400> SEQUENCE: 17

Met Asp Ala Ile Ala Ala Arg Ala Leu Ser Val Val Arg Ala Cys Val
1               5                   10                  15

Thr Val Thr Asp Ala Arg Val Ser Leu Asp Pro Gly Val Met Glu Thr
            20                  25                  30

Leu Gly Ile Ala Ile Asn Arg Tyr Asn Gly Leu Thr Asn His Ser Val
        35                  40                  45

Ser Met Arg Pro Gln Thr Gln Ala Glu Arg Asn Glu Met Phe Phe Met
    50                  55                  60

Cys Thr Asp Met Val Leu Ala Ala Leu Asn Val Gln Ile Gly Asn Ile
65                  70                  75                  80

Ser Pro Asp Tyr Asp Gln Ala Leu Ala Thr Val Gly Ala Leu Ala Thr
                85                  90                  95

Thr Glu Ile Pro Tyr Asn Val Gln Ala Met Asn Asp Ile Val Arg Ile
            100                 105                 110

Thr Gly Gln Met Gln Thr Phe Gly Pro Ser Lys Val Gln Thr Gly Tyr
        115                 120                 125

Ala Gly Ala Val Glu Val Gln Gln Ser Gly Arg Tyr Tyr Val Pro Gln
    130                 135                 140

Gly Arg Thr Arg Gly Gly Tyr Ile Asn Ser Asn Ile Ala Glu Val Cys
145                 150                 155                 160

Met Asp Ala Gly Ala Ala Gly Gln Val Asn Gly Leu Leu Ala Pro Arg
                165                 170                 175

Arg Gly Asp Ala Val Met Ile Tyr Phe Val Trp Arg Pro Leu Arg Ile
            180                 185                 190

Phe Cys Asp Pro Gln Gly Ala Ser Leu Glu Ser Ala Pro Gly Thr Phe
        195                 200                 205

Val Thr Val Asp Gly Val Asn Val Ala Ala Gly Asp Val Val Ala Trp
    210                 215                 220

Asn Thr Ile Ala Pro Val Asn Val Gly Asn Pro Gly Ala Arg Arg Ser
225                 230                 235                 240

Ile Leu Gln Phe Glu Val Leu Trp Tyr Thr Ser Leu Asp Arg Leu Asp
                245                 250                 255

Thr Val Pro Glu Leu Ala Pro Thr Leu Thr Arg Cys Tyr Ala Tyr Val
            260                 265                 270

Ser Pro Thr Trp His Ala Leu Arg Ala Val Ile Phe Gln Gln Met Asn
        275                 280                 285

Met Gln Pro Ile Asn Pro Pro Ile Phe Pro Pro Thr Glu Arg Asn Glu
    290                 295                 300

Ile Val Ala Tyr Leu Leu Val Ala Ser Leu Ala Asp Val Tyr Ala Ala
305                 310                 315                 320

Leu Arg Pro Asp Phe Arg Met Asn Gly Val Val Ala Pro Val Gly Gln
                325                 330                 335

Ile Asn Arg Ala Leu Val Leu Ala Ala Tyr His
            340                 345

<210> SEQ ID NO 18
<211> LENGTH: 1040
<212> TYPE: PRT
<213> ORGANISM: African horse sickness virus

<400> SEQUENCE: 18

Met Ala Ser Glu Phe Gly Ile Leu Leu Thr Glu Arg Ile Phe Asp Glu
1               5                   10                  15

-continued

```
Thr Leu Glu Lys Thr Asn Cys Asp Val Ile Ile Thr Glu Lys Lys
             20                  25                  30

Val Lys Arg Lys Glu Val Glu Gly Val Leu Gly Tyr Val Trp Glu Glu
         35                  40                  45

Thr Asn His Arg Phe Gly Leu Cys Glu Gly Asn Tyr Asp Leu Ala Phe
     50                  55                  60

Ser Asp Thr Met Tyr Cys Gln Thr Lys Cys Asp Gly Ser Tyr Pro Val
65                  70                  75                  80

Phe Pro His Tyr Ile Ile Asp Ala Leu Arg Tyr Gly Val Met Ile Asp
                 85                  90                  95

Arg Asn Asp Asn Gln Val Arg Val Asp Leu Asp Lys Arg Leu Met
            100                 105                 110

Lys Ile Lys Ile Gln Pro Tyr Leu Gly Glu Met Tyr Phe Ser Pro Tyr
        115                 120                 125

Ser Thr Val Phe Cys Lys Arg Gln Ala Leu Ala Leu Gly Val Asp Asp
    130                 135                 140

Leu Arg His Ser Val Asp Val Arg Asn Glu Phe Glu Glu Thr Asn His
145                 150                 155                 160

Gln Thr Lys Gly Val Leu Asn Gly Asn Lys Gln Arg Ala Leu Glu Val
                165                 170                 175

Trp Lys Glu Met Ala Tyr Gln Arg Met Arg Lys Glu Gly Ser Arg Gly
            180                 185                 190

Arg Cys Ile Gly His Asp Asp Val Met Tyr Gln Leu Ile Lys Lys
        195                 200                 205

Leu Arg Tyr Gly Met Met Tyr Pro His His Tyr Ala Leu Asn Ala Arg
    210                 215                 220

Tyr Glu Val Ser Asn Pro Ser Ala Ala Arg Ile Lys Asp Trp Leu Leu
225                 230                 235                 240

Lys Val Arg Val Asn Val Gly Arg Ala Gln Glu Lys Ala Gln Gly Pro
                245                 250                 255

Leu Ala Glu Met Ala Arg Ser Ile Glu Asn Asp Glu Leu Ser Arg Gln
            260                 265                 270

Val Val Asp Gln Ile Ile Gln Tyr Gly Gly Gln Phe Ser Ser Cys Ser
        275                 280                 285

Gly Ala Arg Glu Asp Asp Ile Pro Ile Asn Ile Leu Leu Glu Tyr Cys
    290                 295                 300

Glu Ser Leu Thr Thr Phe Val His Arg Lys Lys Arg Lys Glu Gly Asp
305                 310                 315                 320

Asp Leu Thr Ala Arg Asn Thr Phe Arg Gln Ala Leu Ile Lys Ser Met
            325                 330                 335

Pro Thr Met Asn Phe Lys Asn Gln Met Lys Met Thr Arg Gly Trp Gly
        340                 345                 350

Asn Tyr Thr Phe Phe Ser Tyr Ile Asp Arg Phe Ser Arg Ile Tyr Asn
    355                 360                 365

Met Asn Ile Asp Pro Asn Gly Lys Leu Trp Ile His Lys Thr Val Ser
370                 375                 380

Glu Gln Leu Lys Lys Lys Gln Glu Asn Arg Ala Pro Leu Thr Val
                385                 390                 395                 400

Gln Ile Asp Gly Val His Ile Arg Thr Asp Glu Thr Tyr Gly Thr Val
            405                 410                 415

Asp His Trp Val Glu Trp Val Val Asp Thr Ile Met Leu Arg Glu Thr
        420                 425                 430

Glu Lys Met Ile Lys Asp Tyr Arg Phe Lys Lys Leu Lys Arg Glu Glu
```

-continued

```
            435                 440                 445
Leu Ile Ser Gly Met Asn Lys Leu Glu Asp Gly Leu Arg Cys Ile Val
    450                 455                 460

Tyr Cys Leu Ile Leu Ala Leu Tyr Asp Tyr Tyr Glu Gly Asp Ile Glu
465                 470                 475                 480

Gly Phe Lys Lys Gly Thr Ile Ala Ser Ser Ile Val Glu Thr Val Ser
                485                 490                 495

Gln Met Phe Pro Asn Phe Arg Ser Asp Ile Asp Lys Gly Ile Ser Leu
            500                 505                 510

Lys Val Lys Thr Glu Ala Glu Glu Leu Phe Leu Pro Lys Asn Met Lys
        515                 520                 525

Ser Ser Met Asn Val Gly Glu Glu Arg Gly Tyr Lys Tyr Lys Phe Gly
        530                 535                 540

Trp Lys Asp Asn Glu Glu Arg Val Met Ser Asp Tyr Gly Glu Ile Leu
545                 550                 555                 560

Thr Glu Ser Val Glu Ile Leu Phe Lys Lys Leu Leu Lys Gly Glu Lys
                565                 570                 575

Trp Lys Ile Ile Val Asp Asp Pro Gln Thr Tyr Phe Glu Asp Asp Leu
            580                 585                 590

Phe Val Asp Arg Ala Asn Lys Ile Phe Ser Arg Gly Gly Gln Thr Val
        595                 600                 605

Asn Gln Leu Ile Ser Ile Lys Val Asn Ala Gln Ser Asn Asn Val Glu
    610                 615                 620

Gly Thr Thr Tyr Phe Ser Lys Phe Val Ser Tyr Phe Arg Ile Glu His
625                 630                 635                 640

Phe Ser Ile Thr Thr Ala Lys Lys Arg Thr Asp Ile Arg Asp Lys Lys
                645                 650                 655

Thr Glu Tyr Asn Glu Phe Asp Phe Glu Asp Phe Lys Pro Ala Cys Ile
            660                 665                 670

Gly Glu Leu Gly Ile His Ala Ser Thr Tyr Ile Tyr Gln Asp Leu Leu
        675                 680                 685

Val Gly Lys Ser Arg Gly Glu Arg Val Lys Asp Ala Lys Glu Leu Val
        690                 695                 700

Trp Met Asp Leu Ser Leu Ala Asn Phe Gly Cys Ser Arg Cys Tyr Asp
705                 710                 715                 720

Arg Cys Trp Pro Ala Ser Cys Val Glu Ala Glu Ile Ser Leu Arg Tyr
                725                 730                 735

Tyr Leu Val Thr Ser Ile Phe Ala Arg Tyr Leu Asn Arg Glu Gly Leu
            740                 745                 750

Ser Phe Ser Lys Ile Ile Ser Leu Lys Asp Ser Asp Arg Leu Trp Phe
        755                 760                 765

Pro Thr Tyr Lys His Phe Tyr Val Ala Val Gln Lys Val Leu Arg
        770                 775                 780

Asp Asp Arg Arg Leu Asp Tyr Val Leu Phe Cys Ser Arg Val Ser Ala
785                 790                 795                 800

Ile Thr Thr Arg Arg Ala Thr Leu Met Glu Phe Ser Thr Phe Lys Gln
                805                 810                 815

Met Val Gly Ser Thr Arg Leu Leu Asp Thr Leu Phe Leu Asn Phe Leu
            820                 825                 830

Leu Trp Ile Ile Phe Glu Gln Glu Asn Ile Asp Val Asp Phe Ala Asn
        835                 840                 845

Lys Trp His Pro Leu Leu Ile Ser Thr Glu Lys Gly Leu Arg Val Ile
        850                 855                 860
```

```
Ala Val Asp Val Phe Asn Ser Ser Leu Thr Leu Ser Thr Ser Gly Trp
865                 870                 875                 880

Leu Pro Tyr Glu Arg Ile Cys Ser Glu Ala Met Asp Arg Ala Leu Thr
            885                 890                 895

Ala Asp Glu Ile Asn Leu Lys Arg Trp Phe Val Asp Tyr Tyr Met Glu
        900                 905                 910

Leu Lys Leu Glu Arg Arg Ala Glu Pro Arg Met Ser Phe Lys Ser Glu
            915                 920                 925

Ala Leu Ile Thr Trp Ile Gly Ser Asn Cys Gly Gly Val Thr Asp Tyr
        930                 935                 940

Val Val Gln Leu Leu Pro Val Arg Lys Pro Lys Pro Gly Leu Leu Val
945                 950                 955                 960

Val Val Tyr Ser Glu Asp Gly Gly Glu Lys Trp Ala Glu Trp Ala Leu
            965                 970                 975

Arg Asp Tyr Leu Glu Ile Asp Gly Ser Leu Gly Leu Val Phe Ile Thr
        980                 985                 990

Arg Lys Ala Val Lys Asn Lys Ser  Lys Leu Gly Val Arg Asp Leu Lys
            995                 1000                1005

Ile Asn Arg Gly Arg Val Asp Arg Ile Leu Ile Ser  Ser Gly Val
    1010                1015                1020

Tyr Thr Phe Gly Asn Lys Phe  Leu Phe Ser Lys Leu  Leu Ser Lys
    1025                1030                1035

Ile Glu
    1040

<210> SEQ ID NO 19
<211> LENGTH: 1049
<212> TYPE: PRT
<213> ORGANISM: African horse sickness virus

<400> SEQUENCE: 19

Met Ala Ser Glu Phe Gly Ile Leu Tyr Thr Asp Gln Ile Tyr Glu Gln
1               5                   10                  15

Thr Leu Glu Lys Thr Ser Cys Asp Val Ile Val Thr Lys Glu Asn Ala
            20                  25                  30

Val Lys Arg Val Glu Ile Asp Gly Val Leu Gly Tyr Glu Trp Gly Ala
        35                  40                  45

Thr Asn His Arg Leu Gly Leu Cys Glu Ile Glu His Val Lys Thr Ile
    50                  55                  60

Ser Glu Phe Met Tyr Glu Gln Ile Lys Cys Gly Ala Tyr Pro Val
65                  70                  75                  80

Phe Pro His Tyr Val Ile Asp Ala Leu Lys Tyr Asn Lys Val Ile Glu
                85                  90                  95

Arg Asn Asp Asn Gln Val Arg Val Asp Arg Asp Glu Arg Leu Gln
            100                 105                 110

Lys Ile Lys Ile Gln Pro Tyr Phe Gly Glu Ala Phe Phe Ser Pro Thr
        115                 120                 125

Tyr Ser Ser Thr Phe Cys Lys Arg Gln Ala Ile Arg Gly His Val Ala
    130                 135                 140

Lys Met Arg Thr Phe Ala Lys Asp Arg Ile Asp Phe Glu Glu Ser Ser
145                 150                 155                 160

Ala Gln Thr Lys Tyr Val Asn Gly Asn Lys Val Lys Ile Leu Glu Glu
                165                 170                 175

Trp Lys Gly Arg Thr Asp Ala Arg Met Leu Met Glu Gly Gln Gln Glu
```

```
            180                 185                 190
Lys Cys Val Ala His Glu Val Asp Pro Ile Tyr Gln Leu Ile Lys Lys
            195                 200                 205

Met Arg Tyr Gly Met Met Tyr Pro Thr His Tyr Met Leu Ser Gln Arg
            210                 215                 220

Tyr Arg Ile Ile Ser Glu Arg Lys Met Gly Ile Glu Lys Trp Leu
225                 230                 235                 240

Leu Glu Lys Val Glu Arg Gly Val Gln Arg Gly Val Ala Gly Lys Gly
                    245                 250                 255

Asn Glu Ser Leu Val Arg Leu Glu Lys Leu Met Gln Lys Glu Glu Leu
                260                 265                 270

Glu Asn Ser Val Ile Glu Asn Val Ile Arg Tyr Gly Ser Gln Phe Ser
                275                 280                 285

Thr His Ala Gly Glu Lys Thr Asn Asp Met Pro Leu Ser Val Leu Ile
                290                 295                 300

Lys Tyr Cys Glu Ser Leu Thr Thr Phe Val His Lys Lys Asn Arg Glu
305                 310                 315                 320

Gly Gly Asp Asn Gln Thr Ala Arg Asp Glu Ile Arg Lys Ala Met Val
                    325                 330                 335

His Asn Met Pro Thr Met Asn His Asn Asn Pro Met Lys Val Thr Lys
                    340                 345                 350

Asn Phe Lys Asn Phe Leu Phe Phe Ala Tyr Leu Asp Gly Phe Lys Arg
                355                 360                 365

Asn Asn Gly Val Asp Ile Asn Pro Asn Ser Thr Trp Glu His Lys
                370                 375                 380

Lys Lys Met Ala Glu Lys Leu Lys Asp Glu Gln Gln Lys Asn Gln Asn
385                 390                 395                 400

Arg Pro Met Leu Val Pro Ile Asp Gly Val Tyr Val Ser Thr Ser Val
                    405                 410                 415

Glu Tyr Gly Thr Val Thr His Trp Val Asp Trp Val Asp Ile Ile
                420                 425                 430

Met Thr Thr Gln Val Glu Arg Met Ile Lys Glu Tyr Asp Phe Lys Arg
                435                 440                 445

Leu Glu Arg Lys Gln Leu Ile Ser Gly Met Asn Lys Leu Glu Asp Gly
            450                 455                 460

Val Lys Cys Tyr Ala Tyr Cys Leu Ile Leu Ala Leu Tyr Asp Tyr Tyr
465                 470                 475                 480

Gly Asp Ala Ile Glu Gly Phe Ala Gln Gly Thr Arg Ala Gly Ser Ile
                485                 490                 495

Val Glu Thr Ile Ser Gln Met Phe Pro Glu Phe Arg Asp Val Ala Glu
                500                 505                 510

Lys Phe Gly Ile Lys Leu Thr Ile Lys Asp Glu Ser Glu Glu Leu Phe
            515                 520                 525

Val Gln Lys Asp Met Asn Ser Glu Phe Leu Asp Glu Gly Glu Met Gly
            530                 535                 540

Tyr Lys Phe Val Phe Gly Trp Lys Asn Thr Asp Phe Lys Val Gln Ser
545                 550                 555                 560

Asn Tyr Gly Glu Ile Val Ser Glu Glu Val Arg Leu Phe Lys Val
                565                 570                 575

Ile Leu Glu Gly Lys Glu Trp Ser Asn Glu Val Glu Asp Pro Glu Asp
                580                 585                 590

Tyr Phe Val Asp Asn Leu Phe Asn Lys Thr Pro Asp Ala Val Phe Glu
                595                 600                 605
```

Arg Asp Gly Met Asp Gly Ser Asn Arg Ile Ile Val Lys Asn Lys Thr
610                 615                 620

Thr Leu Arg Glu Gly Gln Arg His Phe Ser Ala Phe Val Ser Tyr Trp
625                 630                 635                 640

Tyr Thr Phe Glu Lys Val Glu Val Gly Arg Ala Met Ala Arg Ile Asp
          645                 650                 655

Ile His Asp Arg Glu Thr Lys Phe Ser Glu Phe Asp Val Asp Asp Tyr
          660                 665                 670

Lys Pro Cys Ser Val Ala Glu Met Gly Leu His Ser Ser Thr Tyr Ile
          675                 680                 685

Tyr Gln Asp Leu Leu Ile Gly Pro Asn Arg Gly Glu His Val Ile Asp
690                 695                 700

Ala Lys Glu Leu Val Trp Tyr Asp Ile Ala Leu Thr Asn Tyr Gly Thr
705                 710                 715                 720

Thr Arg Tyr Phe Asp Gln Cys Trp Pro Ser Ser Cys Ser Thr Thr Glu
          725                 730                 735

Leu Ser Met Arg Tyr Phe Leu Ile Thr Glu Ile Phe Gln Arg Tyr Arg
          740                 745                 750

Thr Asp Asp Arg Ser Ser Phe Ala Asp Ile Glu Arg Met Arg Lys Asn
          755                 760                 765

Gly Tyr Pro Arg Arg Asn Phe Leu Thr Tyr Lys His Tyr Tyr Val Ala
770                 775                 780

Val Ile Gln Glu Val Phe Gly Asp Gln Arg Pro Ile Asp Val Tyr Ser
785                 790                 795                 800

Phe Cys Thr Asp Ile Phe Lys Lys Glu Arg Arg Gly Val Leu Ser
          805                 810                 815

Met Phe Pro Thr Phe Ser Thr Leu Ile Lys Ser Glu Lys Leu Ile Asp
          820                 825                 830

Ala Leu Phe Leu Asn Phe Phe Leu Trp Val Val Phe Glu Met Glu Asn
          835                 840                 845

Val Asp Val Ser Phe Ala Asn Lys Arg His Pro Leu Leu Ile Ser His
850                 855                 860

Asp Lys Gly Leu Arg Leu Ile Gly Val Asp Leu Phe Asn Ser Ala Leu
865                 870                 875                 880

Ser Ile Ser Met Gly Gly Trp Ile Pro Val Glu Arg Ile Cys His Ala
                    885                 890                 895

Asp His Ala Ala Arg Lys Leu Asn Ala Asp Glu Leu Lys Ile Lys Arg
          900                 905                 910

Trp Phe Ile Asp Tyr Tyr Met Asp Leu Ser Leu Asp Arg Arg Ala Glu
          915                 920                 925

Pro Arg Met Ser Phe Lys Tyr Glu Gly Leu Ala Thr Trp Val Gly Ser
          930                 935                 940

Asn Cys Gly Gly Val Arg Asp Tyr Ile Ile Gln Glu Leu Pro Met Arg
945                 950                 955                 960

Lys Pro Lys Pro Gly Leu Leu Ile Leu Val Tyr Gly Glu Asp Gly Asp
                    965                 970                 975

Pro Lys Trp Val Glu Trp Ala Ile Lys Asp Phe Thr Gln Ile Glu Gly
          980                 985                 990

Ser Leu Gly Phe Ile Tyr Ile Asp Pro Ile Ser Val Val Asn Lys Ser
          995                 1000                1005

Thr Phe Arg Thr Arg Glu Met Lys Tyr Asn Arg Gly Arg Leu Asp
   1010                1015                1020

```
Arg Leu Ile Leu Ile Ser Ser Gly Asn Tyr Thr Phe Gly Asn Lys
    1025                1030                1035

Phe Leu Leu Ser Lys Leu Leu Ser Lys Ala Glu
    1040                1045

<210> SEQ ID NO 20
<211> LENGTH: 505
<212> TYPE: PRT
<213> ORGANISM: African horse sickness virus

<400> SEQUENCE: 20

Met Gly Lys Phe Thr Ser Phe Leu Lys Arg Ala Gly Ser Ala Thr Lys
1               5                   10                  15

Lys Ala Leu Thr Ser Asp Ala Ala Lys Arg Met Tyr Lys Met Ala Gly
            20                  25                  30

Arg Thr Leu Gln Lys Ala Val Glu Ser Glu Val Gly Ser Ala Ala Ile
        35                  40                  45

Asp Gly Val Met Gln Gly Thr Ile Gln Ser Ile Ile Gln Gly Glu Asn
    50                  55                  60

Leu Gly Asp Ser Ile Lys Gln Ala Val Ile Leu Asn Val Ala Gly Thr
65                  70                  75                  80

Leu Glu Ser Ala Pro Asp Pro Leu Ser Pro Gly Glu Gln Leu Leu Tyr
                85                  90                  95

Asn Lys Val Ser Glu Leu Glu Arg Met Glu Lys Glu Asp Arg Val Ile
            100                 105                 110

Glu Thr His Ser Glu Lys Ile Val Glu Lys Tyr Gly Arg Glu Leu Val
        115                 120                 125

Asp Ile Arg Lys Ile Met Arg Gly Glu Ala Gln Ala Glu Lys Leu Glu
    130                 135                 140

Gly Lys Glu Met Phe Tyr Ile Glu Lys Ala Leu Lys Gly Ile Leu Gln
145                 150                 155                 160

Ile Gly Lys Asp Gln Ser Asp Arg Ile Thr Arg Leu Tyr Arg Ala Leu
                165                 170                 175

Gln Thr Glu Glu Glu Leu Arg Thr Ala Asp Glu Thr Lys Ile Ile Ser
            180                 185                 190

Glu Tyr Arg Glu Lys Phe Asn Ala Leu Lys Gln Ala Ile Glu Leu Glu
        195                 200                 205

Gln Gln Ala Thr His Glu Glu Ala Val Gln Met Leu Asp Leu Ser
    210                 215                 220

Ala Glu Val Leu Glu Thr Ala Ala Glu Glu Val Pro Ile Phe Gly Ala
225                 230                 235                 240

Gly Ala Ala Asn Val Val Ala Thr Thr Arg Ala Val Gln Gly Gly Leu
                245                 250                 255

Arg Leu Lys Glu Ile Ile Asp Lys Leu Thr Gly Ile Asp Leu Ser His
            260                 265                 270

Leu Lys Val Ala Asp Ile His Pro His Ile Ile Glu Lys Ala Met Leu
        275                 280                 285

Lys Asp Ala Val Thr Asp Ser Asp Leu Ala Met Ala Val Lys Ser Lys
    290                 295                 300

Val Asp Val Val Asp Glu Val Asn Ala Glu Thr Glu His Ile Ile Asp
305                 310                 315                 320

Thr Ile Met Pro Leu Val Lys Lys Glu Tyr Asp Lys His Glu Asn Lys
                325                 330                 335

Phe His Ile Glu Ile Pro Ser Ala Leu Lys Ile His Ser Glu His Thr
            340                 345                 350
```

```
Pro Lys Val His Ile Tyr Thr Thr Pro Trp Asp Ser Asp Lys Val Phe
        355                 360                 365
Ile Cys Arg Cys Ile Ala Pro His His Gln Gln Arg Ser Phe Met Ile
    370                 375                 380
Gly Phe Asp Leu Glu Ile Glu Phe Val Phe Tyr Glu Asp Thr Ser Val
385                 390                 395                 400
Glu Ser His Val Met His Gly Gly Ala Ile Ser Ile Glu Gly Arg Gly
                405                 410                 415
Phe Arg Gln Ala Tyr Ser Glu Phe Met Ser Ala Ala Trp Ser Met Pro
            420                 425                 430
Ala Ala Pro Glu Leu His Lys Arg Arg Leu Gln Arg Ser Leu Gly Ser
        435                 440                 445
His Pro Ile Tyr Met Gly Ser Met Asp Tyr Thr Val Ser Tyr Glu Gln
    450                 455                 460
Leu Val Ser Asn Ala Met Lys Leu Val Tyr Asp Thr Asp Leu Gln Met
465                 470                 475                 480
His Cys Leu Arg Gly Pro Leu Lys Phe Gln Arg Arg Thr Leu Met Asn
                485                 490                 495
Ala Leu Leu Phe Gly Val Arg Ile Ala
            500                 505

<210> SEQ ID NO 21
<211> LENGTH: 1410
<212> TYPE: DNA
<213> ORGANISM: Artificial sequence
<220> FEATURE:
<223> OTHER INFORMATION: N. benthamiana optimised BTV-8 VP3

<400> SEQUENCE: 21
ttaattaatc gcgaccggta tggctgctca aaatgagcaa aggccagaga ggattaagac      60
tactccatac cttgagggtg atgtgctttc ttctgattct ggaccacttc tttctgtttt     120
cgctctccaa gagattatgc agaaggttag gcaagttcag gctgattaca tgactgctac     180
tagggaagtt gatttcactg ttccagatgt gcagaaaatc ctcgatgata tcaaggctct     240
tgctgctgag caagtgtaca agattgtgaa ggtgccatcc atttctttca ggcacattgt     300
gatgcaatct agggataggg ttctcagagt ggatacttac tacgaagaga tgtctcaggt     360
tggagatgtg attactgaag atgagccaga gaagttctac tccactatca tcaagaaggt     420
gagattcatt aggggaaagg gatctttcat tctccacgat atcccaacta gagatcacag     480
aggaatggaa gttgctgagc cagaagttct tggagttgag ttcaagaatg tgcttccagt     540
tcttactgct gaacacaggg ctatgattca gaatgctctc gatggatcta ttatcgagaa     600
cggaaacgtt gcaactaggg atgtggatgt gtttattgga gcttgctctg agccaatcta     660
caggatctac aacaggcttc aggatatat tgaggctgtt cagcttcaag aactcaggaa     720
ctctattggt tggcttgaaa ggcttggaca gaggaagagg attacttact ctcaagaggt     780
gctcactgat tttagaaggc aggatacaat ttgggttttg gctctccagc ttccagttaa     840
cccacaagtt gtttgggatg ttccaaggtc ctctattgct aacctcatca tgaacattgc     900
tacttgcctt ccaactggtg agtacattgc tccaaaccca aggatttctt ccattactct     960
cactcagagg atcactacta ctggaccatt cgctattctt actggatcta ctccaactgc    1020
tcagcagctt aacgatgtga ggaagatcta ccttgctctt atgttcccag acacagattat    1080 tctcgatctc aagatcgatc caggtgaaag aatggatcca gctgttagaa tggttgctgg    1140
```

| | |
|---|---|
| tgttgttgga caccttctttt ttactgctgg tggaaggttc actaacctca cacagaatat | 1200 |
| ggctaggcag cttgatattg ctctcaacga ttacctcctc tatatgtaca acactagggt | 1260 |
| tcaggttaac tatggaccaa ctggtgaacc actcgatttt cagattggta ggaaccagta | 1320 |
| cgattgcaat gttttcaggg ctgatttcgc tactggaact ggatacaatg gatgggctac | 1380 |
| tattgatgtg gagtacagag atccagctcc | 1410 |

<210> SEQ ID NO 22
<211> LENGTH: 2718
<212> TYPE: DNA
<213> ORGANISM: Artificial sequence
<220> FEATURE:
<223> OTHER INFORMATION: Plant Codon Optimised BTV-8 VP3

<400> SEQUENCE: 22

| | |
|---|---|
| accggtatgg cagcacaaaa cgaacagaga ccagaaagaa tcaagacgac accataccta | 60 |
| gaaggtgacg tactaagttc tgatagtggt ccactactat ctgtattcgc attgcaagaa | 120 |
| atcatgcaga aagtcagaca ggtccaagca gattacatga cagctactag agaagtagac | 180 |
| ttcacagtgc cagatgtaca gaagatcctg gatgatatca aggctctagc agcagaacaa | 240 |
| gtatacaaga tcgtaaaggt cccttctatc tccttcagac acatcgttat gcagtctaga | 300 |
| gatcgagttc taagagtaga tacctactac gaggaaatga gccaggtagg agatgtaatc | 360 |
| acggaagatg aaccagaaaa gttctactcc acgatcatca gaaggtacg tttcatcaga | 420 |
| ggaaagggat cattcatcct acacgatatc ccaacgcgag atcatcgagg tatggaagta | 480 |
| gcagaacctg aagttttagg agttgaattc aagaacgtac taccagtctt gacagcagaa | 540 |
| catagagcaa tgatccagaa cgcacttgat ggttcaatca ttgaaaacgg aaacgtggca | 600 |
| acacgagatg ttgatgtttt catcggagca tgttcagaac caatataccg tatatacaac | 660 |
| aggctgcagg gatacataga ggcagttcag ttacaggaac tgcgaaacag tattggttgg | 720 |
| cttgaaagac tgggacaacg aaaacgaatt acatactccc aagaagttct gacagatttc | 780 |
| cgtagacagg atacgatttg ggttctggca ttacagttac cagttaaccc acaggttgtt | 840 |
| tgggatgttc cacgatctag tatagcaaac ctgattatga acattgccac gtgcttacct | 900 |
| acaggagaat acatagctcc aaaccctaga ataagctcca ttaccttaac ccagcgaatt | 960 |
| accaccactg gtccatttgc aatactgact ggaagtactc caactgctca caattgaac | 1020 |
| gatgttagaa agatataacct cgccctgatg ttcccaggac aaattatact cgacttaaag | 1080 |
| atagaccctg gagagagaat ggacccagca gttagaatgg ttgctggagt tgttggacat | 1140 |
| tgttgttca ctgctggtgg tcgttttact aatctgacac aaaacatggc acgtcaatta | 1200 |
| gatattgcct taaacgacta cctcctctac atgtacaaca ccagagtcca ggttaattac | 1260 |
| ggtccaacag gtgaacctct tgatttccag attggtagaa atcagtacga ctgcaatgtg | 1320 |
| ttcagagctg atttcgcaac aggtacaggt tacaatggtt gggctacaat agatgttgag | 1380 |
| tatcgtgacc ctgcaccta tgttcatgct caaagatata aaggtattg tggcattgac | 1440 |
| tcccgtgagt tgataaatcc caccacatat gggattggta tgacctatca ctgttataat | 1500 |
| gagatgctcc ggatgctcgt ggctgctggc aaagattctg aagcagctta tttccgttca | 1560 |
| atgcttcctt tccatatggt tcgttttgct agaattaatc agattattaa tgaggacctc | 1620 |
| cactccgtgt ttagcctccc tgacgatatg tttaatgccc tcctccctga tctcattgct | 1680 |
| ggggctcatc aaaaatgctga tcctgttgtt ttggatgtta gttggattag cttgtggttt | 1740 |
| gcttttaatc ggagctttga gcctacccat agaaatgaga tgcttgagat tgctcctttg | 1800 |

```
attgagagcg tttatgccag tgaactttca gtgatgaagg tggatatgcg tcatttgtca    1860
ttgatgcagc gtaggtttcc tgatgtcttg attcaggcta ggccttctca ttttt ggaag   1920 gctgttttga atgactcacc tgaagctgtt aaagctgtga tgaatttgtc tcactctcac   1980
aattttatta atattcggga catgatgagg tgggtgttgt tgccctctct tcagccgtct   2040
cttaaacttg tgttggagga ggaggcttgg gctgctgcta atgattttga agatcttatg   2100
ttgaccgatc aagtgtatat gcatagggac atgttgcctg agccgaggtt agatgatatt   2160
gagaggttta ggcaagaagg gttttattat accaatatgc ttgaggcccc gcccgagatt   2220
gatagggttg ttcaatatac ttatgagatt gccaggttgc aagctaatat gggccaattt   2280
cgggctgctc ttaggagaat tatggatgat gacgattggg tgaggtttgg ggggtgctt    2340 aggactgtca gggtgaaatt tttcgatgct aggcccccgg atgatatttt acaagggttg   2400 cccttt agtt atgacactaa tgagaaaggg ggccttt ctt atgccactat caaatatgcc   2460
actgagacta ctatatttta tcttatatat aatgtggagt tttcaaatac tcccgactca   2520
cttgtgctta ttaatccgac atatactatg acaaaagtct ttattaataa gcggattgtc   2580
gagcgggtga gggtcggcca aattcttgcc gtgcttaatc ggcggtttgt cgcctataag   2640
ggcaaaatga ggattatgga cattactcaa tcacttaaaa tgggcactaa acttgccgcc   2700
ccgactgtct gactcgag                                                 2718

<210> SEQ ID NO 23
<211> LENGTH: 1618
<212> TYPE: DNA
<213> ORGANISM: Artificial sequence
<220> FEATURE:
<223> OTHER INFORMATION: N. benthamiana optimised BTV-8 VP5

<400> SEQUENCE: 23
ttaattaatc gcgaccggta tgggaaagat tattaagtcc ctctcaaggt tcggaaagaa     60
ggttggaaac gctcttactt ccaacactgc taagaagatc tactccacta ttggaaaggc    120
tgctgagaga tttgctgagt ctgagattgg atccgctgct attgatggac ttgttcaggg    180
atctgtgcac tctcttatga ctggtgagtc ttacggtgag tctgttaagc aagctgtgct    240
tcttaacgtt atgggatctg gtgaagaact tccagatcca ctttctccag gtgaaagggg    300
aatgcagact aagattcgtg aacttgagga tgaacagagg aacgagctta ttaggctcaa    360
gtacaacgat aagatcaagc agaagttcgg aaaagagctt gaagaggttt acgagttcat    420
gaacggtgtt gctaagcaag aggaagatga agagaagcac tacgatgtgc ttaagaaggc    480
tgttaactcc tacgataaga tccttactga ggaagagaag cagatgagga ttcttgctac    540
tgctctccag aaagaggtga agaaaggac tggaactgag gctgttatgg tgaaagagta    600
caggaacaag atcgacgctc tcaaagaggc tattgaggtt gaaagggatg gaatgcagga    660
agaagctatc caagagatcg ctggaatgac tgctgatgtt cttgaagctg cttctgaaga    720
ggttccactt attggagctg gaatggctac tgctgttgct actggaaggg ctattgaggg    780
agcttacaag cttaagaagg tgatcaacgc tctttctgga attgatctca ctcacctcag    840
gactccaaag attgagccaa ctatcgtgtc tactgtgctc gatcacaagt tcaaggatat    900
cccagatgag atgcttgctg tgtctgtgct ttctaagaat agggctatcg aagagaacca    960
caaagagatc atccacctca gaacgaaat tctcccaagg ttcaagaaag ctatggatga   1020
agagaaagag atttgcggaa tcgaggataa gaagatccac ccaaaggtta tgatgaagtt   1080
```

| | | | | |
|---|---|---|---|---|
| caagatccca | aggactcaac | aaccacagat | tcacatctat | tccgcacctt ggqattctga | 1140 |
| tgatgtgttc | ttcttccact | gcatttctca | tcatcacgct | aacgagtctt tcttcatcgg | 1200 |
| attcgatctt | ggaattgatt | tggtgcacta | cgaggatctt | actgctcatt ggcatgctct | 1260 |
| tggagctgct | caagctgctg | ttggaagatc | tcttaacgag | gtgtacaaag agttccttaa | 1320 |
| cctcgctatc | aacaacactt | actcctctca | aatgcacgct | agaaggatga ttaggtccaa | 1380 |
| gactgttcac | ccaatctacc | ttggatctct | ccactacgat | atctcattct ctactctcag | 1440 |
| gtctaatgct | cagaggattg | tgtacgatga | ggaacttcag | atgcacattc ttaggggacc | 1500 |
| acttcatttt | cagagaaggg | ctattctcgg | agctattaag | cacggtgtga agattcttgg | 1560 |
| aactgaagtg | gatattccac | tcttccttag | gaacgcttga | ctcgaggcct ggcgcgcc | 1618 |

<210> SEQ ID NO 24
<211> LENGTH: 1593
<212> TYPE: DNA
<213> ORGANISM: Artificial sequence
<220> FEATURE:
<223> OTHER INFORMATION: Plant Codon Optimised BTV-8 VP5

<400> SEQUENCE: 24

| | | | | |
|---|---|---|---|---|
| accggtatgg | aaagatcat | caagtccctg | tctagattcg | gtaaaaaggt aggaaacgca | 60 |
| ctgacaagta | acacagctaa | gaagatctac | tccacaatcg | gaaaggctgc tgaacgattt | 120 |
| gctgaaagtg | aaatcggaag | tgctgcaata | gatggtcttg | tacaaggatc tgtacattct | 180 |
| ctaatgacag | gagaatccta | cggagaaagt | gtaaagcaag | ctgtactatt gaacgttatg | 240 |
| ggaagtggag | aagaactacc | agatcctctt | agtcctggag | aacgaggaat gcaaactaaa | 300 |
| atccgtgaac | tagaagatga | acaaagatcc | gaactaatca | ggctgaagta caacgataag | 360 |
| atcaagcaga | agttcggtaa | agaactggaa | gaagtttacg | aattcatgaa cggtgttgca | 420 |
| aagcaagaag | aagacgaaga | aaagcactac | gacgttctga | gaaggcagt taactcatac | 480 |
| gacaagatcc | tcacagaaga | gggagaagcaa | atgcgaatcc | tcgcaacagc tttacaaaaa | 540 |
| gaggttaaag | agcgtacagg | tactgaagca | gttatggtta | agagtaccg taataagatc | 600 |
| gacgccctca | agaggcaat | cgaagttgaa | agagacggta | tgcaagaaga agctattcag | 660 |
| gaaattgcag | gtatgactgc | agacgttttg | gaagcagcat | ctgaagaggt tccacttata | 720 |
| ggtgctggta | tggcaactgc | agtggctact | ggtagagcaa | ttgagggtgc ttataagctt | 780 |
| aaaaaggtta | ttaatgcttt | gtctggtata | gatttgactc | atctcagaac tccaaaaatt | 840 |
| gagcctacta | ttgtcagcac | ggttctcgat | cataagttca | aagacatacc ggacgagatg | 900 |
| ttggcagtgt | cagtgctttc | taaaaatcgt | gctattgagg | agaatcataa agagattata | 960 |
| caccttaaaa | atgagatact | ccctaggttc | aagaaagcca | tggatgagga gaaagagatt | 1020 |
| tgcggcatag | aggataagaa | aattcaccct | aaagtcatga | tgaagtttaa aattccgagg | 1080 |
| acccagcagc | cacagataca | catatatagc | gctccttggg | atagcgatga tgtcttttc | 1140 |
| tttcactgta | ttagccacca | tcacgctaat | gagagcttt | tcattgggtt tgatttgggc | 1200 |
| attgatcttg | tgcactatga | ggatcttacg | gcccattggc | atgctcttgg cgctgctcaa | 1260 |
| gctgctgtcg | gcagatctct | taatgagtg | tataaggagt | ttttgaactt ggccattaat | 1320 |
| aataccttatt | catcacagat | gcatgccagg | aggatgatta | ggtcaaaaac cgtgcatcca | 1380 |
| atatatttgg | ggtcacttca | ttatgatatt | tcattttcta | ccttgcggtc taatgcccag | 1440 |
| aggattgtct | atgatgagga | gttgcagatg | catattcttc | ggggcccctt acattttcag | 1500 |
| agacgggcca | ttttaggggc | cattaagcat | ggggtgaaaa | ttttagggac cgaggtggat | 1560 |

```
attcccttat ttttaagaaa tgcctgactc gag                                1593
```

<210> SEQ ID NO 25
<211> LENGTH: 1087
<212> TYPE: DNA
<213> ORGANISM: Artificial sequence
<220> FEATURE:
<223> OTHER INFORMATION: N. benthamiana optimised VP7

<400> SEQUENCE: 25

```
ttaattaatc gcgaccggta tggatacaat tgctgctagg gctcttactg ttatgagagc     60
ttgcgctact cttcaagagg ctaggattgt gcttgaggct aacgtgatgg aaattctcgg    120
aatcgctatc aataggtaca acggacttac tcttaggggt gttactatga ggccaacttc    180
tcttgctcag aggaacgaga tgttcttcat gtgcctcgat atgatgcttt ctgctgctgg    240
tattaacgtg ggaccaatct ctccagatta cactcagcac atggctacta ttggagttct    300
tgctactcca gagatcccct ttactactga ggctgctaat gagattgcta gggtgacagg    360
tgaaacttct acttggggac cagctagaca accatacgga ttttttcttgg agactgaaga    420
gactttcaa ccaggacgtt ggtttatgag agctgctcaa gctgttactg ctgttgtttg    480
cggaccagat atgattcagg tgtcccttaa tgctggtgct agaggtgatg ttcagcagat    540
tttccagggt aggaacgatc caatgatgat ctaccttgtg tggagaagga ttgagaattt    600
cgctatggct cagggaaatt ctcaacaaac tcaggctggt gttactgttt ctgttggagg    660
tgttgatatg agagctggaa ggattattgc ttgggatgga caagctgcac ttcatgttca    720
taacccaact cagcagaatg ctatggttca gattcaggtg tgttctaca tctctatgga    780
taagactctc aaccagtacc cagctcttac tgctgagatc ttcaacgttt actccttcag    840
ggatcatact tggcatggac tcaggactgc tattctcaac aggactactc ttccaaatat    900
gctcccacca atcttcccac caaacgatag ggattctatc cttactttgc tccttcttag    960
cactcttgct gatgtgtaca ctgttcttag gccagagttc gctattcatg tgttaatcc   1020
aatgccagga ccacttacta gagctattgc tagggctgct tatgtgtgac tcgaggcctg   1080
gcgcgcc                                                             1087
```

<210> SEQ ID NO 26
<211> LENGTH: 1062
<212> TYPE: DNA
<213> ORGANISM: Artificial sequence
<220> FEATURE:
<223> OTHER INFORMATION: Plant Codon Optimised BTV-8 VP7

<400> SEQUENCE: 26

```
accggtatgg atacgatcgc tgctcgtgct ctaactgtaa tgagagcatg tgctacacta     60
caagaagcac gaatcgtact ggaagctaac gtcatggaaa tcctgggaat cgccataaat    120
cgatacaacg gtctgacgct acggggagta acaatgagac tactagtct tgcacaaaga    180
aacgaaatgt tcttcatgtg cctcgacatg atgctctccg cagctggaat taacgtcggt    240
ccaatatccc cagattacac acaacatatg gcaacaatcg gtgtgctcgc aacacctgaa    300
atccctttca ctacagaagc agctaacgaa atagcacgtg taaccggaga gacaagtaca    360
tggggaccag caagacaacc atatggattc ttcttggaga cagaggagac atttcaacca    420
ggtagatggt ttatgagggc tgctcaagca gttactgctg ttgtttgtgg accagatatg    480
atacaggtga gccttaacgc tggtgcaaga ggtgacgttc aacaaatatt tcagggtaga    540
```

```
aacgaccta  tgatgatata  cctcgtgtgg  aggagaattg  agaattttgc  tatggcccag    600
ggcaatagcc  agcaaaccca  agctggtgtt  actgtttctg  tgggcggcgt  tgatatgagg    660
gcagggcgaa  ttattgcttg  ggatgggcag  gctgcacttc  atgttcataa  tccaactcag    720
cagaatgcta  tggttcagat  tcaggttgtt  ttctatattt  caatggacaa  gaccttgaat    780
cagtacccgg  ctcttacggc  tgagattttt  aatgtctatt  catttcgtga  tcacacctgg    840
cacgggttga  ggaccgctat  tttgaatcgg  accactttgc  ctaatatgtt  gcctcctatt    900 tttccccga   atgatagggga ttctattctt  actcttttgc  ttttatctac  tttagccgat    960
gtctatactg  tgttacgtcc  tgagtttgcc  attcatggcg  tgaatccgat  gcccgggccc   1020
ttaactaggg  ccattgcccg  ggccgcctat  gtgtgactcg  ag                      1062
```

<210> SEQ ID NO 27
<211> LENGTH: 2923
<212> TYPE: DNA
<213> ORGANISM: Artificial sequence
<220> FEATURE:
<223> OTHER INFORMATION: N. benthamiana optimised BTV-8 VP2

<400> SEQUENCE: 27

```
ttaattaatc  gcgaccggta  tggaagaact  cgctatccca  atctacacta  acgttttccc    60
agctgagctt  cttgatggat  acgattacat  catcgatgtt  tcttctaggg  ttgaagaaga   120
aggcgacgag  ccagttaaga  ggcatgatgt  gactgagatt  cctaggaact  ccatgttcga   180
tatcaaggat  gagcacatca  gggatgctat  tatctacaag  ccagtgaaca  acgatggata   240
cgttttgcca  aggtgctcg   atattactct  caaggctttc  gatgatagga  agcgtgttgt   300
tcttaacgat  ggacactctg  agtttcacac  taagactaac  tgggtgcagt  ggatgattga   360
tgatgctatg  gatgtgcagc  cactcaaagt  tgatattgct  cacactaggt  ctaggatttc   420
tcacgctctc  ttcaattgca  ctgtgaggct  tcattctaag  aaggctgata  ctgcttctta   480
tcacgttgag  ccagtggaaa  ttgaatcttg  gggatgcaat  cacacttggc  tttctaggat   540
tcaccacctt  gttaacgttg  agcttttcca  ctgttctcaa  gaggctgctt  acactcttaa   600
gccaacttac  aagatcattt  ccaacgctga  aagggcttct  acttccgatt  ctttcaacgg   660
aactatgatc  gagcttggta  ggaatcatca  gatccagatg  ggagatcaag  ataccagaa    720 gcttaaagag  ggacttgttc  aggttagaat  cgagggaaag  actccacttg  ttatccagga   780
agagatcact  gctctcaaca  agattcgtga  gcaatggatt  gctaggaatt  cgatcagcg    840 tgagattaag  gttttggatt  tgtgcaggct  tctttcaact  atcggtagga  agatgtgcaa   900
tactgaagag  gaacctaaga  cgaggctga   tctttctgtt  aagttccaga  tggaactcga   960
tgagattttc  aggccaggaa  ataacgagag  gactaacatt  atgggaggtg  gagttcatag  1020
aaagaacgag  gacaggttct  acgtgctcat  tatgattgct  gcttccgata  caaacaaggg  1080
aaggatttgg  tggtctaatc  catatccatg  tcttaggggt  gctcttattg  ctgctgaggt  1140
tcagcttgga  gatgtgtaca  accttctccg  taattggttc  caatggtctg  ttaggccaac  1200
ttacgttcca  tacgatagga  acagagagtc  cgataagtac  atctactcca  ggatcaacct  1260
tttcgattct  actcttaggc  caggtgataa  gattgtgcac  tggagtaca   agcttttgaa   1320 cgaggttaga  gaggtgtcaa  tcaacaaggg  aaacgagtgt  gatttgttcc  cagaggatga  1380
agagttcact  actaagttcc  atgaggctag  gtatactgag  atgaagaacc  agattattca  1440
gtctggatgg  aaccagagag  atttcaagat  gcacaagatc  cttgaggatg  gtgctaacgt  1500
gctcacaatc  gatttgagga  aggatgctca  cattggaact  ggatctgctc  tttctctccc  1560
```

```
tgattactac aacaagtgga ttatcgctcc aatgttcaac gctaagctca ggattactga    1620
ggttgtgatt ggaactgctc acactgatga tccagctgtt ggaagatctg ctaaggcttt    1680
cactcacgat ccattcgatc ttcaaaggta ctgtctcgct aggtattatg atgttaggcc    1740
aggaatgatg ggtagagctt tgtctaagca gcagaatatg tcctccatga ctgataagct    1800
ttccaagcaa gaggattacg ctggaattgt gtcaagaagg cttgagtaca agagagaga    1860 gaaccgttgt cttactgaga ctgctcagta cgttttcgaa aagacttgcc tctacgtttt    1920
ggagcttctt tctaggcata caatgccatc tgaggattct gaagtgactt tcgagcaccc    1980
aactattgat ccatctgtgg atatcgagac ttggaagatc attgatgtgt cccagctcat    2040
tatcttcgtg ttcgattacc ttttcgagaa ccgtaagatc gttagggata caactgaagc    2100
taggtggact cttttcaaga ttaggtctga ggttggaagg gctaggattg atgctatcga    2160
gatgactttt ccaaggttcg gaaggatgct taggaatgct tctcaggcta agatcaacca    2220
ggatatcgct tgccttaact tccttccact cctcttcatt atcggtgata acatctctta    2280
cgctcatagg caatggtcta ttccagtgct tctttacgct cacgatatca ggattatccc    2340
acttgaggtt ggagcttaca ataacaggtt cggacttact tcttaccttg agtacatggc    2400
tttcttccca tcttatgcta ctagggtggc aaagattgat gagtccatca agagtgcgc    2460 tattgctatg gctgagttct acatgaacac tgatattcac tctggatccg tgatgtctaa    2520
cgtgatcact actaagaggc ttctctacga gacttacctt gcttctcttt gcggtggata    2580
ctctgatgga cttctctggt acttgccaat tactcaccca tctaagtgcc ttgttgcttt    2640
cgaagttgct gatgatgttg tgccactttc tgttagaaga gagaggattc tttctaggtt    2700 cccacttttct tcaaggcacg tgaagggaat tgctcttatt tccgtggata ggaaccagaa    2760
agtttctgtt cagactgagg gaattgtgac tcataggctc tgcaagaaga accttctcaa    2820
gtacgtttgt gatgtgatcc tcttcaagtt ctctggtcac gttttcggaa acgatgagat    2880
gcttactaag ctcctcaacg tttgactcga ggcctggcgc gcc                      2923

<210> SEQ ID NO 28
<211> LENGTH: 2889
<212> TYPE: DNA
<213> ORGANISM: Artificial sequence
<220> FEATURE:
<223> OTHER INFORMATION: Plant Codon Optimised BTV-2 VP2

<400> SEQUENCE: 28
atggatgaat taggaatacc aatctacgga aggaattacc cagaacactt actcaaagga      60
tacgaatttt taatcaatac aggagttagg tatccatctc aaggaggtag acatgatgtt     120
tcaaagattc ctgaaatgtt cgcttatgat attaaggatg agggaataag agaagcattg     180
aaatacatgc caactaggaa tgatggagtt gtgttgccta gatcgtggat tattagttta     240
aagggttacg atatcaggaa atccgttatt gaagctaata agagtaactc cttccacact     300
gatacaaatt gggttcagtg gatgattaag gattctatgg atcaacagcc attgaaaatc     360
tcaattgatg aagagcatag tagagttgtg cactccctt ttaactgtca ggttaagatc     420
gatgctaaga aagcagatac tctctcttat catcttgaag ctattgagga tgctgaaaaa     480 gcatgttttgc atacaagggg tcaattgtgc aatcatcttg ctaggatgga tcttttgcat     540
gctgcacaag aaattgctta tgctattaag cctacttacc agcttattgt gcactcagag     600
agggcttcta catcagataa ctttgaactc ggaagacaag atgttattac tcttagaagg     660
```

-continued

| | |
|---|---|
| ggacatagga tacagatggg agatgaggca tatactaagt tgatggaaag acttgttagg | 720 |
| ttgacagtgc agggtaacgt tccaagaaaa atccaatctg aaattgagca gcttgaagct | 780 |
| attagaacta ggtgggcaac aggaagatac gatcctgctc acatcaacag tcaagatctc | 840 |
| tgtaggattc tttccagaat tggtaggatc atgcttgatc aagaagctga gccagttgat | 900 |
| gaagatagtc tttccttgag attccagagg gcactcgatg agaagtttag gcttaacgat | 960 |
| tctgagagaa acaaaatctt cgaacctaag tcacatagaa aggatgaaga taggttttat | 1020 |
| gttttactcg ctatagctgc atctgatact tataattcaa gaatctggtg gagtaaccca | 1080 |
| taccettgct tgaggggaac tttaattgct gcagagacaa agctcggaga tgtttatttt | 1140 |
| actcttaggt cctggtacga ttggtctgtg agatcttcat atgttccaag agaaagggag | 1200 |
| agagaaacag agaagtacat attctctaaa atcaatttgt tcgattacga agctggacct | 1260 |
| agttccaagg ttattcattg ggagtatcag ctttacaaaa gggagagagt tgtgactttg | 1320 |
| gaaagaggta acccatgtga tctttatcct gatgaggatg atgaagtgat tataacaaag | 1380 |
| ttcgatgatg caaagtactc agagatggtt ggagaaatca ttgatggagg ttggaatgat | 1440 |
| gaagagttca agatgtataa gcttttgcaa gagaagggta atgttttgac tatagatttc | 1500 |
| gaaaaggata ctaagctcaa ctctacatca gaggttgtgc ttccagatta ttacggaaag | 1560 |
| tggattgttg ctcctatgtt caactctaaa atgagaatta ttgaaactga gattgcaaca | 1620 |
| aacaggtcag atgatccaat gataaagaga actttgaaac caatgacaga tgatcctgtt | 1680 |
| gaattgcaaa gatatacttt agctaggtac tacgatatta gacctggact catgggtaga | 1740 |
| tctcttaata ggactcaaac acagtcaaca ttcgatgcaa aggttagtga gctttccgat | 1800 |
| tacgaaaaag ttgtgtcaag atttggagtg ataagaaac caactaggcc ttgcgttact | 1860 |
| ttgacaggta gatacatctt agaaaagtac agtctcctcc ttatcgatat cttgaagtac | 1920 |
| cacactgagg ttgaagagaa cccacaagaa gagttcacac atcctagaat agatcttcaa | 1980 |
| ttcaagttta atggtaacac tttatctgat ctcaaccaaa cagttgtgtt tattgttgat | 2040 |
| tatcttcacg aaaagagaaa ctacgttagg agtgtgtatg aggctagata cattatatcc | 2100 |
| aggataagat cttcaacagg tgctgcaagg atgagtatct tggaattcta cttcccaact | 2160 |
| tttgctaggc tcatatctaa tgcaagagag cctacatacg tgaaagatct tatggcattg | 2220 |
| aatttcttac cattgctttt tattgttgga gataacatga tctataagca tagacaatgg | 2280 |
| tcaattccac tcctttttgta cactgatagg gttaaagtga tacctttgga agtgggaagt | 2340 |
| tccaataaca gacagggtct cgttagttat cttgagtata tgttttttctt tccttccctt | 2400 |
| gctgatagga catcaaaggt ggatgagagt atgataaagg tttccaagga agttgtgaac | 2460 |
| tactacatga agactacaat ctctgaagga ggtgttaatt tgaacgttgt gtctactaag | 2520 |
| tcactcctct acgatatata tctttcttct gtgtgtggag gtgtttcaga tggtgttgtg | 2580 |
| tggtatttgc caatcacaca cccttacaaa tgtgttgtgg ctattgaagt gtgcgatgat | 2640 |
| agagttccag caaggcttag atgcgatagg ttaagactca ggttcccttt gtctgctcaa | 2700 |
| catcttaagg gaatagttgt gattcaaatt aatgaggagg gaggttttga tgtttatact | 2760 |
| gagggtattg tgcacacacag ggtttgtaag aaatcacttt tgaagcatgt ttgtgatatc | 2820 |
| gttttactca agttccacgg tcacgttttc ggtaatgatg agatgcttac aaagttatta | 2880 |
| aatgtgtga | 2889 |

<210> SEQ ID NO 29
<211> LENGTH: 2890

```
<212> TYPE: DNA
<213> ORGANISM: Artificial sequence
<220> FEATURE:
<223> OTHER INFORMATION: Plant Codon Optimised BTV-3 VP2

<400> SEQUENCE: 29
accggtatgg aggaactggt aatccctgta attagccggc aattcgataa gaagctggta      60
ggtagatacg aatacgttat cgaactagca gaaccagaac aagatgaatg gactaaccat     120
gacgtaacac aaatccctgg acgtagaatg tttgatgtag cacaacaagg aatccgagaa     180
gctataatct acaagccatt ggataacgac ggtgaagttt tgcctagaat actagacatg     240
agtatcgctt gttacgatat gagaaagacg atgatgaaga aggagggtgt tgatttcgtg     300
tctaacacaa gatggcttga atggatgatc caagactcta tggatgttca accacttaga     360
gtacaaatga aggaggacca ttctacagtg caatatgaca tgttctccgc taaggtacat     420
atcgacagtc gaaaagctga tactacttcc taccatgcta ttgcagttga aacaaaggca     480
gagagaaagt gttgtcatgt aagaacagaa gtctggaatt ccgtagtcag aaatcatctt     540
ttcaacaccg cacaagagag ttgttacacg ttcaagcaaa cgtacgaact gatcgtaaac     600
tccgaacgac taagtacaga ggaggaattt cgagtaggag ctccacagtt tcacactata     660
caaagaaatc accgaatgca actaggagat aacgcttatg ataagttcct aaagggattg     720
gtacaactgc gagtttctgg aactactcca gcaaagatta gagatgaagt tgctgctctt     780
gatgttatta gggataactg gataagagga tcattcgatc gtagtcatat caaaagcctg     840
gaactgtgta gacttctaag ttctattggg cgtaagatgg ttaacatgga ggaggagcct     900
aaagatgaaa aggatctgtc cgttaaattc cagttccgac tagatgagaa gttctcccca     960
aatgatccag aaagaaacgt tatctttacc agtaagaccc atagaaccaa cgaagatcga    1020
ttttacgtcc tactggtcat cgcagctagt gatacaaata acggaagagt ttggtggtct    1080
aatccatacc cttgtctaag aggagcactt attgcagcag aatgtaaact tggtgatgtt    1140
taccatacgc tgagatcaaa gtatgaatgg ggagttagac caacttacaa acctaaggat    1200
ttggaacgtg aacgtgagaa atacgttgtt ggaagggtga atctgtttga tctggaagga    1260
gagcctgcaa ctaaagttat acactgggaa tacgaactca tttcacctac ttacagtgtt    1320
agtaaccaca aggtaatca ctgtgatctc tacccagatg atgttgaaat aaccacgaag    1380
tttaatgagg atcggtaccg tgagatgata cagtccgtga ttgatgatgg ttgggatcaa    1440
aagaacttga agatgtacaa gatattggag gaagaaggga atcctttgct ctatgatctc    1500
gaaaaggaca taaagctcga ttcacagagt caagttgttt tcccatcata ctataataag    1560
tggacccacg ctccaatgtt caatgcaaga gttaagcctt gtgatatcga gttggctgag    1620
cgaaaaaatg atgatccctt cgttaagcgt acattgaagc ctataaaggc tgattgtgtc    1680
gatctcttga ggtatcatat gtcacattac tacgacctca gccttcact taagggtgtt    1740
tcactttcaa acaagcagac accatcaggt atacatcagg ctcttgttca ggatgatctt    1800
tattcccgtc ttttaaggcg tcgtgatgtg gatttagact attcatctcc ttgcccgatt    1860
ataactaatt attttctctt ggagaaattc cacatactca tcttgaccat catggagaaa    1920
cactattggg aactcgacga ctcagacgat gtttatgagt tccctaagat cgacgcaagc    1980
gcttttgagg ttgatggtac tctttatgat attagccaga caattgtgca tatgtatgac    2040
aggttcttcg agaaaaggag agtgctccgt tctatagatg aatccaggtg gattttgcat    2100
ctcatcagga tttctcaggg tagggaaagg ttagaagtta ttgagaggtt ttttcctaat    2160
```

```
tatgggaaag ccatgaggca gagggatttt aaaaaagtcc gggatgttat gtttcttaat    2220
tttttgccgt tctttttttct taccggcgac aatattagct atgagcaccg gcagtggagc    2280
attccgatta ttttgtatgc cgacaaattg cggattcttc cgattgaggt cggtgcccat    2340
tataataggt ttggtgttac ttgcatactt gagttattaa attttttcc gagctatgaa    2400 aaaagggagg aaaaattgga agaggacatt gtgttgtgcg ccgacgccat tgtgaatttt    2460
tatcttcaga ccacaattag caatggcggc gtgcagacct ctattgtgtc tactaaggcc    2520
cttttatatg agatgtattt gtcttctatt tgcggcgggt attctgaggg tgtcctttgg    2580
tatcttccca ttacacaccc cgtgaaatgc ttagttgctt tggaggtgtc agatgccttg    2640
gtgggtgctg atgtgaggat tgataaaatt aggaggcggt ttcccttatc tgctaaacat    2700 cttaaggggaa ttgtccagat ttctgtgcat cccaatcgga catttctgt cacaacttgc    2760 ggcattgtca aacacaaagt gtgcaaaaaa actttattaa aacatcggtg cgacgtcatt    2820
ttacttcaga ctccagggta tgtgtttggc aatgacgagc ttttgacaaa attattgaat    2880
atttgactcg                                                          2890

<210> SEQ ID NO 30
<211> LENGTH: 2883
<212> TYPE: DNA
<213> ORGANISM: Artificial sequence
<220> FEATURE:
<223> OTHER INFORMATION: Plant Codon Optimised BTV-4 VP2

<400> SEQUENCE: 30
accggtatgg aagaattcgt catcccagtt ttcagtgaac gggaaatccc atatgcacta      60
atcaaccagt acccattagc aatccaaaca gatgtacggg tagttgatgt agatggtaac     120
cataacctag tcaagatccc agaaagtgat atgatcgacg tacctaaact agacatcgtt     180
agtgcactta actacaagcc aactagaaac gacggaatag tagtcccaag actacttgat     240
atcactctaa aggcatacga cgatagaaag tccgttaaga acgcaagagg agtagatttc     300
atgacagacg caaaatggat gaagtgggca atagatgata gaatggacat ccaaccattg     360
aagatcacac tggatgaaca ttactccgta aaccatcaat tgttcaactg catcgtcaag     420
gcaaagacag caaacgcaga tacaatctac tacgattact tcccattgga agaccgagct     480
aaaaagtgta accatacaaa cctggaacta ctacgaagtc tgacaacaat cgaagcattc     540
catatcctac aaggagcagc ttatagtcta agtccaact acgacctgat agctaattcc     600
gaaagagaat ccctggaaga tcttaccct ataggtagtg aaaagtgggt tcatttgaca     660
agacgaacaa agatcggaaa ctctggactt agttacaatc gtttcatcag cagtatggta     720
caggtcgttg taagaggaaa ggttcctgat atcatcagag gtgaaatcac acaattgaac     780
cgaattagga cagaatggat tggagcaagt tacgacagaa ctagaatacg tgctctggaa     840
ctttgtaata tactgtccgc tataggtaga aagatgatgg acacacacga agaaccaaag     900
gacgaaatgg acctgtcaac aagattccag tttaagttag acgaaaagtt caatacgagc     960
gactccgaac atgtcaatat tttccgaacc agtggagctg ctacaaatga aggtagattc    1020
tacgctctga tagcaattgc tgcaactgat actcaaaagg acgagttttg agaactaat    1080 ccatatcctt gttaagagg tgcttaata gctagcgaat gtgaactggg agatgtttac    1140 tacacttaa ggcacgtata tcagtggagt ttgcgaccag aatacggaca acgagaacaa    1200
caattggaag ataacaagta cgtattcggt agagtcaatc tcttcgactc agacttggca    1260
gttggagatc aaattataca ctggcaatac gaaattaccg agccagttaa gactacttac    1320
```

```
gacgatggat acatatgtaa tccggaagaa gaggacgatg agctcctttg taaaattgac   1380
gacgagcgtt acaaagagat gatggagcgt ttaatagagg gaggatggga tcaagagagg   1440
tttaaattac attccattct cactgagcct aatcttctca ctattgattt cgagaaggat   1500
gcttacctca attcccgttc tgagttggta ttccctaatt acttcgataa gtggattaat   1560
agcccgatgt ttaatgcccg tttaaggatt acccacggtg agataggttc ttcaaagact   1620
attgatcctt ggaatcgtag agtggtttac ggttatgtga agactagcat tgagagctta   1680
gattatgccc tcggtcgtta ttatgatatt cggctccaac tctttgggga tactctttct   1740
caaaagcaaa ctcagagcgc tgttttact tatctcagcg agcaagatga ttttcctgct   1800
cttaccaatt atagcaaggg tgaggctgtt tgtcctcatg ctggtggtgc tgtttatacg   1860
tttagaaaag ttgctctttc tttgatagcc aattatgaga agctctctcc tgagatgcat   1920
gagggtttgg agcatcaaat gtatgttcat ccttcagcta ataccaccta tcaaaagcaa   1980
gttaaggata tgaaggattt ttcacagctc atttgcttta ttattgattg cattttgag    2040 aagagggtgc agattagggg cgtcggggag gctaggcgta taatatatct tattcagaat   2100
tctacgggct ctcagcgtca ggaagttctt aagaaaacct ttcctaactt ctttatgagg   2160
atttttaaat tgagggaggt caaacggatt tgcgatcttt ctgtgattaa tttcttcct   2220 ttgttgtttc ttgtgcagga taatatttca tattggcaca ggcagtggtc tgtgcccatg   2280 attcttttg atgatgccgt gaggcttatt cccgtggagg tgggcgctta tgccaatagg   2340
tttgggctta aatcttttta taattttgtg cggtttcacc cgggcgattc aaagaaaaaa   2400
caggatgccg atgatatgca caaagagtat ggcgtggctt gttttaaata ttatatgaat   2460
accaaaattt cacagggcgg ggtgaatgtg ccggtcgtca cgtctaaatt ggatacgctt   2520
aaaattcact tggcctcatt gtgccttggg ttggccgatt ctattgtcta taccttgcct   2580
gttgcccatc cgaaaaaatg tattgtgctt attgtggtgg gcgatgataa attggatccc   2640
caggttaggt cagagcaggt tttatctaaa tattattatt caaggcggca tatttgcggt   2700
attgtggccg tttctgttgg gcaggagggg cagttgcagg tttattcatc tggtattgtt   2760
aggcatagga tttgtgagaa atcaattctt aaatataagt gcaaagtggt tttggttcgg   2820
atgcccggcc acgttttggg gaatgatgag cttatgacca aattacttaa tgtttgactc   2880
gag                                                                  2883
```

<210> SEQ ID NO 31
<211> LENGTH: 2898
<212> TYPE: DNA
<213> ORGANISM: Artificial sequence
<220> FEATURE:
<223> OTHER INFORMATION: Plant Codon Optimised BTV-8 VP2

<400> SEQUENCE: 31

```
accggtatgg aagaactggc aatcccaatc tacacaaacg tattccctgc agaactacta     60
gatggatacg attacatcat cgatatctcc tccagagtag aagaagaagg agatgaacca    120
gttaagcgac atgatgttac agaaatccct agaaactcca tgttcgatat caaggatgag    180
cacatcagag atgcaatcat ctacaagcca gtaaacaacg atggttacgt actgccaaga    240
gtacttgata tcacactgaa ggcattcgat gatagaaaga gagtaatcct caacgatgga    300
cacagtgaat tccacactaa gtcaaactgg gtacaatgga tgatcgatga tgcaatggat    360
gtacaaccac taaaggtaga tatcgcacac actagaagtc gaatcagtca tgctttgttc    420
```

```
aactgcactg taagactaca cagtaagaag gcagatacag caagttacca tgttgagcca    480
gttgaaatcg aatcacgagg atgtaatcat acatggctag gtagaatcca tcatctagtt    540
aacgttgagc tgttccattg ctctcaagaa gcagcatatg cacttaagcc tacttacaag    600
atcatctcta acgctgaacg agcatctaca agtgatagtt tcaacggaac aatgatcgaa    660
ctaggaagaa accaccaaat ccaaatggga gatcaaggat accaaaagct gaaggaagga    720
ctagttcaag ttagaataga gggaaagaca ccactggcaa tacaagaaga aattacggca    780
ttgaacaaga ttagggagca atggattgca cgaaacttcg atcaacgaga gataaaggtt    840
ctggatttgt gccgattatt atccacaatt ggcagaaaga tgtgcaacac agaggaagaa    900
cctaagaacg aagctgatct gtctgttaag ttccaaatgg aactggatga aattttcagg    960
ccaggaaaca atgagagaac gaatatatg ggcggaggtg ttcacagaaa gaatgaggat     1020
agattctacg tcctgattat gattgctgct tccgatacga caagggaag aatttggtgg     1080 tcaaatccat acccatgttt gagaggtgct ttaattgctg ctgaagttca actcggagat    1140
gtttacaatc tcctcagaaa ttggttccaa tggtctataa ggccaacata cgttccatac    1200
gatagaaatc gagagagtga taagtacata tacagcagga ttaatctctt cgactccacc    1260
ctcaagcctg gagataagat agttcactgg gaatacgaac tcttgaatga agtgcgtgaa    1320
gtttccatta gtaagggtaa tgagtgcgat ctcttccctg aagatgaaga gttcactaca    1380
aagtttcacg aagctagata cacagaaatg aagaatcaga ttattcagtc cgggtggaat    1440
cagcgtgatt ttaagatgca caaaatactt gaggacggtg ctaatgtgct cacgattgac    1500
tttgagaaag acgctcacat tggtacgggt tctgcacttt ctcttcctga ttattacaac    1560
aaatggatta ttgctcccat gtttaatgcc aaactccgga ttaccgaggt tgttataggg    1620
acagcacata cagatgatcc tgctgttggt agatctgcta aagcttttac gcatgatcct    1680
tttgatctcc agaggtattg tttggcaagg tattatgacg ttcgtcctgg tatgatgggt    1740
agggctttat ctaaacagca gaatatgagt tctatgactg ataaactttc caaacaggag    1800
gattatagcg gtattgtgag ccgtcgtctt gaatatcgtg aaagggaatc aaggtgtctt    1860
acagaaaccg ctcagtatgt ttttgaaaaa acctgccttt atgtgcttga gttgttgagc    1920
aaacatacca tgcctagcga agatagcgaa gttacctttg agcatcctac tgttgatcct    1980
aatattgaca tagagacctg gaaaataata gacgtgagcc agcttataat ttttgtcttt    2040
gactatcttt ttgagaatcg gaaaattgtc cgggacacca ccgaggcccg ttggactctt    2100
tttaaaattc ggagcgaggt tggtcgtgct aggatagatg ctattgagat gacttttcct    2160
aggtttggtc gtatgttgcg taatgttagc caggctaaaa ttaatcagga gattgcctgt    2220
ttgaatttct gccgcttttt gtttataatt ggcgacaata taagttatgc ccatcggcag    2280
tggtctatac ccgttctttt gtatgcccat gacatacgta ttattccgct tgaggtgggt    2340
gcttataata tcggtttgg gttgacctca tatttggagt atatgacctt ctttccgtca     2400
tatgccacta ggttggctaa aattgacgag tcaattaagg agtgcgctat agctatggct    2460
gagttttata tgaatactga cattcattca ggcggggtca tgtctaatgt gattactact    2520
aaacggttgc tttatgagac ttatttggcc tctttgtgtg cggctattc tgacggtctt     2580 ctttggtatg tgccgattac tcatccctca aaatgtcttg tggcctttga ggtcgccgac    2640
gacgtggtcc ccttatctgt gaggagggag aggattttat ctaggtttcc gttatcatct    2700
aggcatgtca aagggattgc cttaatttca gtggacagga atcagaaagt ctcagtccag    2760
actgagggga ttgtgactca tcggttatgt aaaaagaatt tgttaaaata tgtctgtgac    2820
```

```
gtcattttgt ttaaattttc agggcatgtg tttggcaatg acgagatgct tactaaatta    2880
cttaatgtgt gactcgag                                                  2898
```

<210> SEQ ID NO 32
<211> LENGTH: 1593
<212> TYPE: DNA
<213> ORGANISM: Artificial sequence
<220> FEATURE:
<223> OTHER INFORMATION: Plant Codon Optimised BTV-3 VP5

<400> SEQUENCE: 32

```
accggtatgg gaaagatcat caagagccta tccagattcg gtaagaaggt cggtaatgct      60
cttaccagta acacagctaa gaagatctac tccacaatcg gaaaggcagc tgaaaggttc     120
gcagaaagtg aaatcggttc tgctgctatt gatggactag tacaaggatc agtacattca     180
atcatgacag agagagagtta cggagaaagt gtaaagcagg cagtactact aaacgtctta     240
ggtgctggag atgaaatccc agatccactt tcaccaggtg aaagaggtat tcaaatgaag     300
atcaaagaga tcgaggagga acagagaaac gaactggtac gattgaagca tggtaaggaa     360
attgcaaaga agtttggcga tgagctagag gaaatctacc aattcatgaa cggtgaagtc     420
aaggaggagg ttcaacagga agaacagtac aaagtgctgt gtaaggcagt taacagttac     480
gagaagttgc tgttagctga gaacgatgag atgagaacac tggctcgtgc acttcaacga     540
gaagctacag aacgaacaga aacagaatct aaaatggtta aggagtaccg tcaaaaaatt     600
gacgcattaa aggccgcaat cgaggttgaa agagacggaa tgcaagaaga agcaatacag     660
gagattgctg gaatgactgc agatgtttta gaggctgctt cagaagaagt tcctcttgtt     720
ggttctggaa tggcaactgc tatagctact ggacgtgcaa ttgaaggtgc ttataaattg     780
aagaaggtta taaatgccct gtcaggtatt gacctctcac acttgcgtac tcctaaaatt     840
gagcctacta tggtcgcaac tactttggag catcgtttca gagatattcc agacaaggaa     900
ctcgctgttt ctatactcgc aaagaataat gccatagtgg ctaataccag ggaagttcag     960
cacattaaag aggagatact tcccaaattc aagaaaataa tggacgagga gaaagagctc    1020
gaaggcatag acgacaaaaa aattcacccc agggtcatga tgaggtttaa agtgcctagg    1080
ccacagcaac ctcagattca catttattcc gccccatggg attctgatga tgttttcttt    1140
tttcactgcg ttagtcactt ccacgttaat gagtctttct ttctcgggtt tgacctcggt    1200
atagatgtcg tgcatttga ggatcttgca gctcattggc atgcacttgg ggctgctcaa    1260
gaagctaaag ggaggacttt gaatgaagct tataaggaat tcttaatct tagcattggc    1320 tctgcctata cgtctcctat gcatgcccgg aggatgatta gaagcaaaac cgtgcatcct    1380
atttatcttg gctccatgca ttatgatatt acctatgaga cgttgaaaag caatgcccaa    1440
agaattgtgt atgatgatga gttgcagatg catattcttc gggggccgtt acattttcag    1500
cggagagcca ttttggggc cttaaaattt ggggttaaag tgttgggcga taagattgat    1560
gtgccgcttt ttttgaaaaa tgcctgactc gag                                1593
```

<210> SEQ ID NO 33
<211> LENGTH: 1593
<212> TYPE: DNA
<213> ORGANISM: Artificial sequence
<220> FEATURE:
<223> OTHER INFORMATION: Plant Codon Optimised BTV-4 VP5

<400> SEQUENCE: 33

```
accggtatgg gtaaaatcat caagtccctc tccagattcg gaaagaaggt aggtaacgca        60
ctatcttcaa acacggcaaa gaagatctac tctacgatcg gaaaggcagc agaacgattt       120
gcagaatctg aaattggagc agctactata gatggacttg tacaaggatc tgtacatagt       180
atcatcacag gagaaagtta cggtgaaagt gtcaagcaag ctgtactact aaacgtcctg       240
ggaactggag aagaattgcc tgatccactt tctccaggag aacgaggtat gcaaatgaaa       300
attaaggaac tggaagatga acaacgaaat gagctagtca gactgaagta caacaaggaa       360
atcaccaagg aattcggaaa cgaactggaa gaagtctacg atttcatgaa tggggaagct       420
aaggaagagg aagtagtcca agaacaatac agcatgctct gtaaggctgt tgatagttat       480
gagaagatcc tgaaggcaga agattccaag atgggaatcc tcgcacgagc tttgcaaaga       540
gaagctagtg agagatcaca agatgaaatt aagatggtta aggagtatag gcagaagatc       600
gatgctctca gaatgctatc gaaatcgagc gtgatggta tgcaagaaga agcaattcag        660
gaaatagcag gtatgacagc agatgttttg gaggctgcat cagaagaagt tccattgata       720
ggtgcaggta tggctacagc tgttgcaact ggtcgtgcaa ttgaaggtgc ttacaaattg       780
aaaaaagtta ttaatgccct ctccggtatt gacctctctc atatgaggtc acctaaaata       840
gagccaacaa ttattgccac cactttggag catagattca aagagatacc cgatgagcaa       900
ttggcagtta gtgttcttaa caagaaaacc gctgtgaccg ataattgcaa tgagattgct       960
cacataaaac aggagatact tccgaagttc aaacggatta tggacgagga aaagagatt      1020 gagggcatag aggacaaagt gatacaccct cgtgttatga tgaggttcaa aattccgcgt      1080
actcagcagc ctcagattca tatatatgct gctccttggg attctgatga tgtgttttc      1140 tttcactgtg tgagccatca ccatcgtaat gagtcattct ttttgggggtt tgaccttggt      1200 atagacgtgt tcactttga ggacttgaca tcacactggc atgctttggg ccttgctcag      1260
gaggcttctg gcagaacttt aacagaggct tatagagagt ttcttaatct ttcaatttct      1320
tctacatatt ccagcgctat tcatgccaga agaatgatta ggagcagggc cgttcatcct      1380
atttttcttg gcagcatgca ttatgatatt acttatgagg ccttgaaaaa taatgcccag      1440
cggattgtgt atgacgagga gcttcagatg catattctta gggggccatt acactttcag      1500
aggagggcca ttttaggggc ccttaaattt ggggttaaaa tttaggcga taaaattgac      1560 gtgcccttat ttttacggaa tgcctgactc gag                                   1593
```

<210> SEQ ID NO 34
<211> LENGTH: 1062
<212> TYPE: DNA
<213> ORGANISM: Artificial sequence
<220> FEATURE:
<223> OTHER INFORMATION: Plant Codon Optimised BTV-4 VP7

<400> SEQUENCE: 34

```
accggtatgg acacaatcgc agcaagagct cttacagtaa tgagggcatg tgctacactg        60
caagaagcaa gaatcgtcct tgaagcaaac gtaatggaga tcctaggaat cgccatcaac       120
agatacaacg gtctgacact gagaggagtc acaatgagac tacaagtct cgcacaaaga       180 aacgaaatgt tcttcatgtg cctcgacatg atgctctccg cagctggaat taacgtagga       240
cctatctccc ctgattacac acaacatatg gctacgatag gagtgctcgc tactccagaa       300
atacctttca caacggaagc tgcaaacgaa attgctaggg taacgggtga acctcaact       360 tggggtccag caagacaacc ttatggtttc ttccttgaga ctgaggagac tttccaacca       420
ggaagatggt ttatgagggc tgctcaagca gttactgcag ttgtttgtgg tcctgatatg       480
```

```
atacaagtga gtcttaacgc tggagctcgt ggggatgttc aacaaatttt tcagggtcga      540
aatgacccaa tgatgatata cttggtgtgg cggcgaatag agaattttgc tatggctcag      600
ggcaatagcc agcaaaccca ggctggtgtt actgttagcg ttggtggggt tgatatgcga      660
gcagggcgta ttatagcatg ggatgggcag gctgctttac atgttcataa tccaacacag      720
cagaatgcta tggttcagat tcaggttgtg ttttacattt ctatggacaa gacccttaat      780
cagtatcccg ccctaaccgc tgagattttt aatgtctatt cttttaggga tcacacctgg      840
cacggcttga ggaccgctat tcttaatcgg actactctac cgaatatgtt gccgcccatt      900
tttcctccca atgatcggga ttctattctt actttgttgt tgttgtcaac attagccgat      960
gtgtatactg tgttaaggcc agagtttgcc attcatggcg tcaatccgat gccaggccct     1020
ttaactcgtg ccattgcccg tgccgcctat gtgtgactcg ag                         1062
```

<210> SEQ ID NO 35
<211> LENGTH: 2719
<212> TYPE: DNA
<213> ORGANISM: Artificial sequence
<220> FEATURE:
<223> OTHER INFORMATION: Plant Codon Optimised AHSV1 VP3

<400> SEQUENCE: 35

```
ggtaccggta tgcaaggtaa cgaacgtatt caggataaga atgagaagga aaaagcttat       60
gcaccttatc tggatggagc ttctgttagc acagataatg gtccaatttt gtctgtttcg      120
ccttgcaaga ataatgcaa aagattaggc aaaatcaatc tgatatggca gcacatgcac      180
cagatgttga tggggccatc cctgaggtca tgactattat tagtgggatc aagggccttt      240
tggggaaaag gattataaag ttataaacgc acctccaaat tcattcagaa ccattccaat      300
gcagtctacc gagtatgtgc ttcaagtgaa tactttctat gagcgaatgt cagagattgg      360
aggtccagtt gacgaaactg acccgatagg attctacgct ttgatactcg aaaagcttaa      420
gtttttgaaa tctgagggag atttatcctg caaggtatag ctactaaaga ctatcgaggt      480
gcagaaattg cagatcctga aattataggc gttagtttcc agaacgcatt gtcccatcta      540
gcagctattg acaggcaaat cattcaaata cacttaacgg tatgataata gaaaacggct      600
tggttgccga tcgtaacgtt gatgtatttc gagcagctat gtctgatcct atatacagga      660
tccataatgt gttacaaggt tacatagagg gtatcagtat ggtgaattgc gtgagtctgt      720
gaattggttg atgaggctcg gtctgagaaa aaggatcgag tttgctaacg attttctcac      780
tgatttcagg agggctgata ccatatggat aatcagccaa agctcccaat taatgctaat      840
gttatatgga atgtacccag gtgccatatt gccaacctca ttactaatgt agcattgtgt      900
ctacccactg gggaatatct aatgccaaac cccagaatca actctattca attactcaac      960
gtatcacaca gacaaatcca ttctcaatta tctcaggctt gacaccgact gccgtgcaga     1020
tgaacgacgt tcgaaagatt tatcttgcat taatgttccc taatcagatt atactgatat     1080
aaaaccagat tccagccacg ctgttgaccc tgtactgaga atggtagctg gagtattggg     1140
tcatgtcatg ttcacttatg cccaattat gactaacatc accctactag ggctgaact       1200 tctgatgctg cattatccga ttacttactg tatatgtaca acataggat accaatcaat      1260 tatggaccta ccggacaacc attagatttt agaatcgggg ctcgtaatca atatgattgt     1320
aatgcttttg tgctgaccct cagacaggtc gtggatacaa tggctgggga gtagtcgacg     1380
ttcagagagt gcaaccaagt ccatatgatc acgtacagag ggtgattcgt tactgcgaca     1440
```

-continued

| | |
|---|---|
| ttgattccag ggaaatattg accctagaac ttatggaatg aatatgactt accctatttt | 1500 |
| cagagagatg ctgaggatgc ttgttgctgc tgggaaagat caagaagccg cttacttacg | 1560 |
| tcagatgctc cccttcata tgaccgtttc gctaggatta accaaattat taacgaggat | 1620 |
| cttcttagcg cattcagtct acctgatcag aatttcgatg ttgttttgca taatctcatt | 1680 |
| caaggtaatt tcggcgagac agatcccgtt tactagaagt gtcctgggcc tcaatttggt | 1740 |
| ttgcctttgt tcgaaggttt gagcctatcg ctagatccga cctgcttgag gcagctcctt | 1800 |
| tgattgaggc tcgttatgcc gcagagctta gtactatcag atggatgttc aacaacttag | 1860 |
| aatgatgaga gctagagtgc ctgatacagt cattaatgcc acaccgagtc agtgttggaa | 1920 |
| agctgtcctc aaaaacgctc cggaacctat caagaacctg atgacctatc tcactcattt | 1980 |
| tcatttgtta atgtaagaga tatcgtcaga tggtcacaac agagggacat tcaagaatca | 2040 |
| ctcgcttacg ttcttaatag ggaagcttgg gctatagcta atgattttga ggatttaatg | 2100 |
| ctcgtcgatc acgtctacat tcaaagacaa tgttgccgga accaagactg gatgacatca | 2160 |
| atgaattcag aagacaaggt ttttttcata ctaacatgat tgatggcgca ccacctattg | 2220 |
| gtgacgtgac ccactacact tatgccattg ctaacttcaa gcaaatatgg gacagtttag | 2280 |
| agcagcaata agaagaactt tggatgacaa tggatggatt cagtttgggg aatgttaag | 2340 |
| gaatataaag attaagttct tgattcaag accaccgac gaatccttac agcaatgcct | 2400 |
| tacgtttaca ctgaagaaga gcgtgacgga gtgcgaatgg ttgcctttaa atacgcaaca | 2460 |
| accgctactg cctatttttt gctttataac gtggagtata gcaacacaca gacaccttaa | 2520 |
| taaccgttaa cccaacattt accatgcaa aaattcatat gagaaaaag atcgtcagaa | 2580 |
| gggtccgagc tcccgacgtg ttgtctcagg ttaataagcg acttgtggct tataagggaa | 2640 |
| aatgcgactt atggatgtta ctaagtgcct taaaactgga gtgcaattag caaggccaac | 2700 |
| aatttaactc gagctgcag | 2719 |

<210> SEQ ID NO 36
<211> LENGTH: 1530
<212> TYPE: DNA
<213> ORGANISM: Artificial sequence
<220> FEATURE:
<223> OTHER INFORMATION: Plant Codon Optimised AHSV-1 VP5

<400> SEQUENCE: 36

| | |
|---|---|
| cgtaccggtc catgggaaaa tttacttcat ttcttaagcg tgccggtaca gcaacaaaga | 60 |
| gagctctgtc tagtgacgct gctaaaaaga tgtataaaac agctggtaaa gcactgcaaa | 120 |
| gagttgtaga atcagaaacg ggagcgctgc tatagatggg gtaatgcaag gaacaattca | 180 |
| aagcataatt caaggtgaga atttagggga ttcaattaag caggccgtta ttttgaatgt | 240 |
| agcaggaaca ttggaaagtg ctcctatcct ctctcaccag gtgagcagat cttatacgga | 300 |
| aaagtacacg aaattgaaag gatggaaaaa gaagacagag ttattgctgc ccatgccaac | 360 |
| gatatcgaga aggagtttgg caaagagctt atactataag gaaaattgtt aaaggagagg | 420 |
| aaaagattga ggagttggag gggaaggaag tcgaatacgt ggagaaagca ttagacggtt | 480 |
| tgctcaagat aggtaagaac caatcaaaaa ggattactac ttgtataaag ctcttcagac | 540 |
| tgaggagcag cttcgtactg aggatgagat cgctatgata tccgactata agagaagtt | 600 |
| tggagctcta aaggaggcaa ttcagattga gcaacaagca gctaatagga agctatacag | 660 |
| gagatgctgg acatttctgc tgatgttatt gaaacagcaa gcgaagaggt gccaatattt | 720 |
| ggcgcagcag ctgcaaatgt tgtggcaact acccgagcaa tcgaaggagg cctaaactta | 780 |

-continued

```
aggagattgt cgataaacta actggtatag atctttcaca tctgaaagtt gcagaaatcc        840
acccacatgt tatcggccag gctatcagta aaaatgatgt tgacgacaag accctcgctg        900
agcaattaag tccaaggtgg acgctgtcga tgaaatgaac caggaaaccg aacatgtgat        960
acaaagtatt ctcccattgg tcaaaagaga ataccagaag catgaaaaca agttcaacat       1020
aaagatacat ctgctctaaa aatacattct gaacatacac cgaaagttca catttatacc       1080
acaccctggg attccgataa ggtgttcatc tgtcgttgta tcgcaccaca tcaccagcaa       1140
cgatcattca tgatggattt gatttggaaa tcgagtacgt ctactatgag gatacaagtg       1200
ttgaagccca tattatgcac ggaggtgcag ttatgattga aggtaggggt tttcgacaag       1260
cctactccga attcatgtcc gtgcttggtc aatgcctgaa acacctgaac ttcataaaag       1320
gagaatgcag aggaatcaag gatctcaccc catttatatg ggatctatgg attatactat       1380
ctctttcgat caattatcta ccaatgcctc caattggtgc acaatactga tcttcaaatg       1440
cattgcttac gtggtcctat taagtttcaa agaagaacta ttatgaatgc cttgcttttc       1500
ggcgtgaaga ttagctaact cgagctgcag                                        1530
```

<210> SEQ ID NO 37
<211> LENGTH: 1065
<212> TYPE: DNA
<213> ORGANISM: Artificial sequence
<220> FEATURE:
<223> OTHER INFORMATION: Plant Codon Optimised AHSV-1 VP7

<400> SEQUENCE: 37

```
gctaccggtc catggatgca atagcagcta gggctttatc cgttgttagg gcttgtgtaa         60
ccgttactga cgcccgagta tctctcgacc caggcgttat ggaaactttg ggtatcgcta        120
ttaaccgata taatgggcta ctaaccattc agtctcaatg aggccgcaga cccaagctga        180
acgtaacgaa atgttttca tgtgtacaga tatggttttg gctgccctga atgtgcaaat        240
tggtaatatt agtcctgact acgataagca ttggctacag ttggagcact tgccactacc        300
gaaattcctt acaatgtgca ggctatgaac gatatagtga gaattacagg tcagatgcag        360 actttgggc catccaaggt tcaaactggg cctatgctgg tgcagtcgaa gtacaacaaa        420
gcggcagata ctacgtgccg caaggaagaa caagaggtgg atacataaat tctaacatag        480
ctgaagtctg tatggacgca ggagcagctg gccaggtgat ggactgttag ctcctagaag        540
gggagatgca gttatgattt atttcgtgtg gcgaccactg cgtatctttt gcgatcctca        600
gggtgcaagt ttagagtctg ctccaggtac atttgtcacc gttgatgagt taatgtagcc        660
gctggggatg tggttgcctg aacacaatt gcacctgtca atgttggaaa tcccggcgct        720
cgtaggtcaa tccttcaatt cgaggttcta tggtatactt ctctcgatag gagctcgaca        780
ccgtcccaga gttggctccc acacttacta ggtgctatgc atatgtatca cctacatggc        840
acgctctaag agccgtgatt ttccagcaaa tgaacatgca gccaattaat ccaccaatat        900
tccacccact gagcgtaatg agatcgttgc atatttgctc gtagctagtc ttgccgatgt        960
gtacgcagcc ttacgacctg attttagaat gaacggtgta gttgctcctg tgggacaaat       1020
taatagactt tggttcttgc agcttatcat taactcgagc tgcag                       1065
```

<210> SEQ ID NO 38
<211> LENGTH: 3147
<212> TYPE: DNA
<213> ORGANISM: Artificial sequence
<220> FEATURE:

<223> OTHER INFORMATION: Plant Codon Optimised AHSV-1 VP2

<400> SEQUENCE: 38

| | | | | | |
|---|---|---|---|---|---|
| cgtaccggtc | catggctagt | gaattcggta | ttttgttaac | tgaacgtatt | ttcgatgaga | 60 |
| cactagagaa | gactaactgc | gacgtgatca | ttaccgagga | gaagaaggtc | aagagaaaag | 120 |
| aggtagaggg | agttcttgta | tgtttgggaa | gaaaccaatc | atagattcgg | cttgtgtgaa | 180 |
| ggaaattacg | acttggcttt | ctctgatact | atgtattgcc | aaactaaatg | cgacggctcc | 240 |
| taccccgttt | ttcctcacta | catatgacgc | tttgagatac | ggcgttatga | tagacaggaa | 300 |
| cgacaatcag | gttagagttg | atttagacga | caaaagactc | atgaagataa | agatccaacc | 360 |
| gtacttagga | gaaatgtatt | tttcaccaga | aatactctac | tgtcttttgc | aagaggcagg | 420 |
| cactcgcttt | gggagtagat | gatcttagac | attcagttga | tgttagaaat | gaatttgaag | 480 |
| agacaaatca | ccagacaaaa | ggcgtgttga | acggaataac | aaagggcatt | agaggtttgg | 540 |
| aaagagatgg | cataccaacg | tatgcgaaag | gaaggttcta | ggggaagatg | catcggtcat | 600 |
| gatgatgatg | tgatgtatca | attaattaag | aaattgagat | atgcatatgt | accctcacca | 660 |
| ttatgcactt | aacgcaagat | atgaggtgtc | aaacccttct | gctgctagaa | ttaaagattg | 720 |
| gcttctcaaa | gttagggtta | atgttggccg | agcccaggaa | aaggcagaca | gacggaccac | 780 |
| tcgctgaaat | ggctcgatca | attgagaatg | atgaattaag | cagacaggtg | gtcgatcaaa | 840 |
| ttattcaata | tggaggtcaa | tttagctcct | gttctggtgc | tagagaggat | gacaaccaat | 900 |
| aatattttac | tcgaatactg | cgagagtttg | acaacatttg | ttcacaggaa | gaagaggaaa | 960 |
| gaaggtgatg | atttgactgc | cagaaatact | ttccgacaag | ccctgattaa | gagcatgcct | 1020 |
| caatgaattc | aaaaatcaaa | tgaaaatgac | tcgtggttgg | gggaactata | cttttttttc | 1080 |
| ctacatagat | aggttctcac | gtatttacaa | tatgaatatt | gatcccaatg | gtaagttgtg | 1140 |
| gattgacata | aacaacagtc | tctgaacagc | tgaagaaaaa | gcaggaagag | aacagagccc | 1200 |
| ccttaactgt | gcaaattgac | ggtgttcaca | tacgaaccga | tgaaacatac | ggtacagttg | 1260 |
| atcattgggt | ggatgggtcg | tgatacaatt | atgctgagag | agacagagaa | gatgattaaa | 1320 |
| gactatcgtt | ttaaaaaatt | aaaacgtgag | gagctgattt | ctgggatgaa | caaactcgaa | 1380 |
| gacggactcc | gttgcattgt | ttattgtttg | atactcgctc | tatacgatta | ctatgagggg | 1440 |
| gatattgagg | gatttaagaa | gggtaccatt | gccagctcaa | tcgtggaaag | tctcacaaat | 1500 |
| gtttccaaac | tttaggtcag | atataattga | taaatttggt | atcagtttga | aggtcaaaac | 1560 |
| tgaggctgag | gaactgtttc | tgccaaagaa | tatgaagtcc | tcaatgaatg | tcggaagaaa | 1620 |
| gggggtataa | atacaagttc | ggctggaaag | acaatgagga | gcgagttatg | tctgattatg | 1680 |
| gggagatcct | gaccgagtct | gtggagatcc | tatttaagaa | actcctcaaa | ggtgagaaat | 1740 |
| gaaatcattg | tcgatgatcc | gcagacctat | tttgaagatg | atctcttcgt | tgacagggca | 1800 |
| aacaagatct | tcagcagagg | gggccaaact | gtaaatcagt | tgattagcat | taaggttaat | 1860 |
| gcacagtcaa | acgtcgagg | gaacaactta | ttttagtaag | cgttttgttt | cctattggtt | 1920 |
| caggattgag | cattttagta | ttactactgc | caaaaaaaga | actgatatta | gggataagaa | 1980 |
| aactgaatat | aacaattgac | tttgaagatt | tcaagcctgc | ttgtattgga | gaattgggta | 2040 |
| tccatgcaag | tacttacatt | tatcaagatc | ttttggtagg | aaagtctagg | ggcgaaagag | 2100 |
| taaaggacgc | aaaggagttg | tgtgatggat | ctatctttag | caaatttcgg | gtgttccagg | 2160 |
| tgctatgaca | gatgttggcc | agctagttgt | gttgaagcag | aaatctcact | taggtattat | 2220 |
| cttgttacca | gtatattcgc | tcgttcttga | acgtgaaggg | ctgtcatttt | ctaagatact | 2280 |

```
tatatcactt aaagattttt ctgacaggtt gtggtttcct acttacaagc acttttatgt   2340
agctgttgtc cagaaagtac tcagagatga tgaaggctga ctatgtgctg ttttgttcaa   2400
gggtaagcgc cattacaaca agacgagcaa ccctgatgga attcagtact ttcaaacaaa   2460
tggttgggag caccagactg ctagatacac ttttcctaac ttctctttg gataattttc    2520 gaacaagaaa atattgatgt tgattttgct aataaatggc atcctctact tatttccact   2580
gagaaaggat tgcgtgtcat cgccgtggat gtgttcaact ccttcttaca ctagtacatc   2640
tggatggctt ccttatttgg agcgtatttg tagtgaatca gctatggata gagctttaac   2700
cgcagacgaa atcaatctta acgatggtt tgtagattac tatatggaat gaaacttgaa    2760
ggagagcaga gccaagaatg tcttttaaat ctgaagctct tatcacatgg ataggatcaa   2820
actgtggagg tgtaactgat tacgttgtgc aacttctacc tgtgagaaaa ccaaaccagg   2880
tcttctgtgg tagtttattc cgaggacgga ggcgaaaagt gggccgagtg gctttaagg    2940 gactacttag aaatagatgg aagcttgggt cttgttttta tcacacgtaa agctgtaaag   3000
ataagagtaa actggagtgc gagatttgaa gatctataat cgtggtaggg ttgataggct   3060
catccttatt tcttcaggtg tttacacctt cggtaataaa ttcttgttca gcaaattgct   3120
ttcaaagtag aataactcga gctgcag                                      3147

<210> SEQ ID NO 39
<211> LENGTH: 3176
<212> TYPE: DNA
<213> ORGANISM: Artificial sequence
<220> FEATURE:
<223> OTHER INFORMATION: Plant Codon Optimised AHSV-7 VP2

<400> SEQUENCE: 39
cgtaccggtc catggcatca gagtttggta tcttgtacac agatcagatt tatgaacaaa     60
cacttgagaa gactagttgc gatgttatag tcactaagga gaatgccgtt aagagggtcg    120
aaattgagga gtgctaggtt atgagtgggg agctacgaat cacaggcttg gctctgtga    180 aatcgaacat gttaaaacca tctccgaatt tatgtatgaa cagataaaat gtgaaggtgc    240
ctacccagtg ttccctcatt atgttataga cgcacttaag tacaataagg tgatagaaag    300
aaatgacaac caggtccggt agatcgtgat gatgaacgat tgcaaaagat caaaattcag    360
ccttactttg gggaggcctt tttctctcca gaaacgtatt cttcaacatt tgtaaaaga    420 caggctatcc gtggtcacgt tgctaaatgc gtactttcgc taaagatcgg atagattttg   480
aggagagtag cgctcaaact aaatacgtca atgggaataa agttaagatt ttagaagagt    540
ggaaagggag gactgacgca cgtatgttaa tggggtcaa caagagaagt gcgttgccca    600
tgaggtcgac ccaatctacc agctcatcaa aagatgcgt tatggaatga tgtatccaac     660
ccattacatg ttgtctcaac gatatcgaat cataagcgaa gtaggaagat gggaattgaa    720
aaatggcttc ttgaaaaggt cgagaggggc gttcaacggg gtgtcgccgg ggctaaaggt    780
aatgagtccc ttgtaaggct agaaaagctc atgcagaaag aagagctgag aattcagtta    840
tagagaatgt aattcgttat ggttcacagt tttcaacaca cgccggagaa aagactaatg    900
atatgcctct gtccgtgctg atcaagtact gtgagtcctt gacaactttc gtgctaaaaa   960
gaaccgagaa ggaggtgata accagactgc aagggatgaa atccgaaaag ctatggttca   1020
caatatgcct acaatgaatc acaataatcc tatgaaagtc acgaagaact ttaagaactt   1080
ttcttctttg catatttgga tggatttaaa agaaacaatg gtgttgatat caatcccaac   1140
```

-continued

```
aactcaactt ggatcgagca caagaagaag atggctgaga aacttaagga tgagcagcag    1200
aaaaaccaaa caggccgatg ctcgtgccga ttgatggagt ttatgtgtct acctcagtgg    1260
agtacggaac agtaacccac tgggttgatt gggtggtgga tatcattatg acaactcagg    1320
ttgagaggat gattaggaat atgacttcaa gagacttgag cgaaagcaat tgataagcgg    1380
tatgaataag ctggaggacg gagtcaaatg ttatgcttat tgcctcatat tagcattata    1440
tgattattat ggtgatgcta ttaaggattt gcacaaggaa ctagggctgg ctctatagtc    1500
gagacaatat ctcaaatgtt ccccgaattt cggtctgacg ttgctgaaaa gtttgggatt    1560
aagttaacaa taaggatga gagcgaagat tgtttgtgca gaaagacatg aatagtgaat    1620
tcttggacga gggagaaatg ggttacaagt tcgttttcgg atggaagaat acagatttca    1680
aggttcaaag caattatgga gagatcgtta gtgaggagta gagcgtctat ttaaggttat    1740
acttgagggg aaggaatggt caaacgaagt cgaagatcct gaagattatt ttgtggataa    1800
cttgttcaat aaaacaccgg acgctgtatt tgaacgagat ggatggatgg atctaatcgg    1860
ataatcgtaa agaataagac caccttgcgg gagggccaaa ggcatttttc tgcccggttt    1920
gttagctatt ggtacacctt tgaaaaggtt gaggtgggca gagctatggc agaattgata    1980
ttcatgacag ggagacaaag ttctctgaat tcgacgtcga tgattacaaa ccctgctctg    2040
ttgctgagat gggtcttcac agttctacct acatttacca agacctgttg attggtcgaa    2100
cagaggagag catgttattg acgcaaaaga actggtttgg tatgatattg ctctgaccaa    2160
ctatggcaca actaggtact ttgatcaatg ttggcctagc tcatgttcca ctacggagtt    2220
gagttgagat atttccttat cacagaaatc tttcagagat ataggacgga tgatagaagt    2280
agtttcgcag atattttaga aagaatgaga aaaaatgggt accctagaag gaactttcta    2340
acctacaagc atactacgtg gctgttattc aagaggtttt cggggaccaa cgtccaatcg    2400
acgtgtattc attctgcacg gatattttca agaaagagag gagaaggggc gttctttcca    2460
tgtttcccac ttttagtatt tgattaaatc cgaaaaactt attgatgcac tttttcttgaa   2520 tttcttttta tgggtagttt ttgaaatgga gaatgtagac gtttctttcg ctaataaacg    2580
acatcctctt ctaatttctc atgataggqt ctaagactca ttggcgtgga tctctttaat    2640
tctgctcttt ccattagcat gggtggatgg attccatacg tagagaggat ttgccatgca    2700
gatcatgctg ctagaaaatt gaatgctgat gattgaaaat taagaggtgg ttcattgatt    2760
actatatgga tttgtcactt gatagacgtg ccgaaccaag aatgtccttt aaatacgaag    2820
gtttagcaac atgggtgggt agtaactgtg gcggtgttag gactatatta tccaggaact    2880
accaatgaga aaaccaaagc caggcttgct catttggta tatggggagg atggtgatcc     2940
taaatgggtt gaatgggcta ttaaggattt tacccaaatt gaaggtgcct cggatttata    3000
tacattgatc ctattagtgt agtgaacaaa tctactttca ggactagaga aatgaagatt    3060
tacaatagag gcagactgga caggcttata ttaattagct caggtaacta tacttcggaa    3120
ataagtttct gctttctaag ctgttatcaa aggcagaatg aggatccctc gagcag        3176
```

<210> SEQ ID NO 40
<211> LENGTH: 1533
<212> TYPE: DNA
<213> ORGANISM: Artificial sequence
<220> FEATURE:
<223> OTHER INFORMATION: Plant Codon Optimised AHSV-7 VP5

<400> SEQUENCE: 40

```
cgtaccggta tgggaaagtt cacatccttc ctaaagcgtg caggttctgc tactaaaaag     60
```

```
gcattgacat ccgatgcagc taaaagaatg tacaagatgg caggacgaac actacaaaag      120
gctgtagagt cagaagtcgg aagtgcagca attgatggaa taatgcaagg aacaatccaa      180
tctatcatcc aaggagagaa cctaggtgac tccataaagc aagctgttat cctaaacgtc      240
gcaggtacat tagagtcagc acctgatcca cttagtcctg gtgaacaact tttgtataac      300
aaggtatccg aactggaaag aatggagaag gaagatagag tcatcgagac tcattccgag      360
aaaatcgtcg aaagtacgg acgagaatta gtcgatatca gaaagatcat gcggggagaa       420
gcacaagcag aaaagttaga gggaaaggaa atgttctaca tcgagaaggc tctgaagggt      480
attttacaga ttggcaagga ccaaagcgat cgaataacga gattataccg ggctttacaa      540
accgaagaag agttgagaac cgcagatgaa acgaagataa ttagcgagta cagggaaaag      600
ttcaatgctc tgaagcaggc tattgagctg aacaacagg ctacacatga agaagctgtg       660
caagaaatgt tggatctgag cgcagaagtt cttgaaacag cagctgaaga agttccaatt      720
ttcggtgcag gtgctgctaa tgtagttgca acaactagag ctgttcaggg tggtcttcgt      780
ttgaaagaaa ttatagacaa gttgaccggc atagatctca gtcatctcaa ggttgcagat      840
attcacccac atattataga gaaagccatg ctcaaagacg ctgtgacgga ttctgatctc      900
gctatggctg ttaaaagcaa agtggatgtg gtagatgaag tgaatgctga aaccgaacat      960
attattgaca ccattatgcc gctcgtgaag aaagagtacg acaaacacga gaataagttt     1020
cacattgaga ttcccagcgc cctcaaaatt cactcagagc acaccccaaa agtgcacata     1080
tatactactc cgtgggattc tgacaaagtg tttatctgca ggtgtattgc ccctcaccat     1140
cagcagagat cttttatgat agggtttgac ttggagattg agtttgtttt ctatgaggat     1200
acttctgttg agtcacatgt tatgcatggg ggggccattt caattgaggg gaggggtttt     1260
aggcaggctt attctgagtt tatgtcagcc gcttggtcaa tgccagctgc ccctgaactt     1320
cataaacgta ggcttcagag gagtttgggg tctcatccta tatatatggg cagtatggat     1380
tatactgtta gttatgagca gcttgttcct aatgccatga aacttgttta tgatactgat     1440
ttgcagatgc attgtttgcg gggccccttg aaatttcaga ggcgtactct tatgaatgcc     1500 cttcttttg gcgttcgtat tgcctagctc gag                                   1533

<210> SEQ ID NO 41
<211> LENGTH: 30
<212> TYPE: DNA
<213> ORGANISM: Artificial sequence
<220> FEATURE:
<223> OTHER INFORMATION: Oligonucleotide

<400> SEQUENCE: 41
gcaccggtat ggaagaactc gctatcccaa                                        30

<210> SEQ ID NO 42
<211> LENGTH: 32
<212> TYPE: DNA
<213> ORGANISM: Artificial sequence
<220> FEATURE:
<223> OTHER INFORMATION: Oligonucleotide

<400> SEQUENCE: 42
gcctcgagtc aaacgttgag gagcttagta ag                                     32

<210> SEQ ID NO 43
<211> LENGTH: 31
<212> TYPE: DNA
```

<213> ORGANISM: Artificial sequence
<220> FEATURE:
<223> OTHER INFORMATION: Oligonucleotide

<400> SEQUENCE: 43
gcaccggtat ggctgctcaa aatgagcaaa g                       31

<210> SEQ ID NO 44
<211> LENGTH: 30
<212> TYPE: DNA
<213> ORGANISM: Artificial sequence
<220> FEATURE:
<223> OTHER INFORMATION: Oligonucleotide

<400> SEQUENCE: 44
gcctcgagtt aaacagttgg agcagcaagc                         30

<210> SEQ ID NO 45
<211> LENGTH: 34
<212> TYPE: DNA
<213> ORGANISM: Artificial sequence
<220> FEATURE:
<223> OTHER INFORMATION: Oligonucleotide

<400> SEQUENCE: 45
gcaccggtat gggaaagatt attaagtccc tctc                    34

<210> SEQ ID NO 46
<211> LENGTH: 29
<212> TYPE: DNA
<213> ORGANISM: Artificial sequence
<220> FEATURE:
<223> OTHER INFORMATION: Oligonucleotide

<400> SEQUENCE: 46
gcctcgagtc aagcgttcct aaggaagag                          29

<210> SEQ ID NO 47
<211> LENGTH: 30
<212> TYPE: DNA
<213> ORGANISM: Artificial sequence
<220> FEATURE:
<223> OTHER INFORMATION: Oligonucleotide

<400> SEQUENCE: 47
gcaccggtat ggatacaatt gctgctaggg                         30

<210> SEQ ID NO 48
<211> LENGTH: 28
<212> TYPE: DNA
<213> ORGANISM: Artificial sequence
<220> FEATURE:
<223> OTHER INFORMATION: Oligonucleotide

<400> SEQUENCE: 48
gcctcgagtc acacataagc agccctag                           28

<210> SEQ ID NO 49
<211> LENGTH: 30
<212> TYPE: DNA
<213> ORGANISM: Artificial sequence
<220> FEATURE:
<223> OTHER INFORMATION: Oligonucleotide

<400> SEQUENCE: 49
acttgttacg attctgctga ctttcggcgg                         30

<210> SEQ ID NO 50
<211> LENGTH: 28
<212> TYPE: DNA
<213> ORGANISM: Artificial sequence
<220> FEATURE:
<223> OTHER INFORMATION: Oligonucleotide

<400> SEQUENCE: 50
cgacctgcta aacaggagct cacaaaga                                          28

<210> SEQ ID NO 51
<211> LENGTH: 33
<212> TYPE: DNA
<213> ORGANISM: Artificial sequence
<220> FEATURE:
<223> OTHER INFORMATION: Oligonucleotide

<400> SEQUENCE: 51
caaattcgcg accggtccat ggctagtgaa ttc                                    33

<210> SEQ ID NO 52
<211> LENGTH: 35
<212> TYPE: DNA
<213> ORGANISM: Artificial sequence
<220> FEATURE:
<223> OTHER INFORMATION: Oligonucleotide

<400> SEQUENCE: 52
agttaaaggc ctcgagttat tctatctttg aaagc                                  35

<210> SEQ ID NO 53
<211> LENGTH: 29
<212> TYPE: DNA
<213> ORGANISM: Artificial sequence
<220> FEATURE:
<223> OTHER INFORMATION: Oligonucleotide

<400> SEQUENCE: 53
cgtaccggtc catggctagt gaattcggt                                         29

<210> SEQ ID NO 54
<211> LENGTH: 29
<212> TYPE: DNA
<213> ORGANISM: Artificial sequence
<220> FEATURE:
<223> OTHER INFORMATION: Oligonucleotide

<400> SEQUENCE: 54
gcagctcgag ttattctatc tttgaaagc                                         29

<210> SEQ ID NO 55
<211> LENGTH: 27
<212> TYPE: DNA
<213> ORGANISM: Artificial sequence
<220> FEATURE:
<223> OTHER INFORMATION: Oligonucleotide

<400> SEQUENCE: 55
ggtaccggta tgcaaggtaa cgaacgt                                           27

<210> SEQ ID NO 56
<211> LENGTH: 27
<212> TYPE: DNA
<213> ORGANISM: Artificial sequence
<220> FEATURE:

<223> OTHER INFORMATION: Oligonucleotide

<400> SEQUENCE: 56
cagctcgagt taaattgttg gccttgc                              27

<210> SEQ ID NO 57
<211> LENGTH: 28
<212> TYPE: DNA
<213> ORGANISM: Artificial sequence
<220> FEATURE:
<223> OTHER INFORMATION: Oligonucleotide

<400> SEQUENCE: 57
cgtaccggtc catgggaaaa tttacttc                             28

<210> SEQ ID NO 58
<211> LENGTH: 27
<212> TYPE: DNA
<213> ORGANISM: Artificial sequence
<220> FEATURE:
<223> OTHER INFORMATION: Oligonucleotide

<400> SEQUENCE: 58
cagctcgagt tagctaatct tcacgcc                              27

<210> SEQ ID NO 59
<211> LENGTH: 28
<212> TYPE: DNA
<213> ORGANISM: Artificial sequence
<220> FEATURE:
<223> OTHER INFORMATION: Oligonucleotide

<400> SEQUENCE: 59
gctaccggtc catggatgca atagcagc                             28

<210> SEQ ID NO 60
<211> LENGTH: 27
<212> TYPE: DNA
<213> ORGANISM: Artificial sequence
<220> FEATURE:
<223> OTHER INFORMATION: Oligonucleotide

<400> SEQUENCE: 60
cagctcgagt taatgataag ctgcaag                              27

<210> SEQ ID NO 61
<211> LENGTH: 23
<212> TYPE: DNA
<213> ORGANISM: Artificial sequence
<220> FEATURE:
<223> OTHER INFORMATION: Oligonucleotide

<400> SEQUENCE: 61
ccatggcatc agagtttggt atc                                  23

<210> SEQ ID NO 62
<211> LENGTH: 24
<212> TYPE: DNA
<213> ORGANISM: Artificial sequence
<220> FEATURE:
<223> OTHER INFORMATION: Oligonucleotide

<400> SEQUENCE: 62
cctcattctg cctttgataa cagc                                 24

```
<210> SEQ ID NO 63
<211> LENGTH: 18
<212> TYPE: DNA
<213> ORGANISM: Artificial sequence
<220> FEATURE:
<223> OTHER INFORMATION: Oligonucleotide

<400> SEQUENCE: 63
accggtatgg gaaagttc                                                       18

<210> SEQ ID NO 64
<211> LENGTH: 18
<212> TYPE: DNA
<213> ORGANISM: Artificial sequence
<220> FEATURE:
<223> OTHER INFORMATION: Oligonucleotide

<400> SEQUENCE: 64
ctcgagggca atacgaac                                                       18

<210> SEQ ID NO 65
<211> LENGTH: 1518
<212> TYPE: DNA
<213> ORGANISM: Artificial sequence
<220> FEATURE:
<223> OTHER INFORMATION: Plant codon optimised AHSV-3 VP5

<400> SEQUENCE: 65
atgggaaagt tcacgagttt cctgaagaga gcaggtagtg caacaaagaa agcactaact         60
tccgatgcag ctaaaagaat gtacaagatg gctggtaaga cactacaaaa ggtagtcgag        120
agtgaggtag gaagtgcagc aattgatgga gtaatgcaag gaacaatcca atcaatcatc        180
caaggtgaga acttgggaga ttcaatcaag caagcagtaa tcctgaacgt agctggaaca        240
ctagaatctg ctccagatcc attaagtcca ggtgaacaac tactgtataa caaggtttcc        300
gagatcgaaa gagcagaaaa ggaggataga gttatcgaga cacacaacaa gaagatcgtt        360
gagaagtacg gagaggatct gttgaagatc cgaaagatca tgaagggaga agctcaagca        420
gaacaattag agggaaagga aatgaatac gttgagaagg cattaggagg tttgttgaag         480
ataggtaagg accaatccga gagaattacg cgattgtaca gagctttaca gacagaggaa        540
gatttaagga cgtccgatga aacaagaatt ataagcgagt accgtgagaa gttcgacgca        600
ttgaagcaag caattgagct ggagcaacag gctacacatg aagaagctgt tcaggaaatg        660
ttggatctta gtgctgaagt tattgagact gctgctgaag aagttccagt tttcggtgca        720
ggtgctgcta atgttgttgc tactactcgt gctattcagg gtggtttaaa attgaaagag        780
ataatagaca agctcactgg tatagacttg agccacttga aggttgctga tattcaccct        840
cacataattg agaaggctat gctcaaggac aaaattccg acaatgagct cgcaatggct         900
ataaaaagca agtcgaggt tgttgacgag atgaataccg agactgagca tgttatagaa         960
agcataatgc ctctcgtgaa aaaagaatac gaaaaacacg acaataaata ccacgtgaat       1020
attccaagcg ccctcaaaat tcactcagaa catacccta aagtccatat ttataccacc        1080
ccgtgggatt ctgataaagt gttcatttgc cggtgtattg cccctcatca tcagcagagg       1140
tctttcatga ttgggtttga tctcgaaatt gaatttgtgt tttatgaaga tacctctgtc       1200
gtgggccata ttatgcatgg gggcgccgtg tctattgaag ggcggggctt tcgtcaggct       1260
tattctgaat ttatgaatgc cgcctggtct atgccttcaa ctcctgaact tcataaaagg       1320
aggcttcagc gttctcttgg ctcacatccg atttatatgg ggtcaatgga ttatactatt       1380
```

```
tcttatgaac agcttgtgtc aaatgccatg aaacttgtct atgataccga tcttcagatg    1440
cattgtttga ggggccccct taaatttcag aggcgaactc ttatgaatgc ccttcttttt    1500
ggggtgaaag tcgcctga                                                   1518
```

<210> SEQ ID NO 66
<211> LENGTH: 505
<212> TYPE: PRT
<213> ORGANISM: African Horse Sickness Virus

<400> SEQUENCE: 66

```
Met Gly Lys Phe Thr Ser Phe Leu Lys Arg Ala Gly Ser Ala Thr Lys
1               5                   10                  15

Lys Ala Leu Thr Ser Asp Ala Ala Lys Arg Met Tyr Lys Met Ala Gly
            20                  25                  30

Lys Thr Leu Gln Lys Val Val Glu Ser Glu Val Gly Ser Ala Ala Ile
        35                  40                  45

Asp Gly Val Met Gln Gly Thr Ile Gln Ser Ile Ile Gln Gly Glu Asn
    50                  55                  60

Leu Gly Asp Ser Ile Lys Gln Ala Val Ile Leu Asn Val Ala Gly Thr
65                  70                  75                  80

Leu Glu Ser Ala Pro Asp Pro Leu Ser Pro Gly Glu Gln Leu Leu Tyr
                85                  90                  95

Asn Lys Val Ser Glu Ile Glu Arg Ala Glu Lys Glu Asp Arg Val Ile
            100                 105                 110

Glu Thr His Asn Lys Lys Ile Val Glu Lys Tyr Gly Glu Asp Leu Leu
        115                 120                 125

Lys Ile Arg Lys Ile Met Lys Gly Glu Ala Gln Ala Glu Gln Leu Glu
    130                 135                 140

Gly Lys Glu Met Glu Tyr Val Glu Lys Ala Leu Gly Gly Leu Leu Lys
145                 150                 155                 160

Ile Gly Lys Asp Gln Ser Glu Arg Ile Thr Arg Leu Tyr Arg Ala Leu
                165                 170                 175

Gln Thr Glu Glu Asp Leu Arg Thr Ser Asp Glu Thr Arg Ile Ile Ser
            180                 185                 190

Glu Tyr Arg Glu Lys Phe Asp Ala Leu Lys Gln Ala Ile Glu Leu Glu
        195                 200                 205

Gln Gln Ala Thr His Glu Glu Ala Val Gln Glu Met Leu Asp Leu Ser
    210                 215                 220

Ala Glu Val Ile Glu Thr Ala Ala Glu Glu Val Pro Val Phe Gly Ala
225                 230                 235                 240

Gly Ala Ala Asn Val Val Ala Thr Thr Arg Ala Ile Gln Gly Gly Leu
                245                 250                 255

Lys Leu Lys Glu Ile Ile Asp Lys Leu Thr Gly Ile Asp Leu Ser His
            260                 265                 270

Leu Lys Val Ala Asp Ile His Pro His Ile Ile Glu Lys Ala Met Leu
        275                 280                 285

Lys Asp Lys Ile Pro Asp Asn Glu Leu Ala Met Ala Ile Lys Ser Lys
    290                 295                 300

Val Glu Val Val Asp Glu Met Asn Thr Glu Thr Glu His Val Ile Glu
305                 310                 315                 320

Ser Ile Met Pro Leu Val Lys Lys Glu Tyr Glu Lys His Asp Asn Lys
                325                 330                 335

Tyr His Val Asn Ile Pro Ser Ala Leu Lys Ile His Ser Glu His Thr
            340                 345                 350
```

```
Pro Lys Val His Ile Tyr Thr Thr Pro Trp Asp Ser Asp Lys Val Phe
        355                 360                 365
Ile Cys Arg Cys Ile Ala Pro His His Gln Gln Arg Ser Phe Met Ile
370                 375                 380
Gly Phe Asp Leu Glu Ile Glu Phe Val Phe Tyr Glu Asp Thr Ser Val
385                 390                 395                 400
Val Gly His Ile Met His Gly Gly Ala Val Ser Ile Glu Gly Arg Gly
                405                 410                 415
Phe Arg Gln Ala Tyr Ser Glu Phe Met Asn Ala Ala Trp Ser Met Pro
                420                 425                 430
Ser Thr Pro Glu Leu His Lys Arg Arg Leu Gln Arg Ser Leu Gly Ser
                435                 440                 445
His Pro Ile Tyr Met Gly Ser Met Asp Tyr Thr Ile Ser Tyr Glu Gln
            450                 455                 460
Leu Val Ser Asn Ala Met Lys Leu Val Tyr Asp Thr Asp Leu Gln Met
465                 470                 475                 480
His Cys Leu Arg Gly Pro Leu Lys Phe Gln Arg Arg Thr Leu Met Asn
                485                 490                 495
Ala Leu Leu Phe Gly Val Lys Val Ala
                500                 505

<210> SEQ ID NO 67
<211> LENGTH: 3156
<212> TYPE: DNA
<213> ORGANISM: Artificial sequence
<220> FEATURE:
<223> OTHER INFORMATION: Plant codon optimised AHSV-6 VP2

<400> SEQUENCE: 67
atggcttctg aattcggtat cttgatctgc gataagctaa aggaaaacac actggagaag      60
acaaactgcg atgttatcat cacaggagta ggaaaggtta gtgtaagaga agaagatggt     120
atcctaggtt atgagtggga agaaactaac catagattgg gattgtgtga atcgagaac     180 acagtatcca tcagtgattt cgtatacaag cagatcagat gcgaaggagc atatccaatt     240
ctaccacatt acgtaacaga tgtcatcaag tacggaatgg taatcgatag aaacgaccac     300
caaatcagag tcgatagaga tgagaagagt atcggaaaga tccaaatcca accatacttc     360
ggagatatgt acttctcccc agaatattac cctgcaactt cgttaagag aaacctcta     420 ccaatttccg tagatatgat cagagattac atcggagcaa gaatgagaaa gatcgaggca     480
agagcaggaa gaattaagga aggtggaggt aatttgttgg aatgtgcaag aagatgggaa     540
aaggcagcat atgaaagaat cgaaaacgaa agagcactac gatgtgtagt acacgaaaca     600
gatcctacat accaaattct gaagaagcta cgattcggat tcatataccc tcactactac     660
gtcttgaaca cggactataa cccaactact gtaacgagaa cttctcgaat taacgattgg     720
ctgttgaagg agaaaacgca aggagttgtt aaggcagctg aagcatattc agataacgca     780
gaattgaaaa ccctagcaga acgaatggaa gaggaggaac taactgttga tattattcgg     840
gctgttatta ggtacggagc aaagtacgct actcgatctg gtatgcgaga agatacatta     900
tcactacaag aactggatag atactgcgat tctctaacaa cgttcgttca caagaaaaag     960
aaagatgaag gagatgatga aacggctaga acaattattc gaaccagtg gattaaggga    1020 atgccacgaa tggatttcaa gaaggaaatg aagataacga gggtcctat tgctaactgg    1080 tcattcttca tgtctataga cgctttcaag cgtaacaaca aggttgatat taaccctaat    1140
```

-continued

```
catcagacct ggaaggatca catcaaagag gttaccgatc aaatgaatcg ggcacaacaa    1200
ggtaataata acaagcctct gaagattcag attgacggag ttagcatact caccaatgag    1260
aagtacggta ccgttggtca ttgggttgat tgggttgttg acttaattat gctggctcaa    1320
gttaagatgt tgataaagga gtacaagttt aagcgtctga atagccagaa tctgatgtcc    1380
ggtatgaaca agctggtagg tgcattaaga tgttacgctt actgtttgat tctcgctttg    1440
tacgattact acggtcaaga tattgagggt ttcaagaaag gatccaattc ctccgctata    1500
ctggaaactg ttattcagat gttcccaaat ttcaaacagg agattcaggc taatttcggg    1560
ataaacctga acataaaaga caagaaacag tccctctttg tggagcggac aatgcactcc    1620
gattttagca gcaatgaaga atatggctac aaatttgtgt ttgggtgggc tgctagagga    1680
gaagaagttt tgagtaatta tggggatatt ctcagcgatg aagttgagga actcttcacc    1740
aagcttagaa agaaagagca ctgggataaa gttgttgagg atccagaatc ttattttgtc    1800
gacgagctgt atcagaagaa tcctgctgaa gtgttcttta gcgctggtta tgatactgac    1860
caaaatgttg ttattgacgg aaaaatgacc gagggagtta cctatttttc taaaaggttt    1920
gtgagctatt ggtatcgtgt ggagaaaata accaccaaac atctcgaatt tctcaatgag    1980
gagggtcgta aagtggctca gtttgacttt gaggactaca acctatggc tattggagaa     2040 atgggtattc atgctagcac ctataagtat gagagcctcc ttcttggtaa aaatcgtggt    2100
cagaaagtta aagactctat tgccctctgc aattatgacc tcgctcttac taattttgag    2160
gtctctaggc gtcaagattg ctgttggatt tcatcttgct cagctattga actctctatg    2220
cgtgctaata ttactattgc cattttagg aggattgagg acaggcggta tgaaagtttt     2280
gccaaaatac tctcaggtct ttcacagcag caagaccttt actttcctac ttataagcat    2340
tattatttgt ttgtgcttca gaaagtgctt cgggacgaga ggaggataga ccagaatagg    2400
atgtgtacag agttgtttga catacaaagg cgtaggggta ttttgcttag ttttactact    2460
ttgaggtttt ggaatgactc agagtttttg ggcgacactt tgatgatgaa ttttcttttg    2520
tgggtggtct ttgagatgga gaatattgat gtggattatg ggaagaaatg gcatccgttg    2580
ttggtgagtt cagagaaagg gcttcgagtg atagccgttg atgtgttcaa ttcaatgatg    2640
ggggtttcaa ctagtggttg gcttccgtat gttgaacgga tttgttctga atctgatatg    2700
cggagacgtc ttaatgccga tgaattagag ttgaaaaggt ggttctttga ttattatgcc    2760
acattgttgc ttgagaggag gggtgaaccg cgtttatctt tcaaatatga gggcttaaca    2820
acttggattg gctcaaattg tggcggcgtt cgtgattatg tggtccaatt acttcccatg    2880
cgtaaaccca aacccgggct tctttgtata gcctatggcg atgatgtcaa tgtccaatgg    2940
gtggaacatg agttaaggga ttttcttaca catgagggca gtcttgggtt agtggtcatt    3000
tctggcaaaa tgttagtgaa taagagtaaa cttagggtca ggaatcttaa aatatataat    3060
cgggggactc ttgattctct tttttcttata agtgggggct cttatacatt tgggaataag    3120
tttttacttt caaaattaat ggccaaagcc gagtga                              3156
```

<210> SEQ ID NO 68
<211> LENGTH: 600
<212> TYPE: PRT
<213> ORGANISM: African Horse SIckness Virus

<400> SEQUENCE: 68

```
Met Ala Ser Glu Phe Gly Ile Leu Ile Cys Asp Lys Leu Lys Glu Asn
 1               5                  10                  15
```

```
Thr Leu Glu Lys Thr Asn Cys Asp Val Ile Ile Thr Gly Val Gly Lys
             20                  25                  30
Val Ser Val Arg Glu Glu Asp Gly Ile Leu Gly Tyr Glu Trp Glu Glu
         35                  40                  45
Thr Asn His Arg Leu Gly Leu Cys Glu Ile Glu Asn Thr Val Ser Ile
     50                  55                  60
Ser Asp Phe Val Tyr Lys Gln Ile Arg Cys Glu Gly Ala Tyr Pro Ile
65                  70                  75                  80
Leu Pro His Tyr Val Thr Asp Val Ile Lys Tyr Gly Met Val Ile Asp
                 85                  90                  95
Arg Asn Asp His Gln Ile Arg Val Asp Arg Asp Glu Lys Ser Ile Gly
             100                 105                 110
Lys Ile Gln Ile Gln Pro Tyr Phe Gly Asp Met Tyr Phe Ser Pro Glu
         115                 120                 125
Tyr Tyr Pro Ala Thr Phe Val Lys Arg Glu Pro Leu Pro Ile Ser Val
     130                 135                 140
Asp Met Ile Arg Asp Tyr Ile Gly Ala Arg Met Arg Lys Ile Glu Ala
145                 150                 155                 160
Arg Ala Gly Arg Ile Lys Glu Gly Gly Asn Leu Leu Glu Cys Ala
                 165                 170                 175
Arg Arg Trp Glu Lys Ala Ala Tyr Glu Arg Ile Glu Asn Glu Arg Ala
             180                 185                 190
Leu Arg Cys Val Val His Glu Thr Asp Pro Thr Tyr Gln Ile Leu Lys
         195                 200                 205
Lys Leu Arg Phe Gly Phe Ile Tyr Pro His Tyr Tyr Val Leu Asn Thr
     210                 215                 220
Asp Tyr Asn Pro Thr Thr Val Thr Arg Thr Ser Arg Ile Asn Asp Trp
225                 230                 235                 240
Leu Leu Lys Glu Lys Thr Gln Gly Val Val Lys Ala Ala Glu Ala Tyr
                 245                 250                 255
Ser Asp Asn Ala Glu Leu Lys Thr Leu Ala Glu Arg Met Glu Glu Glu
             260                 265                 270
Glu Leu Thr Val Asp Ile Ile Arg Ala Val Ile Arg Tyr Gly Ala Lys
         275                 280                 285
Tyr Ala Thr Arg Ser Gly Met Arg Glu Asp Thr Leu Ser Leu Gln Glu
     290                 295                 300
Leu Asp Arg Tyr Cys Asp Ser Leu Thr Thr Phe Val His Lys Lys Lys
305                 310                 315                 320
Lys Asp Glu Gly Asp Asp Glu Thr Ala Arg Thr Ile Ile Arg Asn Gln
                 325                 330                 335
Trp Ile Lys Gly Met Pro Arg Met Asp Phe Lys Lys Glu Met Lys Ile
             340                 345                 350
Thr Arg Gly Pro Ile Ala Asn Trp Ser Phe Phe Met Ser Ile Asp Ala
         355                 360                 365
Phe Lys Arg Asn Asn Lys Val Asp Ile Asn Pro Asn His Gln Thr Trp
     370                 375                 380
Lys Asp His Ile Lys Glu Val Thr Asp Gln Met Asn Arg Ala Gln Gln
385                 390                 395                 400
Gly Asn Asn Asn Lys Pro Leu Lys Ile Gln Ile Asp Gly Val Ser Ile
                 405                 410                 415
Leu Thr Asn Glu Lys Tyr Gly Thr Val Gly His Trp Val Asp Trp Val
             420                 425                 430
Val Asp Leu Ile Met Leu Ala Gln Val Lys Met Leu Ile Lys Glu Tyr
```

```
                435                 440                 445
Lys Phe Lys Arg Leu Asn Ser Gln Asn Leu Met Ser Gly Met Asn Lys
450                 455                 460

Leu Val Gly Ala Leu Arg Cys Tyr Ala Tyr Cys Leu Ile Leu Ala Leu
465                 470                 475                 480

Tyr Asp Tyr Tyr Gly Gln Asp Ile Glu Gly Phe Lys Lys Gly Ser Asn
                485                 490                 495

Ser Ser Ala Ile Leu Glu Thr Val Ile Gln Met Phe Pro Asn Phe Lys
            500                 505                 510

Gln Glu Ile Gln Ala Asn Phe Gly Ile Asn Leu Asn Ile Lys Asp Lys
                515                 520                 525

Lys Gln Ser Leu Phe Val Glu Arg Thr Met His Ser Asp Phe Ser Ser
530                 535                 540

Asn Glu Glu Tyr Gly Tyr Lys Phe Val Phe Gly Trp Ala Ala Arg Gly
545                 550                 555                 560

Glu Glu Val Leu Ser Asn Tyr Gly Asp Ile Leu Ser Asp Glu Val Glu
                565                 570                 575

Glu Leu Phe Thr Lys Leu Arg Lys Lys Glu His Trp Asp Lys Val Val
            580                 585                 590

Glu Asp Pro Glu Ser Tyr Phe Val
595                 600

<210> SEQ ID NO 69
<211> LENGTH: 36
<212> TYPE: DNA
<213> ORGANISM: Artificial sequence
<220> FEATURE:
<223> OTHER INFORMATION: Oligonucleotide

<400> SEQUENCE: 69
caaattcgcg accggtccat ggttcagaat tcggtg                         36

<210> SEQ ID NO 70
<211> LENGTH: 35
<212> TYPE: DNA
<213> ORGANISM: Artificial sequence
<220> FEATURE:
<223> OTHER INFORMATION: Oligonucleotide

<400> SEQUENCE: 70
agttaaaggc ctcgagtcat ttctcggttt tggcc                          35

<210> SEQ ID NO 71
<211> LENGTH: 36
<212> TYPE: DNA
<213> ORGANISM: Artificial sequence
<220> FEATURE:
<223> OTHER INFORMATION: Oligonucleotide

<400> SEQUENCE: 71
caaattcgcg accggtccat ggcttctgaa ttcggt                         36

<210> SEQ ID NO 72
<211> LENGTH: 34
<212> TYPE: DNA
<213> ORGANISM: Artificial sequence
<220> FEATURE:
<223> OTHER INFORMATION: Oligonucleotide

<400> SEQUENCE: 72
agttaaaggc ctcgagtcac tcggctttgg ccat                           34
```

<210> SEQ ID NO 73
<211> LENGTH: 20
<212> TYPE: DNA
<213> ORGANISM: Artificial sequence
<220> FEATURE:
<223> OTHER INFORMATION: Oligonucleotide

<400> SEQUENCE: 73
ggttttcgaa cttggagaaa                                                20

<210> SEQ ID NO 74
<211> LENGTH: 24
<212> TYPE: DNA
<213> ORGANISM: Artificial sequence
<220> FEATURE:
<223> OTHER INFORMATION: Oligonucleotide

<400> SEQUENCE: 74
agaaaaccgc tcaccaaaca taga                                           24

<210> SEQ ID NO 75
<211> LENGTH: 20
<212> TYPE: DNA
<213> ORGANISM: Artificial sequence
<220> FEATURE:
<223> OTHER INFORMATION: Oligonucleotide

<400> SEQUENCE: 75
ggttttcgaa cttggagaaa                                                20

<210> SEQ ID NO 76
<211> LENGTH: 24
<212> TYPE: DNA
<213> ORGANISM: Artificial sequence
<220> FEATURE:
<223> OTHER INFORMATION: Oligonucleotide

<400> SEQUENCE: 76
agaaaaccgc tcaccaaaca taga                                           24

<210> SEQ ID NO 77
<211> LENGTH: 1050
<212> TYPE: DNA
<213> ORGANISM: Artificial sequence
<220> FEATURE:
<223> OTHER INFORMATION: Oligonucleotide

<400> SEQUENCE: 77
atggacgcta tcgctgctag ggcactctct gttgtgaggg cttgtgttac tgtgactgat      60
gctagggtgt ctcttgatcc tggtgttatg gaaactttgg gtattgctat caatagatat    120
aacggactta caaaccattc tgtttcaatg agacctcaaa cccaggcaga aggaatgag     180 atgttttca tgtgtaccga tatggttctt gctgcattga atgtgcaaat tggtaacatc    240
tcacctgatt atgatcaggc tcttgcaaca gttggagctt ggcaactac agaaattcca    300 tacaatgttc aagctatgaa cgatattgtg agaatcactg gtcaaatgca gacatttgga    360
ccttctaagg ttcaaactgg tccatatgct ggagctgtgg aagttcaaca gtcaggaagg   420
tattacgtgc cacagggaag aacaagggggt ggatacatta atagtaacat cgctgaggtt    480
tgtatggatg caggtgctgc aggacaagtg aatgctcttt tggctcctag aagaggagat   540
gctgttatga tctatttgt gtggagacct cttaggatct tctgcgatcc acagggtgct     600

```
agtttggagt ctgcaccagg aacatttgtt accgtggatg gtgttaatgt ggctgcagga    660
gatgttgtgg cttggaacac aattgcacct gttaatgtgg gtaacccagg agctagaagg    720
agtattttac aattcgaagt tctctggtac acctcattag atagaagtct cgatactgtt    780
cctgagcttg ctccaacctt gactagatgc tatgcatacg tttctcatac ttggcacgct    840
cttagggcag tgatttttca acagatgaat atgcagccaa ttaaccctcc aatcttccct    900
ccaacagaaa ggaatgagat tgttgcttat cttctcgtgg cttctttagc agatgtttac    960
gctgcactta gacctgattt cgcgatgaat ggtgttaatc cgatgccagg gccgatcaat   1020
agggctttgg ttcttgctgc ttatcattag                                    1050
```

<210> SEQ ID NO 78
<211> LENGTH: 349
<212> TYPE: PRT
<213> ORGANISM: Artificial sequence
<220> FEATURE:
<223> OTHER INFORMATION: Peptide

<400> SEQUENCE: 78

```
Met Asp Ala Ile Ala Ala Arg Ala Leu Ser Val Val Arg Ala Cys Val
1               5                   10                  15

Thr Val Thr Asp Ala Arg Val Ser Leu Asp Pro Gly Val Met Glu Thr
                20                  25                  30

Leu Gly Ile Ala Ile Asn Arg Tyr Asn Gly Leu Thr Asn His Ser Val
            35                  40                  45

Ser Met Arg Pro Gln Thr Gln Ala Glu Arg Asn Glu Met Phe Phe Met
        50                  55                  60

Cys Thr Asp Met Val Leu Ala Ala Leu Asn Val Gln Ile Gly Asn Ile
65                  70                  75                  80

Ser Pro Asp Tyr Asp Gln Ala Leu Ala Thr Val Gly Ala Leu Ala Thr
                85                  90                  95

Thr Glu Ile Pro Tyr Asn Val Gln Ala Met Asn Asp Ile Val Arg Ile
            100                 105                 110

Thr Gly Gln Met Gln Thr Phe Gly Pro Ser Lys Val Gln Thr Gly Pro
        115                 120                 125

Tyr Ala Gly Ala Val Glu Val Gln Ser Gly Arg Tyr Tyr Val Pro
    130                 135                 140

Gln Gly Arg Thr Arg Gly Gly Tyr Ile Asn Ser Asn Ile Ala Glu Val
145                 150                 155                 160

Cys Met Asp Ala Gly Ala Gly Gln Val Asn Ala Leu Leu Ala Pro
                165                 170                 175

Arg Arg Gly Asp Ala Val Met Ile Tyr Phe Val Trp Arg Pro Leu Arg
            180                 185                 190

Ile Phe Cys Asp Pro Gln Gly Ala Ser Leu Glu Ser Ala Pro Gly Thr
        195                 200                 205

Phe Val Thr Val Asp Gly Val Asn Val Ala Ala Gly Asp Val Val Ala
    210                 215                 220

Trp Asn Thr Ile Ala Pro Val Asn Val Gly Asn Pro Gly Ala Arg Arg
225                 230                 235                 240

Ser Ile Leu Gln Phe Glu Val Leu Trp Tyr Thr Ser Leu Asp Arg Ser
                245                 250                 255

Leu Asp Thr Val Pro Glu Leu Ala Pro Thr Leu Thr Arg Cys Tyr Ala
            260                 265                 270

Tyr Val Ser His Thr Trp His Ala Leu Arg Ala Val Ile Phe Gln Gln
        275                 280                 285
```

```
Met Asn Met Gln Pro Ile Asn Pro Pro Ile Phe Pro Pro Thr Glu Arg
        290                 295                 300

Asn Glu Ile Val Ala Tyr Leu Leu Val Ala Ser Leu Ala Asp Val Tyr
305                 310                 315                 320

Ala Ala Leu Arg Pro Asp Phe Ala Met Asn Gly Val Asn Pro Met Pro
                325                 330                 335

Gly Pro Ile Asn Arg Ala Leu Val Leu Ala Ala Tyr His
            340                 345
```

<210> SEQ ID NO 79
<211> LENGTH: 1050
<212> TYPE: DNA
<213> ORGANISM: Artificial sequence
<220> FEATURE:
<223> OTHER INFORMATION: Oligonucleotide

<400> SEQUENCE: 79

| | | | | | |
|---|---|---|---|---|---|
| atggacgcta | tcgctgctag | ggcactctct | gttgtgaggg | cttgtgttac | tgtgactgat | 60 |
| gctagggtgt | ctcttgatcc | tggtgttatg | gaaactttgg | gtattgctat | caatagatat | 120 |
| aacggactta | caaaccattc | tgtttcaatg | agacctcaaa | cccaggcaga | aaggaatgag | 180 |
| atgttttca | tgtgtaccga | tatggttctt | gctgcattga | atgtgcaaat | tggtaacatc | 240 |
| tcacctgatt | atgatcaggc | tcttgcaaca | gttggagctt | tggcaactac | agaaattcca | 300 |
| tacaatgttc | aagctatgaa | cgatattgtg | agaatcactg | gtcaaatgca | gacatttgga | 360 |
| ccttctaagg | ttcaaactgg | tccatatgct | ggagctgcag | aagttcaaca | gtcaggaagg | 420 |
| tattacgtgc | cacagggaag | aacaaggggt | ggatacatta | atagtaacat | cgctgaggtt | 480 |
| tgtatggatg | caggtgctgc | aggacaagtg | aatgctcttt | tggctcctag | aagaggagat | 540 |
| gctgttatga | tctattttgt | gtggagacct | cttaggatct | tctgcgatcc | acagggtgct | 600 |
| agtttggagt | ctgcaccagg | aacatttgtt | accgtggatg | tgttaatgt | ggctgcagga | 660 |
| gatgttgtgg | cttggaacac | aattgcacct | gttaatgtgg | gtaacccagg | agctagaagg | 720 |
| agtattttac | aattcgaagt | tctctggtac | acctcattag | atagaagtct | cgatactgtt | 780 |
| cctgagcttg | ctccaacctt | gactagatgc | tatgcatacg | tttctcatac | ttggcacgct | 840 |
| cttagggcag | tgattttca | acagatgaat | atgcagccaa | ttaaccctcc | aatcttccct | 900 |
| ccaacagaaa | ggaatgagat | tgttgcttat | cttctcgtgg | cttctttagc | agatgtttac | 960 |
| gctgcactta | gacctgattt | cgcgatgaat | ggtgttaatc | cgatgccagg | gccgatcaat | 1020 |
| agggctttgg | ttcttgctgc | ttatcattag | | | | 1050 |

<210> SEQ ID NO 80
<211> LENGTH: 349
<212> TYPE: PRT
<213> ORGANISM: Artificial sequence
<220> FEATURE:
<223> OTHER INFORMATION: Peptide

<400> SEQUENCE: 80

```
Met Asp Ala Ile Ala Ala Arg Ala Leu Ser Val Val Arg Ala Cys Val
1               5                   10                  15

Thr Val Thr Asp Ala Arg Val Ser Leu Asp Pro Gly Val Met Glu Thr
                20                  25                  30

Leu Gly Ile Ala Ile Asn Arg Tyr Asn Gly Leu Thr Asn His Ser Val
            35                  40                  45

Ser Met Arg Pro Gln Thr Gln Ala Glu Arg Asn Glu Met Phe Phe Met
```

```
              50                  55                  60
Cys Thr Asp Met Val Leu Ala Ala Leu Asn Val Gln Ile Gly Asn Ile
 65                  70                  75                  80

Ser Pro Asp Tyr Asp Gln Ala Leu Ala Thr Val Gly Ala Leu Ala Thr
                 85                  90                  95

Thr Glu Ile Pro Tyr Asn Val Gln Ala Met Asn Asp Ile Val Arg Ile
            100                 105                 110

Thr Gly Gln Met Gln Thr Phe Gly Pro Ser Lys Val Gln Thr Gly Pro
            115                 120                 125

Tyr Ala Gly Ala Ala Glu Val Gln Gln Ser Gly Arg Tyr Tyr Val Pro
            130                 135                 140

Gln Gly Arg Thr Arg Gly Gly Tyr Ile Asn Ser Asn Ile Ala Glu Val
145                 150                 155                 160

Cys Met Asp Ala Gly Ala Gly Gln Val Asn Ala Leu Leu Ala Pro
                165                 170                 175

Arg Arg Gly Asp Ala Val Met Ile Tyr Phe Val Trp Arg Pro Leu Arg
            180                 185                 190

Ile Phe Cys Asp Pro Gln Gly Ala Ser Leu Glu Ser Ala Pro Gly Thr
            195                 200                 205

Phe Val Thr Val Asp Gly Val Asn Val Ala Ala Gly Asp Val Val Ala
            210                 215                 220

Trp Asn Thr Ile Ala Pro Val Asn Val Gly Asn Pro Gly Ala Arg Arg
225                 230                 235                 240

Ser Ile Leu Gln Phe Glu Val Leu Trp Tyr Thr Ser Leu Asp Arg Ser
                245                 250                 255

Leu Asp Thr Val Pro Glu Leu Ala Pro Thr Leu Thr Arg Cys Tyr Ala
            260                 265                 270

Tyr Val Ser His Thr Trp His Ala Leu Arg Ala Val Ile Phe Gln Gln
            275                 280                 285

Met Asn Met Gln Pro Ile Asn Pro Pro Ile Phe Pro Pro Thr Glu Arg
            290                 295                 300

Asn Glu Ile Val Ala Tyr Leu Leu Val Ala Ser Leu Ala Asp Val Tyr
305                 310                 315                 320

Ala Ala Leu Arg Pro Asp Phe Ala Met Asn Gly Val Asn Pro Met Pro
                325                 330                 335

Gly Pro Ile Asn Arg Ala Leu Val Leu Ala Ala Tyr His
            340                 345

<210> SEQ ID NO 81
<211> LENGTH: 956
<212> TYPE: PRT
<213> ORGANISM: Bluetongue virus

<400> SEQUENCE: 81

Met Glu Glu Phe Val Ile Pro Val Tyr Ser Glu Thr Asp Ile Pro Tyr
 1                5                  10                  15

Ser Leu Leu Ser His Tyr Pro Leu Ala Ile Arg Thr Asp Val Lys Ile
                 20                  25                  30

Ala Asp Thr Asp Glu Gly His Asp Val Val Lys Ile Pro Glu Ser Asp
             35                  40                  45

Met Ile Asp Val Pro Arg Val Asp Ile Val Glu Ala Leu Ala Ala Lys
     50                  55                  60

Pro Met Arg Asn Asp Gly Ile Val Val Pro Arg Leu Leu Asp Ile Thr
 65                  70                  75                  80
```

```
Leu Arg Ala Tyr Asp Asp Arg Lys Ala Ile Lys Ser Ala Arg Gly Val
                85                  90                  95

Glu Phe Met Thr Asn Ala Lys Trp Met Lys Trp Ala Ile Asp Asp Arg
            100                 105                 110

Met Asp Ile Gln Pro Leu Lys Val Ala Ile Asp His Tyr Asn Ala Val
            115                 120                 125

Asn His Gln Leu Phe Asn Cys Ile Val Lys Ala Arg Ser Ala Asn Ala
            130                 135                 140

Asp Thr Ile Tyr Tyr Asp Tyr Phe Pro Leu Glu Ser Lys Val Lys Lys
145                 150                 155                 160

Cys Asn His Ala Asn Leu Asp Leu Leu Arg Ser Leu Thr Asn Thr Glu
                165                 170                 175

Met Phe His Met Leu Gln Gly Ala Ala Tyr Ser Leu Lys Ser Asn Tyr
            180                 185                 190

Glu Leu Ile Thr Asn Ser Glu Arg Asn Ser Thr Glu Thr Tyr Ala
            195                 200                 205

Pro Gly Val His Asn Gln Ile Arg Leu Val Arg Gly Thr Arg Ile Gly
210                 215                 220

Tyr Lys Gly Glu Ala Tyr Ser Arg Phe Val Ser Ser Leu Val Gln Val
225                 230                 235                 240

Arg Ile Gln Gly Arg Thr Pro Pro Glu Ile Val Asp Asp Ile Ala Arg
                245                 250                 255

Leu Asn Val Ile Arg Thr Glu Trp Ile Asn Ala Gln Phe Asp Ser Thr
                260                 265                 270

Lys Ile Arg Ala Leu Glu Leu Cys Lys Ile Leu Ser Ala Ile Gly Arg
            275                 280                 285

Lys Met Leu Asn Thr His Glu Glu Pro Lys Asp Glu Met Asp Leu Ser
290                 295                 300

Thr Lys Phe Gln Phe Lys Leu Asp Asp Lys Phe Lys Lys Thr Asp Ser
305                 310                 315                 320

Glu His Ile Asn Ile Phe Asn Val Arg Ala Pro Ala Thr His Glu Gly
                325                 330                 335

Arg Phe Tyr Ala Leu Ile Ala Ile Ala Ala Thr Asp Thr Gln Arg Gly
            340                 345                 350

Arg Ile Trp Arg Thr Asn Pro Tyr Pro Cys Leu Arg Gly Ala Leu Ile
            355                 360                 365

Ala Ala Glu Cys Glu Leu Gly Asp Val Tyr His Thr Leu Arg Gln Val
370                 375                 380

Tyr Lys Trp Ser Leu Arg Gln Asp Tyr Gly Arg Thr Glu Val Pro Leu
385                 390                 395                 400

Glu Asn Asn Lys Tyr Val Phe Ser Arg Ile Asn Leu Phe Asp Ser Asn
                405                 410                 415

Leu Asp Val Gly Asp Gln Val Val His Trp Met Tyr Glu Val Asp Gly
            420                 425                 430

Pro Ala Glu Thr Thr Tyr Asp Asn Gly Tyr Met Cys Lys Thr Glu Arg
            435                 440                 445

Glu Asp Glu Glu Leu Val Cys Lys Ile Ser Glu Glu Lys Tyr Lys Thr
450                 455                 460

Met Leu Asp Arg Met Ile Gln Gly Gly Trp Asp Gln Glu Arg Phe Lys
465                 470                 475                 480

Leu Tyr Ser Ile Leu Thr Asp Pro Asn Leu Leu Thr Ile Asp Phe Glu
                485                 490                 495

Lys Asp Ala His Leu Asn Ile Arg Ser Glu Phe Val Leu Pro Ser Tyr
```

```
              500                 505                 510
Phe Asp Gln Trp Ile Tyr Ser Pro Met Phe Asn Ala Arg Leu Arg Ile
            515                 520                 525
Thr His Gly Glu Ile Ala Thr Arg Lys Ser Ala Asp Pro Trp Asn Lys
            530                 535                 540
Arg Val Val Phe Gly Tyr Ile Lys Ala Ser Thr Glu Ser Pro Glu Tyr
545                 550                 555                 560
Ala Leu Gly Gln Tyr Phe Asp Met Arg Ile Gln Phe Tyr Gly Asp Ala
            565                 570                 575
Leu Ser Ser Lys Gln Asn Gln Ser Ala Val Phe Gln Tyr Leu Ser Gln
            580                 585                 590
Gln Glu Asp Phe Pro Thr Leu Thr Ser Tyr Ala Lys Gly Asp Val Val
            595                 600                 605
Cys Pro His Ser Gly Gly Ala Leu Tyr Thr Phe Arg Arg Val Ala Leu
            610                 615                 620
Met Leu Met Ala Asn Tyr Glu Lys Leu Ser Pro Asp Leu His Glu Gly
625                 630                 635                 640
Met Glu Asp Tyr Thr Tyr Thr His Pro Ser Ile Gly Gly Ala Tyr Gln
            645                 650                 655
Lys Arg Ile Leu Glu Met Arg Asp Phe Ser Gln Leu Ile Cys Phe Ile
            660                 665                 670
Ile Asp Tyr Ile Phe Glu Arg His Asp Gln Leu Arg Asp Ala Lys Glu
            675                 680                 685
Ala Arg Arg Ile Leu Tyr Leu Ile Gln Asn Leu Asp Glu Pro Gln Arg
            690                 695                 700
Leu Glu Met Leu Asn Val Thr Phe Pro Asn Phe Arg His Phe Leu
705                 710                 715                 720
Lys Leu Lys Asp Val Gln Leu Ile Ser Asp Leu Asn Val Ile Asn Phe
            725                 730                 735
Leu Pro Leu Leu Phe Leu Val Gln Asp Asn Ile Ser Tyr Trp His Arg
            740                 745                 750
Gln Trp Ala Val Pro Met Ile Leu Tyr Asp Asp Val Ile Arg Leu Ile
            755                 760                 765
Pro Val Glu Val Gly Ala Tyr Ala Asn Arg Phe Gly Ile Lys Ser Phe
770                 775                 780
Phe Asn Phe Thr Arg Phe His Pro Gly Asp Ala Lys Lys Arg Gln Lys
785                 790                 795                 800
Ala Asp Asp Thr His Lys Glu Phe Gly Ser Ile Ser Phe Asn Tyr Tyr
            805                 810                 815
Ala Ser Thr Lys Ile Ala Gln Gly Gly Val His Thr Pro Val Val Thr
            820                 825                 830
Thr Lys Leu Asp Thr Leu Lys Ile His Leu Ser Ser Leu Cys Ala Gly
            835                 840                 845
Leu Ala Asp Ser Ile Val Tyr Thr Leu Pro Val Ala His Pro Lys Lys
            850                 855                 860
Cys Ile Val Leu Ile Ile Val Gly Asp Asp Lys Leu Glu Pro His Val
865                 870                 875                 880
Arg Ser Glu Gln Val Ser Tyr Tyr Phe Ser Arg Arg His Val
            885                 890                 895
Ser Gly Ile Val Ser Ile Cys Val Gly Gln Asp Asn Gln Leu Lys Val
            900                 905                 910
Tyr Ser Ser Gly Ile Val Arg His Arg Val Cys Glu Lys Phe Ile Leu
            915                 920                 925
```

```
Lys Tyr Lys Cys Lys Val Val Leu Val Lys Met Pro Gly Tyr Val Phe
            930                 935                 940

Gly Asn Asp Glu Leu Met Thr Lys Leu Leu Asn Val
945                 950                 955
```

<210> SEQ ID NO 82
<211> LENGTH: 956
<212> TYPE: PRT
<213> ORGANISM: Bluetongues virus

<400> SEQUENCE: 82

```
Met Glu Glu Phe Val Ile Pro Val Phe Ser Glu Arg Asp Ile Pro Tyr
1               5                   10                  15

Ser Leu Leu Asn His Tyr Pro Leu Ala Ile Arg Ile Asp Val Lys Val
            20                  25                  30

Asp Asp Glu Asp Gly Arg His Asn Leu Ile Lys Ile Pro Glu Ser Asp
        35                  40                  45

Met Ile Asp Val Pro Lys Leu Ser Val Ile Glu Ala Leu Asn Tyr Arg
50                  55                  60

Pro Lys Arg Asn Asp Gly Val Val Pro Arg Leu Leu Asp Ile Thr
65                  70                  75                  80

Leu His Ala Tyr Asp Lys Arg Lys Ser Thr Lys Ser Ala Lys Gly Val
                85                  90                  95

Glu Phe Thr Thr Asp Ala Lys Trp Met Lys Trp Ala Ile Asp Asp Lys
            100                 105                 110

Met Asp Ile Gln Pro Leu Lys Val Thr Leu Asp Asn His Tyr Ser Val
        115                 120                 125

Asn His Gln Leu Phe Asn Cys Ile Val Lys Ala Arg Ser Ala Asn Ala
130                 135                 140

Asp Thr Ile Tyr Tyr Asp Tyr Pro Leu Glu Asn Gly Ala Lys Lys
145                 150                 155                 160

Cys Asn His Thr Asn Leu Asp Leu Leu Arg Ser Leu Thr Thr Thr Glu
                165                 170                 175

Met Phe His Ile Leu Gln Gly Ala Ala Tyr Ala Leu Lys Thr Thr His
            180                 185                 190

Glu Leu Val Ala His Ser Glu Arg Glu Ser Thr Ser Glu Thr Tyr Gln
        195                 200                 205

Val Gly Thr Gln Arg Trp Ile Gln Leu Arg Lys Gly Thr Lys Ile Gly
210                 215                 220

Tyr Arg Gly Gln Pro Tyr Glu Arg Phe Ile Ser Ser Leu Val Gln Val
225                 230                 235                 240

Ile Ile Lys Gly Arg Val Pro Asp Glu Ile Arg Asp Glu Ile Ala Glu
                245                 250                 255

Leu Asn Arg Ile Lys Asp Glu Trp Lys Asn Ala Ala Tyr Asp Arg Thr
            260                 265                 270

Lys Ile Arg Ala Leu Glu Leu Cys Lys Ile Leu Ser Ala Ile Gly Arg
        275                 280                 285

Lys Met Leu Asp Val Gln Glu Pro Lys Asp Glu Met Ala Leu Ser
290                 295                 300

Thr Arg Phe Gln Phe Lys Leu Asp Glu Lys Phe Ile Arg Thr Asp Gln
305                 310                 315                 320

Glu His Val Asn Ile Phe Glu Val Gly Gly Pro Ala Thr Asp Asp Gly
                325                 330                 335

Arg Phe Tyr Ala Leu Ile Ala Ile Ala Ala Thr Asp Thr Gln Gln Gly
```

```
                340              345              350
Arg Val Trp Arg Thr Asn Pro Tyr Pro Cys Leu Arg Gly Ala Leu Ile
            355                  360              365
Ala Ala Glu Cys Glu Leu Gly Asp Val Tyr Phe Thr Leu Arg Gln Thr
            370                  375                  380
Tyr Lys Trp Ser Leu Arg Ser Glu Tyr Gly Gln Glu Arg Pro Leu
385                      390                  395                  400
Glu Asp Asn Lys Tyr Val Phe Ser Arg Leu Asn Leu Phe Asp Thr Asn
                405                  410                  415
Leu Ala Ile Gly Asp Glu Ile Ile His Trp Arg Tyr Glu Ile Tyr Arg
            420                  425                  430
Pro Lys Glu Thr Thr His Asp Asp Gly Tyr Ile Cys Val Ser Gln Lys
            435                  440                  445
Asp Asp Asp Glu Leu Leu Cys Glu Ile Asp Gly Asp Arg Tyr Lys Glu
            450                  455                  460
Met Phe Asp Arg Met Ile Gln Gly Gly Trp Asp Gln Glu Arg Phe Lys
465                      470                  475                  480
Leu His Asn Ile Leu Thr Glu Pro Asn Leu Leu Thr Ile Asp Phe Glu
                485                  490                  495
Lys Asp Ala Tyr Leu Gly Ser Arg Ser Glu Leu Val Phe Pro Pro Tyr
                500                  505                  510
Tyr Asp Lys Trp Ile Asn Ser Pro Met Phe Asn Ala Lys Leu Lys Ile
                515                  520                  525
Ala Arg Gly Glu Ile Ala Thr Arg Lys Val Asp Asp Pro Trp Asn Asn
            530                  535                  540
Arg Ala Val His Gly Tyr Ile Lys Thr Ser Ala Glu Ser Leu Gly Tyr
545                      550                  555                  560
Val Leu Gly Pro Tyr Tyr Asp Leu Arg Leu Gln Leu Phe Gly Asp Ala
                565                  570                  575
Leu Ser Leu Glu Gln Lys Gln Ser Ala Val Phe Glu Tyr Met Ala Gln
                580                  585                  590
Gln Asp Asp Phe Pro Ala Leu Thr Asp Tyr Thr Lys Glu Lys Asn Gly
            595                  600                  605
Cys Pro His Ser Gly Gly Thr Phe Tyr Thr Phe Arg Lys Val Ala Leu
            610                  615                  620
Ile Ile Leu Ser Ser Tyr Glu Arg Leu Asp Pro Ser Leu His Glu Gly
625                      630                  635                  640
Arg Glu His Glu Thr Tyr Met His Pro Ala Ile Asn Asp Val Phe Arg
                645                  650                  655
Arg Tyr Ala Leu Glu Met Lys Glu Phe Ser Gln Leu Ile Cys Phe Val
                660                  665                  670
Phe Asp Tyr Ile Phe Glu Lys His Val Gln Leu Arg Asn Ala Lys Glu
                675                  680                  685
Ala Arg Arg Ile Ile Tyr Leu Ile Gln Asn Thr Ser Gly Val His Arg
            690                  695                  700
Leu Asp Ile Leu Arg Glu Thr Phe Pro Asn Phe Leu Arg His Val Met
705                      710                  715                  720
Asn Leu Arg Asp Val Lys Arg Ile Cys Asp Leu Asn Val Ile Asn Phe
                725                  730                  735
Phe Pro Leu Leu Phe Leu Ile Gln Asp Asn Ile Ser Tyr Trp His Arg
                740                  745                  750
Gln Trp Ser Ile Pro Met Ile Leu Phe Gly Glu Val Val Arg Leu Ile
            755                  760                  765
```

```
Pro Ile Glu Val Gly Ala Tyr Ala Asn Arg Phe Gly Phe Lys Ser Phe
            770                 775                 780

Leu Asn Phe Ile Arg Phe His Pro Gly Asp Ser Lys Lys Lys Gln Asp
785                 790                 795                 800

Ala Asp Asp Thr His Lys Glu Phe Gly Ser Ile Cys Phe Glu Tyr Tyr
            805                 810                 815

Thr Thr Thr Lys Ile Ser Gln Gly Glu Ile Asp Val Pro Val Ile Thr
            820                 825                 830

Ser Lys Leu Asp Thr Leu Lys Leu His Ile Ala Ser Leu Cys Ala Gly
            835                 840                 845

Leu Ala Asp Ser Leu Val Tyr Thr Leu Pro Val Ala His Pro Lys Lys
        850                 855                 860

Ser Ile Val Leu Ile Ile Val Gly Asp Asp Lys Leu Glu Pro Gln Val
865                 870                 875                 880

Arg Ser Glu Gln Ile Val Asn Lys Tyr His Tyr Ser Arg Arg His Ile
            885                 890                 895

Ser Gly Val Val Ser Ile Cys Val Asp Gln Asn Gly Gln Leu Lys Val
            900                 905                 910

His Ser Met Gly Ile Thr Arg His Arg Ile Cys Asp Lys Ser Ile Leu
        915                 920                 925

Lys Tyr Lys Cys Lys Val Val Leu Val Arg Met Pro Gly His Val Phe
    930                 935                 940

Gly Asn Asp Glu Leu Met Thr Lys Leu Leu Asn Val
945                 950                 955

<210> SEQ ID NO 83
<211> LENGTH: 955
<212> TYPE: PRT
<213> ORGANISM: Bluetongue virus

<400> SEQUENCE: 83

Met Glu Glu Phe Val Ile Pro Val Tyr Ser Asp Glu Ile Pro Tyr
1               5                   10                  15

Ala Leu Leu Ser Arg Tyr Pro Leu Ala Ile Gln Thr Asn Val Lys Ile
            20                  25                  30

Glu Asp Val Glu Gly Lys His Asn Val Val Lys Ile Pro Glu Ser Asp
        35                  40                  45

Met Ile Asp Ile Pro Lys Leu Thr Ile Val Glu Ala Met Asn Tyr Lys
    50                  55                  60

Pro Ala Arg Asn Asp Gly Ile Val Val Pro Arg Leu Leu Asp Ile Thr
65                  70                  75                  80

Leu Arg Ala Tyr Asp Asp Arg Lys Ser Thr Lys Ser Ala Arg Gly Ile
                85                  90                  95

Glu Phe Met Thr Asn Ala Arg Trp Met Lys Trp Ala Ile Asp Asp Arg
            100                 105                 110

Met Asp Ile Gln Pro Leu Lys Val Thr Leu Asp His Tyr Cys Ser Val
        115                 120                 125

Asn His Gln Leu Phe Asn Cys Val Val Lys Ala Asn Ala Ala Asn Ala
    130                 135                 140

Asp Thr Ile Tyr Tyr Asp Tyr Phe Pro Leu Glu Asp Tyr Lys Lys Arg
145                 150                 155                 160

Cys Asn His Thr Asn Leu Asp Leu Leu Arg Ser Leu Thr Asn Met Glu
                165                 170                 175

Leu Phe His Ala Leu Gln Gly Ala Ala Tyr Ser Ile Lys Ser Ser Tyr
```

```
            180                 185                 190
Glu Leu Val Ala Tyr Ser Glu Arg Gly Ser Leu Glu Glu Thr Tyr Val
            195                 200                 205
Val Gly Gln Pro Lys Trp Ile His Leu Thr Arg Gly Thr Arg Ile Gly
            210                 215                 220
Asn Ser Gly Leu Ser Tyr Glu Arg Phe Ile Ser Ser Met Val Gln Val
225                 230                 235                 240
Ser Val Asn Gly Lys Ile Pro Asp Glu Ile Ala Asn Glu Ile Ala Gln
            245                 250                 255
Leu Asn Arg Ile Arg Ala Glu Trp Ile Thr Ala Thr Tyr Asp Arg Gly
            260                 265                 270
Arg Ile Arg Ala Leu Glu Leu Cys Asn Ile Leu Ser Thr Ile Gly Arg
            275                 280                 285
Lys Met Leu Asn Thr His Glu Glu Pro Lys Asp Glu Met Asp Leu Ser
            290                 295                 300
Thr Arg Phe Gln Phe Lys Leu Asp Glu Lys Phe Asn Arg Ala Asp Ser
305                 310                 315                 320
Glu His Val Asn Ile Phe Gly Val Arg Gly Pro Ala Thr Asp Glu Gly
            325                 330                 335
Arg Phe Tyr Ala Leu Ile Ala Ile Ala Ala Thr Asp Thr Gln Lys Gly
            340                 345                 350
Arg Val Trp Arg Thr Asn Pro Tyr Pro Cys Leu Arg Gly Ala Leu Val
            355                 360                 365
Ala Ala Glu Cys Glu Leu Gly Asp Val Tyr Ser Thr Leu Arg Arg Val
            370                 375                 380
Tyr Arg Trp Ser Leu Arg Pro Glu Tyr Gly Gln His Glu Arg Gln Leu
385                 390                 395                 400
Glu Asn Asn Lys Tyr Val Phe Asn Arg Ile Asn Leu Phe Asp Ser Asn
            405                 410                 415
Leu Ala Val Gly Asp Gln Ile Ile His Trp Arg Tyr Glu Val Lys Ala
            420                 425                 430
Ser Ala Glu Thr Thr Tyr Asp Ser Gly Tyr Met Cys Arg His Glu Ala
            435                 440                 445
Glu Glu Asp Glu Leu Leu Cys Lys Ile Asn Glu Asp Lys Tyr Lys Glu
            450                 455                 460
Met Leu Asp Arg Met Ile Gln Gly Gly Trp Asp Gln Glu Arg Phe Lys
465                 470                 475                 480
Leu His Asn Ile Leu Thr Asp Pro Asn Leu Leu Thr Ile Asp Phe Glu
            485                 490                 495
Lys Asp Ala Tyr Leu Asn Ser Arg Ser Glu Leu Val Leu Pro Asp Tyr
            500                 505                 510
Phe Asp Lys Trp Ile Ser Ser Pro Met Phe Asn Ala Arg Leu Arg Ile
            515                 520                 525
Thr Lys Gly Glu Ile Gly Thr Ser Lys Lys Asp Pro Trp Asn Asn
            530                 535                 540
Arg Ala Val Arg Gly Tyr Ile Lys Ser Pro Ala Glu Ser Leu Asp Phe
545                 550                 555                 560
Val Leu Gly Pro Tyr Tyr Asp Leu Arg Leu Phe Phe Gly Glu Thr
            565                 570                 575
Leu Ser Leu Lys Gln Glu Gln Ser Ala Val Phe Gln Tyr Leu Ser Gln
            580                 585                 590
Leu Asp Asp Phe Pro Ala Leu Thr Gln Leu Thr Gly Asp Ala Val Cys
            595                 600                 605
```

Pro His Ser Gly Gly Ala Leu Tyr Thr Phe Arg Lys Val Ala Leu Phe
          610                 615                 620

Leu Ile Gly Asn Tyr Glu Lys Leu Ser Pro Asp Leu His Glu Gly Met
625                 630                 635                 640

Glu His Gln Arg Tyr Val His Pro Ser Thr Gly Gly Thr Tyr Gln Lys
                645                 650                 655

Arg Val Leu Glu Met Lys Asp Pro Cys Gln Leu Thr Cys Phe Val Ile
            660                 665                 670

Asp Tyr Ile Phe Glu Lys Arg Glu Gln Leu Arg Asp Thr Lys Glu Ala
        675                 680                 685

Arg Tyr Ile Val Tyr Leu Ile Gln Ser Leu Thr Gly Thr Gln Arg Leu
    690                 695                 700

Ser Val Leu Arg Ser Thr Phe Pro Asn Phe Phe Gln Arg Leu Leu Met
705                 710                 715                 720

Leu Lys Glu Ile Lys Phe Val Arg Asp Leu Asn Val Ile Asn Phe Leu
                725                 730                 735

Pro Leu Met Phe Leu Val His Asp Asn Ile Ser Tyr Trp His Arg Gln
                740                 745                 750

Trp Ser Ile Pro Met Val Leu Phe Asp Thr Ile Lys Leu Ile Pro
            755                 760                 765

Val Glu Val Gly Ala Tyr Ala Asn Arg Phe Gly Phe Lys Ser Phe Met
770                 775                 780

Asn Phe Thr Arg Phe His Pro Gly Glu Leu Lys Lys Gln Ile Ala
785                 790                 795                 800

Glu Asp Ile His Lys Glu Phe Gly Val Val Ala Phe Glu Tyr Tyr Thr
                805                 810                 815

Asn Thr Lys Ile Ser Gln Gly Asn Val His Thr Pro Val Met Thr Thr
            820                 825                 830

Lys Met Asp Val Leu Arg Val His Leu Ser Ser Leu Cys Ala Gly Leu
        835                 840                 845

Ala Asp Ser Val Val Tyr Thr Leu Pro Val Ala His Pro Lys Lys Cys
    850                 855                 860

Ile Val Leu Ile Val Gly Asp Asp Lys Leu Glu Pro His Thr Arg
865                 870                 875                 880

Ser Glu Gln Ile Val Ser Arg Tyr Asn Tyr Ser Arg Lys His Ile Cys
                885                 890                 895

Gly Ile Val Ser Val Thr Ile Gly Gln Asn Ser Gln Leu Arg Val His
                900                 905                 910

Thr Ser Gly Ile Val Lys His Arg Val Cys Asp Lys Phe Ile Leu Lys
            915                 920                 925

His Lys Cys Lys Val Ile Leu Val Arg Met Pro Gly Tyr Val Phe Gly
        930                 935                 940

Asn Asp Glu Leu Met Thr Lys Leu Leu Asn Val
945                 950                 955

<210> SEQ ID NO 84
<211> LENGTH: 956
<212> TYPE: PRT
<213> ORGANISM: Bluetongue virus

<400> SEQUENCE: 84

Met Glu Glu Phe Val Ile Pro Val Phe Ser Glu Arg Glu Ile Pro Tyr
1               5                   10                  15

Ala Leu Ile Asn Gln Tyr Pro Leu Ala Ile Gln Thr Asp Val Arg Val

```
            20                  25                  30
Val Asp Val Asp Asn His Asn Leu Val Lys Ile Pro Glu Ser Asp
        35                  40                  45
Met Ile Asp Val Pro Lys Leu Asp Ile Val Ser Ala Leu Asn Tyr Lys
    50                  55                  60
Pro Thr Arg Asn Asp Gly Ile Val Val Pro Arg Leu Leu Asp Ile Thr
65                  70                  75                  80
Leu Lys Ala Tyr Asp Asp Arg Lys Ser Val Lys Asn Ala Arg Gly Val
                85                  90                  95
Asp Phe Met Thr Asp Ala Lys Trp Met Lys Trp Ala Ile Asp Asp Arg
            100                 105                 110
Met Asp Ile Gln Pro Leu Lys Ile Thr Leu Asp Glu His Tyr Ser Val
        115                 120                 125
Asn His Gln Leu Phe Asn Cys Ile Val Lys Ala Lys Thr Ala Asn Ala
    130                 135                 140
Asp Thr Ile Tyr Tyr Asp Tyr Phe Pro Leu Glu Asp Arg Ala Lys Lys
145                 150                 155                 160
Cys Asn His Thr Asn Leu Glu Leu Leu Arg Ser Leu Thr Thr Ile Glu
                165                 170                 175
Ala Phe His Ile Leu Gln Gly Ala Ala Tyr Ser Leu Lys Ser Asn Tyr
            180                 185                 190
Asp Leu Ile Ala Asn Ser Glu Arg Glu Ser Leu Glu Glu Ser Tyr Pro
        195                 200                 205
Ile Gly Ser Glu Lys Trp Val His Leu Thr Arg Arg Thr Lys Ile Gly
    210                 215                 220
Asn Ser Gly Leu Ser Tyr Asn Arg Ser Ile Ser Ser Met Val Gln Val
225                 230                 235                 240
Val Val Arg Gly Lys Val Pro Asp Ile Ile Arg Gly Glu Ile Thr Gln
                245                 250                 255
Leu Asn Arg Ile Arg Thr Glu Trp Ile Gly Ala Ser Tyr Asp Arg Thr
            260                 265                 270
Arg Ile Arg Ala Leu Glu Leu Cys Asn Ile Leu Ser Ala Ile Gly Arg
        275                 280                 285
Lys Met Met Asp Thr His Glu Glu Pro Lys Asp Glu Met Asp Leu Ser
    290                 295                 300
Thr Arg Phe Gln Phe Lys Leu Asp Glu Lys Phe Asn Thr Ser Asp Phe
305                 310                 315                 320
Glu His Val Asn Ile Phe Arg Thr Ser Gly Ala Ala Thr Asn Glu Gly
                325                 330                 335
Arg Phe Tyr Ala Leu Ile Ala Ile Ala Ala Thr Asp Thr Gln Lys Gly
            340                 345                 350
Arg Val Trp Arg Thr Asn Pro Tyr Pro Cys Leu Arg Gly Ala Leu Ile
        355                 360                 365
Ala Ser Glu Cys Glu Leu Gly Asp Val Tyr Tyr Thr Leu Arg His Val
    370                 375                 380
Tyr Arg Trp Ser Leu Arg Pro Glu Tyr Gly Gln Arg Glu Arg Gln Leu
385                 390                 395                 400
Glu Asp Asn Lys Tyr Val Phe Gly Arg Val Asn Leu Phe Asp Ser Asp
                405                 410                 415
Leu Ala Val Gly Asp Gln Ile Ile His Trp Gln Tyr Glu Ile Thr Glu
            420                 425                 430
Pro Val Lys Thr Thr Tyr Asp Asp Gly Tyr Ile Cys Asn Pro Glu Glu
        435                 440                 445
```

```
Lys Asp Asp Glu Leu Leu Cys Lys Ile Asp Glu Arg Tyr Lys Glu
    450                 455                 460

Met Met Glu Arg Leu Ile Glu Gly Gly Trp Asp Gln Glu Arg Phe Lys
465                 470                 475                 480

Leu His Ser Ile Leu Thr Glu Pro Asn Leu Leu Thr Ile Asp Phe Glu
                485                 490                 495

Lys Asp Ala Tyr Leu Asn Ser Arg Ser Glu Leu Val Phe Pro Asn Tyr
                500                 505                 510

Phe Asp Lys Trp Ile Asn Ser Pro Met Phe Asn Ala Arg Leu Arg Ile
            515                 520                 525

Thr His Gly Glu Ile Gly Ser Ser Lys Thr Ile Asp Pro Trp Asn Arg
    530                 535                 540

Arg Val Val Tyr Gly Tyr Val Lys Thr Ser Ile Glu Ser Leu Asp Tyr
545                 550                 555                 560

Ala Leu Gly Arg Tyr Tyr Asp Ile Arg Leu Gln Leu Phe Gly Asp Thr
                565                 570                 575

Leu Ser Gln Lys Gln Thr Gln Ser Ala Val Phe Thr Tyr Leu Ser Glu
                580                 585                 590

Gln Asp Asp Phe Pro Ala Leu Thr Asn Tyr Ser Lys Gly Glu Ala Val
    595                 600                 605

Cys Pro His Ala Gly Gly Ala Val Tyr Thr Phe Arg Lys Val Ala Leu
610                 615                 620

Ser Leu Ile Ala Asn Tyr Glu Lys Leu Ser Pro Glu Met His Glu Gly
625                 630                 635                 640

Leu Glu His Gln Met Tyr Val His Pro Ser Ala Asn Thr Thr Tyr Gln
                645                 650                 655

Lys Gln Val Lys Asp Met Lys Asp Phe Ser Gln Leu Ile Cys Phe Ile
                660                 665                 670

Ile Asp Cys Ile Phe Glu Lys Arg Val Gln Ile Arg Gly Val Gly Glu
            675                 680                 685

Ala Arg Arg Ile Ile Tyr Leu Ile Gln Asn Ser Thr Gly Ser Gln Arg
    690                 695                 700

Gln Glu Val Leu Lys Lys Thr Phe Pro Asn Phe Phe Met Arg Ile Phe
705                 710                 715                 720

Lys Leu Arg Glu Val Lys Arg Ile Cys Asp Leu Ser Val Ile Asn Phe
                725                 730                 735

Leu Pro Leu Leu Phe Leu Val Gln Asp Asn Ile Ser Tyr Trp His Arg
                740                 745                 750

Gln Trp Ser Val Pro Met Ile Leu Phe Asp Asp Ala Val Arg Leu Ile
            755                 760                 765

Pro Val Glu Val Gly Ala Tyr Ala Asn Arg Phe Gly Leu Lys Ser Phe
    770                 775                 780

Tyr Asn Phe Val Arg Phe His Pro Gly Asp Ser Lys Lys Gln Asp
785                 790                 795                 800

Ala Asp Asp Met His Lys Glu Tyr Gly Val Ala Cys Phe Glu Tyr Tyr
                805                 810                 815

Met Asn Thr Lys Ile Ser Gln Gly Gly Val Asn Val Pro Val Val Thr
                820                 825                 830

Ser Lys Leu Asp Thr Leu Lys Ile His Leu Ala Ser Leu Cys Leu Gly
            835                 840                 845

Leu Ala Asp Ser Ile Val Tyr Thr Leu Pro Val Ala His Pro Lys Lys
    850                 855                 860
```

-continued

```
Cys Ile Val Leu Ile Val Val Gly Asp Asp Lys Leu Asp Pro Gln Val
865                 870             875                 880

Arg Ser Glu Gln Val Leu Ser Lys Tyr Tyr Ser Arg Arg His Ile
            885                 890             895

Cys Gly Ile Val Ala Val Ser Val Gly Gln Glu Gly Gln Leu Gln Val
            900             905                 910

Tyr Ser Ser Gly Ile Val Arg His Arg Ile Cys Glu Lys Ser Ile Leu
        915             920                 925

Lys Tyr Lys Cys Lys Val Val Leu Val Arg Met Pro Gly His Val Phe
    930             935                 940

Gly Asn Asp Glu Leu Met Thr Lys Leu Leu Asn Val
945                 950             955
```